(12) United States Patent
Butt et al.

(10) Patent No.: US 7,820,384 B2
(45) Date of Patent: *Oct. 26, 2010

(54) METHODS AND COMPOSITIONS FOR PROTEIN EXPRESSION AND PURIFICATION

(75) Inventors: Tauseef R. Butt, Audubon, PA (US);
Steven D. Weeks, Philadelphia, PA (US);
Hiep T. Tran, West Chester, PA (US);
Michael P. Malakhov, West Chester, PA (US); Oxana A. Malakhova, West Chester, PA (US)

(73) Assignee: Lifesensors, Inc., Malvern, PA (US)

( * ) Notice: Subject to any disclaimer, the term of this patent is extended or adjusted under 35 U.S.C. 154(b) by 182 days.

This patent is subject to a terminal disclaimer.

(21) Appl. No.: 11/363,660

(22) Filed: Feb. 28, 2006

(65) Prior Publication Data

US 2006/0216785 A1   Sep. 28, 2006

Related U.S. Application Data

(62) Division of application No. 10/338,411, filed on Jan. 7, 2003, now Pat. No. 7,060,461.

(60) Provisional application No. 60/346,449, filed on Jan. 7, 2002.

(51) Int. Cl.
  *C12Q 1/68* (2006.01)
  *C12N 1/21* (2006.01)
  *C12N 1/15* (2006.01)
  *C07K 14/00* (2006.01)

(52) U.S. Cl. .................. 435/6; 435/252.3; 435/252.11; 530/350

(58) Field of Classification Search ........................ None
See application file for complete search history.

(56) References Cited

U.S. PATENT DOCUMENTS

| 6,576,469 | B1 | 6/2003 | Struhl |
| 6,872,551 | B2 * | 3/2005 | Lima et al. ................. 435/69.7 |
| 7,060,461 | B2 | 6/2006 | Butt et al. |
| 7,220,576 | B2 | 5/2007 | Butt et al. |
| 2007/0259414 | A1 | 11/2007 | Butt et al. |

FOREIGN PATENT DOCUMENTS

WO   02/090495 A2   11/2002

OTHER PUBLICATIONS

Wada et al. Cleavage of the C-terminus of NEDD8 by UCH-L3. Biochem Biophys Res Commun. Oct. 29, 1998;251(3):688-92.*
Li et al. A new protease required for cell-cycle progression in yeast. Nature 398, 246-251 (Mar. 18, 1999).*
Hochstrasser, M. Biochemistry. All in the ubiquitin family. Science. Jul. 28, 2000;289(5479):563-4.*
Johnsson, N., "A split-ubiquitin-based assay detects the influence of mutations on the conformational stability of . . . ," FEBS Letters, 531:259-264, (2002).
Genebank Accession No. U37458 (Printed on Jul. 25, 2006).
Bachmair, et al., In vivo half-life of a protein is a function of its amino-terminal residue, Science 234:179-186, (1986).
pQE-30 Xa Vector, Qiagen product cataglog on the world wide web (2005).
Muller, S., et al., "Conjugation with the ubiquitin-related modifier SUMO-1 regulates the partioning of . . . ," EMBO J., 17:61-70, (1998).
Kamitani, et al. Characterization of NEDD8, a Developmentally Down-regulated Ubiquitin-like Protein; Journal of Biological Chemistry; 272: 45 28557-28562 (Nov. 7, 2007).
Hochstrasser, M. "All in the Ubiquitin Family," Science, 289:563-564, 2000.

* cited by examiner

*Primary Examiner*—Michele K Joike
(74) *Attorney, Agent, or Firm*—Dann, Dorfman, Herrell & Skillman; Robert C. Netter, Jr.

(57) ABSTRACT

Methods for enhancing expression levels and secretion of heterologous fusion proteins in a host cell are disclosed.

9 Claims, 87 Drawing Sheets

Figure 3

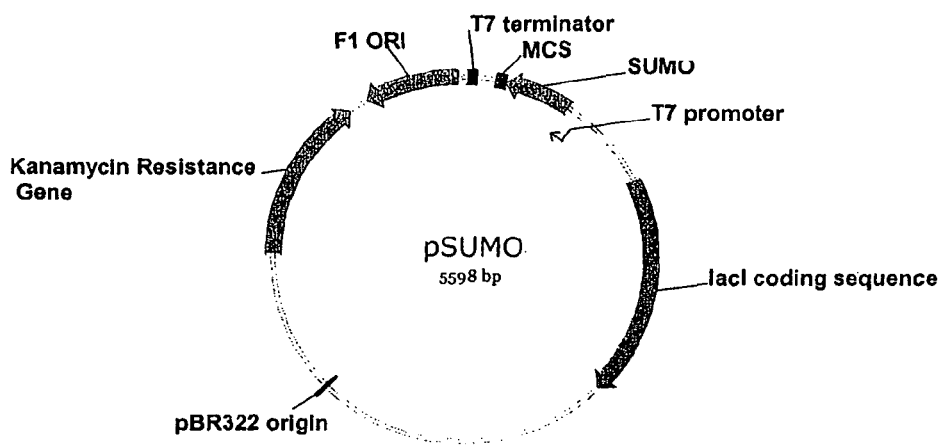

Multiple Cloning Site:

```
           BglII                                                              XbaI
           -----                                                              ----
  1   AGATCTCGATCCCGCGAAATTAATACGACTCACTATAGGGGAATTGTGAGCGGATAACAATTCCCCTCTAGAAATAATTTTGTTTAACTTTAAGAAGGAG

NcoI
           ----
              MetGlyHisHisHisHisHisHisGlySerAspSerGluValAsnGlnGluAlaLysProGluValLysProGluValLysProGluThrHis
101   ATATACCATGGGTCATCACCATCATCATCACGGGTCGGACTCAGAAGTCAATCAAGAAGCTAAGCCAGAGGTCAAGCCAGAAGTCAAGCCTGAGACTCAC

BglII
                        -----
       IleAsnLeuLysValSerAspGlySerSerGluIlePhePheLysIleLysLysThrThrProLeuArgArgLeuMetGluAlaPheAlaLysArgGlnGly·
201   ATCAATTTAAAGGTGTCCGATGGATCTTCAGAGATCTTCTTCAAGATCAAAAAGACCACTCCTTTAAGAAGGCTGATGGAAGCGTTCGCTAAAAGACAGG

EcoRI
                                   -----
      ·GLysGluMetAspSerLeuArgPheLeuTyrAspGlyIleArgIleGlnAlaAspGlnThrProGluAspLeuAspMetGluAspAsnAspIleIleGlu·
301   GTAAGGAAATGGACTCCTTAAGATTCTTGTACGACGGTATTAGAATTCAAGCTGATCAGACCCCTGAAGATTTGGACATGGAGGATAACGATATTATTGA

SacI    SalI         NotI
                                         ----    ----         ----
                                                              EagI
                                                              ----
                         BsaI BamHI EcoRI          HindIII         XhoI
                         -------------------       -------         ----
      ·AlaHisArgGluGlnIleGlyGly***
401   GGCTCACCGCGAACAGATTGGAGGTTGAGACCGGATCCGAATTCGAGCTCCGTCGACAAGCTTGCGGCCGCACTCGAG
                          ↑
                     Hydrolase Cleavage Site
```

Sumo-LXR-fusion expression

Ubl-GFP co-translational cleavage
YPD, 30°C, 3.5 h induction, 100 μM CuSO$_4$

Figure 14
SUMO-GFP fusion proteins expression in Hi-Five cells fluorescence micrographs
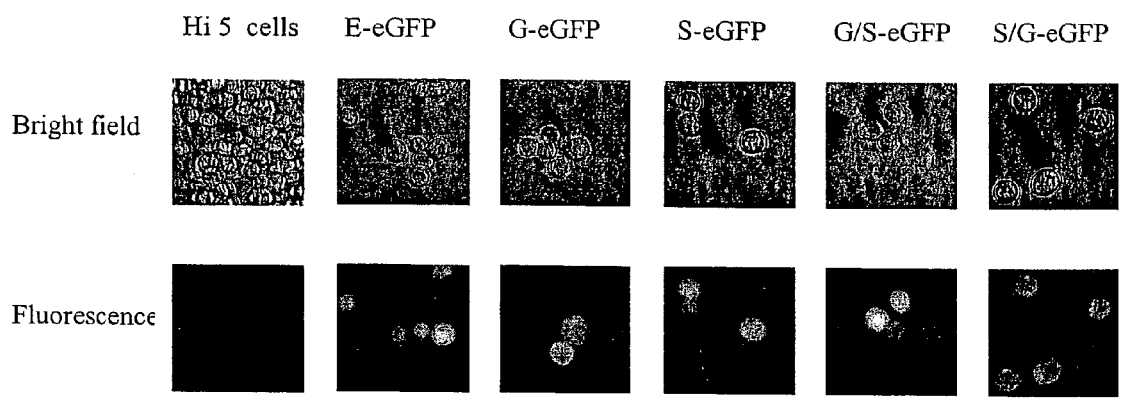
Ubiquitin-GFP fusion proteins expression in Hi-Five cells fluorescence micrographs
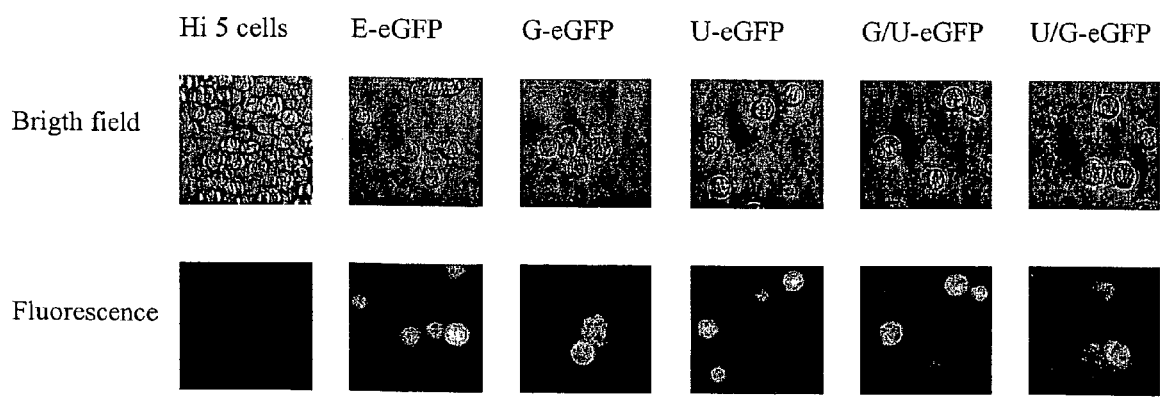

Figure 15
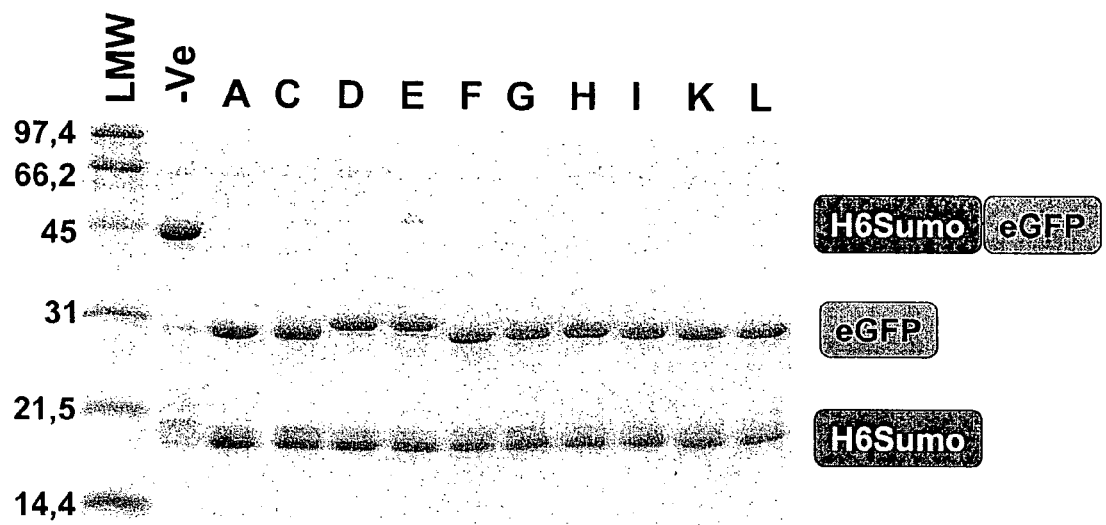
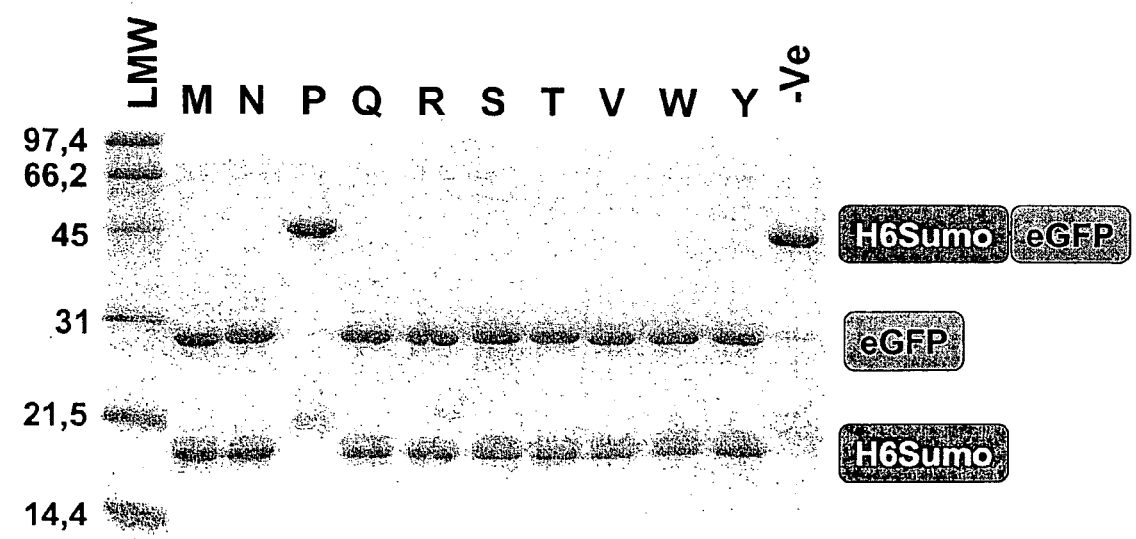

```
                               SUMO
                     SUMO NCBI ACCESSION# Q12306
           NcoI
           ~~~~~~
              M   G   H   H   H   H   H   G   S   D   S   E   V   N   Q
      1   CCATGGGTCA TCACCATCAT CATCACGGGT CGGACTCAGA AGTCAATCAA
          GGTACCCAGT AGTGGTAGTA GTAGTGCCCA GCCTGAGTCT TCAGTTAGTT
              E   A   K   P   E   V   K   P   E   V   K   P   E   T   H   I   N ·
     51   GAAGCTAAGC CAGAGGTCAA GCCAGAAGTC AAGCCTGAGA CTCACATCAA
          CTTCGATTCG GTCTCCAGTT CGGTCTTCAG TTCGGACTCT GAGTGTAGTT
            · L   K   V   S   D   G   S   S   E   I   F   F   K   I   K   K   T ·
    101   TTTAAAGGTG TCCGATGGAT CTTCAGAGAT CTTCTTCAAG ATCAAAAAGA
          AAATTTCCAC AGGCTACCTA GAAGTCTCTA GAAGAAGTTC TAGTTTTTCT
            · T   P   L   R   R   L   M   E   A   F   A   K   R   Q   G   K
    151   CCACTCCTTT AAGAAGGCTG ATGGAAGCGT TCGCTAAAAG ACAGGGTAAG
          GGTGAGGAAA TTCTTCCGAC TACCTTCGCA AGCGATTTTC TGTCCCATTC
              E   M   D   S   L   R   F   L   Y   D   G   I   R   I   Q   A   D ·
    201   GAAATGGACT CCTTAAGATT CTTGTACGAC GGTATTAGAA TTCAAGCTGA
          CTTTACCTGA GGAATTCTAA GAACATGCTG CCATAATCTT AAGTTCGACT
            · Q   A   P   E   D   L   M   E   D   N   D   I   I   E   A   H ·
    251   TCAGGCCCCT GAAGATTTGG ACATGGAGGA TAACGATATT ATTGAGGCTC
          AGTCCGGGGA CTTCTAAACC TGTACCTCCT ATTGCTATAA TAACTCCGAG
            · R   E   Q   I   G   G
    301   ACCGCGAACA GATTGGAGGT
          TGGCGCTTGT CTAACCTCCA
```

GFP
GFP NCBI ACCESSION# P42212

```
          M   V   S   K   G   E   E   L   F   T
  1   ATGGTGAGCA AGGGCGAGGA GCTGTTCACC
      TACCACTCGT TCCCGCTCCT CGACAAGTGG
          G   V   V   P   I   L   V   E   L   D   G   D   V   N   G   H   K ·
 31   GGGGTGGTGC CCATCCTGGT CGAGCTGGAC GGCGACGTAA ACGGCCACAA
      CCCCACCACG GGTAGGACCA GCTCGACCTG CCGCTGCATT TGCCGGTGTT
        · F   S   V   S   G   E   G   E   G   D   A   T   Y   G   K   L   T ·
 81   GTTCAGCGTG TCCGGCGAGG GCGAGGGCGA TGCCACCTAC GGCAAGCTGA
      CAAGTCGCAC AGGCCGCTCC CGCTCCCGCT ACGGTGGATG CCGTTCGACT
        · L   K   F   I   C   T   T   G   K   L   P   V   P   W   P   T
131   CCCTGAAGTT CATCTGCACC ACCGGCAAGC TGCCCGTGCC CTGGCCCACC
      GGGACTTCAA GTAGACGTGG TGGCCGTTCG ACGGGCACGG GACCGGGTGG
          L   V   T   T   L   T   Y   G   V   Q   C   F   S   R   Y   P   D ·
181   CTCGTGACCA CCCTGACCTA CGGCGTGCAG TGCTTCAGCC GCTACCCCGA
      GAGCACTGGT GGGACTGGAT GCCGCACGTC ACGAAGTCGG CGATGGGGCT
        · H   M   K   Q   H   D   F   F   K   S   A   M   P   E   G   Y   V ·
201   CCACATGAAG CAGCACGACT TCTTCAAGTC CGCCATGCCC GAAGGCTACG
      GGTGTACTTC GTCGTGCTGA AGAAGTTCAG GCGGTACGGG CTTCCGATGC
        · Q   E   R   T   I   F   F   K   D   D   G   N   Y   K   T   R
231   TCCAGGAGCG CACCATCTTC TTCAAGGACG ACGGCAACTA CAAGACCCGC
      AGGTCCTCGC GTGGTAGAAG AAGTTCCTGC TGCCGTTGAT GTTCTGGGCG

A   E   V   K   F   E   G   D   T   L   V   N   R   I   E   L   K ·
281   GCCGAGGTGA AGTTCGAGGG CGACACCCTG GTGAACCGCA TCGAGCTGAA
      CGGCTCCACT TCAAGCTCCC GCTGTGGGAC CACTTGGCGT AGCTCGACTT
        · G   I   D   F   K   E   D   G   N   I   L   G   H   K   L   E   Y ·
331   GGGCATCGAC TTCAAGGAGG ACGGCAACAT CCTGGGGCAC AAGCTGGAGT
      CCCGTAGCTG AAGTTCCTCC TGCCGTTGTA GGACCCCGTG TTCGACCTCA
        · N   Y   N   S   H   N   V   Y   I   M   A   D   K   Q   K   N
381   ACAACTACAA CAGCCACAAC GTCTATATCA TGGCCGACAA GCAGAAGAAC
      TGTTGATGTT GTCGGTGTTG CAGATATAGT ACCGGCTGTT CGTCTTCTTG
          G   I   K   V   N   F   K   I   R   H   N   I   E   D   G   S   V ·
431   GGCATCAAGG TGAACTTCAA GATCCGCCAC AACATCGAGG ACGGCAGCGT
      CCGTAGTTCC ACTTGAAGTT CTAGGCGGTG TTGTAGCTCC TGCCGTCGCA
        · Q   L   A   D   H   Y   Q   Q   N   T   P   I   G   D   G   P   V ·
481   GCAGCTCGCC GACCACTACC AGCAGAACAC CCCCATCGGC GACGGCCCCG
      CGTCGAGCGG CTGGTGATGG TCGTCTTGTG GGGGTAGCCG CTGCCGGGGC
        · L   L   P   D   N   H   Y   L   S   T   Q   S   A   L   S   K
531   TGCTGCTGCC CGACAACCAC TACCTGAGCA CCCAGTCCGC CCTGAGCAAA
      ACGACGACGG GCTGTTGGTG ATGGACTCGT GGGTCAGGCG GGACTCGTTT
```

Figure 24B

```
        D   P   N   E    K   R   D    H   M   V    L   L   E    F   V   T   A  ·
581   GACCCCAACG  AGAAGCGCGA  TCACATGGTC  CTGCTGGAGT  TCGTGACCGC
      CTGGGGTTGC  TCTTCGCGCT  AGTGTACCAG  GACGACCTCA  AGCACTGGCG
                                                          HindIII
                                                          ~~~~~~~
      · A   G   I    T   L   G    M   D   E    L   Y   K   *    *
631   CGCCGGGATC  ACTCTCGGCA  TGGACGAGCT  GTACAAGTAA  TAAGCTT
      GCGGCCCTAG  TGAGAGCCGT  ACCTGCTCGA  CATGTTCATT  ATTCGAA
```

Figure 25A

SUMO-GFP
SUMO NCBI ACCESSION# Q12306

```
     NcoI
     ~~~~~~
          M   G   H   H   H   H   H   G   S   D   S   E   V   N   Q
  1  CCATGGGTCA TCACCATCAT CATCACGGGT CGGACTCAGA AGTCAATCAA
     GGTACCCAGT AGTGGTAGTA GTAGTGCCCA GCCTGAGTCT TCAGTTAGTT
      E   A   K   P   E   V   K   P   E   V   K   P   E   T   H   I   N  ·
 51  GAAGCTAAGC CAGAGGTCAA GCCAGAAGTC AAGCCTGAGA CTCACATCAA
     CTTCGATTCG GTCTCCAGTT CGGTCTTCAG TTCGGACTCT GAGTGTAGTT
     ·  L   K   V   S   D   G   S   S   E   I   F   F   K   I   K   K   T
101  TTTAAAGGTG TCCGATGGAT CTTCAGAGAT CTTCTTCAAG ATCAAAAAGA
     AAATTTCCAC AGGCTACCTA GAAGTCTCTA GAAGAAGTTC TAGTTTTTCT
     ·  T   P   L   R   R   L   M   E   A   F   A   K   R   Q   G   K
151  CCACTCCTTT AAGAAGGCTG ATGGAAGCGT TCGCTAAAAG ACAGGGTAAG
     GGTGAGGAAA TTCTTCCGAC TACCTTCGCA AGCGATTTTC TGTCCCATTC
         E   M   D   S   L   R   F   L   Y   D   G   I   R   I   Q   A   D  ·
201  GAAATGGACT CCTTAAGATT CTTGTACGAC GGTATTAGAA TTCAAGCTGA
     CTTTACCTGA GGAATTCTAA GAACATGCTG CCATAATCTT AAGTTCGACT
     ·  Q   A   P   E   D   L   D   M   E   D   N   D   I   I   E   A   H
251  TCAGGCCCCT GAAGATTTGG ACATGGAGGA TAACGATATT ATTGAGGCTC
     AGTCCGGGGA CTTCTAAACC TGTACCTCCT ATTGCTATAA TAACTCCGAG
     ·  R   E   Q   I   G   G   M   V   S   K   G   E   E   L   F   T
301  ACCGCGAACA GATTGGAGGT ATGGTGAGCA AGGGCGAGGA GCTGTTCACC
     TGGCGCTTGT CTAACCTCCA TACCACTCGT TCCCGCTCCT CGACAAGTGG
         G   V   V   P   I   L   V   E   L   D   G   D   V   N   G   H   K  ·
351  GGGGTGGTGC CCATCCTGGT CGAGCTGGAC GGCGACGTAA ACGGCCACAA
     CCCCACCACG GGTAGGACCA GCTCGACCTG CCGCTGCATT TGCCGGTGTT
     ·  F   S   V   S   G   E   G   E   G   D   A   T   Y   G   K   L   T
401  GTTCAGCGTG TCCGGCGAGG GCGAGGGCGA TGCCACCTAC GGCAAGCTGA
     CAAGTCGCAC AGGCCGCTCC CGCTCCCGCT ACGGTGGATG CCGTTCGACT
     ·  L   K   F   I   C   T   T   G   K   L   P   V   P   W   P   T
451  CCCTGAAGTT CATCTGCACC ACCGGCAAGC TGCCCGTGCC CTGGCCCACC
     GGGACTTCAA GTAGACGTGG TGGCCGTTCG ACGGGCACGG GACCGGGTGG
         L   V   T   T   L   T   Y   G   V   Q   C   F   S   R   Y   P   D  ·
501  CTCGTGACCA CCCTGACCTA CGGCGTGCAG TGCTTCAGCC GCTACCCCGA
     GAGCACTGGT GGGACTGGAT GCCGCACGTC ACGAAGTCGG CGATGGGGCT
     ·  H   M   K   Q   H   D   F   F   K   S   A   M   P   E   G   Y   V
551  CCACATGAAG CAGCACGACT TCTTCAAGTC CGCCATGCCC GAAGGCTACG
     GGTGTACTTC GTCGTGCTGA AGAAGTTCAG GCGGTACGGG CTTCCGATGC
     ·  Q   E   R   T   I   F   F   K   D   D   G   N   Y   K   T   R
601  TCCAGGAGCG CACCATCTTC TTCAAGGACG ACGGCAACTA CAAGACCCGC
     AGGTCCTCGC GTGGTAGAAG AAGTTCCTGC TGCCGTTGAT GTTCTGGGCG
         A   E   V   K   F   E   G   D   T   L   V   N   R   I   E   L   K  ·
651  GCCGAGGTGA AGTTCGAGGG CGACACCCTG GTGAACCGCA TCGAGCTGAA
     CGGCTCCACT TCAAGCTCCC GCTGTGGGAC CACTTGGCGT AGCTCGACTT
     ·  G   I   D   F   K   E   D   G   N   I   L   G   H   K   L   E   Y
701  GGGCATCGAC TTCAAGGAGG ACGGCAACAT CCTGGGGCAC AAGCTGGAGT
```

```
          CCCGTAGCTG AAGTTCCTCC TGCCGTTGTA GGACCCCGTG TTCGACCTCA
           · N  Y  N  S  H  N  V  Y  I  M  A  D  K  Q  K  N
      751 ACAACTACAA CAGCCACAAC GTCTATATCA TGGCCGACAA GCAGAAGAAC
          TGTTGATGTT GTCGGTGTTG CAGATATAGT ACCGGCTGTT CGTCTTCTTG
             G  I  K  V  N  F  K  I  R  H  N  I  E  D  G  S  V ·
      801 GGCATCAAGG TGAACTTCAA GATCCGCCAC AACATCGAGG ACGGCAGCGT
          CCGTAGTTCC ACTTGAAGTT CTAGGCGGTG TTGTAGCTCC TGCCGTCGCA
           · Q  L  A  D  H  Y  Q  N  T  P  I  G  D  G  P  V ·
      851 GCAGCTCGCC GACCACTACC AGCAGAACAC CCCCATCGGC GACGGCCCCG
          CGTCGAGCGG CTGGTGATGG TCGTCTTGTG GGGGTAGCCG CTGCCGGGGC
           · L  L  P  D  N  H  Y  L  S  T  Q  S  A  L  S  K
      901 TGCTGCTGCC CGACAACCAC TACCTGAGCA CCCAGTCCGC CCTGAGCAAA
          ACGACGACGG GCTGTTGGTG ATGGACTCGT GGGTCAGGCG GGACTCGTTT
             D  P  N  E  K  R  D  H  M  V  L  L  E  F  V  T  A ·
      951 GACCCCAACG AGAAGCGCGA TCACATGGTC CTGCTGGAGT TCGTGACCGC
          CTGGGGTTGC TCTTCGCGCT AGTGTACCAG GACGACCTCA AGCACTGGCG
                                                    HindIII
                                                    ------
           · A  G  I  T  L  G  M  D  E  L  Y  K *  *
     1001 CGCCGGGATC ACTCTCGGCA TGGACGAGCT GTACAAGTAA TAAGCTT
          GCGGCCCTAG TGAGAGCCGT ACCTGCTCGA CATGTTCATT ATTCGAA
```

Ub-GFP
Ub NCBI ACCESSION# 751846A

```
     NcoI
     ~~~~~~
          M  G  H  H  H   H  H  G  Q  I   F  V  K  T  L
  1  CCATGGGTCA TCACCATCAT CATCACGGGC AGATCTTCGT CAAGACGTTA
     GGTACCCAGT AGTGGTAGTA GTAGTGCCCG TCTAGAAGCA GTTCTGCAAT
          T  G  K  T  I   T  L  E  V  E   P  S  D  T  I  E  N ·
 51  ACCGGTAAAA CCATAACTCT AGAAGTTGAA CCATCCGATA CCATCGAAAA
     TGGCCATTTT GGTATTGAGA TCTTCAACTT GGTAGGCTAT GGTAGCTTTT
        · V  K  A  K  I   Q  D  K  E  G   I  P  P  D  Q  Q  R ·
101  CGTTAAGGCT AAAATTCAAG ACAAGGAAGG CATTCCACCT GATCAACAAA
     GCAATTCCGA TTTTAAGTTC TGTTCCTTCC GTAAGGTGGA CTAGTTGTTT
        · L  I  F  A  G   K  Q  L  E  D   G  R  T  L  S  D
151  GATTGATCTT TGCCGGTAAG CAGCTCGAGG ACGGTAGAAC GCTGTCTGAT
     CTAACTAGAA ACGGCCATTC GTCGAGCTCC TGCCATCTTG CGACAGACTA
          Y  N  I  Q  K   E  S  T  L  H   L  V  L  R  L  R  G ·
201  TACAACATTC AGAAGGAGTC GACCTTACAT CTTGTCTTAC GCCTACGTGG
     ATGTTGTAAG TCTTCCTCAG CTGGAATGTA GAACAGAATG CGGATGCACC
        · G  M  V  S  K   G  E  E  L  F   T  G  V  V  P  I  L ·
251  AGGTATGGTG AGCAAGGGCG AGGAGCTGTT CACCGGGGTG GTGCCCATCC
     TCCATACCAC TCGTTCCCGC TCCTCGACAA GTGGCCCCAC CACGGGTAGG
        · V  E  L  D  G   D  V  N  G  H   K  F  S  V  S  G
301  TGGTCGAGCT GGACGGCGAC GTAAACGGCC ACAAGTTCAG CGTGTCCGGC
     ACCAGCTCGA CCTGCCGCTG CATTTGCCGG TGTTCAAGTC GCACAGGCCG
          E  G  E  G  D   A  T  Y  G  K   L  T  L  K  F  I  C ·
351  GAGGGCGAGG GCGATGCCAC CTACGGCAAG CTGACCCTGA AGTTCATCTG
     CTCCCGCTCC CGCTACGGTG GATGCCGTTC GACTGGGACT TCAAGTAGAC
        · T  T  G  K  L   P  V  P  W  P   T  L  V  T  T  L  T ·
401  CACCACCGGC AAGCTGCCCG TGCCCTGGCC CACCCTCGTG ACCACCCTGA
     GTGGTGGCCG TTCGACGGGC ACGGGACCGG GTGGGAGCAC TGGTGGGACT
        · Y  G  V  Q  C   F  S  R  Y  P   D  H  M  K  Q  H
451  CCTACGGCGT GCAGTGCTTC AGCCGCTACC CCGACCACAT GAAGCAGCAC
     GGATGCCGCA CGTCACGAAG TCGGCGATGG GGCTGGTGTA CTTCGTCGTG
          D  F  F  K  S   A  M  P  E  G   Y  V  Q  E  R  T  I ·
501  GACTTCTTCA AGTCCGCCAT GCCCGAAGGC TACGTCCAGG AGCGCACCAT
     CTGAAGAAGT TCAGGCGGTA CGGGCTTCCG ATGCAGGTCC TCGCGTGGTA
        · F  F  K  D  D   G  N  Y  K  T   R  A  E  V  K  F  E ·
551  CTTCTTCAAG GACGACGGCA ACTACAAGAC CCGCGCCGAG GTGAAGTTCG
     GAAGAAGTTC CTGCTGCCGT TGATGTTCTG GGCGCGGCTC CACTTCAAGC
        · G  D  T  L  V   N  R  I  E  L   K  G  I  D  F  K
601  AGGGCGACAC CCTGGTGAAC CGCATCGAGC TGAAGGGCAT CGACTTCAAG
     TCCCGCTGTG GGACCACTTG GCGTAGCTCG ACTTCCCGTA GCTGAAGTTC
          E  D  G  N  I   L  G  H  K  L   E  Y  N  Y  N  S  H ·
651  GAGGACGGCA ACATCCTGGG GCACAAGCTG GAGTACAACT ACAACAGCCA
     CTCCTGCCGT TGTAGGACCC CGTGTTCGAC CTCATGTTGA TGTTGTCGGT
        · N  V  Y  I  M   A  D  K  Q  K   N  G  I  K  V  N  F ·
701  CAACGTCTAT ATCATGGCCG ACAAGCAGAA GAACGGCATC AAGGTGAACT
     GTTGCAGATA TAGTACCGGC TGTTCGTCTT CTTGCCGTAG TTCCACTTGA
        · K  I  R  H  N   I  E  D  G  S   V  Q  L  A  D  H
751  TCAAGATCCG CCACAACATC GAGGACGGCA GCGTGCAGCT CGCCGACCAC
```

```
              AGTTCTAGGC GGTGTTGTAG CTCCTGCCGT CGCACGTCGA GCGGCTGGTG
                Y  Q  Q   N  T  P  I   G  D  G   P  V  L  L   P  D  N  ·
        801   TACCAGCAGA ACACCCCCAT CGGCGACGGC CCCGTGCTGC TGCCCGACAA
              ATGGTCGTCT TGTGGGGGTA GCCGCTGCCG GGGCACGACG ACGGGCTGTT
              · H  Y  L  S  T  Q  S  A  L  S   K  D  P   N  E  K  R  ·
        851   CCACTACCTG AGCACCCAGT CCGCCCTGAG CAAAGACCCC AACGAGAAGC
              GGTGATGGAC TCGTGGGTCA GGCGGGACTC GTTTCTGGGG TTGCTCTTCG

·  D  H  M   V  L  L   E  F  V  T  A  A  G   I  T  L
        901   GCGATCACAT GGTCCTGCTG GAGTTCGTGA CCGCCGCCGG GATCACTCTC
              CGCTAGTGTA CCAGGACGAC CTCAAGCACT GGCGGCGGCC CTAGTGAGAG
                                                  HindIII
                                                  ~~~~~~~
                G  M  D   E  L  Y  K  *  *
        951   GGCATGGACG AGCTGTACAA GTAATAAGCT T
              CCGTACCTGC TCGACATGTT CATTATTCGA A
```

Urm1-GFP
Urm1 NCBI ACCESSION# NP_587744

```
        NcoI
        ~~~~~
             M   G   H   H   H   H   H   H   G   V   N   V   K   V   E   F
  1   CCATGGGTCA TCACCATCAT CATCACGGGG TAAACGTGAA AGTGGAGTTT
      GGTACCCAGT AGTGGTAGTA GTAGTGCCCC ATTTGCACTT TCACCTCAAA
             L   G   G   L   D   A   I   F   G   K   Q   R   V   H   K   I   K  ·
 51   CTAGGTGGAC TTGATGCTAT TTTTGGAAAA CAAAGAGTAC ATAAAATTAA
      GATCCACCTG AACTACGATA AAAACCTTTT GTTTCTCATG TATTTTAATT
         ·  M   D   K   E   D   P   V   T   V   G   D   L   I   D   H   I   V  ·
101   GATGGACAAA GAAGATCCTG TCACAGTGGG CGATTTGATT GACCACATTG
      CTACCTGTTT CTTCTAGGAC AGTGTCACCC GCTAAACTAA CTGGTGTAAC
         ·  S   T   M   I   N   N   P   N   D   V   S   I   F   I   E   D
151   TATCTACTAT GATCAATAAC CCTAATGACG TTAGTATCTT CATCGAAGAT
      ATAGATGATA CTAGTTATTG GGATTACTGC AATCATAGAA GTAGCTTCTA
             D   S   I   R   P   G   I   I   T   L   I   N   D   T   D   W   E  ·
201   GATTCTATAA GACCCGGTAT CATCACATTA ATCAACGACA CCGACTGGGA
      CTAAGATATT CTGGGCCATA GTAGTGTAAT TAGTTGCTGT GGCTGACCCT
         ·  L   E   G   E   K   D   Y   I   L   E   D   G   D   I   I   S   F  ·
251   GCTCGAAGGC GAAAAAGACT ACATATTGGA AGACGGTGAC ATCATCTCTT
      CGAGCTTCCG CTTTTTCTGA TGTATAACCT TCTGCCACTG TAGTAGAGAA
         ·  T   S   T   L   H   G   M   V   S   K   G   E   E   L   F
301   TTACTTCAAC ATTACATGGA GGTATGGTGA GCAAGGGCGA GGAGCTGTTC
      AATGAAGTTG TAATGTACCT CCATACCACT CGTTCCCGCT CCTCGACAAG
             T   G   V   V   P   I   L   V   E   L   D   G   D   V   N   G   H  ·
351   ACCGGGGTGG TGCCCATCCT GGTCGAGCTG GACGGCGACG TAAACGGCCA
      TGGCCCCACC ACGGGTAGGA CCAGCTCGAC CTGCCGCTGC ATTTGCCGGT
         ·  K   F   S   V   S   G   E   G   E   G   D   A   T   Y   G   K   L  ·
401   CAAGTTCAGC GTGTCCGGCG AGGGCGAGGG CGATGCCACC TACGGCAAGC
      GTTCAAGTCG CACAGGCCGC TCCCGCTCCC GCTACGGTGG ATGCCGTTCG
         ·  T   L   K   F   I   C   T   T   G   K   L   P   V   P   W   P
451   TGACCCTGAA GTTCATCTGC ACCACCGGCA AGCTGCCCGT GCCCTGGCCC
      ACTGGGACTT CAAGTAGACG TGGTGGCCGT TCGACGGGCA CGGGACCGGG
             T   L   V   T   T   L   T   Y   G   V   Q   C   F   S   R   Y   P  ·
501   ACCCTCGTGA CCACCCTGAC CTACGGCGTG CAGTGCTTCA GCCGCTACCC
      TGGGAGCACT GGTGGGACTG GATGCCGCAC GTCACGAAGT CGGCGATGGG
         ·  D   H   M   K   Q   H   D   F   F   K   S   A   M   P   E   G   Y  ·
551   CGACCACATG AAGCAGCACG ACTTCTTCAA GTCCGCCATG CCCGAAGGCT
      GCTGGTGTAC TTCGTCGTGC TGAAGAAGTT CAGGCGGTAC GGGCTTCCGA
         ·  V   Q   E   R   T   I   F   F   K   D   D   G   N   Y   K   T
601   ACGTCCAGGA GCGCACCATC TTCTTCAAGG ACGACGGCAA CTACAAGACC
      TGCAGGTCCT CGCGTGGTAG AAGAAGTTCC TGCTGCCGTT GATGTTCTGG
             R   A   E   V   K   F   E   G   D   T   L   V   N   R   I   E   L  ·
651   CGCGCCGAGG TGAAGTTCGA GGGCGACACC CTGGTGAACC GCATCGAGCT
      GCGCGGCTCC ACTTCAAGCT CCCGCTGTGG GACCACTTGG CGTAGCTCGA
         ·  K   G   I   D   F   K   E   D   G   N   I   L   G   H   K   L   E  ·
701   GAAGGGCATC GACTTCAAGG AGGACGGCAA CATCCTGGGG CACAAGCTGG
      CTTCCCGTAG CTGAAGTTCC TCCTGCCGTT GTAGGACCCC GTGTTCGACC
```

```
           · Y  N  Y   N  S  H   N  V  Y   I  M  A   D  K  Q  K
       751 AGTACAACTA CAACAGCCAC AACGTCTATA TCATGGCCGA CAAGCAGAAG
           TCATGTTGAT GTTGTCGGTG TTGCAGATAT AGTACCGGCT GTTCGTCTTC
             N  G  I   K  V  N   F  K  I   R  H  N   I  E  D  G  S ·
       801 AACGGCATCA AGGTGAACTT CAAGATCCGC CACAACATCG AGGACGGCAG
           TTGCCGTAGT TCCACTTGAA GTTCTAGGCG GTGTTGTAGC TCCTGCCGTC
           · V  Q  L   A  D  H   Y  Q  Q   N  T  P   I  G  D  G  P ·
       851 CGTGCAGCTC GCCGACCACT ACCAGCAGAA CACCCCCATC GGCGACGGCC
           GCACGTCGAG CGGCTGGTGA TGGTCGTCTT GTGGGGGTAG CCGCTGCCGG
           · V  L  L   P  D  N   H  Y  L   S  T  Q   S  A  L  S
       901 CCGTGCTGCT GCCCGACAAC CACTACCTGA GCACCCAGTC CGCCCTGAGC
           GGCACGACGA CGGGCTGTTG GTGATGGACT CGTGGGTCAG GCGGGACTCG
              K  D  P   N  E  K   R  D  H   M  V  L   L  E  F  V  T ·
       951 AAAGACCCCA ACGAGAAGCG CGATCACATG GTCCTGCTGG AGTTCGTGAC
           TTTCTGGGGT TGCTCTTCGC GCTAGTGTAC CAGGACGACC TCAAGCACTG
                                                             HindIII
                                                             ~~~~~~
           · A  A  G   I  T  L   G  M  D  E   L  Y  K  * *
      1001 CGCCGCCGGG ATCACTCTCG GCATGGACGA GCTGTACAAG TAATAAGCTT
           GCGGCGGCCC TAGTGAGAGC CGTACCTGCT CGACATGTTC ATTATTCGAA
```

Hub1-GFP
Hub1 NCBI ACCESSION# XM_114578

```
         NcoI
         ~~~~~~
          M   G   H   H   Y   H   H   H   G   M   I   E   V   V   V   N
  1  CCATGGGTCA TCACTATCAT CATCACGGGA TGATTGAGGT AGTTGTGAAT
     GGTACCCAGT AGTGATAGTA GTAGTGCCCT ACTAACTCCA TCAACACTTA
          D   R   L   G   K   K   V   R   V   K   C   L   A   E   D   S   V ·
 51  GACCGATTAG GCAAAAAAGT CAGAGTGAAG TGCCTTGCTG AAGATAGTGT
     CTGGCTAATC CGTTTTTTCA GTCTCACTTC ACGGAACGAC TTCTATCACA
        · G   D   F   K   K   V   L   S   L   Q   I   G   T   Q   P   N   K ·
101  AGGTGATTTC AAAAAAGTAT TGTCCTTGCA AATTGGCACC CAACCAAACA
     TCCACTAAAG TTTTTTCATA ACAGGAACGT TTAACCGTGG GTTGGTTTGT
        · I   V   L   Q   K   G   G   S   V   L   K   D   H   I   S   L
151  AAATTGTGTT GCAGAAGGGT GGAAGTGTTT TAAAAGACCA TATCTCTCTG
     TTTAACACAA CGTCTTCCCA CCTTCACAAA ATTTTCTGGT ATAGAGAGAC
          E   D   Y   E   V   H   D   Q   T   N   L   E   L   Y   M   V ·
201  GAAGATTATG AGGTACATGA TCAGACAAAT TTGGAGCTGT ATTACATGGT
     CTTCTAATAC TCCATGTACT AGTCTGTTTA AACCTCGACA TAATGTACCA
        · S   K   G   E   E   L   F   T   G   V   V   P   I   L   V   E   L ·
251  GAGCAAGGGC GAGGAGCTGT TCACCGGGGT GGTGCCCATC CTGGTCGAGC
     CTCGTTCCCG CTCCTCGACA AGTGGCCCCA CCACGGGTAG GACCAGCTCG
        · D   G   D   V   N   G   H   K   F   S   V   S   G   E   G   E
301  TGGACGGCGA CGTAAACGGC CACAAGTTCA GCGTGTCCGG CGAGGGCGAG
     ACCTGCCGCT GCATTTGCCG GTGTTCAAGT CGCACAGGCC GCTCCCGCTC
          G   D   A   T   Y   G   K   L   T   L   K   F   I   C   T   T   G ·
351  GGCGATGCCA CCTACGGCAA GCTGACCCTG AAGTTCATCT GCACCACCGG
     CCGCTACGGT GGATGCCGTT CGACTGGGAC TTCAAGTAGA CGTGGTGGCC
        · K   L   P   V   P   W   P   T   L   V   T   T   L   T   Y   G   V ·
401  CAAGCTGCCC GTGCCCTGGC CCACCCTCGT GACCACCCTG ACCTACGGCG
     GTTCGACGGG CACGGGACCG GGTGGGAGCA CTGGTGGGAC TGGATGCCGC
        · Q   C   F   S   R   Y   P   D   H   M   K   Q   H   D   F   F
451  TGCAGTGCTT CAGCCGCTAC CCCGACCACA TGAAGCAGCA CGACTTCTTC
     ACGTCACGAA GTCGGCGATG GGGCTGGTGT ACTTCGTCGT GCTGAAGAAG
          K   S   A   M   P   E   G   Y   V   Q   E   R   T   I   F   F   K ·
501  AAGTCCGCCA TGCCCGAAGG CTACGTCCAG GAGCGCACCA TCTTCTTCAA
     TTCAGGCGGT ACGGGCTTCC GATGCAGGTC CTCGCGTGGT AGAAGAAGTT
        · D   D   G   N   Y   K   T   R   A   E   V   K   F   E   G   D   T ·
551  GGACGACGGC AACTACAAGA CCCGCGCCGA GGTGAAGTTC GAGGGCGACA
     CCTGCTGCCG TTGATGTTCT GGGCGCGGCT CCACTTCAAG CTCCCGCTGT
        · L   V   N   R   I   E   L   K   G   I   D   F   K   E   D   G
601  CCCTGGTGAA CCGCATCGAG CTGAAGGGCA TCGACTTCAA GGAGGACGGC
     GGGACCACTT GGCGTAGCTC GACTTCCCGT AGCTGAAGTT CCTCCTGCCG
          N   I   L   G   H   K   L   E   Y   N   Y   N   S   H   N   V   Y ·
651  AACATCCTGG GGCACAAGCT GGAGTACAAC TACAACAGCC ACAACGTCTA
     TTGTAGGACC CCGTGTTCGA CCTCATGTTG ATGTTGTCGG TGTTGCAGAT
        · I   M   A   D   K   Q   K   N   G   I   K   V   N   F   K   I   R ·
701  TATCATGGCC GACAAGCAGA AGAACGGCAT CAAGGTGAAC TTCAAGATCC
```

```
              ATAGTACCGG CTGTTCGTCT TCTTGCCGTA GTTCCACTTG AAGTTCTAGG
               · H   N   I   E   D   G   S   V   Q   L   A   D   H   Y   Q   Q
         751  GCCACAACAT CGAGGACGGC AGCGTGCAGC TCGCCGACCA CTACCAGCAG
              CGGTGTTGTA GCTCCTGCCG TCGCACGTCG AGCGGCTGGT GATGGTCGTC
                 N   T   P   I   G   D   G   P   V   L   L   P   D   N   H   Y   L  ·
         801  AACACCCCCA TCGGCGACGG CCCCGTGCTG CTGCCCGACA ACCACTACCT
              TTGTGGGGGT AGCCGCTGCC GGGGCACGAC GACGGGCTGT TGGTGATGGA
               · S   T   Q   S   A   L   S   K   D   P   N   E   K   R   D   H   M ·
         851  GAGCACCCAG TCCGCCCTGA GCAAAGACCC CAACGAGAAG CGCGATCACA
              CTCGTGGGTC AGGCGGGACT CGTTTCTGGG GTTGCTCTTC GCGCTAGTGT
               · V   L   L   E   F   V   T   A   A   G   I   T   L   G   M   D
         901  TGGTCCTGCT GGAGTTCGTG ACCGCCGCCG GGATCACTCT CGGCATGGAC
              ACCAGGACGA CCTCAAGCAC TGGCGGCGGC CCTAGTGAGA GCCGTACCTG
                               HindIII
                               ~~~~~~~
                 E   L   Y   K   *   *
         951  GAGCTGTACA AGTAATAAGC TT
              CTCGACATGT TCATTATTCG AA
```

Rub1-GFP
Rub1 NCBI Accession# Y16890

```
      NcoI
      ~~~~~~
              M   G   H   H   H   H   H   H   G   I   V   K   X   K   T   L
  1   CCATGGGTCA TCACCATCAT CATCACGGGA TTGTTAAAGN GAAGACACTG
      GGTACCCAGT AGTGGTAGTA GTAGTGCCCT AACAATTTCN CTTCTGTGAC
          T   G   K   E   I   S   V   E   L   K   E   S   D   L   V   Y   H  ·
 51   ACTGGGAAGG AGATCTCTGT TGAGCTGAAG GAATCAGATC TCGTATATCA
      TGACCCTTCC TCTAGAGACA ACTCGACTTC CTTAGTCTAG AGCATATAGT
      ·   I   K   E   L   L   E   E   K   E   G   I   P   P   S   Q   Q   R  ·
101   CATCAAGGAA CTTTTGGAGG AAAAAGAAGG GATTCCACCA TCTCAACAAA
      GTAGTTCCTT GAAAACCTCC TTTTTCTTCC CTAAGGTGGT AGAGTTGTTT
      ·   L   I   F   Q   G   K   Q   I   D   D   K   L   T   V   T   D
151   GACTTATATT CCAGGGAAAA CAAATTGATG ATAAATTAAC AGTAACGGAT
      CTGAATATAA GGTCCCTTTT GTTTAACTAC TATTTAATTG TCATTGCCTA
          A   H   X   V   E   G   M   Q   L   H   L   V   L   T   L   R   G  ·
201   GCACATNTAG TAGAGGGAAT GCAACTCCAC TTGGTATTAA CACTACGCGG
      CGTGTANATC ATCTCCCTTA CGTTGAGGTG AACCATAATT GTGATGCGCC
      ·   G   M   V   S   K   G   E   E   L   F   T   G   V   V   P   I   L  ·
251   AGGTATGGTG AGCAAGGGCG AGGAGCTGTT CACCGGGGTG GTGCCCATCC
      TCCATACCAC TCGTTCCCGC TCCTCGACAA GTGGCCCCAC CACGGGTAGG
      ·   V   E   L   D   G   D   V   N   G   H   K   F   S   V   S   G
301   TGGTCGAGCT GGACGGCGAC GTAAACGGCC ACAAGTTCAG CGTGTCCGGC
      ACCAGCTCGA CCTGCCGCTG CATTTGCCGG TGTTCAAGTC GCACAGGCCG
          E   G   E   G   D   A   T   Y   G   K   L   T   L   K   F   I   C  ·
351   GAGGGCGAGG GCGATGCCAC CTACGGCAAG CTGACCCTGA AGTTCATCTG
      CTCCCGCTCC CGCTACGGTG GATGCCGTTC GACTGGGACT TCAAGTAGAC
      ·   T   T   G   K   L   P   V   P   W   P   T   L   V   T   T   L   T  ·
401   CACCACCGGC AAGCTGCCCG TGCCCTGGCC CACCCTCGTG ACCACCCTGA
      GTGGTGGCCG TTCGACGGGC ACGGGACCGG GTGGGAGCAC TGGTGGGACT
      ·   Y   G   V   Q   C   F   S   R   Y   P   D   H   M   K   Q   H
451   CCTACGGCGT GCAGTGCTTC AGCCGCTACC CCGACCACAT GAAGCAGCAC
      GGATGCCGCA CGTCACGAAG TCGGCGATGG GGCTGGTGTA CTTCGTCGTG
              D   F   F   K   S   A   M   P   E   G   Y   V   Q   E   R   T   I  ·
501   GACTTCTTCA AGTCCGCCAT GCCCGAAGGC TACGTCCAGG AGCGCACCAT
      CTGAAGAAGT TCAGGCGGTA CGGGCTTCCG ATGCAGGTCC TCGCGTGGTA
      ·   F   F   K   D   D   G   N   Y   K   T   R   A   E   V   K   F   E  ·
551   CTTCTTCAAG GACGACGGCA ACTACAAGAC CCGCGCCGAG GTGAAGTTCG
      GAAGAAGTTC CTGCTGCCGT TGATGTTCTG GGCGCGGCTC CACTTCAAGC
      ·   G   D   T   L   V   N   R   I   E   L   K   G   I   D   F   K
601   AGGGCGACAC CCTGGTGAAC CGCATCGAGC TGAAGGGCAT CGACTTCAAG
      TCCCGCTGTG GGACCACTTG GCGTAGCTCG ACTTCCCGTA GCTGAAGTTC
          E   D   G   N   I   L   G   H   K   L   E   Y   N   Y   N   S   H  ·
651   GAGGACGGCA ACATCCTGGG GCACAAGCTG GAGTACAACT ACAACAGCCA
      CTCCTGCCGT TGTAGGACCC CGTGTTCGAC CTCATGTTGA TGTTGTCGGT
      ·   N   V   Y   I   M   A   D   K   Q   K   N   G   I   K   V   N   F  ·
701   CAACGTCTAT ATCATGGCCG ACAAGCAGAA GAACGGCATC AAGGTGAACT
```

```
         GTTGCAGATA TAGTACCGGC TGTTCGTCTT CTTGCCGTAG TTCCACTTGA
        · K   I   R   H   N   I   E   D   G   S   V   Q   L   A   D   H
    751 TCAAGATCCG CCACAACATC GAGGACGGCA GCGTGCAGCT CGCCGACCAC
        AGTTCTAGGC GGTGTTGTAG CTCCTGCCGT CGCACGTCGA GCGGCTGGTG
          Y   Q   N   T   P   I   G   D   G   P   V   L   L   P   D   N ·
    801 TACCAGCAGA ACACCCCCAT CGGCGACGGC CCCGTGCTGC TGCCCGACAA
        ATGGTCGTCT TGTGGGGGTA GCCGCTGCCG GGGCACGACG ACGGGCTGTT
        · H   Y   L   S   T   Q   S   A   L   S   K   D   P   N   E   K   R ·
    851 CCACTACCTG AGCACCCAGT CCGCCCTGAG CAAAGACCCC AACGAGAAGC
        GGTGATGGAC TCGTGGGTCA GGCGGGACTC GTTTCTGGGG TTGCTCTTCG
        · D   H   M   V   L   L   E   F   V   T   A   A   G   I   T   L
    901 GCGATCACAT GGTCCTGCTG GAGTTCGTGA CCGCCGCCGG GATCACTCTC
        CGCTAGTGTA CCAGGACGAC CTCAAGCACT GGCGGCGGCC CTAGTGAGAG

HindIII
                                                  ~~~~~~~
          G   M   D   E   L   Y   K   *   *
    951 GGCATGGACG AGCTGTACAA GTAATAAGCT T
        CCGTACCTGC TCGACATGTT CATTATTCGA A
```

Apg8-GFP
Apg8 NCBI ACCESSION# P38182

```
      NcoI
      ~~~~
         M   G   H   H   H   H   H   H   G   K   S   T   F   K   S   E
  1   ATGGGTCA TCACCATCAT CATCACGGGA AGTCTACATT TAAGTCTGAA
      TACCCAGT AGTGGTAGTA GTAGTGCCCT TCAGATGTAA ATTCAGACTT
       Y   P   F   E   K   R   K   A   E   S   E   R   I   A   D   R   F·
 51   TATCCATTTG AAAAAAGGAA GGCGGAGTCG GAGAGGATTG CTGACAGGTT
      ATAGGTAAAC TTTTTTCCTT CCGCCTCAGC CTCTCCTAAC GACTGTCCAA
      ·K   N   R   I   P   V   I   C   E   K   A   E   K   S   D   I   P·
101   CAAGAATAGG ATACCTGTGA TTTGCGAAAA AGCTGAAAAG TCAGATATTC
      GTTCTTATCC TATGGACACT AAACGCTTTT TCGACTTTTC AGTCTATAAG
      ·E   I   D   K   R   K   Y   L   V   P   A   D   L   T   V   G
151   CAGAGATTGA TAAGCGTAAA TATCTAGTTC CTGCTGACCT TACCGTAGGG
      GTCTCTAACT ATTCGCATTT ATAGATCAAG GACGACTGGA ATGGCATCCC
         Q   F   V   Y   V   I   R   K   I   M   L   P   P   E   K   A·
201   CAATTTGTTT ATGTTATAAG AAAGAGGATT ATGCTACCCC CTGAGAAGGC
      GTTAAACAAA TACAATATTC TTTCTCCTAA TACGATGGGG GACTCTTCCG
      ·I   F   I   F   V   N   D   T   L   P   P   T   A   A   L   M   S·
251   CATCTTCATT TTTGTCAATG ATACTTTGCC ACCTACTGCG GCGTTGATGT
      GTAGAAGTAA AAACAGTTAC TATGAAACGG TGGATGACGC CGCAACTACA
      ·A   I   Y   Q   E   H   K   D   K   D   G   F   L   Y   V   T
301   CTGCCATATA TCAAGAACAC AAGGATAAGG ACGGGTTTTT GTATGTCACT
      GACGGTATAT AGTTCTTGTG TTCCTATTCC TGCCCAAAAA CATACAGTGA
         Y   S   G   E   N   T   F   G   M   V   S   K   G   E   E   L   F·
351   TACTCAGGAG AAAATACATT TGGTATGGTG AGCAAGGGCG AGGAGCTGTT
      ATGAGTCCTC TTTTATGTAA ACCATACCAC TCGTTCCCGC TCCTCGACAA
      ·T   G   V   V   P   I   L   V   E   L   D   G   D   V   N   G   H·
401   CACCGGGGTG GTGCCCATCC TGGTCGAGCT GGACGGCGAC GTAAACGGCC
      GTGGCCCCAC CACGGGTAGG ACCAGCTCGA CCTGCCGCTG CATTTGCCGG
      ·K   F   S   V   S   G   E   G   E   G   D   A   T   Y   G   K
451   ACAAGTTCAG CGTGTCCGGC GAGGGCGAGG GCGATGCCAC CTACGGCAAG
      TGTTCAAGTC GCACAGGCCG CTCCCGCTCC CGCTACGGTG GATGCCGTTC
         L   T   L   K   F   I   C   T   T   G   K   L   P   V   P   W·
501   CTGACCCTGA AGTTCATCTG CACCACCGGC AAGCTGCCCG TGCCCTGGCC
      GACTGGGACT TCAAGTAGAC GTGGTGGCCG TTCGACGGGC ACGGGACCGG
      ·T   L   V   T   T   L   T   Y   G   V   Q   C   F   S   R   Y   P·
551   CACCCTCGTG ACCACCCTGA CCTACGGCGT GCAGTGCTTC AGCCGCTACC
      GTGGGAGCAC TGGTGGGACT GGATGCCGCA CGTCACGAAG TCGGCGATGG
      ·D   H   M   K   Q   H   D   F   F   K   S   A   M   P   E   G
601   CCGACCACAT GAAGCAGCAC GACTTCTTCA AGTCCGCCAT GCCCGAAGGC
      GGCTGGTGTA CTTCGTCGTG CTGAAGAAGT TCAGGCGGTA CGGGCTTCCG
         Y   V   Q   E   R   T   I   F   F   K   D   D   G   N   Y   K   T·
```

```
 651  TACGTCCAGG  AGCGCACCAT  CTTCTTCAAG  GACGACGGCA  ACTACAAGAC
      ATGCAGGTCC  TCGCGTGGTA  GAAGAAGTTC  CTGCTGCCGT  TGATGTTCTG
       · R  A  E     V  K  F     E  G  D     T  L  V     N  R  I  E  L ·
 701  CCGCGCCGAG  GTGAAGTTCG  AGGGCGACAC  CCTGGTGAAC  CGCATCGAGC
      GGCGCGGCTC  CACTTCAAGC  TCCCGCTGTG  GGACCACTTG  GCGTAGCTCG
       · K  G  I     D  F  K     E  D  G     N  I  L     G  H  K  L
 751  TGAAGGGCAT  CGACTTCAAG  GAGGACGGCA  ACATCCTGGG  GCACAAGCTG
      ACTTCCCGTA  GCTGAAGTTC  CTCCTGCCGT  TGTAGGACCC  CGTGTTCGAC
         E  Y  N     Y  N  S     H  N  V     Y  I  M     A  D  K  Q  K ·
 801  GAGTACAACT  ACAACAGCCA  CAACGTCTAT  ATCATGGCCG  ACAAGCAGAA
      CTCATGTTGA  TGTTGTCGGT  GTTGCAGATA  TAGTACCGGC  TGTTCGTCTT
       · N  G  I     K  V  N     F  K  I     R  H  N     I  E  D  G  S ·
 851  GAACGGCATC  AAGGTGAACT  TCAAGATCCG  CCACAACATC  GAGGACGGCA
      CTTGCCGTAG  TTCCACTTGA  AGTTCTAGGC  GGTGTTGTAG  CTCCTGCCGT
       · V  Q  L     A  D  H     Y  Q  Q     N  T  P     I  G  D  G
 901  GCGTGCAGCT  CGCCGACCAC  TACCAGCAGA  ACACCCCCAT  CGGCGACGGC
      CGCACGTCGA  GCGGCTGGTG  ATGGTCGTCT  TGTGGGGGTA  GCCGCTGCCG
          P  V  L     L  P  D     N  H  Y     L  S  T     Q  S  A  L  S ·
 951  CCCGTGCTGC  TGCCCGACAA  CCACTACCTG  AGCACCCAGT  CCGCCCTGAG
      GGGCACGACG  ACGGGCTGTT  GGTGATGGAC  TCGTGGGTCA  GGCGGGACTC
       · K  D  P     N  E  K  R     D  H  M     V  L  L     E  F  V  T ·
1001  CAAAGACCCC  AACGAGAAGC  GCGATCACAT  GGTCCTGCTG  GAGTTCGTGA
      GTTTCTGGGG  TTGCTCTTCG  CGCTAGTGTA  CCAGGACGAC  CTCAAGCACT
                                                              HindIII
                                                              ~~~~
       · A  A  G     I  T  L     G  M  D     E  L  Y  K     *  *  A
1051  CCGCCGCCGG  GATCACTCTC  GGCATGGACG  AGCTGTACAA  GTAATAAGCTT
      GGCGGCGGCC  CTAGTGAGAG  CCGTACCTGC  TCGACATGTT  CATTATTCGAA
```

Apg12-GFP
Apg12 NCBI ACCESSION# P38316

```
    NcoI
    ~~~~~~
         M  G  H  H  H  H  H  H  G  S  R  I  L  E  S  E
  1  CCATGGGTCA TCACCATCAT CATCACGGGA GTAGGATCCT AGAGAGCGAA
     GGTACCCAGT AGTGGTAGTA GTAGTGCCCT CATCCTAGGA TCTCTCGCTT
      N  E  T  E  S  D  E  S  S  I  I  S  T  N  N  G  T ·
 51  AATGAAACAG AAAGTGACGA AAGCTCCATC ATATCCACAA ATAATGGAAC
     TTACTTTGTC TTTCACTGCT TTCGAGGTAG TATAGGTGTT TATTACCTTG
     · A  M  E  R  S  R  N  N  Q  E  L  R  S  S  P  H  T ·
101  GGCAATGGAA AGATCCAGAA ATAATCAAGA ATTAAGATCA TCTCCTCATA
     CCGTTACCTT TCTAGGTCTT TATTAGTTCT TAATTCTAGT AGAGGAGTAT
     · V  Q  N  R  L  E  L  F  S  R  R  L  S  Q  L  G
151  CCGTTCAAAA TAGATTGGAA CTTTTTAGCA GGAGATTGTC TCAGCTTGGT
     GGCAAGTTTT ATCTAACCTT GAAAAATCGT CCTCTAACAG AGTCGAACCA
      L  A  S  D  I  S  V  D  Q  Q  V  E  D  S  S  S  G ·
201  TTGGCGAGTG ACATTTCTGT CGACCAGCAA GTTGAAGATT CCTCTAGTGG
     AACCGCTCAC TGTAAAGACA GCTGGTCGTT CAACTTCTAA GGAGATCACC
     · T  Y  E  Q  E  E  T  I  K  T  N  A  Q  T  S  K  Q ·
251  CACTTATGAA CAGGAAGAGA CAATCAAAAC GAATGCACAA ACAAGCAAAC
     GTGAATACTT GTCCTTCTCT GTTAGTTTTG CTTACGTGTT TGTTCGTTTG
     · K  S  H  K  D  E  K  N  I  Q  K  I  Q  I  K  F
301  AAAAAAGCCA TAAAGACGAA AAAAACATAC AAAAGATACA GATAAAATTT
     TTTTTTCGGT ATTTCTGCTT TTTTTGTATG TTTTCTATGT CTATTTAAA
      Q  P  I  G  S  I  G  Q  L  K  P  S  V  C  K  I  S ·
351  CAGCCCATTG GTTCTATTGG GCAGTTAAAA CCATCTGTTT GTAAAATATC
     GTCGGGTAAC CAAGATAACC CGTCAATTTT GGTAGACAAA CATTTTATAG
     · M  S  Q  S  F  A  M  V  I  L  F  L  K  R  R  L  K ·
401  NATGTCACAG TCTTTTGCAA TGGTTATTTT ATTTCTTAAG AGACGGCTGA
     NTACAGTGTC AGAAAACGTT ACCAATAAAA TAAAGAATTC TCTGCCGACT
     · M  D  H  V  Y  C  Y  I  N  N  S  F  A  P  S  P
451  AAATGGACCA TGTTTATTGT TATATAAATA ATTCGTTTGC GCCAAGTCCG
     TTTACCTGGT ACAAATAACA ATATATTTAT TAAGCAAACG CGGTTCAGGC
      Q  Q  N  I  G  E  L  W  M  X  F  K  T  N  D  E  L ·
501  CAGCAAAATA TTGGTGAACT TTGGATGCNA TTCAAGACTA ATGATGAGCT
     GTCGTTTTAT AACCACTTGA AACCTACGNT AAGTTCTGAT TACTACTCGA
     · I  V  S  Y  C  A  S  V  A  F  G  M  V  S  K  G  E ·
551  TATTGTAAGT TATTGTGCAT CCGTAGCGTT TGGTATGGTG AGCAAGGGCG
     ATAACATTCA ATAACACGTA GGCATCGCAA ACCATACCAC TCGTTCCCGC
     · E  L  F  T  G  V  V  P  I  L  V  E  L  D  G  D
601  AGGAGCTGTT CACCGGGGTG GTGCCCATCC TGGTCGAGCT GGACGGCGAC
     TCCTCGACAA GTGGCCCCAC CACGGGTAGG ACCAGCTCGA CCTGCCGCTG
      V  N  G  H  K  F  S  V  S  G  E  G  E  G  D  A  T ·
651  GTAAACGGCC ACAAGTTCAG CGTGTCCGGC GAGGGCGAGG GCGATGCCAC
     CATTTGCCGG TGTTCAAGTC GCACAGGCCG CTCCCGCTCC CGCTACGGTG
     · Y  G  K  L  T  L  K  F  I  C  T  T  G  K  L  P  V ·
701  CTACGGCAAG CTGACCCTGA AGTTCATCTG CACCACCGGC AAGCTGCCCG
     GATGCCGTTC GACTGGGACT TCAAGTAGAC GTGGTGGCCG TTCGACGGGC
```

```
              ·  P  W  P     T  L  V     T  T  L     T  Y  G  V     Q  C  F
   751  TGCCCTGGCC CACCCTCGTG ACCACCCTGA CCTACGGCGT GCAGTGCTTC
        ACGGGACCGG GTGGGAGCAC TGGTGGGACT GGATGCCGCA CGTCACGAAG
              S  R  Y  P     D  H  M     K  Q  H     D  F  F  K     S  A  M  ·
   801  AGCCGCTACC CCGACCACAT GAAGCAGCAC GACTTCTTCA AGTCCGCCAT
        TCGGCGATGG GGCTGGTGTA CTTCGTCGTG CTGAAGAAGT TCAGGCGGTA
           ·  P  E  G     Y  V  Q     E  R  T     I  F  F  K     D  D  G  N  ·
   851  GCCCGAAGGC TACGTCCAGG AGCGCACCAT CTTCTTCAAG GACGACGGCA
        CGGGCTTCCG ATGCAGGTCC TCGCGTGGTA GAAGAAGTTC CTGCTGCCGT
           ·  Y  K  T     R  A  E     V  K  F     E  G  D     T  L  V  N
   901  ACTACAAGAC CCGCGCCGAG GTGAAGTTCG AGGGCGACAC CCTGGTGAAC
        TGATGTTCTG GGCGCGGCTC CACTTCAAGC TCCCGCTGTG GGACCACTTG
           R  I  E  L     K  G  I     D  F  K     E  D  G     N  I  L  G  ·
   951  CGCATCGAGC TGAAGGGCAT CGACTTCAAG GAGGACGGCA ACATCCTGGG
        GCGTAGCTCG ACTTCCCGTA GCTGAAGTTC CTCCTGCCGT TGTAGGACCC
           ·  H  K  L     E  Y  N  Y     N  S  H     N  V  Y     I  M  A  D  ·
  1001  GCACAAGCTG GAGTACAACT ACAACAGCCA CAACGTCTAT ATCATGGCCG
        CGTGTTCGAC CTCATGTTGA TGTTGTCGGT GTTGCAGATA TAGTACCGGC
           ·  K  Q  K     N  G  I     K  V  N  F     K  I  R     H  N  I
  1051  ACAAGCAGAA GAACGGCATC AAGGTGAACT TCAAGATCCG CCACAACATC
        TGTTCGTCTT CTTGCCGTAG TTCCACTTGA AGTTCTAGGC GGTGTTGTAG
           E  D  G  S     V  Q  L     A  D  H     Y  Q  Q  N     T  P  I  ·
  1101  GAGGACGGCA GCGTGCAGCT CGCCGACCAC TACCAGCAGA ACACCCCCAT
        CTCCTGCCGT CGCACGTCGA GCGGCTGGTG ATGGTCGTCT TGTGGGGGTA
           ·  G  D  G     P  V  L  L     P  D  N     H  Y  L     S  T  Q  S  ·
  1151  CGGCGACGGC CCCGTGCTGC TGCCCGACAA CCACTACCTG AGCACCCAGT
        GCCGCTGCCG GGGCACGACG ACGGGCTGTT GGTGATGGAC TCGTGGGTCA

·  A  L  S     K  D  P     N  E  K  R     D  H  M     V  L  L
  1201  CCGCCCTGAG CAAAGACCCC AACGAGAAGC GCGATCACAT GGTCCTGCTG
        GGCGGGACTC GTTTCTGGGG TTGCTCTTCG CGCTAGTGTA CCAGGACGAC
           E  F  V  T     A  A  G     I  T  L     G  M  D  E     L  Y  K  ·
  1251  GAGTTCGTGA CCGCCGCCGG GATCACTCTC GGCATGGACG AGCTGTACAA
        CTCAAGCACT GGCGGCGGCC CTAGTGAGAG CCGTACCTGC TCGACATGTT
                    HindIII
                    ~~~~~~~
          ·  *  *
  1301  GTAATAAGCT T
        CATTATTCGA A
```

ISG15-GFP
ISG15 NCBI ACCESSION# P05161

```
    NcoI
    ~~~~~
         M   G   H   H   H   H   H   H   G   G   W   D   L   T   V   K
  1  CCATGGGTCA TCACCATCAT CATCACGGGG GCTGGGACCT GACGGTGAAG
     GGTACCCAGT AGTGGTAGTA GTAGTGCCCC CGACCCTGGA CTGCCACTTC
         M   L   A   G   N   E   F   Q   V   S   L   S   S   S   M   S   V  ·
 51  ATGCTGGCGG GCAACGAATT CCAGGTGTCC CTGAGCAGCT CCATGTCGGT
     TACGACCGCC CGTTGCTTAA GGTCCACAGG GACTCGTCGA GGTACAGCCA
       · S   E   L   K   A   Q   I   T   Q   K   I   G   V   H   A   F   Q  ·
101  GTCAGAGCTG AAGGCGCAGA TCACCCAGAA GATTGGCGTG CACGCCTTCC
     CAGTCTCGAC TTCCGCGTCT AGTGGGTCTT CTAACCGCAC GTGCGGAAGG
       · Q   R   L   A   V   H   P   S   G   V   A   L   Q   D   R   V
151  AGCAGCGTCT GGCTGTCCAC CCGAGCGGTG TGGCGCTGCA GGACAGGGTC
     TCGTCGCAGA CCGACAGGTG GGCTCGCCAC ACCGCGACGT CCTGTCCCAG
         P   L   A   S   Q   G   L   G   P   G   S   T   V   L   L   V   V  ·
201  CCCCTTGCCA GCCAGGGCCT GGGCCCTGGC AGCACGGTCC TGCTGGTGGT
     GGGGAACGGT CGGTCCCGGA CCCGGGACCG TCGTGCCAGG ACGACCACCA
       · D   K   C   D   E   P   L   S   I   L   V   R   N   N   K   G   R  ·
251  GGACAAATGC GACGAACCTC TGAGCATCCT GGTGAGGAAT AACAAGGGCC
     CCTGTTTACG CTGCTTGGAG ACTCGTAGGA CCACTCCTTA TTGTTCCCGG
       · S   S   T   Y   E   V   R   L   T   Q   T   V   A   H   L   K
301  GCAGCAGCAC CTACGAGGTC CGGCTGACGC AGACCGTGGC CCACCTGAAG
     CGTCGTCGTG GATGCTCCAG GCCGACTGCG TCTGGCACCG GGTGGACTTC
         Q   Q   V   S   G   L   E   G   V   Q   D   D   L   F   W   L   T  ·
351  CAGCAAGTGA GCGGGCTGGA GGGTGTGCAG GACGACCTGT TCTGGCTGAC
     GTCGTTCACT CGCCCGACCT CCCACACGTC CTGCTGGACA AGACCGACTG
       · F   E   G   K   P   L   E   D   Q   L   P   L   G   E   Y   G   L  ·
401  CTTCGAGGGG AAGCCCCTGG AGGACCAGCT CCCGCTGGGG GAGTACGGCC
     GAAGCTCCCC TTCGGGGACC TCCTGGTCGA GGGCGACCCC CTCATGCCGG
       · K   P   L   S   T   V   F   M   N   L   R   G   G
451  TCAAGCCCCT GAGCACCGTG TTCATGAATC TGCGCCTGCG GGGAGGCGGC
     AGTTCGGGGA CTCGTGGCAC AAGTACTTAG ACGCGGACGC CCCTCCGCCG
         T   E   P   G   G   M   V   S   K   G   E   E   L   F   T   G   V  ·
501  ACAGAGCCTG GAGGTATGGT GAGCAAGGGC GAGGAGCTGT TCACCGGGGT
     TGTCTCGGAC CTCCATACCA CTCGTTCCCG CTCCTCGACA AGTGGCCCCA
       · V   P   I   L   V   E   L   D   G   D   V   N   G   H   K   F   S  ·
551  GGTGCCCATC CTGGTCGAGC TGGACGGCGA CGTAAACGGC CACAAGTTCA
     CCACGGGTAG GACCAGCTCG ACCTGCCGCT GCATTTGCCG GTGTTCAAGT
       · V   S   G   E   G   E   G   D   A   T   Y   G   K   L   T   L
601  GCGTGTCCGG CGAGGGCGAG GGCGATGCCA CCTACGGCAA GCTGACCCTG
     CGCACAGGCC GCTCCCGCTC CCGCTACGGT GGATGCCGTT CGACTGGGAC
         K   F   I   C   T   T   G   K   L   P   V   P   W   P   T   L   V  ·
651  AAGTTCATCT GCACCACCGG CAAGCTGCCC GTGCCCTGGC CCACCCTCGT
     TTCAAGTAGA CGTGGTGGCC GTTCGACGGG CACGGGACCG GGTGGGAGCA
       · T   T   L   T   Y   G   V   Q   C   F   S   R   Y   P   D   H   M  ·
701  GACCACCCTG ACCTACGGCG TGCAGTGCTT CAGCCGCTAC CCCGACCACA
```

```
                CTGGTGGGAC TGGATGCCGC ACGTCACGAA GTCGGCGATG GGGCTGGTGT
                 · K  Q  H   D  F  F    K  S  A  M    P  E  G  Y    V  Q
          751   TGAAGCAGCA CGACTTCTTC AAGTCCGCCA TGCCCGAAGG CTACGTCCAG
                ACTTCGTCGT GCTGAAGAAG TTCAGGCGGT ACGGGCTTCC GATGCAGGTC
                 E  R  T  I   F  F  K   D  D  G    N  Y  K  T    R  A  E ·
          801   GAGCGCACCA TCTTCTTCAA GGACGACGGC AACTACAAGA CCCGCGCCGA
                CTCGCGTGGT AGAAGAAGTT CCTGCTGCCG TTGATGTTCT GGGCGCGGCT
                 · V  K  F   E  G  D    L  V  N    R  I  E   L  K  G  I ·
          851   GGTGAAGTTC GAGGGCGACA CCCTGGTGAA CCGCATCGAG CTGAAGGGCA
                CCACTTCAAG CTCCCGCTGT GGGACCACTT GGCGTAGCTC GACTTCCCGT
                 · D  F  K   E  D  G    N  I  L   G  H  K  L    E  Y  N
          901   TCGACTTCAA GGAGGACGGC AACATCCTGG GGCACAAGCT GGAGTACAAC
                AGCTGAAGTT CCTCCTGCCG TTGTAGGACC CCGTGTTCGA CCTCATGTTG
                   Y  N  S  H   N  V  Y    I  M  A    D  K  Q   K  N  G  I ·
          951   TACAACAGCC ACAACGTCTA TATCATGGCC GACAAGCAGA AGAACGGCAT
                ATGTTGTCGG TGTTGCAGAT ATAGTACCGG CTGTTCGTCT TCTTGCCGTA
                 · K  V  N   F  K  I  R    H  N  I    E  D  G    S  V  Q  L ·
         1001   CAAGGTGAAC TTCAAGATCC GCCACAACAT CGAGGACGGC AGCGTGCAGC
                GTTCCACTTG AAGTTCTAGG CGGTGTTGTA GCTCCTGCCG TCGCACGTCG
                 · A  D  H   Y  Q  Q    N  T  P  I    G  D  G    P  V  L
         1051   TCGCCGACCA CTACCAGCAG AACACCCCCA TCGGCGACGG CCCCGTGCTG
                AGCGGCTGGT GATGGTCGTC TTGTGGGGGT AGCCGCTGCC GGGGCACGAC
                  L  P  D  N   H  Y  L    S  T  Q    S  A  L   S  K  D  P ·
         1101   CTGCCCGACA ACCACTACCT GAGCACCCAG TCCGCCCTGA GCAAAGACCC
                GACGGGCTGT TGGTGATGGA CTCGTGGGTC AGGCGGGACT CGTTTCTGGG
                 · N  E  K   R  D  H  M    V  L  L    E  F  V    T  A  A  G ·
         1151   CAACGAGAAG CGCGATCACA TGGTCCTGCT GGAGTTCGTG ACCGCCGCCG
                GTTGCTCTTC GCGCTAGTGT ACCAGGACGA CCTCAAGCAC TGGCGGCGGC
                                                                HindIII
                                                              ~~~~~~~
                 · I  T  L   G  M  D    E  L  Y  K   *   *
         1201   GGATCACTCT CGGCATGGAC GAGCTGTACA AGTAATAAGC TT
                CCTAGTGAGA GCCGTACCTG CTCGACATGT CATTATTCG AA
```

SUMO-Protein G
Protein G NCBI Accession# X53324

```
     NcoI
     ~~~~~~
         M   G   H   H   H   H   H   G   S   D   S   E   V   N   Q
  1  CCATGGGTCA TCACCATCAT CATCACGGGT CGGACTCAGA AGTCAATCAA
     GGTACCCAGT AGTGGTAGTA GTAGTGCCCA GCCTGAGTCT TCAGTTAGTT
         E   A   K   P   E   V   K   P   E   V   K   P   E   T   H   I   N ·
 51  GAAGCTAAGC CAGAGGTCAA GCCAGAAGTC AAGCCTGAGA CTCACATCAA
     CTTCGATTCG GTCTCCAGTT CGGTCTTCAG TTCGGACTCT GAGTGTAGTT
     · L   K   V   S   D   G   S   E   I   F   F   K   I   K   K   T ·
101  TTTAAAGGTG TCCGATGGAT CTTCAGAGAT CTTCTTCAAG ATCAAAAAGA
     AAATTTCCAC AGGCTACCTA GAAGTCTCTA GAAGAAGTTC TAGTTTTTCT
     · T   P   L   R   R   L   M   E   A   F   A   K   R   Q   G   K
151  CCACTCCTTT AAGAAGGCTG ATGGAAGCGT TCGCTAAAAG ACAGGGTAAG
     GGTGAGGAAA TTCTTCCGAC TACCTTCGCA AGCGATTTTC TGTCCCATTC
         E   M   D   S   L   R   F   L   Y   D   G   I   R   I   Q   A   D ·
201  GAAATGGACT CCTTAAGATT CTTGTACGAC GGTATTAGAA TTCAAGCTGA
     CTTTACCTGA GGAATTCTAA GAACATGCTG CCATAATCTT AAGTTCGACT
     · Q   T   P   E   D   L   D   M   E   D   N   D   I   I   E   A   H ·
251  TCAGACCCCT GAAGATTTGG ACATGGAGGA TAACGATATT ATTGAGGCTC
     AGTCTGGGGA CTTCTAAACC TGTACCTCCT ATTGCTATAA TAACTCCGAG
     · R   E   Q   I   G   G   T   P   A   V   T   T   Y   K   L   V
301  ACCGCGAACA GATTGGAGGT ACGCCGGCGG TGACCACCTA TAAACTGGTG
     TGGCGCTTGT CTAACCTCCA TGCGGCCGCC ACTGGTGGAT ATTTGACCAC
         I   N   G   K   T   L   K   G   E   T   T   K   A   V   D   A ·
351  ATTAACGGCA AAACCCTGAA AGGCGAAACC ACCACCAAAG CGGTGGATGC
     TAATTGCCGT TTTGGGACTT TCCGCTTTGG TGGTGGTTTC GCCACCTACG
     · E   T   A   E   K   A   F   K   Q   Y   A   N   D   N   G   V   D ·
401  GGAAACCGCG GAAAAAGCGT TTAAACAGTA TGCGAACGAT AACGGCGTGG
     CCTTTGGCGC CTTTTTCGCA AATTTGTCAT ACGCTTGCTA TTGCCGCACC
     · G   V   W   T   Y   D   D   A   T   K   T   F   T   V   T   E
451  ATGGCGTGTG GACCTATGAT GATGCGACCA AAACCTTTAC CGTGACCGAA
     TACCGCACAC CTGGATACTA CTACGCTGGT TTTGGAAATG GCACTGGCTT
         HindIII
         ~~~~~~~
         *   *
501  TAATAAGCTT
     ATTATTCGAA
```

Figure 34A
SUMO β-GUS
β-GUS NCBI Accession# U12640

```
        M   G   H   H    H   H   H   H    G   S   D   S    E   V   N   Q   E ·
  1   ATGGGTCATC ACCATCATCA TCACGGGTCG GACTCAGAAG TCAATCAAGA
      TACCCAGTAG TGGTAGTAGT AGTGCCCAGC CTGAGTCTTC AGTTAGTTCT
      · A   K   P    E   V   K   P    E   V   K    P   E   T    H   I   N   L ·
 51   AGCTAAGCCA GAGGTCAAGC CAGAAGTCAA GCCTGAGACT CACATCAATT
      TCGATTCGGT CTCCAGTTCG GTCTTCAGTT CGGACTCTGA GTGTAGTTAA
      · K   V   S    D   G   S    E   I   F    F   K   I   K    K   T
101   TAAAGGTGTC CGATGGATCT TCAGAGATCT TCTTCAAGAT CAAAAAGACC
      ATTTCCACAG GCTACCTAGA AGTCTCTAGA AGAAGTTCTA GTTTTTCTGG
        T   P   L   R    R   L   M    E   A   F    A   K   R    Q   G   K   E ·
151   ACTCCTTTAA GAAGGCTGAT GGAAGCGTTC GCTAAAAGAC AGGGTAAGGA
      TGAGGAAATT CTTCCGACTA CCTTCGCAAG CGATTTTCTG TCCCATTCCT
      · M   D   S    L   R   F   L    Y   D   G    I   R   I    Q   A   D   Q ·
201   AATGGACTCC TTAAGATTCT TGTACGACGG TATTAGAATT CAAGCTGATC
      TTACCTGAGG AATTCTAAGA ACATGCTGCC ATAATCTTAA GTTCGACTAG
      · T   P   E    D   L   D    M   E   D   N    D   I   I    E   A   H
251   AGACCCCTGA AGATTTGGAC ATGGAGGATA ACGATATTAT TGAGGCTCAC
      TCTGGGGACT TCTAAACCTG TACCTCCTAT TGCTATAATA ACTCCGAGTG
        R   E   Q   I    G   G   M    E   F   M    L   R   P    V   E   T   P ·
301   CGCGAACAGA TTGGAGGTAT GGAATTCATG TTACGTCCTG TAGAAACCCC
      GCGCTTGTCT AACCTCCATA CCTTAAGTAC AATGCAGGAC ATCTTTGGGG
      · T   R   E    I   K   K   L    D   G   L    W   A   F    S   L   D   R ·
351   AACCCGTGAA ATCAAAAAAC TCGACGGCCT GTGGGCATTC AGTCTGGATC
      TTGGGCACTT TAGTTTTTTG AGCTGCCGGA CACCCGTAAG TCAGACCTAG
      · E   N   C    G   I   D    Q   R   W   W    E   S   A    L   Q   E
401   GCGAAAACTG TGGAATTGAT CAGCGTTGGT GGGAAAGCGC GTTACAAGAA
      CGCTTTTGAC ACCTTAACTA GTCGCAACCA CCCTTTCGCG CAATGTTCTT
        S   R   A   I    A   V   P    G   S   F    N   D   Q    F   A   D   A ·
451   AGCCGGGCAA TTGCTGTGCC AGGCAGTTTT AACGATCAGT TCGCCGATGC
      TCGGCCCGTT AACGACACGG TCCGTCAAAA TTGCTAGTCA AGCGGCTACG
      · D   I   R    N   Y   A   G    N   V   W    Y   Q   R    E   V   F   I ·
501   AGATATTCGT AATTATGCGG GCAACGTCTG GTATCAGCGC GAAGTCTTTA
      TCTATAAGCA TTAATACGCC CGTTGCAGAC CATAGTCGCG CTTCAGAAAT
      · P   K   G    W   A   G    Q   R   I   V    L   R   F    D   A   V
551   TACCGAAAGG TTGGGCAGGC CAGCGTATCG TGCTGCGTTT CGATGCGGTC
      ATGGCTTTCC AACCCGTCCG GTCGCATAGC ACGACGCAAA GCTACGCCAG
        T   H   Y   G    K   V   W    V   N   N    Q   E   V    M   E   H   Q ·
601   ACTCATTACG GCAAAGTGTG GGTCAATAAT CAGGAAGTGA TGGAGCATCA
      TGAGTAATGC CGTTTCACAC CCAGTTATTA GTCCTTCACT ACCTCGTAGT
      · G   G   Y    T   P   F   E    A   D   V    T   P   Y    V   I   A   G ·
651   GGGCGGCTAT ACGCCATTTG AAGCCGATGT CACGCCGTAT GTTATTGCCG
      CCCGCCGATA TGCGGTAAAC TTCGGCTACA GTGCGGCATA CAATAACGGC
      · K   S   V    R   I   T    V   C   V   N    N   E   L    N   W   Q
```

Figure 34B

```
 701 GGAAAAGTGT ACGTATCACC GTTTGTGTGA ACAACGAACT GAACTGGCAG
     CCTTTTCACA TGCATAGTGG CAAACACACT TGTTGCTTGA CTTGACCGTC
        T  I  P  P   G  M  V   I  T  D   E  N  G   K  K  Q  ·
 751 ACTATCCCGC CGGGAATGGT GATTACCGAC GAAAACGGCA AGAAAAAGCA
     TGATAGGGCG GCCCTTACCA CTAATGGCTG CTTTTGCCGT TCTTTTTCGT
      · S  Y  F   H  D  F   F  N  Y   A  G  I  H   R  S  V  M  ·
 801 GTCTTACTTC CATGATTTCT TTAACTATGC CGGAATCCAT CGCAGCGTAA
     CAGAATGAAG GTACTAAAGA AATTGATACG GCCTTAGGTA GCGTCGCATT
      · L  Y  T   T  P  N   T  W  V   D  D  I  T   V  V  T
 851 TGCTCTACAC CACGCCGAAC ACCTGGGTGG ACGATATCAC CGTGGTGACG
     ACGAGATGTG GTGCGGCTTG TGGACCCACC TGCTATAGTG GCACCACTGC
        H  V  A   Q  D  C   N  H  A   S  V  D   W  Q  V  V  A  ·
 901 CATGTCGCGC AAGACTGTAA CCACGCGTCT GTTGACTGGC AGGTGGTGGC
     GTACAGCGCG TTCTGACATT GGTGCGCAGA CAACTGACCG TCCACCACCG
      · N  G  D   V  S  V  E   L  R  D   A  D  Q   Q  V  V  A  ·
 951 CAATGGTGAT GTCAGCGTTG AACTGCGTGA TGCGGATCAA CAGGTGGTTG
     GTTACCACTA CAGTCGCAAC TTGACGCACT ACGCCTAGTT GTCCACCAAC
      · T  G  Q   G  T  S   G  T  L   Q  V  V  N   P  H  L
1001 CAACTGGACA AGGCACTAGC GGGACTTTGC AAGTGGTGAA TCCGCACCTC
     GTTGACCTGT TCCGTGATCG CCCTGAAACG TTCACCACTT AGGCGTGGAG
        W  Q  P   G  E  G   Y  L  Y   E  L  C   V  T  A  K  S  ·
1051 TGGCAACCGG GTGAAGGTTA CTCTATGAA CTGTGCGTCA CAGCCAAAAG
     ACCGTTGGCC CACTTCCAAT AGAGATACTT GACACGCAGT GTCGGTTTTC
      · Q  T  E   C  D  I  Y   P  L  R   V  G  I   R  S  V  A  ·
1101 CCAGACAGAG TGTGATATCT ACCCGCTTCG CGTCGGCATC CGGTCAGTGG
     GGTCTGTCTC ACACTATAGA TGGGCGAAGC GCAGCCGTAG GCCAGTCACC
      · V  K  G   Q  Q  F   L  I  N   H  K  P   F  Y  F  T
1151 CAGTGAAGGG CCAACAGTTC CTGATTAACC ACAAACCGTT CTACTTTACT
     GTCACTTCCC GGTTGTCAAG GACTAATTGG TGTTTGGCAA GATGAAATGA
        G  F  G  R   H  E  D   A  D  L   R  G  K   G  F  D  N  ·
1201 GGCTTTGGTC GTCATGAAGA TGCGGACTTA CGTGGCAAAG GATTCGATAA
     CCGAAACCAG CAGTACTTCT ACGCCTGAAT GCACCGTTTC CTAAGCTATT
      · V  L  M   V  H  D  H   A  L  M   D  W  I   G  A  N  S  ·
1251 CGTGCTGATG GTGCACGACC ACGCATTAAT GGACTGGATT GGGGCCAACT
     GCACGACTAC CACGTGCTGG TGCGTAATTA CCTGACCTAA CCCCGGTTGA
      · Y  R  T   S  H  Y   P  Y  A  E   E  M  L   D  W  A
1301 CCTACCGTAC CTCGCATTAC CCTTACGCTG AAGAGATGCT CGACTGGGCA
     GGATGGCATG GAGCGTAATG GGAATGCGAC TTCTCTACGA GCTGACCCGT
        D  E  H  G   I  V  V   I  D  E   T  A  A  V   G  F  N  ·
1351 GATGAACATG GCATCGTGGT GATTGATGAA ACTGCTGCTG TCGGCTTTAA
     CTACTTGTAC CGTAGCACCA CTAACTACTT TGACGACGAC AGCCGAAATT
      · L  S  L   G  I  G  F   E  A  G   N  K  P   K  E  L  Y  ·
1401 CCTCTCTTTA GGCATTGGTT TCGAAGCGGG CAACAAGCCG AAAGAACTGT
     GGAGAGAAAT CCGTAACCAA AGCTTCGCCC GTTGTTCGGC TTTCTTGACA
      · S  E  E   A  V  N   G  E  T   Q  A  H   L  Q  A
1451 ACAGCGAAGA GGCAGTCAAC GGGGAAACTC AGCAAGCGCA CTTACAGGCG
     TGTCGCTTCT CCGTCAGTTG CCCCTTTGAG TCGTTCGCGT GAATGTCCGC
        I  K  E  L   I  A  R   D  K  N   H  P  S   V  M  W  ·
1501 ATTAAAGAGC TGATAGCGCG TGACAAAAAC CACCCAAGCG TGGTGATGTG
     TAATTTCTCG ACTATCGCGC ACTGTTTTTG GTGGGTTCGC ACCACTACAC
      · S  I  A   N  E  P  D   T  R  P   Q  V  H   G  N  I  S  ·
1551 GAGTATTGCC AACGAACCGG ATACCCGTCC GCAAGTGCAC GGGAATATTT
```

```
              CTCATAACGG TTGCTTGGCC TATGGGCAGG CGTTCACGTG CCCTTATAAA
               · P  L  A    E  A  T    R  K  L    D  P  T    P  I  T
       1601   CGCCACTGGC GGAAGCAACG CGTAAACTCG ACCCGACGCG TCCGATCACC
              GCGGTGACCG CCTTCGTTGC GCATTTGAGC TGGGCTGCGC AGGCTAGTGG

C  V  N  V    M  F  C    D  A  H    T  D  T  I    S  D  L ·
       1651   TGCGTCAATG TAATGTTCTG CGACGCTCAC ACCGATACCA TCAGCGATCT
              ACGCAGTTAC ATTACAAGAC GCTGCGAGTG TGGCTATGGT AGTCGCTAGA
               · F  D  V    L  C  L  N    R  Y  Y    G  W  Y    V  Q  S  G ·
       1701   CTTTGATGTG CTGTGCCTGA ACCGTTATTA CGGATGGTAT GTCCAAAGCG
              GAAACTACAC GACACGGACT TGGCAATAAT GCCTACCATA CAGGTTTCGC
               · D  L  E    T  A  E    K  V  L  E    K  E  L    L  A  W
       1751   GCGATTTGGA AACGGCAGAG AAGGTACTGG AAAAAGAACT TCTGGCCTGG
              CGCTAAACCT TTGCCGTCTC TTCCATGACC TTTTTCTTGA AGACCGGACC
                 Q  E  K  L    H  Q  P    I  I  I    T  E  Y  G    V  D  T ·
       1801   CAGGAGAAAC TGCATCAGCC GATTATCATC ACCGAATACG GCGTGGATAC
              GTCCTCTTTG ACGTAGTCGG CTAATAGTAG TGGCTTATGC CGCACCTATG
               · L  A  G    L  H  S  M    Y  T  D    M  W  S    E  E  Y  Q ·
       1851   GTTAGCCGGG CTGCACTCAA TGTACACCGA CATGTGGAGT GAAGAGTATC
              CAATCGGCCC GACGTGAGTT ACATGTGGCT GTACACCTCA CTTCTCATAG
               · C  A  W    L  D  M    Y  H  R  V    F  D  R    V  S  A
       1901   AGTGTGCATG GCTGGATATG TATCACCGCG TCTTTGATCG CGTCAGCGCC
              TCACACGTAC CGACCTATAC ATAGTGGCGC AGAAACTAGC GCAGTCGCGG
                 V  V  G  E    Q  V  W    N  F  A    D  F  A  T    S  Q  G ·
       1951   GTCGTCGGTG AACAGGTATG GAATTTCGCC GATTTTGCGA CCTCGCAAGG
              CAGCAGCCAC TTGTCCATAC CTTAAAGCGG CTAAAACGCT GGAGCGTTCC
               · I  L  R    V  G  G    N  K  K  G    I  F  T    R  D  R  K ·
       2001   CATATTGCGC GTTGGCGGTA ACAAGAAAGG GATCTTCACT CGCGACCGCA
              GTATAACGCG CAACCGCCAT TGTTCTTTCC CTAGAAGTGA GCGCTGGCGT
               · P  K  S    A  A  F    L  L  Q  K    R  W  T    G  M  N
       2051   AACCGAAGTC GGCGGCTTTT CTGCTGCAAA AACGCTGGAC TGGCATGAAC
              TTGGCTTCAG CCGCCGAAAA GACGACGTTT TTGCGACCTG ACCGTACTTG
                  F  G  E  K    P  Q  Q    G  G  K    Q
       2101   TTCGGTGAAA AACCGCAGCA GGGAGGCAAA CAA
              AAGCCACTTT TTGGCGTCGT CCCTCCGTTT GTT
```

SUMO-Liver X Receptor α
Liver X Receptor A NCBI Accession# NM_005693

```
           M   G   H   H    H   H   H    H   G   S    D   S   E   V    N   Q   E  ·
  1   ATGGGTCATC ACCATCATCA TCACGGGTCG GACTCAGAAG TCAATCAAGA
      TACCCAGTAG TGGTAGTAGT AGTGCCCAGC CTGAGTCTTC AGTTAGTTCT
      ·  A   K   P    E   V   K   P    E   V   K    P   E   T    H   I   N   L  ·
 51   AGCTAAGCCA GAGGTCAAGC CAGAAGTCAA GCCTGAGACT CACATCAATT
      TCGATTCGGT CTCCAGTTCG GTCTTCAGTT CGGACTCTGA GTGTAGTTAA
      ·  K   V   S    D   G   S    S   E   I   F    F   K   I    K   K   T
101   TAAAGGTGTC CGATGGATCT TCAGAGATCT TCTTCAAGAT CAAAAAGACC
      ATTTCCACAG GCTACCTAGA AGTCTCTAGA AGAAGTTCTA GTTTTTCTGG
           T   P   L    R   R   L    M   E   A   F    A   K   R    Q   G   K   E  ·
151   ACTCCTTTAA GAAGGCTGAT GGAAGCGTTC GCTAAAAGAC AGGGTAAGGA
      TGAGGAAATT CTTCCGACTA CCTTCGCAAG CGATTTTCTG TCCCATTCCT
      ·  M   D   S    L   R   F   L    Y   D   G    I   R   I    Q   A   D   Q  ·
201   AATGGACTCC TTAAGATTCT TGTACGACGG TATTAGAATT CAAGCTGATC
      TTACCTGAGG AATTCTAAGA ACATGCTGCC ATAATCTTAA GTTCGACTAG
      ·  T   P   E    D   L   D    M   E   D   N    I   I   E    A   H
251   AGACCCCTGA AGATTTGGAC ATGGAGGATA ACGATATTAT TGAGGCTCAC
      TCTGGGGACT TCTAAACCTG TACCTCCTAT TGCTATAATA ACTCCGAGTG
           R   E   Q    I   G   G    M   S   L   W    L   G   A    P   V   P   D  ·
301   CGCGAACAGA TTGGAGGTAT GTCCTTGTGG CTGGGGGCCC CTGTGCCTGA
      GCGCTTGTCT AACCTCCATA CAGGAACACC GACCCCCGGG GACACGGACT
      ·  I   P   P    D   S   A   V    E   L   W    K   P   G    A   Q   D   A  ·
351   CATTCCTCCT GACTCTGCGG TGGAGCTGTG GAAGCCAGGC GCACAGGATG
      GTAAGGAGGA CTGAGACGCC ACCTCGACAC CTTCGGTCCG CGTGTCCTAC
      ·  S   S   Q    A   Q   G    G   S   S   C    I   L   R    E   E   A
401   CAAGCAGCCA GGCCCAGGGA GGCAGCAGCT GCATCCTCAG AGAGGAAGCC
      GTTCGTCGGT CCGGGTCCCT CCGTCGTCGA CGTAGGAGTC TCTCCTTCGG
           R   M   P    H   S   A   G    G   T   A    G   V   G    L   E   A   A  ·
451   AGGATGCCCC ACTCTGCTGG GGGTACTGCA GGGGTGGGGC TGGAGGCTGC
      TCCTACGGGG TGAGACGACC CCCATGACGT CCCCACCCCG ACCTCCGACG
      ·  E   P   T    A   L   L   T    R   A   E    P   P   S    E   P   T   E  ·
501   AGAGCCCACA GCCCTGCTCA CCAGGGCAGA GCCCCCTTCA GAACCCACAG
      TCTCGGGTGT CGGGACGAGT GGTCCCGTCT CGGGGGAAGT CTTGGGTGTC
      ·  I   R   P    Q   K   R    K   K   G   P    A   P   K    M   L   G
551   AGATCCGTCC ACAAAAGCGG AAAAAGGGGC CAGCCCCCAA AATGCTGGGG
      TCTAGGCAGG TGTTTTCGCC TTTTTCCCCG GTCGGGGGTT TTACGACCCC
           N   E   L    C   S   V   C    G   D   K    A   S   G    F   H   Y   N  ·
601   AACGAGCTAT GCAGCGTGTG TGGGGACAAG GCCTCGGGCT TCCACTACAA
      TTGCTCGATA CGTCGCACAC ACCCCTGTTC CGGAGCCCGA AGGTGATGTT
      ·  V   L   S    C   E   G   C    K   G   F    R   R   S    V   I   K  ·
651   TGTTCTGAGC TGCGAGGGCT GCAAGGGATT CCGCCGCAGC GTCATCA
      ACAAGACTCG ACGCTCCCGA CGTTCCCTAA GGCGGCGTCG CAGTAGT
      ·  G   A   H    Y   I   C    H   S   G   G    H   C   P    M   D   T
701   AGGGAGCGCA CTACATCTGC CACAGTGGCG GCCACTGCCC CATGGACACC
```

Figure 35B

```
         TCCCTCGCGT GATGTAGACG GTGTCACCGC CGGTGACGGG GTACCTGTGG
            Y   M   R   R    K   Q    E   C   R    L   K   C   R   Q   A  ·
 751    TACATGCGTC GCAAGTGCCA GGAGTGTCGG CTTCGCAAAT GCCGTCAGGC
        ATGTACGCAG CGTTCACGGT CCTCACAGCC GAAGCGTTTA CGGCAGTCCG
         ·  G   M   R    E   E   C   V    L   S   E    E   Q   I    R   L   K   K  ·
 801    TGGCATGCGG GAGGAGTGTG TCCTGTCAGA AGAACAGATC CGCCTGAAGA
        ACCGTACGCC CTCCTCACAC AGGACAGTCT TCTTGTCTAG GCGGACTTCT
         ·  L   K   R    Q   E   E    E   Q   A    H   A   T    S   L   P   P
 851    AACTGAAGCG GCAAGAGGAG GAACAGGCTC ATGCCACATC CTTGCCCCCC
        TTGACTTCGC CGTTCTCCTC CTTGTCCGAG TACGGTGTAG GAACGGGGGG
            R   R   S   S    P   P   Q    I   L   P    Q   L   S    P   E   Q   L  ·
 901    AGGCGTTCCT CACCCCCCCA AATCCTGCCC CAGCTCAGCC CGGAACAACT
        TCCGCAAGGA GTGGGGGGGT TTAGGACGGG GTCGAGTCGG GCCTTGTTGA
         ·  G   M   I    E   K   L   V    A   A   Q    Q   Q   C    N   R   R   S  ·
 951    GGGCATGATC GAGAAGCTCG TCGCTGCCCA GCAACAGTGT AACCGGCGCT
        CCCGTACTAG CTCTTCGAGC AGCGACGGGT CGTTGTCACA TTGGCCGCGA
         ·  F   S    D   R   L   R    V   T   P    W   P   M    A   P   D   P
1001    CCTTTTCTGA CCGGCTTCGA GTCACGCCTT GGCCCATGGC ACCAGATCCC
        GGAAAAGACT GGCCGAAGCT CAGTGCGGAA CCGGGTACCG TGGTCTAGGG
             H   S   R   E    A   R    Q   Q   R    F   A   H    F   T   E   L   A  ·
1051    CATAGCCGGG AGGCCCGTCA GCAGCGCTTT GCCCACTTCA CTGAGCTGGC
        GTATCGGCCC TCCGGGCAGT CGTCGCGAAA CGGGTGAAGT GACTCGACCG
         ·  I   V   S    V   Q   E   I    V   D   F    A   K   Q    L   P   G   F  ·
1101    CATCGTCTCT GTGCAGGAGA TAGTTGACTT TGCTAAACAG ·CTACCCGGCT
        GTAGCAGAGA CACGTCCTCT ATCAACTGAA ACGATTTGTC GATGGGCCGA

·  L   Q   L    S   R   E    D   Q   I    A   L   L   K    T   S   A
1151    TCCTGCAGCT CAGCCGGGAG GACCAGATTG CCCTGCTGAA GACCTCTGCG
        AGGACGTCGA GTCGGCCCTC CTGGTCTAAC GGGACGACTT CTGGAGACGC
            I   E   V   M    L   L   E    T   S   R    R   Y   N   P    G   S   E  ·
1201    ATCGAGGTGA TGCTTCTGGA GACATCTCGG AGGTACAACC CTGGGAGTGA
        TAGCTCCACT ACGAAGACCT CTGTAGAGCC TCCATGTTGG GACCCTCACT
         ·  S   I   T    F   L   K   D    F   S   Y    N   R   E    D   F   A   K  ·
1251    GAGTATCACC TTCCTCAAGG ATTTCAGTTA TAACCGGGAA GACTTTGCCA
        CTCATAGTGG AAGGAGTTCC TAAAGTCAAT ATTGGCCCTT CTGAAACGGT
         ·  A   G   L   Q    V   E   F    I   N   P    I   F   E    F   S   R
1301    AAGCAGGGCT GCAAGTGGAA TTCATCAACC CCATCTTCGA GTTCTCCAGG
        TTCGTCCCGA CGTTCACCTT AAGTAGTTGG GGTAGAAGCT CAAGAGGTCC
            A   M   N   E    L   Q   L    N   D   A    E   F   A   L    L   I   A  ·
1351    GCCATGAATG AGCTGCAACT CAATGATGCC GAGTTTGCCT TGCTCATTGC
        CGGTACTTAC TCGACGTTGA GTTACTACGG CTCAAACGGA ACGAGTAACG
         ·  I   S   I    F   S   A   D    R   P   N    V   Q   D    Q   L   Q   V  ·
1401    TATCAGCATC TTCTCTGCAG ACCGGCCCAA CGTGCAGGAC CAGCTCCAGG
        ATAGTCGTAG AAGAGACGTC TGGCCGGGTT GCACGTCCTG GTCGAGGTCC
         ·  E   R   L    Q   H   T    Y   V   E    A   L   H    A   Y   V   S
1451    TGGAGAGGCT GCAGCACACA TATGTGGAAG CCCTGCATGC CTACGTCTCC
        ACCTCTCCGA CGTCGTGTGT ATACACCTTC GGGACGTACG GATGCAGAGG
            I   H   H   P    H   D   R    L   M   F    P   R   M   L    M   K   L  ·
1501    ATCCACCATC CCCATGACCG ACTGATGTTC CCACGGATGC TAATGAAACT
        TAGGTGGTAG GGGTACTGGC TGACTACAAG GGTGCCTACG ATTACTTTGA
         ·  V   S   L    R   T   L   S    S   V   H    S   E   Q    V   F   A   L  ·
1551    GGTGAGCCTC CGGACCCTGA GCAGCGTCCA CTCAGAGCAA GTGTTTGCAC
```

```
           CCACTCGGAG GCCTGGGACT CGTCGCAGGT GAGTCTCGTT CACAAACGTG
            · R   L   Q    D  K  K    L  P  P    L  S  E    I  W  D
     1601  TGCGTCTGCA GGACAAAAAG CTCCCACCGC TGCTCTCTGA GATCTGGGAT
           ACGCAGACGT CCTGTTTTTC GAGGGTGGCG ACGAGAGACT CTAGACCCTA
             V  H  E  *
     1651  GTGCACGAAT GA
           CACGTGCTTA CT
```

SUMO Tyrosine Kinase
Tyrosin Kinase NCBI Accession# BC039039

```
         M   G   H   H    H   H   H   H   G   S    D   S   E   V    N   Q   E  ·
  1   ATGGGTCATC ACCATCATCA TCACGGGTCG GACTCAGAAG TCAATCAAGA
      TACCCAGTAG TGGTAGTAGT AGTGCCCAGC CTGAGTCTTC AGTTAGTTCT
      · A   K   P    E   V   K   P    E   V   K    P   E   T    H   I   N   L  ·
 51   AGCTAAGCCA GAGGTCAAGC CAGAAGTCAA GCCTGAGACT CACATCAATT
      TCGATTCGGT CTCCAGTTCG GTCTTCAGTT CGGACTCTGA GTGTAGTTAA
         · K   V   S    D   G   S    E   I   F    F   K   I    K   K   T
101   TAAAGGTGTC CGATGGATCT TCAGAGATCT TCTTCAAGAT CAAAAAGACC
      ATTTCCACAG GCTACCTAGA AGTCTCTAGA AGAAGTTCTA GTTTTTCTGG
         T   P   L   R    R   L   M    E   A   F    A   K   R   Q    G   K   E  ·
151   ACTCCTTTAA GAAGGCTGAT GGAAGCGTTC GCTAAAAGAC AGGGTAAGGA
      TGAGGAAATT CTTCCGACTA CCTTCGCAAG CGATTTTCTG TCCCATTCCT
      · M   D   S    L   R   F   L    Y   D   G    I   R   I    Q   A   D   Q  ·
201   AATGGACTCC TTAAGATTCT TGTACGACGG TATTAGAATT CAAGCTGATC
      TTACCTGAGG AATTCTAAGA ACATGCTGCC ATAATCTTAA GTTCGACTAG
      · T   P   E    D   L   D    M   E   D   N    D   I   I    E   A   H
251   AGACCCCTGA AGATTTGGAC ATGGAGGATA ACGATATTAT TGAGGCTCAC
      TCTGGGGACT TCTAAACCTG TACCTCCTAT TGCTATAATA ACTCCGAGTG
         R   E   Q   I    G   G   M    C   P   N    S   S   A   S    N   A   S  ·
301   CGCGAACAGA TTGGAGGTAT GTGCCCCAAC AGCAGTGCCA GCAACGCCTC
      GCGCTTGTCT AACCTCCATA CACGGGGTTG TCGTCACGGT ·CGTTGCGGAG
      · G   A   A    A   P   T   L    P   A   H    P   S   T    L   T   H   P· ·
351   AGGGGCTGCT GCTCCCACAC TCCCAGCCCA CCCATCCACG TTGACTCATC
      TCCCCGACGA CGAGGGTGTG AGGGTCGGGT GGGTAGGTGC AACTGAGTAG
         · Q   R   R    I   D   T    L   N   S   D    G   Y   T    P   E   P
401   CTCAGAGACG AATCGACACC TCAACTCAG ATGGATACAC CCCTGAGCCA
      GAGTCTCTGC TTAGCTGTGG AGTTGAGTC TACCTATGTG GGGACTCGGT
         A   R   I    T   S   P   D    K   P   R    P   M   P   M    D   T   S  ·
451   GCACGCATAA CGTCCCCAGA CAAACCGCGG CCGATGCCCA TGGACACGAG
      CGTGCGTATT GCAGGGGTCT GTTTGGCGCC GGCTACGGGT ACCTGTGCTC
      · V   Y   E    S   P   Y   S    D   P   E    E   L   K    D   K   K   L  ·
501   CGTGTATGAG AGCCCCTACA GCGACCCAGA GGAGCTCAAG GACAAGAAGC
      GCACATACTC TCGGGGATGT CGCTGGGTCT CCTCGAGTTC CTGTTCTTCG
      · F   L   K    R   D   N    L   L   I   A    D   I   E    L   G   C
551   TCTTCCTGAA GCGCGATAAC CTCCTCATAG CTGACATTGA ACTTGGCTGC
      AGAAGGACTT CGCGCTATTG GAGGAGTATC GACTGTAACT TGAACCGACG
         G   N   F    G   S   V   R    Q   G   V    Y   R   M   R    K   K   Q  ·
601   GGCAACTTTG GCTCAGTGCG CCAGGGCGTG TACCGCATGC GCAAGAAGCA
      CCGTTGAAAC CGAGTCACGC GGTCCCGCAC ATGGCGTACG CGTTCTTCGT
      · I   D   V    A   I   K   V    L   K   Q    G   T   E    K   A   D   T  ·
651   GATCGACGTG GCCATCAAGG TGCTGAAGCA GGGCACGGAG AAGGCAGACA
      CTAGCTGCAC CGGTAGTTCC ACGACTTCGT CCCGTGCCTC TTCCGTCTGT
      · E   E   M    M   R   E    A   Q   I   M    H   Q   L    D   N   P
701   CGGAAGAGAT GATGCGCGAG GCGCAGATCA TGCACCAGCT GGACAACCCC
      GCCTTCTCTA CTACGCGCTC CGCGTCTAGT ACGTGGTCGA CCTGTTGGGG
         Y   I   V    R   L   I   G    V   C   Q    A   E   A   L    M   L   V  ·
751   TACATCGTGC GGCTCATTGG CGTCTGCCAG GCCGAGGCCC TCATGCTGGT
```

```
            ATGTAGCACG CCGAGTAACC GCAGACGGTC CGGCTCCGGG AGTACGACCA
             · M  E  M   A  G  G    P  L  H    K  F  L    V  G  K  R ·
      801   CATGGAGATG GCTGGGGGCG GGCCGCTGCA CAAGTTCCTG GTCGGCAAGA
            GTACCTCTAC CGACCCCCGC CCGGCGACGT GTTCAAGGAC CAGCCGTTCT
             · E  E  I   P  V  S    N  V  A    E  L  L    H  Q  V  S
      851   GGGAGGAGAT CCCTGTGAGC AATGTGGCCG AGCTGCTGCA CCAGGTGTCC
            CCCTCCTCTA GGGACACTCG TTACACCGGC TCGACGACGT GGTCCACAGG
               M  G  M   K  Y  L    E  E  K    N  F  V    H  R  D  L  A ·
      901   ATGGGGATGA AGTACCTGGA GGAGAAGAAC TTTGTGCACC GTGACCTGGC
            TACCCCTACT TCATGGACCT CCTCTTCTTG AAACACGTGG CACTGGACCG
             · A  R  N   V  L  L    V  N  R    H  Y  A  K  I  S  D  F ·
      951   GGCCCGCAAC GTCCTGCTGG TTAACCGGCA CTACGCCAAG ATCAGCGACT
            CCGGGCGTTG CAGGACGACC AATTGGCCGT GATGCGGTTC TAGTCGCTGA
             · G  L  S   K  A  L    G  A  D  D  S  Y  Y   T  A  R
     1001   TTGGCCTCTC CAAAGCACTG GGTGCCGACG ACAGCTACTA CACTGCCCGC
            AACCGGAGAG GTTTCGTGAC CCACGGCTGC TGTCGATGAT GTGACGGGCG
               S  A  G  K  W  P    L  K  W  Y   A  P  E    C  I  N  F ·
     1051   TCAGCAGGGA AGTGGCCGCT CAAGTGGTAC GCACCCGAAT GCATCAACTT
            AGTCGTCCCT TCACCGGCGA GTTCACCATG CGTGGGCTTA CGTAGTTGAA

· R  K  F   S  S  R  S  D  V  W    S  Y  G    V  T  M  W ·
     1101   CCGCAAGTTC TCCAGCCGCA GCGATGTCTG GAGCTATGGG GTCACCATGT
            GGCGTTCAAG AGGTCGGCGT CGCTACAGAC CTCGATACCC CAGTGGTACA
             · E  A  L   S  Y  G    Q  K  P  Y   K  K  M    K  G  P
     1151   GGGAGGCCTT GTCCTACGGC CAGAAGCCCT ACAAGAAGAT GAAAGGGCCG
            CCCTCCGGAA CAGGATGCCG GTCTTCGGGA TGTTCTTCTA CTTTCCCGGC
               E  V  M   A  F  I    E  Q  G  K   R  M  E    C  P  P  E ·
     1201   GAGGTCATGG CCTTCATCGA GCAGGGCAAG CGGATGGAGT GCCCACCAGA
            CTCCAGTACC GGAAGTAGCT CGTCCCGTTC GCCTACCTCA CGGGTGGTCT
             · C  P  P   E  L  Y  A  L  M  S    D  C  W    I  Y  K  W ·
     1251   GTGTCCACCC GAACTGTACG CACTCATGAG TGACTGCTGG ATCTACAAGT
            CACAGGTGGG CTTGACATGC GTGAGTACTC ACTGACGACC TAGATGTTCA
             · E  D  R   P  D  F    L  T  V  Q   R  M  R    A  C
     1301   GGGAGGATCG CCCCGACTTC CTGACCGTGG AGCAGCGCAT GCGAGCCTGT
            CCCTCCTAGC GGGGCTGAAG GACTGGCACC TCGTCGCGTA CGCTCGGACA
               Y  Y  S   L  A  S  K   V  E  G    P  P  G    S  T  Q  K ·
     1351   TACTACAGCC TGGCCAGCAA GGTGGAAGGG CCCCCAGGCA GCACACAGAA
            ATGATGTCGG ACCGGTCGTT CCACCTTCCC GGGGGTCCGT CGTGTGTCTT
             · A  E  A   A  C  *
     1401   GGCTGAGGCT GCCTGTGCCT GA
            CCGACTCCGA CGGACACGGA CT
```

Figure 36B

Figure 37A
SUMO MAPKAPK2 Kinase
MAPKAPK2 Kinase NCBI Accession# BC036060

```
        M   G   H   H   H   H   H   H   G   S   D   S   E   V   N   Q   E  ·
  1   ATGGGTCATC ACCATCATCA TCACGGGTCG GACTCAGAAG TCAATCAAGA
        TACCCAGTAG TGGTAGTAGT AGTGCCCAGC CTGAGTCTTC AGTTAGTTCT
      ·  A   K   P   E   V   K   P   E   V   K   P   E   T   H   I   N   L  ·
 51   AGCTAAGCCA GAGGTCAAGC CAGAAGTCAA GCCTGAGACT CACATCAATT
        TCGATTCGGT CTCCAGTTCG GTCTTCAGTT CGGACTCTGA GTGTAGTTAA
      ·  K   V   S   D   G   S   E   I   F   F   K   I   K   K   T
101   TAAAGGTGTC CGATGGATCT TCAGAGATCT TCTTCAAGAT CAAAAAGACC
        ATTTCCACAG GCTACCTAGA AGTCTCTAGA AGAAGTTCTA GTTTTTCTGG
         T   P   L   R   R   L   M   E   A   F   A   K   R   Q   G   K   E  ·
151   ACTCCTTTAA GAAGGCTGAT GGAAGCGTTC GCTAAAAGAC AGGGTAAGGA
        TGAGGAAATT CTTCCGACTA CCTTCGCAAG CGATTTTCTG TCCCATTCCT
      ·  M   D   S   L   R   F   L   Y   D   G   I   R   I   Q   A   D   Q  ·
201   AATGGACTCC TTAAGATTCT TGTACGACGG TATTAGAATT CAAGCTGATC
        TTACCTGAGG AATTCTAAGA ACATGCTGCC ATAATCTTAA GTTCGACTAG
      ·  T   P   E   D   L   D   M   E   D   N   D   I   I   E   A   H
251   AGACCCCTGA AGATTTGGAC ATGGAGGATA ACGATATTAT TGAGGCTCAC
        TCTGGGGACT TCTAAACCTG TACCTCCTAT TGCTATAATA ACTCCGAGTG
         R   E   Q   I   G   G   M   Q   F   H   V   K   S   G   L   Q   I  ·
301   CGCGAACAGA TTGGAGGTAT GCAGTTCCAC GTCAAGTCCG GCCTGCAGAT
        GCGCTTGTCT AACCTCCATA CGTCAAGGTG CAGTTCAGGC CGGACGTCTA
      ·  K   K   N   A   I   I   D   D   Y   K   V   T   S   Q   V   L   G  ·
351   CAAGAAGAAC GCCATCATCG ATGACTACAA GGTCACCAGC CAGGTCCTGG
        GTTCTTCTTG CGGTAGTAGC TACTGATGTT CCAGTGGTCG GTCCAGGACC
      ·  L   G   I   N   G   K   V   L   Q   I   F   N   K   R   T   Q
401   GGCTGGGCAT CAACGGCAAA GTTTTGCAGA TCTTCAACAA GAGGACCCAG
        CCGACCCGTA GTTGCCGTTT CAAAACGTCT AGAAGTTGTT CTCCTGGGTC
         E   K   F   A   L   K   M   L   Q   D   C   P   K   A   R   R   E  ·
451   GAGAAATTCG CCCTCAAAAT GCTTCAGGAC TGCCCCAAGG CCCGCAGGGA
        CTCTTTAAGC GGGAGTTTTA CGAAGTCCTG ACGGGGTTCC GGGCGTCCCT
      ·  V   E   L   H   W   R   A   S   Q   C   P   H   I   V   R   I   V  ·
501   GGTGGAGCTG CACTGGCGGG CCTCCCAGTG CCCGCACATC GTACGGATCG
        CCACCTCGAC GTGACCGCCC GGAGGGTCAC GGGCGTGTAG CATGCCTAGC
      ·  D   V   Y   E   N   L   Y   A   G   R   K   C   L   L   I   V
551   TGGATGTGTA CGAGAATCTG TACGCAGGGA GGAAGTGCCT GCTGATTGTC
        ACCTACACAT GCTCTTAGAC ATGCGTCCCT CCTTCACGGA CGACTAACAG
         M   E   C   L   D   G   G   E   L   F   S   R   I   Q   D   R   G  ·
601   ATGGAATGTT TGGACGGTGG AGAACTCTTT AGCCGAATCC AGGATCGAGG
        TACCTTACAA ACCTGCCACC TCTTGAGAAA TCGGCTTAGG TCCTAGCTCC
      ·  D   Q   A   F   T   E   R   E   A   S   E   I   M   K   S   I   G  ·
651   AGACCAGGCA TTCACAGAAA GAGAAGCATC CGAAATCATG AAGAGCATCG
        TCTGGTCCGT AAGTGTCTTT CTCTTCGTAG GCTTTAGTAC TTCTCGTAGC
      ·  E   A   I   Q   Y   L   H   S   I   N   I   A   H   R   D   V
701   GTGAGGCCAT CCAGTATCTG CATTCAATCA ACATTGCCCA TCGGGATGTC
        CACTCCGGTA GGTCATAGAC GTAAGTTAGT TGTAACGGGT AGCCCTACAG
         K   P   E   N   L   L   Y   T   S   K   R   P   N   A   I   L   K  ·
```

```
 751  AAGCCTGAGA ATCTCTTATA CACCTCCAAA AGGCCCAACG CCATCCTGAA
      TTCGGACTCT TAGAGAATAT GTGGAGGTTT TCCGGGTTGC GGTAGGACTT
       · L   T   D   F   G   F   A   K   E   T   T   S   H   N   S   L   T ·
 801  ACTCACTGAC TTTGGCTTTG CCAAGGAAAC CACCAGCCAC AACTCTTTGA
      TGAGTGACTG AAACCGAAAC GGTTCCTTTG GTGGTCGGTG TTGAGAAACT
       · T   P   C   Y   T   P   Y   Y   V   A   P   E   V   L   G   P
 851  CGACTCCTTG TTATACACCG TACTATGTGG CTCCAGAAGT GCTGGGTCCA
      GCTGAGGAAC AATATGTGGC ATGATACACC GAGGTCTTCA CGACCCAGGT
          E   K   Y   D   K   S   C   D   M   W   S   L   G   V   I   M   Y ·
 901  GAGAAGTATG ACAAGTCCTG TGACATGTGG TCCCTGGGTG TCATCATGTA
      CTCTTCATAC TGTTCAGGAC ACTGTACACC AGGGACCCAC AGTAGTACAT
       · I   L   L   C   G   Y   P   P   F   Y   S   N   H   G   L   A   I ·
 951  CATCCTGCTG TGTGGGTATC CCCCCTTCTA CTCCAACCAC GGCCTTGCCA
      GTAGGACGAC ACACCCATAG GGGGGAAGAT GAGGTTGGTG CCGGAACGGT
       · S   P   G   M   K   T   R   I   R   M   G   Q   Y   E   F   P
1001  TCTCTCCGGG CATGAAGACT CGCATCCGAA TGGGCCAGTA TGAATTTCCC
      AGAGAGGCCC GTACTTCTGA GCGTAGGCTT ACCCGGTCAT ACTTAAAGGG
           N   P   E   W   S   E   V   S   E   E   V   K   M   L   I   R   N ·
1051  AACCCAGAAT GGTCAGAAGT ATCAGAGGAA GTGAAGATGC TCATTCGGAA
      TTGGGTCTTA CCAGTCTTCA TAGTCTCCTT CACTTCTACG AGTAAGCCTT
       · L   L   K   T   E   P   T   Q   R   M   T   I   T   E   F   M   N ·
1101  TCTGCTGAAA ACAGAGCCCA CCCAGAGAAT GACCATCACC GAGTTTATGA
      AGACGACTTT TGTCTCGGGT GGGTCTCTTA CTGGTAGTGG CTCAAATACT
       · H   P   W   I   M   Q   S   T   K   V   P   Q   T   P   L   H
1151  ACCACCCTTG GATCATGCAA TCAACAAAGG TCCCTCAAAC CCCACTGCAC
      TGGTGGGAAC CTAGTACGTT AGTTGTTTCC AGGGAGTTTG GGGTGACGTG
           T   S   R   V   L   K   E   D   K   E   R   W   E   D   V   K   E ·
1201  ACCAGCCGGG TCCTGAAGGA GGACAAGGAG CGGTGGGAGG ATGTCAAGGA
      TGGTCGGCCC AGGACTTCCT CCTGTTCCTC GCCACCCTCC TACAGTTCCT
       · E   M   T   S   A   L   A   T   M   R   V   D   Y   E   Q   I   K ·
1251  GGAGATGACC AGTGCCTTGG CCACAATGCG CGTTGACTAC GAGCAGATCA
      CCTCTACTGG TCACGGAACC GGTGTTACGC GCAACTGATG CTCGTCTAGT

· *
1301  AGTAA
      TCATT
```

Figure 37B

Figure 38A
SUMO β-Gal
β-Gal NCBI Accession# V00296

```
        M   G   H   H    H   H   H    H   G   S    D   S   E    V   N   Q   E  ·
  1   ATGGGTCATC ACCATCATCA TCACGGGTCG GACTCAGAAG TCAATCAAGA
      TACCCAGTAG TGGTAGTAGT AGTGCCCAGC CTGAGTCTTC AGTTAGTTCT
      ·   A   K   P    E   V   K    P   E   V   K    P   E   T    H   I   N   L  ·
 51   AGCTAAGCCA GAGGTCAAGC CAGAAGTCAA GCCTGAGACT CACATCAATT
      TCGATTCGGT CTCCAGTTCG GTCTTCAGTT CGGACTCTGA GTGTAGTTAA
      ·   K   V   S    D   G   S    E   I   F    F   K   I    K   K   T
101   TAAAGGTGTC CGATGGATCT TCAGAGATCT TCTTCAAGAT CAAAAAGACC
      ATTTCCACAG GCTACCTAGA AGTCTCTAGA AGAAGTTCTA GTTTTTCTGG
          T   P   L   R    R   L   M    E   A   F    A   K   R    Q   G   K   E  ·
151   ACTCCTTTAA GAAGGCTGAT GGAAGCGTTC GCTAAAAGAC AGGGTAAGGA
      TGAGGAAATT CTTCCGACTA CCTTCGCAAG CGATTTTCTG TCCCATTCCT
      ·   M   D   S    L   R   F   L    Y   D   G    I   R   I    Q   A   D   Q  ·
201   AATGGACTCC TTAAGATTCT TGTACGACGG TATTAGAATT CAAGCTGATC
      TTACCTGAGG AATTCTAAGA ACATGCTGCC ATAATCTTAA GTTCGACTAG
      ·   T   P   E    D   L   D    M   E   D   N    D   I   I    E   A   H
251   AGACCCCTGA AGATTTGGAC ATGGAGGATA ACGATATTAT TGAGGCTCAC
      TCTGGGGACT TCTAAACCTG TACCTCCTAT TGCTATAATA ACTCCGAGTG
          R   E   Q   I    G   G   M    T   M   I    T   D   S    L   A   V   V  ·
301   CGCGAACAGA TTGGAGGTAT GACCATGATT ACGGATTCAC TGGCCGTCGT
      GCGCTTGTCT AACCTCCATA CTGGTACTAA TGCCTAAGTG ACCGGCAGCA
      ·   L   Q   R    R   D   W    E   N   P   G    V   T   Q    L   N   R   L  ·
351   TTTACAACGT CGTGACTGGG AAAACCCTGG CGTTACCCAA CTTAATCGCC
      AAATGTTGCA GCACTGACCC TTTTGGGACC GCAATGGGTT GAATTAGCGG
      ·   A   A   H    P   P   F    A   S   W   R    N   S   E    A   R
401   TTGCAGCACA TCCCCCTTTC GCCAGCTGGC GTAATAGCGA AGAGGCCCGC
      AACGTCGTGT AGGGGGAAAG CGGTCGACCG CATTATCGCT TCTCCGGGCG
          T   D   R   P    S   Q   Q    L   R   S    L   N   G    E   W   R   F  ·
451   ACCGATCGCC CTTCCCAACA GTTGCGCAGC CTGAATGGCG AATGGCGCTT
      TGGCTAGCGG GAAGGGTTGT CAACGCGTCG GACTTACCGC TTACCGCGAA
      ·   A   W   F    P   A   P   E    A   V   P    E   S   W    L   E   C   D  ·
501   TGCCTGGTTT CCGGCACCAG AAGCGGTGCC GGAAAGCTGG CTGGAGTGCG
      ACGGACCAAA GGCCGTGGTC TTCGCCACGG CCTTTCGACC GACCTCACGC
      ·   L   P   E    A   D   T    V   V   V   P    S   N   W    Q   M   H
551   ATCTTCCTGA GGCCGATACT GTCGTCGTCC CCTCAAACTG GCAGATGCAC
      TAGAAGGACT CCGGCTATGA CAGCAGCAGG GGAGTTTGAC CGTCTACGTG
          G   Y   D   A    P   I   Y    T   N   V    T   Y   P    I   T   V   N  ·
601   GGTTACGATG CGCCCATCTA CACCAACGTA ACCTATCCCA TTACGGTCAA
      CCAATGCTAC GCGGGTAGAT GTGGTTGCAT TGGATAGGGT AATGCCAGTT
      ·   P   P   F    V   P   T    E   N   P   T    G   C   Y    S   L   T   F  ·
651   TCCGCCGTTT GTTCCCACGG AGAATCCGAC GGGTTGTTAC TCGCTCACAT
      AGGCGGCAAA CAAGGGTGCC TCTTAGGCTG CCCAACAATG AGCGAGTGTA
      ·   N   V   D    E   S   W    L   Q   E   G    Q   T   R    I   I   F
701   TTAATGTTGA TGAAAGCTGG CTACAGGAAG GCCAGACGCG AATTATTTTT
      AATTACAACT ACTTTCGACC GATGTCCTTC CGGTCTGCGC TTAATAAAAA
          D   G   V   N    S   A   F    H   L   W    C   N   G    R   W   V   G  ·
751   GATGGCGTTA ACTCGGCGTT TCATCTGTGG TGCAACGGGC GCTGGGTCGG
      CTACCGCAAT TGAGCCGCAA AGTAGACACC ACGTTGCCCG CGACCCAGCC
```

Figure 38B

```
            · Y  G  Q     D  S  R  L     P  S  E     F  D  L     S  A  F  L ·
       801  TTACGGCCAG GACAGTCGTT TGCCGTCTGA ATTTGACCTG AGCGCATTTT
            AATGCCGGTC CTGTCAGCAA ACGGCAGACT TAAACTGGAC TCGCGTAAAA
            ·  R  A  G     E  N  R     L  A  V  M     V  L  R     W  S  D
       851  TACGCGCCGG AGAAAACCGC CTCGCGGTGA TGGTGCTGCG TTGGAGTGAC
            ATGCGCGGCC TCTTTTGGCG GAGCGCCACT ACCACGACGC AACCTCACTG
              G  S  Y  L     E  D  Q     D  M  W     R  M  S     I  F  R ·
       901  GGCAGTTATC TGGAAGATCA GGATATGTGG CGGATGAGCG GCATTTTCCG
            CCGTCAATAG ACCTTCTAGT CCTATACACC GCCTACTCGC CGTAAAAGGC
            · D  V  S     L  L  H  K     P  T  T     Q  I  S     D  F  H  V ·
       951  TGACGTCTCG TTGCTGCATA AACCGACTAC ACAAATCAGC GATTTCCATG
            ACTGCAGAGC AACGACGTAT TTGGCTGATG TGTTTAGTCG CTAAAGGTAC
            ·  A  T  R     F  N  D     D  F  S  R     A  V  L     E  A  E
      1001  TTGCCACTCG CTTTAATGAT GATTTCAGCC GCGCTGTACT GGAGGCTGAA
            AACGGTGAGC GAAATTACTA CTAAAGTCGG CGCGACATGA CCTCCGACTT
              V  Q  M     C  G  E  L     R  D  Y     L  R  V  T     V  S  L ·
      1051  GTTCAGATGT GCGGCGAGTT GCGTGACTAC CTACGGGTAA CAGTTTCTTT
            CAAGTCTACA CGCCGCTCAA CGCACTGATG GATGCCCATT GTCAAAGAAA
            · W  Q  G     E  T  Q  V     A  S  G     T  A  P     F  G  G  E ·
      1101  ATGGCAGGGT GAAACGCAGG TCGCCAGCGG CACCGCGCCT TTCGGCGGTG
            TACCGTCCCA CTTTGCGTCC AGCGGTCGCC GTGGCGCGGA AAGCCGCCAC
            ·  I  I  D     E  R  G     G  Y  A  D     R  V  T     L  R  L
      1151  AAATTATCGA TGAGCGTGGT GGTTATGCCG ATCGCGTCAC ACTACGTCTG
            TTTAATAGCT ACTCGCACCA CCAATACGGC TAGCGCAGTG TGATGCAGAC
              N  V  E  N     P  K  L     W  S  A     E  I  P  N     L  Y  R ·
      1201  AACGTCGAAA ACCCGAAACT GTGGAGCGCC GAAATCCCGA ATCTCTATCG
            TTGCAGCTTT TGGGCTTTGA CACCTCGCGG CTTTAGGGCT TAGAGATAGC
            · A  V  V     E  L  H  T     A  D  G     T  L  I     E  A  E  A ·
      1251  TGCGGTGGTT GAACTGCACA CCGCCGACGG CACGCTGATT GAAGCAGAAG
            ACGCCACCAA CTTGACGTGT GGCGGCTGCC GTGCGACTAA CTTCGTCTTC
            ·  C  D  V     G  F  R     E  V  R  I     E  N  G     L  L  L
      1301  CCTGCGATGT CGGTTTCCGC GAGGTGCGGA TTGAAAATGG TCTGCTGCTG
            GGACGCTACA GCCAAAGGCG CTCCACGCCT AACTTTTACC AGACGACGAC
              L  N  G  K     P  L  L     I  R  G     V  N  R  H     E  H  H ·
      1351  CTGAACGGCA AGCCGTTGCT GATTCGAGGC GTTAACCGTC ACGAGCATCA
            GACTTGCCGT TCGGCAACGA CTAAGCTCCG CAATTGGCAG TGCTCGTAGT
            · P  L  H     G  Q  V  M     D  E  Q     T  M  V     Q  D  I  L ·
      1401  TCCTCTGCAT GGTCAGGTCA TGGATGAGCA GACGATGGTG CAGGATATCC
            AGGAGACGTA CCAGTCCAGT ACCTACTCGT CTGCTACCAC GTCCTATAGG
            ·  L  M  K     Q  N  N     F  N  A  V     R  C  S     H  Y  P
      1451  TGCTGATGAA GCAGAACAAC TTTAACGCCG TGCGCTGTTC GCATTATCCG
            ACGACTACTT CGTCTTGTTG AAATTGCGGC ACGCGACAAG CGTAATAGGC
              N  H  P  L     W  Y  T     L  C  D     R  Y  G  L     Y  V  V ·
      1501  AACCATCCGC TGTGGTACAC GCTGTGCGAC CGCTACGGCC TGTATGTGGT
            TTGGTAGGCG ACACCATGTG CGACACGCTG GCGATGCCGG ACATACACCA
            · D  E  A     N  I  E  T     H  G  M     V  P  M     N  R  L  T ·
      1551  GGATGAAGCC AATATTGAAA CCCACGGCAT GGTGCCAATG AATCGTCTGA
            CCTACTTCGG TTATAACTTT GGGTGCCGTA CCACGGTTAC TTAGCAGACT

·  D  D  P     R  W  L     P  A  M  S     E  R  V     T  R  M
      1601  CCGATGATCC GCGCTGGCTA CCGGCGATGA GCGAACGCGT AACGCGAATG
            GGCTACTAGG CGCGACCGAT GGCCGCTACT CGCTTGCGCA TTGCGCTTAC
```

Figure 38C

```
         V  Q  R  D  R  N  H  P  S  V     I  I  W  S  L  G  N  ·
1651  GTGCAGCGCG ATCGTAATCA CCCGAGTGTG ATCATCTGGT CGCTGGGGAA
      CACGTCGCGC TAGCATTAGT GGGCTCACAC TAGTAGACCA GCGACCCCTT
      ·  E  S  G  H  G  A  N  H  D  A  L  Y  R  W  I  K  S  ·
1701  TGAATCAGGC CACGGCGCTA ATCACGACGC GCTGTATCGC TGGATCAAAT
      ACTTAGTCCG GTGCCGCGAT TAGTGCTGCG CGACATAGCG ACCTAGTTTA
      ·  V  D  P  S  R  P  V  Q  Y  E  G  G  A  D  T
1751  CTGTCGATCC TTCCCGCCCG GTGCAGTATG AAGGCGGCGG AGCCGACACC
      GACAGCTAGG AAGGGCGGGC CACGTCATAC TTCCGCCGCC TCGGCTGTGG
         T  A  T  D  I  I  C  P  M  Y  A  R  V  D  E  D  Q  ·
1801  ACGGCCACCG ATATTATTTG CCCGATGTAC GCGCGCGTGG ATGAAGACCA
      TGCCGGTGGC TATAATAAAC GGGCTACATG CGCGCGCACC TACTTCTGGT
      ·  P  F  P  A  V  P  K  W  S  I  K  K  W  L  S  L  P  ·
1851  GCCCTTCCCG GCTGTGCCGA ATGGTCCAT CAAAAAATGG CTTTCGCTAC
      CGGGAAGGGC CGACACGGCT TTACCAGGTA GTTTTTTACC GAAAGCGATG
      ·  G  E  T  R  P  L  I  L  C  E  Y  A  H  A  M  G
1901  CTGGAGAGAC GCGCCCGCTG ATCCTTTGCG AATACGCCCA CGCGATGGGT
      GACCTCTCTG CGCGGGCGAC TAGGAAACGC TTATGCGGGT GCGCTACCCA
         N  S  L  G  G  F  A  K  Y  W  Q  A  F  R  Q  Y  P  ·
1951  AACAGTCTTG GCGGTTTCGC TAAATACTGG CAGGCGTTTC GTCAGTATCC
      TTGTCAGAAC CGCCAAAGCG ATTTATGACC GTCCGCAAAG CAGTCATAGG
      ·  R  L  Q  G  G  F  V  W  D  W  V  D  Q  S  L  I  K  ·
2001  CCGTTTACAG GGCGGCTTCG TCTGGGACTG GGTGGATCAG TCGCTGATTA
      GGCAAATGTC CCGCCGAAGC AGACCCTGAC CCACCTAGTC AGCGACTAAT
      ·  Y  D  E  N  G  N  P  W  S  A  Y  G  G  D  F  G
2051  AATATGATGA AAACGGCAAC CCGTGGTCGG CTTACGGCGG TGATTTTGGC
      TTATACTACT TTTGCCGTTG GGCACCAGCC GAATGCCGCC ACTAAAACCG
         D  T  P  N  D  R  Q  F  C  M  N  G  L  V  F  A  D  ·
2101  GATACGCCGA ACGATCGCCA GTTCTGTATG AACGGTCTGG TCTTTGCCGA
      CTATGCGGCT TGCTAGCGGT CAAGACATAC TTGCCAGACC AGAAACGGCT
      ·  R  T  P  H  P  A  L  T  E  A  K  H  Q  Q  F  F  ·
2151  CCGCACGCCG CATCCAGCGC TGACGGAAGC AAAACACCAG CAGCAGTTTT
      GGCGTGCGGC GTAGGTCGCG ACTGCCTTCG TTTTGTGGTC GTCGTCAAAA
      ·  Q  F  R  L  S  G  Q  T  I  E  V  T  S  E  Y  L
2201  TCCAGTTCCG TTTATCCGGG CAAACCATCG AAGTGACCAG CGAATACCTG
      AGGTCAAGGC AAATAGGCCC GTTTGGTAGC TTCACTGGTC GCTTATGGAC
         F  R  H  S  D  N  E  L  L  H  W  M  V  A  L  D  G  ·
2251  TTCCGTCATA GCGATAACGA GCTCCTGCAC TGGATGGTGG CGCTGGATGG
      AAGGCAGTAT CGCTATTGCT CGAGGACGTG ACCTACCACC GCGACCTACC
      ·  K  P  L  A  S  G  E  V  P  L  D  V  A  P  Q  G  K  ·
2301  TAAGCCGCTG GCAAGCGGTG AAGTGCCTCT GGATGTCGCT CCACAAGGTA
      ATTCGGCGAC CGTTCGCCAC TTCACGGAGA CCTACAGCGA GGTGTTCCAT
      ·  Q  L  I  E  L  P  E  L  P  Q  P  E  S  A  G  Q
2351  AACAGTTGAT TGAACTGCCT GAACTACCGC AGCCGGAGAG CGCCGGGCAA
      TTGTCAACTA ACTTGACGGA CTTGATGGCG TCGGCCTCTC GCGGCCCGTT
         L  W  L  T  V  R  V  V  Q  P  N  A  T  W  S  E  ·
2401  CTCTGGCTCA CAGTACGCGT AGTGCAACCG AACGCGACCG CATGGTCAGA
      GAGACCGAGT GTCATGCGCA TCACGTTGGC TTGCGCTGGC GTACCAGTCT
      ·  A  G  H  I  S  A  W  Q  Q  W  R  L  A  E  N  L  S  ·
2451  AGCCGGGCAC ATCAGCGCCT GGCAGCAGTG GCGTCTGGCG GAAAACCTCA
      TCGGCCCGTG TAGTCGCGGA CCGTCGTCAC CGCAGACCGC CTTTTGGAGT
```

Figure 38D

```
        V  T  L  P  A  A  S  H  A  T  P  H  L  T  T  S
2501  GTGTGACGCT CCCCGCCGCG TCCCACGCCA TCCCGCATCT GACCACCAGC
      CACACTGCGA GGGGCGGCGC AGGGTGCGGT AGGGCGTAGA CTGGTGGTCG
         E  M  D  F  C  I  E  L  G  N  K  R  W  Q  F  N  R
2551  GAAATGGATT TTTGCATCGA GCTGGGTAAT AAGCGTTGGC AATTTAACCG
      CTTTACCTAA AAACGTAGCT CGACCCATTA TTCGCAACCG TTAAATTGGC
         Q  S  G  F  L  S  Q  M  W  I  G  D  K  Q  L  L
2601  CCAGTCAGGC TTTCTTTCAC AGATGTGGAT TGGCGATAAA AAACAACTGC
      GGTCAGTCCG AAAGAAAGTG TCTACACCTA ACCGCTATTT TTTGTTGACG
         T  P  L  R  D  Q  F  T  R  A  P  L  D  N  D  I
2651  TGACGCCGCT GCGCGATCAG TTCACCCGTG CACCGCTGGA TAACGACATT
      ACTGCGGCGA CGCGCTAGTC AAGTGGGCAC GTGGCGACCT ATTGCTGTAA
         G  V  S  E  A  T  R  I  D  P  N  A  W  V  E  R  W
2701  GGCGTAAGTG AAGCGACCCG CATTGACCCT AACGCCTGGG TCGAACGCTG
      CCGCATTCAC TTCGCTGGGC GTAACTGGGA TTGCGGACCC AGCTTGCGAC
         K  A  A  G  H  Y  Q  A  E  A  A  L  L  Q  C  T  A
2751  GAAGGCGGCG GGCCATTACC AGGCCGAAGC AGCGTTGTTG CAGTGCACGG
      CTTCCGCCGC CCGGTAATGG TCCGGCTTCG TCGCAACAAC GTCACGTGCC
         D  T  L  A  D  A  V  L  I  T  T  A  H  A  W  Q
2801  CAGATACACT TGCTGATGCG GTGCTGATTA CGACCGCTCA CGCGTGGCAG
      GTCTATGTGA ACGACTACGC CACGACTAAT GCTGGCGAGT GCGCACCGTC
         H  Q  G  K  T  L  F  I  S  R  K  T  Y  R  I  D  G
2851  CATCAGGGGA AAACCTTATT TATCAGCCGG AAAACCTACC GGATTGATGG
      GTAGTCCCCT TTTGGAATAA ATAGTCGGCC TTTTGGATGG CCTAACTACC
         S  G  Q  M  A  I  T  V  D  V  E  V  A  S  D  T  P
2901  TAGTGGTCAA ATGGCGATTA CCGTTGATGT TGAAGTGGCG AGCGATACAC
      ATCACCAGTT TACCGCTAAT GGCAACTACA ACTTCACCGC TCGCTATGTG
         H  P  A  R  I  G  L  N  C  Q  L  A  Q  V  A  E
2951  CGCATCCGGC GCGGATTGGC CTGAACTGCC AGCTGGCGCA GGTAGCAGAG
      GCGTAGGCCG CGCCTAACCG GACTTGACGG TCGACCGCGT CCATCGTCTC
         R  V  N  W  L  G  L  G  P  Q  E  N  Y  P  D  R  L
3001  CGGGTAAACT GGCTCGGATT AGGGCCGCAA GAAAACTATC CCGACCGCCT
      GCCCATTTGA CCGAGCCTAA TCCCGGCGTT CTTTTGATAG GGCTGGCGGA
         T  A  A  C  F  D  R  W  D  L  P  L  S  D  M  Y  I
3051  TACTGCCGCC TGTTTTGACC GCTGGGATCT GCCATTGTCA GACATGTATA
      ATGACGGCGG ACAAAACTGG CGACCCTAGA CGGTAACAGT CTGTACATAT
         P  Y  V  F  P  S  E  N  G  L  R  C  G  T  R  E
3101  CCCCGTACGT CTTCCCGAGC GAAAACGGTC TGCGCTGCGG GACGCGCGAA
      GGGGCATGCA GAAGGGCTCG CTTTTGCCAG ACGCGACGCC CTGCGCGCTT
         L  N  Y  G  P  H  Q  W  R  G  D  F  Q  F  N  I  S
3151  TTGAATTATG GCCCACACCA GTGGCGCGGC GACTTCCAGT TCAACATCAG
      AACTTAATAC CGGGTGTGGT CACCGCGCCG CTGAAGGTCA AGTTGTAGTC
         R  Y  S  Q  Q  L  M  E  T  S  H  R  H  L  L  H
3201  CCGCTACAGT CAACAGCAAC TGATGGAAAC CAGCCATCGC CATCTGCTGC
      GGCGATGTCA GTTGTCGTTG ACTACCTTTG GTCGGTAGCG GTAGACGACG
         A  E  E  G  T  W  L  N  I  D  G  F  H  M  G  I
3251  ACGCGGAAGA AGGCACATGG CTGAATATCG ACGGTTTCCA TATGGGGATT
      TGCGCCTTCT TCCGTGTACC GACTTATAGC TGCCAAAGGT ATACCCCTAA

G  G  D  D  S  W  S  P  S  V  S  A  E  F  Q  L  S
3301  GGTGGCGACG ACTCCTGGAG CCCGTCAGTA TCGGCGGAAT TCCAGCTGAG
      CCACCGCTGC TGAGGACCTC GGGCAGTCAT AGCCGCCTTA AGGTCGACTC
```

```
         · A   G   R    Y   H   Y   Q    L   V   W    C   Q   K    *   *
3351  CGCCGGTCGC TACCATTACC AGTTGGTCTG GTGTCAAAAA TAATAA
      GCGGCCAGCG ATGGTAATGG TCAACCAGAC CACAGTTTTT ATTATT
```

```
   1 CGCCTTGTTA CTAGTTAGAA AAAGACATTT TTGCTGTCAG TCACTGTCAA
     GCGGAACAAT GATCAATCTT TTTCTGTAAA AACGACAGTC AGTGACAGTT
  51 GAGATTCTTT TGCTGGCATT TCTTCTAGAA GCAAAAAGAG CGATGCGTCT
     CTCTAAGAAA ACGACCGTAA AGAAGATCTT CGTTTTCTC GCTACGCAGA
 101 TTTCCGCTGA ACCGTTCAG CAAAAAGAC TACCAACGCA ATATGGATTG
     AAAGGCGACT TGGCAAGGTC GTTTTTCTG ATGGTTGCGT TATACCTAAC
 151 TCAGAATCAT ATAAAGAGA AGCAAATAAC TCCTTGTCTT GTATCAATTG
     AGTCTTAGTA TATTTTCTCT TCGTTTATTG AGGAACAGAA CATAGTTAAC
 201 CATTATAATA TCTTCTTGTT AGTGCAATAT CATATAGAAG TCATCGAAAT
     GTAATATTAT AGAAGAACAA TCACGTTATA GTATATCTTC AGTAGCTTTA
                                                NcoI
                                                ~~~~~~~
 251 AGATATTAAG AAAAACAAAC TGTACAATCC ATGGGTCATC ACCATCATCA
     TCTATAATTC TTTTTGTTTG ACATGTTAGG TACCCAGTAG TGGTAGTAGT
 301 TCACGGGTCG GACTCAGAAG TCAATCAAGA AGCTAAGCCA GAGGTCAAGC
     AGTGCCCAGC CTGAGTCTTC AGTTAGTTCT TCGATTCGGT CTCCAGTTCG
 351 CAGAAGTCAA GCCTGAGACT CACATCAATT TAAAGGTGTC CGATGGATCT
     GTCTTCAGTT CGGACTCTGA GTGTAGTTAA ATTTCCACAG GCTACCTAGA
 401 TCAGAGATCT TCTTCAAGAT CAAAAAGACC ACTCCTTTAA GAAGGCTGAT
     AGTCTCTAGA AGAAGTTCTA GTTTTTCTGG TGAGGAAATT CTTCCGACTA
 451 GGAAGCGTTC GCTAAAAGAC AGGGTAAGGA AATGGACTCC TTAAGATTCT
     CCTTCGCAAG CGATTTTCTG TCCCATTCCT TTACCTGAGG AATTCTAAGA
 501 TGTACGACGG TATTAGAATT CAAGCTGATC AGACCCCTGA AGATTTGGAC
     ACATGCTGCC ATAATCTTAA GTTCGACTAG TCTGGGGACT TCTAAACCTG
 551 ATGGAGGATA ACGATATTAT TGAGGCTCAC CGCGAACAGA TTGGAGGTAT
     TACCTCCTAT TGCTATAATA ACTCCGAGTG GCGCTTGTCT AACCTCCATA
 601 GGTGAGCAAG GGCGAGGAGC TGTTCACCGG GGTGGTGCCC ATCCTGGTCG
     CCACTCGTTC CCGCTCCTCG ACAAGTGGCC CCACCACGGG TAGGACCAGC
 651 AGCTGGACGG CGACGTAAAC GGCCACAAGT TCAGCGTGTC CGGCGAGGGC
     TCGACCTGCC GCTGCATTTG CCGGTGTTCA AGTCGCACAG GCCGCTCCCG
 701 GAGGGCGATG CCACCTACGG CAAGCTGACC CTGAAGTTCA TCTGCACCAC
     CTCCCGCTAC GGTGGATGCC GTTCGACTGG GACTTCAAGT AGACGTGGTG
 751 CGGCAAGCTG CCCGTGCCCT GGCCCACCCT CGTGACCACC CTGACCTACG
     GCCGTTCGAC GGGCACGGGA CCGGGTGGGA GCACTGGTGG GACTGGATGC
 801 GCGTGCAGTG CTTCAGCCGC TACCCCGACC ACATGAAGCA GCACGACTTC
     CGCACGTCAC GAAGTCGGCG ATGGGGCTGG TGTACTTCGT CGTGCTGAAG
 851 TTCAAGTCCG CCATGCCCGA AGGCTACGTC CAGGAGCGCA CCATCTTCTT
     AAGTTCAGGC GGTACGGGCT TCCGATGCAG GTCCTCGCGT GGTAGAAGAA
 901 CAAGGACGAC GGCAACTACA AGACCCGCGC CGAGGTGAAG TTCGAGGGCG
     GTTCCTGCTG CCGTTGATGT TCTGGGCGCG GCTCCACTTC AAGCTCCCGC
 951 ACACCCTGGT GAACCGCATC GAGCTGAAGG GCATCGACTT CAAGGAGGAC
     TGTGGGACCA CTTGGCGTAG CTCGACTTCC CGTAGCTGAA GTTCCTCCTG
1001 GGCAACATCC TGGGGCACAA GCTGGAGTAC AACTACAACA GCCACAACGT
     CCGTTGTAGG ACCCCGTGTT CGACCTCATG TTGATGTTGT CGGTGTTGCA
1051 CTATATCATG GCCGACAAGC AGAAGAACGG CATCAAGGTG AACTTCAAGA
     GATATAGTAC CGGCTGTTCG TCTTCTTGCC GTAGTTCCAC TTGAAGTTCT
1101 TCCGCCACAA CATCGAGGAC GGCAGCGTGC AGCTCGCCGA CCACTACCAG
     AGGCGGTGTT GTAGCTCCTG CCGTCGCACG TCGAGCGGCT GGTGATGGTC
1151 CAGAACACCC CCATCGGCGA CGGCCCCGTG CTGCTGCCCG ACAACCACTA
     GTCTTGTGGG GGTAGCCGCT GCCGGGGCAC GACGACGGGC TGTTGGTGAT
```

Figure 40B

```
1201  CCTGAGCACC CAGTCCGCCC TGAGCAAAGA CCCCAACGAG AAGCGCGATC
      GGACTCGTGG GTCAGGCGGG ACTCGTTTCT GGGGTTGCTC TTCGCGCTAG
1251  ACATGGTCCT GCTGGAGTTC GTGACCGCCG CCGGGATCAC TCTCGGCATG
      TGTACCAGGA CGACCTCAAG CACTGGCGGC GGCCCTAGTG AGAGCCGTAC
                                                  XhoI
                                                  ~~~~~~~
1301  GACGAGCTGT ACAAGTAATA AGCTTGCGGC CGCACTCGAG GAGCTCCCTG
      CTGCTCGACA TGTTCATTAT TCGAACGCCG GCGTGAGCTC CTCGAGGGAC
1351  GCGAATTGTA CCAAGATGGC CTTTGGTGGG TTGAAGAAGG AAAAAGACAG
      CGCTTAACAT GGTTCTACCG GAAACCACCC AACTTCTTCC TTTTTCTGTC
1401  AAACGACTTA ATTACCTACT TGAAAAAAGC CTGTGAGTAA ACAGGCCCCT
      TTTGCTGAAT TAATGGATGA ACTTTTTTCG GACACTCATT TGTCCGGGGA
1451  TTTCCTTTGT CGATATCATG TAATTAGTTA TGTCACGCTT ACATTCACGC
      AAAGGAAACA GCTATAGTAC ATTAATCAAT ACAGTGCGAA TGTAAGTGCG
1501  CCTCCCCCCA CATCCGCTCT AACCGAAAAG GAAGGAGTTA GACAACCTGA
      GGAGGGGGGT GTAGGCGAGA TTGGCTTTTC CTTCCTCAAT CTGTTGGACT
1551  AGTCTAGGTC CCTATTTATT TTTTTATAGT TATGTTAGTA TTAAGAACGT
      TCAGATCCAG GGATAAATAA AAAATATCA ATACAATCAT AATTCTTGCA
1601  TATTTATATT TCAAATTTTT CTTTTTTTTC TGTACAGACG CGTGTACGCA
      ATAAATATAA AGTTTAAAAA GAAAAAAAG ACATGTCTGC GCACATGCGT
1651  TGTAACATTA TACTGAAAAC CTTGCTTGAG AAGGTTTTGG GACGCTCGAA
      ACATTGTAAT ATGACTTTTG GAACGAACTC TTCCAAAACC CTGCGAGCTT
1701  GGCTTTAATT TGCAAGCTTA TCGATGATAA GCTGTCAAAC ATGAGAATTC
      CCGAAATTAA ACGTTCGAAT AGCTACTATT CGACAGTTTG TACTCTTAAG
1751  GGTCGAAAAA AGAAAAGGAG AGGGCCAAGA GGGAGGGCAT TGGTGACTAT
      CCAGCTTTTT TCTTTTCCTC TCCCGGTTCT CCCTCCCGTA ACCACTGATA
1801  TGAGCACGTG AGTATACGTG ATTAAGCACA CAAAGGCAGC TTGGAGTATG
      ACTCGTGCAC TCATATGCAC TAATTCGTGT GTTTCCGTCG AACCTCATAC
1851  TCTGTTATTA ATTTCACAGG TAGTTCTGGT CCATTGGTGA AAGTTTGCGG
      AGACAATAAT TAAAGTGTCC ATCAAGACCA GGTAACCACT TTCAAACGCC
1901  CTTGCAGAGC ACAGAGGCCG CAGAATGTGC TCTAGATTCC GATGCTGACT
      GAACGTCTCG TGTCTCCGGC GTCTTACACG AGATCTAAGG CTACGACTGA
1951  TGCTGGGTAT TATATGTGTG CCCAATAGAA AGAGAACAAT TGACCCGGTT
      ACGACCCATA ATATACACAC GGGTTATCTT TCTCTTGTTA ACTGGGCCAA
2001  ATTGCAAGGA AAATTTCAAG TCTTGTAAAA GCATATAAAA ATAGTTCAGG
      TAACGTTCCT TTTAAAGTTC AGAACATTTT CGTATATTTT TATCAAGTCC
2051  CACTCCGAAA TACTTGGTTG GCGTGTTTCG TAATCAACCT AAGGAGGATG
      GTGAGGCTTT ATGAACCAAC CGCACAAAGC ATTAGTTGGA TTCCTCCTAC
2101  TTTTGGCTCT GGTCAATGAT TACGGCATTG ATATCGTCCA ACTGCATGGA
      AAAACCGAGA CCAGTTACTA ATGCCGTAAC TATAGCAGGT TGACGTACCT
2151  GATGAGTCGT GGCAAGAATA CCAAGAGTTC CTCGGTTTGC CAGTTATTAA
      CTACTCAGCA CCGTTCTTAT GGTTCTCAAG GAGCCAAACG GTCAATAATT
2201  AAGACTCGTA TTTCCAAAAG ACTGCAACAT ACTACTCAGT GCAGCTTCAC
      TTCTGAGCAT AAAGGTTTTC TGACGTTGTA TGATGAGTCA CGTCGAAGTG
2251  AGAAACCTCA TTCGTTTATT CCCTTGTTTG ATTCAGAAGC AGGTGGGACA
      TCTTTGGAGT AAGCAAATAA GGGAACAAAC TAAGTCTTCG TCCACCCTGT
2301  GGTGAACTTT TGGATTGGAA CTCGATTTCT GACTGGGTTG GAAGGCAAGA
      CCACTTGAAA ACCTAACCTT GAGCTAAAGA CTGACCCAAC CTTCCGTTCT
2351  GAGCCCCGAA AGCTTACATT TTATGTTAGC TGGTGGACTG ACGCCAGAAA
      CTCGGGGCTT TCGAATGTAA AATACAATCG ACCACCTGAC TGCGGTCTTT
2401  ATGTTGGTGA TGCGCTTAGA TTAAATGGCG TTATTGGTGT TGATGTAAGC
```

Figure 40C

```
           TACAACCACT ACGCGAATCT AATTTACCGC AATAACCACA ACTACATTCG
2451  GGAGGTGTGG AGACAAATGG TGTAAAAGAC TCTAACAAAA TAGCAAATTT
      CCTCCACACC TCTGTTTACC ACATTTTCTG AGATTGTTTT ATCGTTTAAA
2501  CGTCAAAAAT GCTAAGAAAT AGGTTATTAC TGAGTAGTAT TTATTTAAGT
      GCAGTTTTTA CGATTCTTTA TCCAATAATG ACTCATCATA AATAAATTCA
2551  ATTGTTTGTG CACTTGCCTG CAGCTTCTCA ATGATATTCG AATACGCTTT
      TAACAAACAC GTGAACGGAC GTCAAGAGT TACTATAAGC TTATGCGAAA
2601  GAGGAGATAC AGCCTAATAT CCGACAAACT GTTTTACAGA TTTACGATCG
      CTCCTCTATG TCGGATTATA GGCTGTTTGA CAAAATGTCT AAATGCTAGC
2651  TACTTGTTAC CCATCATTGA ATTTTGAACA TCCGAACCTG GGAGTTTTCC
      ATGAACAATG GGTAGTAACT TAAAACTTGT AGGCTTGGAC CCTCAAAAGG
2701  CTGAAACAGA TAGTATATTT GAACCTGTAT AATAATATAT AGTCTAGCGC
      GACTTTGTCT ATCATATAAA CTTGGACATA TTATTATATA TCAGATCGCG
2751  TTTACGGAAG ACAATGTATG TATTTCGGTT CCTGGAGAAA CTATTGCATC
      AAATGCCTTC TGTTACATAC ATAAAGCCAA GGACCTCTTT GATAACGTAG
2801  TATTGCATAG GTAATCTTGC ACGTCGCATC CCCGGTTCAT TTTCTGCGTT
      ATAACGTATC CATTAGAACG TGCAGCGTAG GGGCCAAGTA AAAGACGCAA
2851  TCCATCTTGC ACTTCAATAG CATATCTTTG TTAACGAAGC ATCTGTGCTT
      AGGTAGAACG TGAAGTTATC GTATAGAAAC AATTGCTTCG TAGACACGAA
2901  CATTTTGTAG AACAAAAATG CAACGCGAGA GCGCTAATTT TCAAACAAA
      GTAAAACATC TTGTTTTTAC GTTGCGCTCT CGCGATTAAA AAGTTTGTTT
2951  GAATCTGAGC TGCATTTTTA CAGAACAGAA ATGCAACGCG AAAGCGCTAT
      CTTAGACTCG ACGTAAAAAT GTCTTGTCTT TACGTTGCGC TTTCGCGATA
3001  TTTACCAACG AAGAATCTGT GCTTCATTTT TGTAAAACAA AAATGCAACG
      AAATGGTTGC TTCTTAGACA CGAAGTAAAA ACATTTTGTT TTTACGTTGC
3051  CGAGAGCGCT AATTTTTCAA ACAAAGAATC TGAGCTGCAT TTTTACAGAA
      GCTCTCGCGA TTAAAAAGTT TGTTTCTTAG ACTCGACGTA AAAATGTCTT
3101  CAGAAATGCA ACGCGAGAGC GCTATTTTAC CAACAAAGAA TCTATACTTC
      GTCTTTACGT TGCGCTCTCG CGATAAAATG GTTGTTTCTT AGATATGAAG
3151  TTTTTTGTTC TACAAAAATG CATCCCGAGA GCGCTATTTT TCTAACAAAG
      AAAAAACAAG ATGTTTTTAC GTAGGGCTCT CGCGATAAAA AGATTGTTTC
3201  CATCTTAGAT TACTTTTTTT CTCCTTTGTG CGCTCTATAA TGCAGTCTCT
      GTAGAATCTA ATGAAAAAAA GAGGAAACAC GCGAGATATT ACGTCAGAGA
3251  TGATAACTTT TTGCACTGTA GGTCCGTTAA GGTTAGAAGA AGGCTACTTT
      ACTATTGAAA AACGTGACAT CCAGGCAATT CCAATCTTCT TCCGATGAAA
3301  GGTGTCTATT TTCTCTTCCA TAAAAAAAGC CTGACTCCAC TTCCCGCGTT
      CCACAGATAA AAGAGAAGGT ATTTTTTTCG GACTGAGGTG AAGGGCGCAA
3351  TACTGATTAC TAGCGAAGCT GCGGGTGCAT TTTTCAAGA TAAAGGCATC
      ATGACTAATG ATCGCTTCGA CGCCCACGTA AAAAGTTCT ATTTCCGTAG
3401  CCCGATTATA TTCTATACCG ATGTGGATTG CGCATACTTT GTGAACAGAA
      GGGCTAATAT AAGATATGGC TACACCTAAC GCGTATGAAA CACTTGTCTT
3451  AGTGATAGCG TTGATGATTC TTCATTGGTC AGAAAATTAT GAACGGTTTC
      TCACTATCGC AACTACTAAG AAGTAACCAG TCTTTTAATA CTTGCCAAAG
3501  TTCTATTTTG TCTCTATATA CTACGTATAG GAAATGTTTA CATTTTCGTA
      AAGATAAAAC AGAGATATAT GATGCATATC CTTTACAAAT GTAAAAGCAT
3551  TTGTTTTCGA TTCACTCTAT GAATAGTTCT TACTACAATT TTTTTGTCTA
      AACAAAAGCT AAGTGAGATA CTTATCAAGA ATGATGTTAA AAAAACAGAT
3601  AAGAGTAATA CTAGAGATAA ACATAAAAAA TGTAGAGGTC GAGTTTAGAT
      TTCTCATTAT GATCTCTATT TGTATTTTTT ACATCTCCAG CTCAAATCTA
3651  GCAAGTTCAA GGAGCGAAAG GTGGATGGGT AGGTTATATA GGGATATAGC
      CGTTCAAGTT CCTCGCTTTC CACCTACCCA TCCAATATAT CCCTATATCG
```

Figure 40D

```
3701  ACAGAGATAT ATAGCAAAGA GATACTTTTG AGCAATGTTT GTGGAAGCGG
      TGTCTCTATA TATCGTTTCT CTATGAAAAC TCGTTACAAA CACCTTCGCC
3751  TATTCGCAAT ATTTTAGTAG CTCGTTACAG TCCGGTGCGT TTTTGGTTTT
      ATAAGCGTTA TAAAATCATC GAGCAATGTC AGGCCACGCA AAAACCAAAA
3801  TTGAAAGTGC GTCTTCAGAG CGCTTTTGGT TTTCAAAAGC GCTCTGAAGT
      AACTTTCACG CAGAAGTCTC GCGAAAACCA AAAGTTTTCG CGAGACTTCA
3851  TCCTATACTT TCTAGAGAAT AGGAACTTCG GAATAGGAAC TTCAAAGCGT
      AGGATATGAA AGATCTCTTA TCCTTGAAGC CTTATCCTTG AAGTTTCGCA
3901  TTCCGAAAAC GAGCGCTTCC GAAAATGCAA CGCGAGCTGC GCACATACAG
      AAGGCTTTTG CTCGCGAAGG CTTTTACGTT GCGCTCGACG CGTGTATGTC
3951  CTCACTGTTC ACGTCGCACC TATATCTGCG TGTTGCCTGT ATATATATAT
      GAGTGACAAG TGCAGCGTGG ATATAGACGC ACAACGGACA TATATATATA
4001  ACATGAGAAG AACGGCATAG TGCGTGTTTA TGCTTAAATG CGTACTTATA
      TGTACTCTTC TTGCCGTATC ACGCACAAAT ACGAATTTAC GCATGAATAT
4051  TGCGTCTATT TATGTAGGAT GAAAGGTAGT CTAGTACCTC CTGTGATATT
      ACGCAGATAA ATACATCCTA CTTTCCATCA GATCATGGAG GACACTATAA
4101  ATCCCATTCC ATGCGGGTA  TCGTATGCTT CCTTCAGCAC TACCCTTTAG
      TAGGGTAAGG TACGCCCCAT AGCATACGAA GGAAGTCGTG ATGGGAAATC
4151  CTGTTCTATA TGCTGCCACT CCTCAATTGG ATTAGTCTCA TCCTTCAATG
      GACAAGATAT ACGACGGTGA GGAGTTAACC TAATCAGAGT AGGAAGTTAC
4201  CTATCATTTC CTTTGATATT GGATCATATG CATAGTACCG AGAAACTAGT
      GATAGTAAAG GAAACTATAA CCTAGTATAC GTATCATGGC TCTTTGATCA
4251  GCGAAGTAGT GATCAGGTAT TGCTGTTATC TGATGAGTAT ACGTTGTCCT
      CGCTTCATCA CTAGTCCATA ACGACAATAG ACTACTCATA TGCAACAGGA
4301  GGCCACGGCA GAAGCACGCT TATCGCTCCA ATTTCCCACA ACATTAGTCA
      CCGGTGCCGT CTTCGTGCGA ATAGCGAGGT TAAAGGGTGT TGTAATCAGT
4351  ACTCCGTTAG GCCCTTCATT GAAAGAAATG AGGTCATCAA ATGTCTTCCA
      TGAGGCAATC CGGGAAGTAA CTTTCTTTAC TCCAGTAGTT TACAGAAGGT
4401  ATGTGAGATT TTGGGCCATT TTTTATAGCA AAGATTGAAT AAGGCGCATT
      TACACTCTAA AACCCGGTAA AAAATATCGT TTCTAACTTA TTCCGCGTAA
4451  TTTCTTCAAA GCTTTATTGT ACGATCTGAC TAAGTTATCT TTTAATAATT
      AAAGAAGTTT CGAAATAACA TGCTAGACTG ATTCAATAGA AAATTATTAA
4501  GGTATTCCTG TTTATTGCTT GAAGAATTGC CGGTCCTATT TACTCGTTTT
      CCATAAGGAC AAATAACGAA CTTCTTAACG GCCAGGATAA ATGAGCAAAA
4551  AGGACTGGTT CAGAATTCTT GAAGACGAAA GGGCCTCGTG ATACGCCTAT
      TCCTGACCAA GTCTTAAGAA CTTCTGCTTT CCCGGAGCAC TATGCGGATA
4601  TTTTATAGGT TAATGTCATG ATAATAATGG TTTCTTAGAC GTCAGGTGGC
      AAAATATCCA ATTACAGTAC TATTATTACC AAAGAATCTG CAGTCCACCG
4651  ACTTTTCGGG GAAATGTGCG CGGAACCCCT ATTTGTTTAT TTTTCTAAAT
      TGAAAAGCCC CTTTACACGC GCCTTGGGGA TAAACAAATA AAAAGATTTA
4701  ACATTCAAAT ATGTATCCGC TCATGAGACA ATAACCCTGA TAAATGCTTC
      TGTAAGTTTA TACATAGGCG AGTACTCTGT TATTGGGACT ATTTACGAAG
4751  AATAATATTG AAAAAGGAAG AGTATGAGTA TTCAACATTT CCGTGTCGCC
      TTATTATAAC TTTTTCCTTC TCATACTCAT AAGTTGTAAA GGCACAGCGG
4801  CTTATTCCCT TTTTTGCGGC ATTTTGCCTT CCTGTTTTTG CTCACCCAGA
      GAATAAGGGA AAAAACGCCG TAAAACGGAA GGACAAAAAC GAGTGGGTCT
4851  AACGCTGGTG AAAGTAAAAG ATGCTGAAGA TCAGTTGGGT GCACGAGTGG
      TTGCGACCAC TTTCATTTTC TACGACTTCT AGTCAACCCA CGTGCTCACC
4901  GTTACATCGA ACTGGATCTC AACAGCGGTA AGATCCTTGA GAGTTTTCGC
      CAATGTAGCT TGACCTAGAG TTGTCGCCAT TCTAGGAACT CTCAAAAGCG
4951  CCCGAAGAAC GTTTTCCAAT GATGAGCACT TTTAAAGTTC TGCTATGTGG
```

Figure 40E

```
           GGGCTTCTTG CAAAAGGTTA CTACTCGTGA AAATTTCAAG ACGATACACC
5001  CGCGGTATTA TCCCGTGTTG ACGCCGGGCA AGAGCAACTC GGTCGCCGCA
      GCGCCATAAT AGGGCACAAC TGCGGCCCGT TCTCGTTGAG CCAGCGGCGT
5051  TACACTATTC TCAGAATGAC TTGGTTGAGT ACTCACCAGT CACAGAAAAG
      ATGTGATAAG AGTCTTACTG AACCAACTCA TGAGTGGTCA GTGTCTTTTC
5101  CATCTTACGG ATGGCATGAC AGTAAGAGAA TTATGCAGTG CTGCCATAAC
      GTAGAATGCC TACCGTACTG TCATTCTCTT AATACGTCAC GACGGTATTG
5151  CATGAGTGAT AACACTGCGG CCAACTTACT TCTGACAACG ATCGGAGGAC
      GTACTCACTA TTGTGACGCC GGTTGAATGA AGACTGTTGC TAGCCTCCTG
5201  CGAAGGAGCT AACCGCTTTT TTGCACAACA TGGGGGATCA TGTAACTCGC
      GCTTCCTCGA TTGGCGAAAA AACGTGTTGT ACCCCCTAGT ACATTGAGCG
5251  CTTGATCGTT GGGAACCGGA GCTGAATGAA GCCATACCAA ACGACGAGCG
      GAACTAGCAA CCCTTGGCCT CGACTTACTT CGGTATGGTT TGCTGCTCGC
5301  TGACACCACG ATGCCTGCAG CAATGGCAAC AACGTTGCGC AAACTATTAA
      ACTGTGGTGC TACGGACGTC GTTACCGTTG TTGCAACGCG TTTGATAATT
5351  CTGGCGAACT ACTTACTCTA GCTTCCCGGC AACAATTAAT AGACTGGATG
      GACCGCTTGA TGAATGAGAT CGAAGGGCCG TTGTTAATTA TCTGACCTAC
5401  GAGGCGGATA AAGTTGCAGG ACCACTTCTG CGCTCGGCCC TTCCGGCTGG
      CTCCGCCTAT TTCAACGTCC TGGTGAAGAC GCGAGCCGGG AAGGCCGACC
                                                       BsaI
                                                   ~~~~~~~
5451  CTGGTTTATT GCTGATAAAT CTGGAGCCGG TGAGCGTGGG TCTCGCGGTA
      GACCAAATAA CGACTATTTA GACCTCGGCC ACTCGCACCC AGAGCGCCAT
5501  TCATTGCAGC ACTGGGGCCA GATGGTAAGC CCTCCCGTAT CGTAGTTATC
      AGTAACGTCG TGACCCCGGT CTACCATTCG GGAGGGCATA GCATCAATAG
5551  TACACGACGG GGAGTCAGGC AACTATGGAT GAACGAAATA GACAGATCGC
      ATGTGCTGCC CCTCAGTCCG TTGATACCTA CTTGCTTTAT CTGTCTAGCG
5601  TGAGATAGGT GCCTCACTGA TTAAGCATTG GTAACTGTCA GACCAAGTTT
      ACTCTATCCA CGGAGTGACT AATTCGTAAC CATTGACAGT CTGGTTCAAA
5651  ACTCATATAT ACTTTAGATT GATTTAAAAC TTCATTTTTA ATTTAAAAGG
      TGAGTATATA TGAAATCTAA CTAAATTTTG AAGTAAAAAT TAAATTTTCC
5701  ATCTAGGTGA AGATCCTTTT TGATAATCTC ATGACCAAAA TCCCTTAACG
      TAGATCCACT TCTAGGAAAA ACTATTAGAG TACTGGTTTT AGGGAATTGC
5751  TGAGTTTTCG TTCCACTGAG CGTCAGACCC CGTAGAAAAG ATCAAAGGAT
      ACTCAAAAGC AAGGTGACTC GCAGTCTGGG GCATCTTTTC TAGTTTCCTA
5801  CTTCTTGAGA TCCTTTTTTT CTGCGCGTAA TCTGCTGCTT GCAAACAAAA
      GAAGAACTCT AGGAAAAAAA GACGCGCATT AGACGACGAA CGTTTGTTTT
5851  AAACCACCGC TACCAGCGGT GGTTTGTTTG CCGGATCAAG AGCTACCAAC
      TTTGGTGGCG ATGGTCGCCA CCAAACAAAC GGCCTAGTTC TCGATGGTTG
5901  TCTTTTTCCG AAGGTAACTG GCTTCAGCAG AGCGCAGATA CCAAATACTG
      AGAAAAAGGC TTCCATTGAC CGAAGTCGTC TCGCGTCTAT GGTTTATGAC
5951  TCCTTCTAGT GTAGCCGTAG TTAGGCCACC ACTTCAAGAA CTCTGTAGCA
      AGGAAGATCA CATCGGCATC AATCCGGTGG TGAAGTTCTT GAGACATCGT
6001  CCGCCTACAT ACCTCGCTCT GCTAATCCTG TTACCAGTGG CTGCTGCCAG
      GGCGGATGTA TGGAGCGAGA CGATTAGGAC AATGGTCACC GACGACGGTC
6051  TGGCGATAAG TCGTGTCTTA CCGGGTTGGA CTCAAGACGA TAGTTACCGG
      ACCGCTATTC AGCACAGAAT GGCCCAACCT GAGTTCTGCT ATCAATGGCC
6101  ATAAGGCGCA GCGGTCGGGC TGAACGGGGG GTTCGTGCAC ACAGCCCAGC
      TATTCCGCGT CGCCAGCCCG ACTTGCCCCC AAGCACGTG TGTCGGGTCG
6151  TTGGAGCGAA CGACCTACAC CGAACTGAGA TACCTACAGC GTGAGCTATG
      AACCTCGCTT GCTGGATGTG GCTTGACTCT ATGGATGTCG CACTCGATAC
```

Figure 40F

```
6201 AGAAAGCGCC ACGCTTCCCG AAGGGAGAAA GGCGGACAGG TATCCGGTAA
     TCTTTCGCGG TGCGAAGGGC TTCCCTCTTT CCGCCTGTCC ATAGGCCATT
6251 GCGGCAGGGT CGGAACAGGA GAGCGCACGA GGGAGCTTCC AGGGGGAAAC
     CGCCGTCCCA GCCTTGTCCT CTCGCGTGCT CCCTCGAAGG TCCCCCTTTG
6301 GCCTGGTATC TTTATAGTCC TGTCGGGTTT CGCCACCTCT GACTTGAGCG
     CGGACCATAG AAATATCAGG ACAGCCCAAA GCGGTGGAGA CTGAACTCGC
6351 TCGATTTTTG TGATGCTCGT CAGGGGGGCG GAGCCTATGG AAAAACGCCA
     AGCTAAAAAC ACTACGAGCA GTCCCCCGC CTCGGATACC TTTTTGCGGT
6401 GCAACGCGGC CTTTTTACGG TTCCTGGCCT TTTGCTGGCC TTTTGCTCAC
     CGTTGCGCCG GAAAAATGCC AAGGACCGGA AAACGACCGG AAAACGAGTG
6451 ATGTTCTTTC CTGCGTTATC CCCTGATTCT GTGGATAACC GTATTACCGC
     TACAAGAAAG GACGCAATAG GGGACTAAGA CACCTATTGG CATAATGGCG
6501 CTTTGAGTGA GCTGATACCG CTCGCCGCAG CCGAACGACC GAGCGCAGCG
     GAAACTCACT CGACTATGGC GAGCGGCGTC GGCTTGCTGG CTCGCGTCGC
6551 AGTCAGTGAG CGAGGAAGCG GAAGAGCGCC TGATGCGGTA TTTTCTCCTT
     TCAGTCACTC GCTCCTTCGC CTTCTCGCGG ACTACGCCAT AAAAGAGGAA
6601 ACGCATCTGT GCGGTATTTC ACACCGCATA TGGTGCACTC TCAGTACAAT
     TGCGTAGACA CGCCATAAAG TGTGGCGTAT ACCACGTGAG AGTCATGTTA
6651 CTGCTCTGAT GCCGCATAGT TAAGCCAGTA TACACTCCGC TATCGCTACG
     GACGAGACTA CGGCGTATCA ATTCGGTCAT ATGTGAGGCG ATAGCGATGC
6701 TGACTGGGTC ATGGCTGCGC CCGACACCC GCCAACACCC GCTGACGCGC
     ACTGACCCAG TACCGACGCG GGCTGTGGG CGGTTGTGGG CGACTGCGCG
                                                      Esp3I
                                                      ~
6751 CCTGACGGGC TTGTCTGCTC CCGGCATCCG CTTACAGACA AGCTGTGACC
     GGACTGCCCG AACAGACGAG GGCCGTAGGC GAATGTCTGT TCGACACTGG
     Esp3I
     ~~~~~
6801 GTCTCCGGGA GCTGCATGTG TCAGAGGTTT TCACCGTCAT CACCGAAACG
     CAGAGGCCCT CGACGTACAC AGTCTCCAAA AGTGGCAGTA GTGGCTTTGC
6851 CGCGAGGCAG GGATC
     GCGCTCCGTC CCTAG
```

Figure 42A

```
   1    CCTTGTTACT AGTTAGAAAA AGACATTTTT GCTGTCAGTC ACTGTCAAGA
        GGAACAATGA TCAATCTTTT TCTGTAAAAA CGACAGTCAG TGACAGTTCT
  51    GATTCTTTTG CTGGCATTTC TTCTAGAAGC AAAAAGAGCG ATGCGTCTTT
        CTAAGAAAAC GACCGTAAAG AAGATCTTCG TTTTTCTCGC TACGCAGAAA
 101    TCCGCTGAAC CGTTCCAGCA AAAAGACTA CCAACGCAAT ATGGATTGTC
        AGGCGACTTG GCAAGGTCGT TTTTCTGAT GGTTGCGTTA TACCTAACAG
 151    AGAATCATAT AAAAGAGAAG CAAATAACTC CTTGTCTTGT ATCAATTGCA
        TCTTAGTATA TTTTCTCTTC GTTATTGAG GAACAGAACA TAGTTAACGT
 201    TTATAATATC TTCTTGTTAG TGCAATATCA TATAGAAGTC ATCGAAATAG
        AATATTATAG AAGAACAATC ACGTTATAGT ATATCTTCAG TAGCTTTATC
                                                  NcoI
                                                  ~~~~~~~
 251    ATATTAAGAA AAACAAACTG TACAATCCAT GGGTCATCAC CATCATCATC
        TATAATTCTT TTTGTTTGAC ATGTTAGGTA CCCAGTAGTG GTAGTAGTAG
 301    ACGGGCAGAT CTTCGTCAAG ACGTTAACCG GTAAAACCAT AACTCTAGAA
        TGCCCGTCTA GAAGCAGTTC TGCAATTGGC CATTTTGGTA TTGAGATCTT
 351    GTTGAACCAT CCGATACCAT CGAAAACGTT AAGGCTAAAA TTCAAGACAA
        CAACTTGGTA GGCTATGGTA GCTTTTGCAA TTCCGATTTT AAGTTCTGTT
                                                            XhoI
                                                            ~
 401    GGAAGGCATT CCACCTGATC AACAAAGATT GATCTTTGCC GGTAAGCAGC
        CCTTCCGTAA GGTGGACTAG TTGTTTCTAA CTAGAAACGG CCATTCGTCG
        XhoI
        ~~~~~
 451    TCGAGGACGG TAGAACGCTG TCTGATTACA ACATTCAGAA GGAGTCGACC
        AGCTCCTGCC ATCTTGCGAC AGACTAATGT TGTAAGTCTT CCTCAGCTGG
 501    TTACATCTTG TCTTACGCCT ACGTGGAGGT ATGGAATTCA TGTTACGTCC
        AATGTAGAAC AGAATGCGGA TGCACCTCCA TACCTTAAGT ACAATGCAGG
 551    TGTAGAAACC CCAACCCGTG AAATCAAAAA ACTCGACGGC CTGTGGGCAT
        ACATCTTTGG GGTTGGGCAC TTTAGTTTTT TGAGCTGCCG GACACCCGTA
 601    TCAGTCTGGA TCGCGAAAAC TGTGGAATTG ATCAGCGTTG GTGGGAAAGC
        AGTCAGACCT AGCGCTTTTG ACACCTTAAC TAGTCGCAAC CACCCTTTCG
 651    GCGTTACAAG AAAGCCGGGC AATTGCTGTG CCAGGCAGTT TTAACGATCA
        CGCAATGTTC TTTCGGCCCG TTAACGACAC GGTCCGTCAA AATTGCTAGT
 701    GTTCGCCGAT GCAGATATTC GTAATTATGC GGGCAACGTC TGGTATCAGC
        CAAGCGGCTA CGTCTATAAG CATTAATACG CCCGTTGCAG ACCATAGTCG
 751    GCGAAGTCTT TATACCGAAA GGTTGGGCAG GCCAGCGTAT CGTGCTGCGT
        CGCTTCAGAA ATATGGCTTT CCAACCCGTC CGGTCGCATA GCACGACGCA
 801    TTCGATGCGG TCACTCATTA CGGCAAAGTG TGGGTCAATA ATCAGGAAGT
        AAGCTACGCC AGTGAGTAAT GCCGTTTCAC ACCCAGTTAT TAGTCCTTCA
 851    GATGGAGCAT CAGGGCGGCT ATACGCCATT TGAAGCCGAT GTCACGCCGT
        CTACCTCGTA GTCCCGCCGA TATGCGGTAA ACTTCGGCTA CAGTGCGGCA
 901    ATGTTATTGC CGGGAAAAGT GTACGTATCA CCGTTTGTGT GAACAACGAA
        TACAATAACG GCCCTTTTCA CATGCATAGT GGCAAACACA CTTGTTGCTT
 951    CTGAACTGGC AGACTATCCC GCCGGGAATG GTGATTACCG ACGAAACGG
        GACTTGACCG TCTGATAGGG CGGCCCTTAC CACTAATGGC TGCTTTTGCC
1001    CAAGAAAAAG CAGTCTTACT TCCATGATTT CTTTAACTAT GCCGGAATCC
        GTTCTTTTTC GTCAGAATGA AGGTACTAAA GAAATTGATA CGGCCTTAGG
1051    ATCGCAGCGT AATGCTCTAC ACCACGCCGA ACACCTGGGT GGACGATATC
        TAGCGTCGCA TTACGAGATG TGGTGCGGCT TGTGGACCCA CCTGCTATAG
```

Figure 42B

```
1101  ACCGTGGTGA CGCATGTCGC GCAAGACTGT AACCACGCGT CTGTTGACTG
      TGGCACCACT GCGTACAGCG CGTTCTGACA TTGGTGCGCA GACAACTGAC
1151  GCAGGTGGTG GCCAATGGTG ATGTCAGCGT TGAACTGCGT GATGCGGATC
      CGTCCACCAC CGGTTACCAC TACAGTCGCA ACTTGACGCA CTACGCCTAG
1201  AACAGGTGGT TGCAACTGGA CAAGGCACTA GCGGGACTTT GCAAGTGGTG
      TTGTCCACCA ACGTTGACCT GTTCCGTGAT CGCCCTGAAA CGTTCACCAC
1251  AATCCGCACC TCTGGCAACC GGGTGAAGGT TATCTCTATG AACTGTGCGT
      TTAGGCGTGG AGACCGTTGG CCCACTTCCA ATAGAGATAC TTGACACGCA
1301  CACAGCCAAA AGCCAGACAG AGTGTGATAT CTACCCGCTT CGCGTCGGCA
      GTGTCGGTTT TCGGTCTGTC TCACACTATA GATGGGCGAA GCGCAGCCGT
1351  TCCGGTCAGT GGCAGTGAAG GGCCAACAGT TCCTGATTAA CCACAAACCG
      AGGCCAGTCA CCGTCACTTC CCGGTTGTCA AGGACTAATT GGTGTTTGGC
1401  TTCTACTTTA CTGGCTTTGG TCGTCATGAA GATGCGGACT TACGTGGCAA
      AAGATGAAAT GACCGAAACC AGCAGTACTT CTACGCCTGA ATGCACCGTT
1451  AGGATTCGAT AACGTGCTGA TGGTGCACGA CCACGCATTA ATGGACTGGA
      TCCTAAGCTA TTGCACGACT ACCACGTGCT GGTGCGTAAT TACCTGACCT
1501  TTGGGGCCAA CTCCTACCGT ACCTCGCATT ACCCTTACGC TGAAGAGATG
      AACCCCGGTT GAGGATGGCA TGGAGCGTAA TGGGAATGCG ACTTCTCTAC
1551  CTCGACTGGG CAGATGAACA TGGCATCGTG GTGATTGATG AAACTGCTGC
      GAGCTGACCC GTCTACTTGT ACCGTAGCAC CACTAACTAC TTTGACGACG
1601  TGTCGGCTTT AACCTCTCTT TAGGCATTGG TTTCGAAGCG GGCAACAAGC
      ACAGCCGAAA TTGGAGAGAA ATCCGTAACC AAAGCTTCGC CCGTTGTTCG
1651  CGAAAGAACT GTACAGCGAA GAGGCAGTCA ACGGGGAAAC TCAGCAAGCG
      GCTTTCTTGA CATGTCGCTT CTCCGTCAGT TGCCCCTTTG AGTCGTTCGC
1701  CACTTACAGG CGATTAAAGA GCTGATAGCG CGTGACAAAA CCACCCAAG
      GTGAATGTCC GCTAATTTCT CGACTATCGC GCACTGTTTT TGGTGGGTTC
1751  CGTGGTGATG TGGAGTATTG CCAACGAACC GGATACCCGT CCGCAAGTGC
      GCACCACTAC ACCTCATAAC GGTTGCTTGG CCTATGGGCA GGCGTTCACG
1801  ACGGGAATAT TTCGCCACTG GCGGAAGCAA CGCGTAAACT CGACCCGACG
      TGCCCTTATA AAGCGGTGAC CGCCTTCGTT GCGCATTTGA GCTGGGCTGC
1851  CGTCCGATCA CCTGCGTCAA TGTAATGTTC TGCGACGCTC ACACCGATAC
      GCAGGCTAGT GGACGCAGTT ACATTACAAG ACGCTGCGAG TGTGGCTATG
1901  CATCAGCGAT CTCTTTGATG TGCTGTGCCT GAACCGTTAT TACGGATGGT
      GTAGTCGCTA GAGAAACTAC ACGACACGGA CTTGGCAATA ATGCCTACCA
1951  ATGTCCAAAG CGGCGATTTG GAAACGGCAG AGAAGGTACT GGAAAAAGAA
      TACAGGTTTC GCCGCTAAAC CTTTGCCGTC TCTTCCATGA CCTTTTTCTT
2001  CTTCTGGCCT GGCAGGAGAA ACTGCATCAG CCGATTATCA TCACCGAATA
      GAAGACCGGA CCGTCCTCTT TGACGTAGTC GGCTAATAGT AGTGGCTTAT
2051  CGGCGTGGAT ACGTTAGCCG GGCTGCACTC AATGTACACC GACATGTGGA
      GCCGCACCTA TGCAATCGGC CCGACGTGAG TTACATGTGG CTGTACACCT
2101  GTGAAGAGTA TCAGTGTGCA TGGCTGGATA TGTATCACCG GTCTTTGAT
      CACTTCTCAT AGTCACACGT ACCGACCTAT ACATAGTGGC GCAGAAACTA
2151  CGCGTCAGCG CCGTCGTCGG TGAACAGGTA TGGAATTTCG CCGATTTTGC
      GCGCAGTCGC GGCAGCAGCC ACTTGTCCAT ACCTTAAAGC GGCTAAAACG
2201  GACCTCGCAA GGCATATTGC GCGTTGGCGG TAACAAGAAA GGGATCTTCA
      CTGGAGCGTT CCGTATAACG CGCAACCGCC ATTGTTCTTT CCCTAGAAGT
2251  CTCGCGACCG CAAACCGAAG TCGGCGGCTT TTCTGCTGCA AAAACGCTGG
      GAGCGCTGGC GTTTGGCTTC AGCCGCCGAA AAGACGACGT TTTTGCGACC
2301  ACTGGCATGA ACTTCGGTGA AAAACCGCAG CAGGGAGGCA AACAATAAGC
      TGACCGTACT TGAAGCCACT TTTTGGCGTC GTCCCTCCGT TTGTTATTCG
                XhoI
```

Figure 42C

```
2351  TTGCGGCCGC ACTCGAGGAG CTCCCTGGCG AATTGTACCA AGATGGCCTT
      AACGCCGGCG TGAGCTCCTC GAGGGACCGC TTAACATGGT TCTACCGGAA
2401  TGGTGGGTTG AAGAAGGAAA AAGACAGAAA CGACTTAATT ACCTACTTGA
      ACCACCCAAC TTCTTCCTTT TTCTGTCTTT GCTGAATTAA TGGATGAACT
2451  AAAAAGCCTG TGAGTAAACA GGCCCCTTTT CCTTTGTCGA TATCATGTAA
      TTTTTCGGAC ACTCATTTGT CCGGGGAAAA GGAAACAGCT ATAGTACATT
2501  TTAGTTATGT CACGCTTACA TTCACGCCCT CCCCCCACAT CCGCTCTAAC
      AATCAATACA GTGCGAATGT AAGTGCGGGA GGGGGGTGTA GGCGAGATTG
2551  CGAAAAGGAA GGAGTTAGAC AACCTGAAGT CTAGGTCCCT ATTTATTTTT
      GCTTTTCCTT CCTCAATCTG TTGGACTTCA GATCCAGGGA TAAATAAAAA
2601  TTATAGTTAT GTTAGTATTA AGAACGTTAT TTATATTTCA AATTTTTCTT
      AATATCAATA CAATCATAAT TCTTGCAATA AATATAAAGT TTAAAAAGAA
2651  TTTTTTCTGT ACAGACGCGT GTACGCATGT AACATTATAC TGAAAACCTT
      AAAAAAGACA TGTCTGCGCA CATGCGTACA TTGTAATATG ACTTTTGGAA
2701  GCTTGAGAAG GTTTGGGAC GCTCGAAGGC TTTAATTTGC AAGCTTATCG
      CGAACTCTTC CAAAACCCTG CGAGCTTCCG AAATTAAACG TTCGAATAGC
2751  ATGATAAGCT GTCAAACATG AGAATTCGGT CGAAAAAGA AAAGGAGAGG
      TACTATTCGA CAGTTTGTAC TCTTAAGCCA GCTTTTTTCT TTTCCTCTCC
2801  GCCAAGAGGG AGGGCATTGG TGACTATTGA GCACGTGAGT ATACGTGATT
      CGGTTCTCCC TCCCGTAACC ACTGATAACT CGTGCACTCA TATGCACTAA
2851  AAGCACACAA AGGCAGCTTG GAGTATGTCT GTTATTAATT TCACAGGTAG
      TTCGTGTGTT TCCGTCGAAC CTCATACAGA CAATAATTAA AGTGTCCATC
2901  TTCTGGTCCA TTGGTGAAAG TTTGCGGCTT GCAGAGCACA GAGGCCGCAG
      AAGACCAGGT AACCACTTTC AAACGCCGAA CGTCTCGTGT CTCCGGCGTC
2951  AATGTGCTCT AGATTCCGAT GCTGACTTGC TGGGTATTAT ATGTGTGCCC
      TTACACGAGA TCTAAGGCTA CGACTGAACG ACCCATAATA TACACACGGG
3001  AATAGAAAGA GAACAATTGA CCCGGTTATT GCAAGGAAAA TTTCAAGTCT
      TTATCTTTCT CTTGTTAACT GGGCCAATAA CGTTCCTTTT AAAGTTCAGA
3051  TGTAAAAGCA TATAAAATA GTTCAGGCAC TCCGAAATAC TTGGTTGGCG
      ACATTTTCGT ATATTTTAT CAAGTCCGTG AGGCTTTATG AACCAACCGC
3101  TGTTTCGTAA TCAACCTAAG GAGGATGTTT TGGCTCTGGT CAATGATTAC
      ACAAAGCATT AGTTGGATTC CTCCTACAAA ACCGAGACCA GTTACTAATG
3151  GGCATTGATA TCGTCCAACT GCATGGAGAT GAGTCGTGGC AAGAATACCA
      CCGTAACTAT AGCAGGTTGA CGTACCTCTA CTCAGCACCG TTCTTATGGT
3201  AGAGTTCCTC GGTTTGCCAG TTATTAAAAG ACTCGTATTT CCAAAAGACT
      TCTCAAGGAG CCAAACGGTC AATAATTTTC TGAGCATAAA GGTTTTCTGA
3251  GCAACATACT ACTCAGTGCA GCTTCACAGA AACCTCATTC GTTTATTCCC
      CGTTGTATGA TGAGTCACGT CGAAGTGTCT TTGGAGTAAG CAAATAAGGG
3301  TTGTTTGATT CAGAAGCAGG TGGACAGGT GAACTTTTGG ATTGGAACTC
      ACAAACTAA GTCTTCGTCC ACCCTGTCCA CTTGAAACC TAACCTTGAG
3351  GATTTCTGAC TGGGTTGGAA GGCAAGAGAG CCCCGAAAGC TTACATTTTA
      CTAAAGACTG ACCCAACCTT CCGTTCTCTC GGGGCTTTCG AATGTAAAAT
3401  TGTTAGCTGG TGGACTGACG CCAGAAAATG TTGGTGATGC GCTTAGATTA
      ACAATCGACC ACCTGACTGC GGTCTTTTAC AACCACTACG CGAATCTAAT
3451  AATGGCGTTA TTGGTGTTGA TGTAAGCGGA GGTGTGGAGA CAAATGGTGT
      TTACCGCAAT AACCACAACT ACATTCGCCT CCACACCTCT GTTTACCACA
3501  AAAAGACTCT AACAAAATAG CAAATTTCGT CAAAAATGCT AAGAAATAGG
      TTTTCTGAGA TTGTTTTATC GTTTAAAGCA GTTTTTACGA TTCTTTATCC
3551  TTATTACTGA GTAGTATTTA TTAAGTATT GTTTGTGCAC TTGCCTGCAG
      AATAATGACT CATCATAAAT AAATTCATAA CAAACACGTG AACGGACGTC
```

Figure 42D

```
3601  CTTCTCAATG ATATTCGAAT ACGCTTTGAG GAGATACAGC CTAATATCCG
      GAAGAGTTAC TATAAGCTTA TGCGAAACTC CTCTATGTCG GATTATAGGC
3651  ACAAACTGTT TTACAGATTT ACGATCGTAC TTGTTACCCA TCATTGAATT
      TGTTTGACAA AATGTCTAAA TGCTAGCATG AACAATGGGT AGTAACTTAA
3701  TTGAACATCC GAACCTGGGA GTTTTCCCTG AAACAGATAG TATATTTGAA
      AACTTGTAGG CTTGGACCCT CAAAAGGGAC TTTGTCTATC ATATAAACTT
3751  CCTGTATAAT AATATATAGT CTAGCGCTTT ACGGAAGACA ATGTATGTAT
      GGACATATTA TTATATATCA GATCGCGAAA TGCCTTCTGT TACATACATA
3801  TTCGGTTCCT GGAGAAACTA TTGCATCTAT TGCATAGGTA ATCTTGCACG
      AAGCCAAGGA CCTCTTTGAT AACGTAGATA ACGTATCCAT TAGAACGTGC
3851  TCGCATCCCC GGTTCATTTT CTGCGTTTCC ATCTTGCACT TCAATAGCAT
      AGCGTAGGGG CCAAGTAAAA GACGCAAAGG TAGAACGTGA AGTTATCGTA
3901  ATCTTTGTTA ACGAAGCATC TGTGCTTCAT TTTGTAGAAC AAAAATGCAA
      TAGAAACAAT TGCTTCGTAG ACACGAAGTA AAACATCTTG TTTTTACGTT
3951  CGCGAGAGCG CTAATTTTTC AAACAAAGAA TCTGAGCTGC ATTTTTACAG
      GCGCTCTCGC GATTAAAAAG TTTGTTTCTT AGACTCGACG TAAAAATGTC
4001  AACAGAAATG CAACGCGAAA GCGCTATTTT ACCAACGAAG AATCTGTGCT
      TTGTCTTTAC GTTGCGCTTT CGCGATAAAA TGGTTGCTTC TTAGACACGA
4051  TCATTTTTGT AAAACAAAAA TGCAACGCGA GAGCGCTAAT TTTTCAAACA
      AGTAAAAACA TTTTGTTTTT ACGTTGCGCT CTCGCGATTA AAAAGTTTGT
4101  AAGAATCTGA GCTGCATTTT TACAGAACAG AAATGCAACG CGAGAGCGCT
      TTCTTAGACT CGACGTAAAA ATGTCTTGTC TTTACGTTGC GCTCTCGCGA
4151  ATTTTACCAA CAAAGAATCT ATACTTCTTT TTGTTCTAC AAAAATGCAT
      TAAAATGGTT GTTTCTTAGA TATGAAGAAA AACAAGATG TTTTTACGTA
4201  CCCGAGAGCG CTATTTTTCT AACAAAGCAT CTTAGATTAC TTTTTTTCTC
      GGGCTCTCGC GATAAAAAGA TTGTTTCGTA GAATCTAATG AAAAAAAGAG
4251  CTTTGTGCGC TCTATAATGC AGTCTCTTGA TAACTTTTTG CACTGTAGGT
      GAAACACGCG AGATATTACG TCAGAGAACT ATTGAAAAAC GTGACATCCA
4301  CCGTTAAGGT TAGAAGAAGG CTACTTTGGT GTCTATTTTC TCTTCCATAA
      GGCAATTCCA ATCTTCTTCC GATGAAACCA CAGATAAAAG AGAAGGTATT
4351  AAAAAGCCTG ACTCCACTTC CCGCGTTTAC TGATTACTAG CGAAGCTGCG
      TTTTTCGGAC TGAGGTGAAG GGCGCAAATG ACTAATGATC GCTTCGACGC
4401  GGTGCATTTT TTCAAGATAA AGGCATCCCC GATTATATTC TATACCGATG
      CCACGTAAAA AAGTTCTATT TCCGTAGGGG CTAATATAAG ATATGGCTAC
4451  TGGATTGCGC ATACTTTGTG AACAGAAAGT GATAGCGTTG ATGATTCTTC
      ACCTAACGCG TATGAAACAC TTGTCTTTCA CTATCGCAAC TACTAAGAAG
4501  ATTGGTCAGA AAATTATGAA CGGTTTCTTC TATTTTGTCT CTATATACTA
      TAACCAGTCT TTTAATACTT GCCAAAGAAG ATAAAACAGA GATATATGAT
4551  CGTATAGGAA ATGTTTACAT TTTCGTATTG TTTTCGATTC ACTCTATGAA
      GCATATCCTT TACAAATGTA AAAGCATAAC AAAAGCTAAG TGAGATACTT
4601  TAGTTCTTAC TACAATTTTT TTGTCTAAAG AGTAATACTA GAGATAAACA
      ATCAAGAATG ATGTTAAAAA AACAGATTTC TCATTATGAT CTCTATTTGT
4651  TAAAAAATGT AGAGGTCGAG TTTAGATGCA AGTTCAAGGA GCGAAAGGTG
      ATTTTTTACA TCTCCAGCTC AAATCTACGT TCAAGTTCCT CGCTTTCCAC
4701  GATGGGTAGG TTATATAGGG ATATAGCACA GAGATATATA GCAAAGAGAT
      CTACCCATCC AATATATCCC TATATCGTGT CTCTATATAT CGTTTCTCTA
4751  ACTTTTGAGC AATGTTTGTG GAAGCGGTAT TCGCAATATT TTAGTAGCTC
      TGAAAACTCG TTACAAACAC CTTCGCCATA AGCGTTATAA AATCATCGAG
4801  GTTACAGTCC GGTGCGTTTT TGGTTTTTTG AAAGTGCGTC TTCAGAGCGC
      CAATGTCAGG CCACGCAAAA ACCAAAAAAC TTTCACGCAG AAGTCTCGCG
4851  TTTTGGTTTT CAAAAGCGCT CTGAAGTTCC TATACTTTCT AGAGAATAGG
```

Figure 42E

```
          AAAACCAAAA GTTTTCGCGA GACTTCAAGG ATATGAAAGA TCTCTTATCC
    4901  AACTTCGGAA TAGGAACTTC AAAGCGTTTC CGAAAACGAG CGCTTCCGAA
          TTGAAGCCTT ATCCTTGAAG TTTCGCAAAG GCTTTTGCTC GCGAAGGCTT
    4951  AATGCAACGC GAGCTGCGCA CATACAGCTC ACTGTTCACG TCGCACCTAT
          TTACGTTGCG CTCGACGCGT GTATGTCGAG TGACAAGTGC AGCGTGGATA
    5001  ATCTGCGTGT TGCCTGTATA TATATATACA TGAGAAGAAC GGCATAGTGC
          TAGACGCACA ACGGACATAT ATATATATGT ACTCTTCTTG CCGTATCACG
    5051  GTGTTTATGC TTAAATGCGT ACTTATATGC GTCTATTTAT GTAGGATGAA
          CACAAATACG AATTTACGCA TGAATATACG CAGATAAATA CATCCTACTT
    5101  AGGTAGTCTA GTACCTCCTG TGATATTATC CCATTCCATG CGGGGTATCG
          TCCATCAGAT CATGGAGGAC ACTATAATAG GGTAAGGTAC GCCCCATAGC
    5151  TATGCTTCCT TCAGCACTAC CCTTTAGCTG TTCTATATGC TGCCACTCCT
          ATACGAAGGA AGTCGTGATG GGAAATCGAC AAGATATACG ACGGTGAGGA
    5201  CAATTGGATT AGTCTCATCC TTCAATGCTA TCATTTCCTT TGATATTGGA
          GTTAACCTAA TCAGAGTAGG AAGTTACGAT AGTAAAGGAA ACTATAACCT
    5251  TCATATGCAT AGTACCGAGA AACTAGTGCG AAGTAGTGAT CAGGTATTGC
          AGTATACGTA TCATGGCTCT TTGATCACGC TTCATCACTA GTCCATAACG
    5301  TGTTATCTGA TGAGTATACG TTGTCCTGGC CACGGCAGAA GCACGCTTAT
          ACAATAGACT ACTCATATGC AACAGGACCG GTGCCGTCTT CGTGCGAATA
    5351  CGCTCCAATT TCCCACAACA TTAGTCAACT CCGTTAGGCC CTTCATTGAA
          GCGAGGTTAA AGGGTGTTGT AATCAGTTGA GGCAATCCGG GAAGTAACTT
    5401  AGAAATGAGG TCATCAAATG TCTTCCAATG TGAGATTTTG GGCCATTTTT
          TCTTTACTCC AGTAGTTTAC AGAAGGTTAC ACTCTAAAAC CCGGTAAAAA
    5451  TATAGCAAAG ATTGAATAAG GCGCATTTTT CTTCAAAGCT TTATTGTACG
          ATATCGTTTC TAACTTATTC CGCGTAAAAA GAAGTTTCGA ATAACATGC
    5501  ATCTGACTAA GTTATCTTTT AATAATTGGT ATTCCTGTTT ATTGCTTGAA
          TAGACTGATT CAATAGAAAA TTATTAACCA TAAGGACAAA TAACGAACTT
    5551  GAATTGCCGG TCCTATTTAC TCGTTTTAGG ACTGGTTCAG AATTCTTGAA
          CTTAACGGCC AGGATAAATG AGCAAAATCC TGACCAAGTC TTAAGAACTT
    5601  GACGAAAGGG CCTCGTGATA CGCCTATTTT TATAGGTTAA TGTCATGATA
          CTGCTTTCCC GGAGCACTAT GCGGATAAAA ATATCCAATT ACAGTACTAT
    5651  ATAATGGTTT CTTAGACGTC AGGTGGCACT TTTCGGGGAA ATGTGCGCGG
          TATTACCAAA GAATCTGCAG TCCACCGTGA AAAGCCCCTT TACACGCGCC
    5701  AACCCCTATT TGTTTATTTT CTAAATACA TTCAAATATG TATCCGCTCA
          TTGGGGATAA ACAAATAAAA AGATTTATGT AAGTTTATAC ATAGGCGAGT
    5751  TGAGACAATA ACCCTGATAA ATGCTTCAAT AATATTGAAA AAGGAAGAGT
          ACTCTGTTAT TGGGACTATT TACGAAGTTA TTATAACTTT TTCCTTCTCA
    5801  ATGAGTATTC AACATTTCCG TGTCGCCCTT ATTCCCTTTT TTGCGGCATT
          TACTCATAAG TTGTAAAGGC ACAGCGGGAA TAAGGGAAAA AACGCCGTAA
    5851  TTGCCTTCCT GTTTTTGCTC ACCCAGAAAC GCTGGTGAAA GTAAAAGATG
          AACGGAAGGA CAAAAACGAG TGGGTCTTTG CGACCACTTT CATTTTCTAC
    5901  CTGAAGATCA GTTGGGTGCA CGAGTGGGTT ACATCGAACT GGATCTCAAC
          GACTTCTAGT CAACCCACGT GCTCACCCAA TGTAGCTTGA CCTAGAGTTG
    5951  AGCGGTAAGA TCCTTGAGAG TTTTCGCCCC GAAGAACGTT TTCCAATGAT
          TCGCCATTCT AGGAACTCTC AAAAGCGGGG CTTCTTGCAA AAGGTTACTA
    6001  GAGCACTTTT AAAGTTCTGC TATGTGGCGC GGTATTATCC CGTGTTGACG
          CTCGTGAAAA TTTCAAGACG ATACACCGCG CCATAATAGG CACAACTGC
    6051  CCGGGCAAGA GCAACTCGGT CGCCGCATAC ACTATTCTCA GAATGACTTG
          GGCCCGTTCT CGTTGAGCCA GCGGCGTATG TGATAAGAGT CTTACTGAAC
    6101  GTTGAGTACT CACCAGTCAC AGAAAAGCAT CTTACGGATG GCATGACAGT
          CAACTCATGA GTGGTCAGTG TCTTTTCGTA GAATGCCTAC CGTACTGTCA
```

Figure 42F

```
6151  AAGAGAATTA TGCAGTGCTG CCATAACCAT GAGTGATAAC ACTGCGGCCA
      TTCTCTTAAT ACGTCACGAC GGTATTGGTA CTCACTATTG TGACGCCGGT
6201  ACTTACTTCT GACAACGATC GGAGGACCGA AGGAGCTAAC CGCTTTTTTG
      TGAATGAAGA CTGTTGCTAG CCTCCTGGCT TCCTCGATTG GCGAAAAAAC
6251  CACAACATGG GGGATCATGT AACTCGCCTT GATCGTTGGG AACCGGAGCT
      GTGTTGTACC CCCTAGTACA TTGAGCGGAA CTAGCAACCC TTGGCCTCGA
6301  GAATGAAGCC ATACCAAACG ACGAGCGTGA CACCACGATG CCTGCAGCAA
      CTTACTTCGG TATGGTTTGC TGCTCGCACT GTGGTGCTAC GGACGTCGTT
6351  TGGCAACAAC GTTGCGCAAA CTATTAACTG GCGAACTACT TACTCTAGCT
      ACCGTTGTTG CAACGCGTTT GATAATTGAC CGCTTGATGA ATGAGATCGA
6401  TCCCGGCAAC AATTAATAGA CTGGATGGAG GCGGATAAAG TTGCAGGACC
      AGGGCCGTTG TTAATTATCT GACCTACCTC CGCCTATTTC AACGTCCTGG
6451  ACTTCTGCGC TCGGCCCTTC CGGCTGGCTG GTTATTGCT GATAAATCTG
      TGAAGACGCG AGCCGGGAAG GCCGACCGAC CAAATAACGA CTATTTAGAC
                      BsaI
                      ~~~~~~~
6501  GAGCCGGTGA GCGTGGGTCT CGCGGTATCA TTGCAGCACT GGGGCCAGAT
      CTCGGCCACT CGCACCCAGA GCGCCATAGT AACGTCGTGA CCCCGGTCTA
6551  GGTAAGCCCT CCCGTATCGT AGTTATCTAC ACGACGGGGA GTCAGGCAAC
      CCATTCGGGA GGGCATAGCA TCAATAGATG TGCTGCCCCT CAGTCCGTTG
6601  TATGGATGAA CGAAATAGAC AGATCGCTGA GATAGGTGCC TCACTGATTA
      ATACCTACTT GCTTTATCTG TCTAGCGACT CTATCCACGG AGTGACTAAT
6651  AGCATTGGTA ACTGTCAGAC CAAGTTTACT CATATATACT TTAGATTGAT
      TCGTAACCAT TGACAGTCTG GTTCAAATGA GTATATATGA AATCTAACTA
6701  TTAAAACTTC ATTTTTAATT TAAAAGGATC TAGGTGAAGA TCCTTTTTGA
      AATTTTGAAG TAAAAATTAA ATTTTCCTAG ATCCACTTCT AGGAAAAACT
6751  TAATCTCATG ACCAAAATCC CTTAACGTGA GTTTTCGTTC CACTGAGCGT
      ATTAGAGTAC TGGTTTTAGG GAATTGCACT CAAAAGCAAG GTGACTCGCA
6801  CAGACCCCGT AGAAAAGATC AAAGGATCTT CTTGAGATCC TTTTTTTCTG
      GTCTGGGGCA TCTTTTCTAG TTTCCTAGAA GAACTCTAGG AAAAAAAGAC
6851  CGCGTAATCT GCTGCTTGCA AACAAAAAAA CCACCGCTAC CAGCGGTGGT
      GCGCATTAGA CGACGAACGT TTGTTTTTTT GGTGGCGATG GTCGCCACCA
6901  TTGTTTGCCG GATCAAGAGC TACCAACTCT TTTTCCGAAG GTAACTGGCT
      AACAAACGGC CTAGTTCTCG ATGGTTGAGA AAAAGGCTTC CATTGACCGA
6951  TCAGCAGAGC GCAGATACCA AATACTGTCC TTCTAGTGTA GCCGTAGTTA
      AGTCGTCTCG CGTCTATGGT TTATGACAGG AAGATCACAT CGGCATCAAT
7001  GGCCACCACT TCAAGAACTC TGTAGCACCG CCTACATACC TCGCTCTGCT
      CCGGTGGTGA AGTTCTTGAG ACATCGTGGC GGATGTATGG AGCGAGACGA
7051  AATCCTGTTA CCAGTGGCTG CTGCCAGTGG CGATAAGTCG TGTCTTACCG
      TTAGGACAAT GGTCACCGAC GACGGTCACC GCTATTCAGC ACAGAATGGC
7101  GGTTGGACTC AAGACGATAG TTACCGGATA AGGCGCAGCG GTCGGGCTGA
      CCAACCTGAG TTCTGCTATC AATGGCCTAT TCCGCGTCGC CAGCCCGACT
7151  ACGGGGGGTT CGTGCACACA GCCCAGCTTG GAGCGAACGA CCTACACCGA
      TGCCCCCCAA GCACGTGTGT CGGGTCGAAC CTCGCTTGCT GGATGTGGCT
7201  ACTGAGATAC CTACAGCGTG AGCTATGAGA AAGCGCCACG CTTCCCGAAG
      TGACTCTATG GATGTCGCAC TCGATACTCT TTCGCGGTGC GAAGGGCTTC
7251  GGAGAAAGGC GGACAGGTAT CCGGTAAGCG GCAGGGTCGG AACAGGAGAG
      CCTCTTTCCG CCTGTCCATA GGCCATTCGC CGTCCCAGCC TTGTCCTCTC
7301  CGCACGAGGG AGCTTCCAGG GGGAAACGCC TGGTATCTTT ATAGTCCTGT
      GCGTGCTCCC TCGAAGGTCC CCCTTTGCGG ACCATAGAAA TATCAGGACA
7351  CGGGTTTCGC CACCTCTGAC TTGAGCGTCG ATTTTTGTGA TGCTCGTCAG
```

Figure 42G

```
         GCCCAAAGCG GTGGAGACTG AACTCGCAGC TAAAAACACT ACGAGCAGTC
7401     GGGGGCGGAG CCTATGGAAA AACGCCAGCA ACGCGGCCTT TTTACGGTTC
         CCCCCGCCTC GGATACCTTT TTGCGGTCGT TGCGCCGGAA AAATGCCAAG
7451     CTGGCCTTTT GCTGGCCTTT TGCTCACATG TTCTTTCCTG CGTTATCCCC
         GACCGGAAAA CGACCGGAAA ACGAGTGTAC AAGAAAGGAC GCAATAGGGG
7501     TGATTCTGTG GATAACCGTA TTACCGCCTT TGAGTGAGCT GATACCGCTC
         ACTAAGACAC CTATTGGCAT AATGGCGGAA ACTCACTCGA CTATGGCGAG
7551     GCCGCAGCCG AACGACCGAG CGCAGCGAGT CAGTGAGCGA GGAAGCGGAA
         CGGCGTCGGC TTGCTGGCTC GCGTCGCTCA GTCACTCGCT CCTTCGCCTT
7601     GAGCGCCTGA TGCGGTATTT TCTCCTTACG CATCTGTGCG GTATTTCACA
         CTCGCGGACT ACGCCATAAA AGAGGAATGC GTAGACACGC CATAAAGTGT
7651     CCGCATATGG TGCACTCTCA GTACAATCTG CTCTGATGCC GCATAGTTAA
         GGCGTATACC ACGTGAGAGT CATGTTAGAC GAGACTACGG CGTATCAATT
7701     GCCAGTATAC ACTCCGCTAT CGCTACGTGA CTGGGTCATG GCTGCGCCCC
         CGGTCATATG TGAGGCGATA GCGATGCACT GACCCAGTAC CGACGCGGGG
7751     GACACCCGCC AACACCCGCT GACGCGCCCT GACGGGCTTG TCTGCTCCCG
         CTGTGGGCGG TTGTGGGCGA CTGCGCGGGA CTGCCCGAAC AGACGAGGGC
                                                  Esp3I
                                           --------
7801     GCATCCGCTT ACAGACAAGC TGTGACCGTC TCCGGGAGCT GCATGTGTCA
         CGTAGGCGAA TGTCTGTTCG ACACTGGCAG AGGCCCTCGA CGTACACAGT
7851     GAGGTTTTCA CCGTCATCAC CGAAACGCGC GAGGCAGGGA TCCG
         CTCCAAAAGT GGCAGTAGTG GCTTTGCGCG CTCCGTCCCT AGGC
```

Figure 44A

```
   1 ATCATGGAGA TAATTAAAAT GATAACCATC TCGCAAATAA ATAAGTATTT
     TAGTACCTCT ATTAATTTTA CTATTGGTAG AGCGTTTATT TATTCATAAA
  51 TACTGTTTTC GTAACAGTTT TGTAATAAAA AAACCTATAA ATATTCCGGA
     ATGACAAAAG CATTGTCAAA ACATTATTTT TTTGGATATT TATAAGGCCT
 101 TTATTCATAC CGTCCCACCA TCGGGCGCGA TGGGTCATCA CCATCATCAT
     AATAAGTATG GCAGGGTGGT AGCCCGCGCT ACCCAGTAGT GGTAGTAGTA
 151 CACGGGTCGG ACTCAGAAGT CAATCAAGAA GCTAAGCCAG AGGTCAAGCC
     GTGCCCAGCC TGAGTCTTCA GTTAGTTCTT CGATTCGGTC TCCAGTTCGG
 201 AGAAGTCAAG CCTGAGACTC ACATCAATTT AAAGGTGTCC GATGGATCTT
     TCTTCAGTTC GGACTCTGAG TGTAGTTAAA TTTCCACAGG CTACCTAGAA
 251 CAGAGATCTT CTTCAAGATC AAAAAGACCA CTCCTTTAAG AAGGCTGATG
     GTCTCTAGAA GAAGTTCTAG TTTTTCTGGT GAGGAAATTC TTCCGACTAC
 301 GAAGCGTTCG CTAAAAGACA GGGTAAGGAA ATGGACTCCT TAAGATTCTT
     CTTCGCAAGC GATTTTCTGT CCCATTCCTT TACCTGAGGA ATTCTAAGAA
 351 GTACGACGGT ATTAGAATTC AAGCTGATCA GACCCCTGAA GATTTGGACA
     CATGCTGCCA TAATCTTAAG TTCGACTAGT CTGGGGACTT CTAAACCTGT
 401 TGGAGGATAA CGATATTATT GAGGCTCACC GCAACAGAT  TGGAGGTATG
     ACCTCCTATT GCTATAATAA CTCGAGTGG  CGCTTGTCTA ACCTCCATAC
 451 GTGAGCAAGG GCGAGGAGCT GTTCACCGGG GTGGTGCCCA TCCTGGTCGA
     CACTCGTTCC CGCTCCTCGA CAAGTGGCCC CACCACGGGT AGGACCAGCT
 501 GCTGGACGGC GACGTAAACG GCCACAAGTT CAGCGTGTCC GGCGAGGGCG
     CGACCTGCCG CTGCATTTGC CGGTGTTCAA GTCGCACAGG CCGCTCCCGC
 551 AGGGCGATGC CACCTACGGC AAGCTGACCC TGAAGTTCAT CTGCACCACC
     TCCCGCTACG GTGGATGCCG TTCGACTGGG ACTTCAAGTA GACGTGGTGG
 601 GGCAAGCTGC CCGTGCCCTG GCCCACCCTC GTGACCACCC TGACCTACGG
     CCGTTCGACG GGCACGGGAC CGGGTGGGAG CACTGGTGGG ACTGGATGCC
 651 CGTGCAGTGC TTCAGCCGCT ACCCCGACCA CATGAAGCAG CACGACTTCT
     GCACGTCACG AAGTCGGCGA TGGGGCTGGT GTACTTCGTC GTGCTGAAGA
 701 TCAAGTCCGC CATGCCCGAA GGCTACGTCC AGGAGCGCAC CATCTTCTTC
     AGTTCAGGCG GTACGGGCTT CCGATGCAGG TCCTCGCGTG GTAGAAGAAG
 751 AAGGACGACG GCAACTACAA GACCCGCGCC GAGGTGAAGT TCGAGGGCGA
     TTCCTGCTGC CGTTGATGTT CTGGGCGCGG CTCCACTTCA AGCTCCCGCT
 801 CACCCTGGTG AACCGCATCG AGCTGAAGGG CATCGACTTC AAGGAGGACG
     GTGGGACCAC TTGGCGTAGC TCGACTTCCC GTAGCTGAAG TTCCTCCTGC
 851 GCAACATCCT GGGGCACAAG CTGGAGTACA ACTACAACAG CCACAACGTC
     CGTTGTAGGA CCCCGTGTTC GACCTCATGT TGATGTTGTC GGTGTTGCAG
 901 TATATCATGG CCGACAAGCA GAAGAACGGC ATCAAGGTGA ACTTCAAGAT
     ATATAGTACC GGCTGTTCGT CTTCTTGCCG TAGTTCCACT TGAAGTTCTA
 951 CCGCCACAAC ATCGAGGACG GCAGCGTGCA GCTCGCCGAC CACTACCAGC
     GGCGGTGTTG TAGCTCCTGC CGTCGCACGT CGAGCGGCTG GTGATGGTCG
1001 AGAACACCCC CATCGGCGAC GGCCCCGTGC TGCTGCCCGA CAACCACTAC
     TCTTGTGGGG GTAGCCGCTG CCGGGGCACG ACGACGGGCT GTTGGTGATG
1051 CTGAGCACCC AGTCCGCCCT GAGCAAAGAC CCCAACGAGA AGCGCGATCA
     GACTCGTGGG TCAGGCGGGA CTCGTTTCTG GGGTTGCTCT TCGCGCTAGT
1101 CATGGTCCTG CTGGAGTTCG TGACCGCCGC CGGGATCACT CTCGGCATGG
     GTACCAGGAC GACCTCAAGC ACTGGCGGCG GCCCTAGTGA GAGCCGTACC
                              Esp3I
                           ~~~~~~~
1151 ACGAGCTGTA CAAGTAATGA GACGGAATTC AAAGGCCTAC GTCGACGAGC
     TGCTCGACAT GTTCATTACT CTGCCTTAAG TTTCCGGATG CAGCTGCTCG
```

Figure 44B

```
                      XbaI              XhoI
                    ~~~~~~~          ~~~~~~~
1201  TCACTAGTCG CGGCCGCTTT CGAATCTAGA GCCTGCAGTC TCGAGGCATG
      AGTGATCAGC GCCGGCGAAA GCTTAGATCT CGGACGTCAG AGCTCCGTAC
                 HindIII
                 ~~~~~~~
1251  CGGTACCAAG CTTGTCGAGA AGTACTAGAG GATCATAATC AGCCATACCA
      GCCATGGTTC GAACAGCTCT TCATGATCTC CTAGTATTAG TCGGTATGGT
1301  CATTTGTAGA GGTTTTACTT GCTTTAAAAA ACCTCCACA CCTCCCCCTG
      GTAAACATCT CCAAAATGAA CGAAATTTTT TGGAGGGTGT GGAGGGGGAC
1351  AACCTGAAAC ATAAAATGAA TGCAATTGTT GTTGTTAACT TGTTTATTGC
      TTGGACTTTG TATTTTACTT ACGTTAACAA CAACAATTGA ACAAATAACG
1401  AGCTTATAAT GGTTACAAAT AAAGCAATAG CATCACAAAT TTCACAAATA
      TCGAATATTA CCAATGTTTA TTTCGTTATC GTAGTGTTTA AAGTGTTTAT
1451  AAGCATTTTT TTCACTGCAT TCTAGTTGTG GTTTGTCCAA ACTCATCAAT
      TTCGTAAAAA AAGTGACGTA AGATCAACAC CAAACAGGTT TGAGTAGTTA
1501  GTATCTTATC ATGTCTGGAT CTGATCACTG CTTGAGCCTA GGAGATCCGA
      CATAGAATAG TACAGACCTA GACTAGTGAC GAACTCGGAT CCTCTAGGCT
1551  ACCAGATAAG TGAAATCTAG TTCCAAACTA TTTTGTCATT TTTAATTTTC
      TGGTCTATTC ACTTTAGATC AAGGTTTGAT AAAACAGTAA AAATTAAAAG
1601  GTATTAGCTT ACGACGCTAC ACCCAGTTCC CATCTATTTT GTCACTCTTC
      CATAATCGAA TGCTGCGATG TGGGTCAAGG GTAGATAAAA CAGTGAGAAG
1651  CCTAAATAAT CCTTAAAAAC TCCATTTCCA CCCCTCCCAG. TTCCCAACTA
      GGATTTATTA GGAATTTTTG AGGTAAAGGT GGGGAGGGTC AAGGGTTGAT
1701  TTTTGTCCGC CCACAGCGGG GCATTTTTCT TCCTGTTATG TTTTTAATCA
      AAAACAGGCG GGTGTCGCCC CGTAAAAAGA AGGACAATAC AAAAATTAGT
1751  AACATCCTGC CAACTCCATG TGACAAACCG TCATCTTCGG CTACTTTTC
      TTGTAGGACG GTTGAGGTAC ACTGTTTGGC AGTAGAAGCC GATGAAAAAG
1801  TCTGTCACAG AATGAAAATT TTTCTGTCAT CTCTTCGTTA TTAATGTTTG
      AGACAGTGTC TTACTTTTAA AAAGACAGTA GAGAAGCAAT AATTACAAAC
1851  TAATTGACTG AATATCAACG CTTATTTGCA GCCTGAATGG CGAATGGGAC
      ATTAACTGAC TTATAGTTGC GAATAAACGT CGGACTTACC GCTTACCCTG
1901  GCGCCCTGTA GCGGCGCATT AAGCGCGGCG GGTGTGGTGG TTACGCGCAG
      CGCGGGACAT CGCCGCGTAA TTCGCGCCGC CCACACCACC AATGCGCGTC
1951  CGTGACCGCT ACACTTGCCA GCGCCCTAGC GCCCGCTCCT TTCGCTTTCT
      GCACTGGCGA TGTGAACGGT CGCGGGATCG CGGGCGAGGA AAGCGAAAGA
2001  TCCCTTCCTT TCTCGCCACG TTCGCCGGCT TTCCCCGTCA AGCTCTAAAT
      AGGGAAGGAA AGAGCGGTGC AAGCGGCCGA AAGGGGCAGT TCGAGATTTA
2051  CGGGGGCTCC CTTTAGGGTT CCGATTTAGT GCTTTACGGC ACCTCGACCC
      GCCCCCGAGG GAAATCCCAA GGCTAAATCA CGAAATGCCG TGGAGCTGGG
2101  CAAAAAACTT GATTAGGGTG ATGGTTCACG TAGTGGGCCA TCGCCCTGAT
      GTTTTTTGAA CTAATCCCAC TACCAAGTGC ATCACCCGGT AGCGGGACTA
2151  AGACGGTTTT TCGCCCTTTG ACGTTGGAGT CCACGTTCTT TAATAGTGGA
      TCTGCCAAAA AGCGGGAAAC TGCAACCTCA GGTGCAAGAA ATTATCACCT
2201  CTCTTGTTCC AAACTGGAAC AACACTCAAC CCTATCTCGG TCTATTCTTT
      GAGAACAAGG TTTGACCTTG TTGTGAGTTG GGATAGAGCC AGATAAGAAA
2251  TGATTTATAA GGGATTTTGC CGATTTCGGC CTATTGGTTA AAAAATGAGC
      ACTAAATATT CCCTAAAACG GCTAAAGCCG GATAACCAAT TTTTTACTCG
2301  TGATTTAACA AAAATTTAAC GCGAATTTTA ACAAAATATT AACGTTTACA
      ACTAAATTGT TTTTAAATTG CGCTTAAAAT TGTTTTATAA TTGCAAATGT
2351  ATTTCAGGTG GCACTTTTCG GGGAAATGTG CGCGGAACCC CTATTTGTTT
```

Figure 44C

```
              TAAAGTCCAC CGTGAAAAGC CCCTTTACAC GCGCCTTGGG GATAAACAAA
2401   ATTTTTCTAA ATACATTCAA ATATGTATCC GCTCATGAGA CAATAACCCT
       TAAAAAGATT TATGTAAGTT TATACATAGG CGAGTACTCT GTTATTGGGA
2451   GATAAATGCT TCAATAATAT TGAAAAAGGA AGAGTATGAG TATTCAACAT
       CTATTTACGA AGTTATTATA ACTTTTTCCT TCTCATACTC ATAAGTTGTA
2501   TTCCGTGTCG CCCTTATTCC CTTTTTTGCG GCATTTTGCC TTCCTGTTTT
       AAGGCACAGC GGGAATAAGG GAAAAAACGC CGTAAAACGG AAGGACAAAA
2551   TGCTCACCCA GAAACGCTGG TGAAAGTAAA AGATGCTGAA GATCAGTTGG
       ACGAGTGGGT CTTTGCGACC ACTTTCATTT TCTACGACTT CTAGTCAACC
2601   GTGCACGAGT GGGTTACATC GAACTGGATC TCAACAGCGG TAAGATCCTT
       CACGTGCTCA CCCAATGTAG CTTGACCTAG AGTTGTCGCC ATTCTAGGAA
2651   GAGAGTTTTC GCCCCGAAGA ACGTTTTCCA ATGATGAGCA CTTTTAAAGT
       CTCTCAAAAG CGGGGCTTCT TGCAAAAGGT TACTACTCGT GAAAATTTCA
2701   TCTGCTATGT GGCGCGGTAT TATCCCGTAT TGACGCCGGG CAAGAGCAAC
       AGACGATACA CCGCGCCATA ATAGGGCATA ACTGCGGCCC GTTCTCGTTG
2751   TCGGTCGCCG CATACACTAT TCTCAGAATG ACTTGGTTGA GTACTCACCA
       AGCCAGCGGC GTATGTGATA AGAGTCTTAC TGAACCAACT CATGAGTGGT
2801   GTCACAGAAA AGCATCTTAC GGATGGCATG ACAGTAAGAG AATTATGCAG
       CAGTGTCTTT TCGTAGAATG CCTACCGTAC TGTCATTCTC TTAATACGTC
2851   TGCTGCCATA ACCATGAGTG ATAACACTGC GGCCAACTTA CTTCTGACAA
       ACGACGGTAT TGGTACTCAC TATTGTGACG CCGGTTGAAT GAAGACTGTT
2901   CGATCGGAGG ACCGAAGGAG CTAACCGCTT TTTTGCACAA CATGGGGGAT
       GCTAGCCTCC TGGCTTCCTC GATTGGCGAA AAAACGTGTT GTACCCCCTA
2951   CATGTAACTC GCCTTGATCG TTGGGAACCG GAGCTGAATG AAGCCATACC
       GTACATTGAG CGGAACTAGC AACCCTTGGC CTCGACTTAC TTCGGTATGG
3001   AAACGACGAG CGTGACACCA CGATGCCTGT AGCAATGGCA ACAACGTTGC
       TTTGCTGCTC GCACTGTGGT GCTACGGACA TCGTTACCGT TGTTGCAACG
3051   GCAAACTATT AACTGGCGAA CTACTTACTC TAGCTTCCCG GCAACAATTA
       CGTTTGATAA TTGACCGCTT GATGAATGAG ATCGAAGGGC CGTTGTTAAT
3101   ATAGACTGGA TGGAGGCGGA TAAAGTTGCA GGACCACTTC TGCGCTCGGC
       TATCTGACCT ACCTCCGCCT ATTTCAACGT CCTGGTGAAG ACGCGAGCCG
3151   CCTTCCGGCT GGCTGGTTTA TTGCTGATAA ATCTGGAGCC GGTGAGCGTG
       GGAAGGCCGA CCGACCAAAT AACGACTATT TAGACCTCGG CCACTCGCAC
       BsaI
       ~~~~~~
3201   GGTCTCGCGG TATCATTGCA GCACTGGGGC CAGATGGTAA GCCCTCCCGT
       CCAGAGCGCC ATAGTAACGT CGTGACCCCG GTCTACCATT CGGGAGGGCA
3251   ATCGTAGTTA TCTACACGAC GGGGAGTCAG GCAACTATGG ATGAACGAAA
       TAGCATCAAT AGATGTGCTG CCCCTCAGTC CGTTGATACC TACTTGCTTT
3301   TAGACAGATC GCTGAGATAG GTGCCTCACT GATTAAGCAT TGGTAACTGT
       ATCTGTCTAG CGACTCTATC CACGGAGTGA CTAATTCGTA ACCATTGACA
3351   CAGACCAAGT TTACTCATAT ATACTTTAGA TTGATTTAAA ACTTCATTTT
       GTCTGGTTCA AATGAGTATA TATGAAATCT AACTAAATTT TGAAGTAAAA
3401   TAATTTAAAA GGATCTAGGT GAAGATCCTT TTTGATAATC TCATGACCAA
       ATTAAATTTT CCTAGATCCA CTTCTAGGAA AAACTATTAG AGTACTGGTT
3451   AATCCCTTAA CGTGAGTTTT CGTTCCACTG AGCGTCAGAC CCCGTAGAAA
       TTAGGGAATT GCACTCAAAA GCAAGGTGAC TCGCAGTCTG GGGCATCTTT
3501   AGATCAAAGG ATCTTCTTGA GATCCTTTTT TTCTGCGCGT AATCTGCTGC
       TCTAGTTTCC TAGAAGAACT CTAGGAAAAA AGACGCGCA TTAGACGACG
3551   TTGCAAACAA AAAAACCACC GCTACCAGCG GTGGTTTGTT TGCCGGATCA
       AACGTTTGTT TTTTTGGTGG CGATGGTCGC CACCAAACAA ACGGCCTAGT
```

Figure 44D

```
3601  AGAGCTACCA ACTCTTTTTC CGAAGGTAAC TGGCTTCAGC AGAGCGCAGA
      TCTCGATGGT TGAGAAAAAG GCTTCCATTG ACCGAAGTCG TCTCGCGTCT
3651  TACCAAATAC TGTCCTTCTA GTGTAGCCGT AGTTAGGCCA CCACTTCAAG
      ATGGTTTATG ACAGGAAGAT CACATCGGCA TCAATCCGGT GGTGAAGTTC
3701  AACTCTGTAG CACCGCCTAC ATACCTCGCT CTGCTAATCC TGTTACCAGT
      TTGAGACATC GTGGCGGATG TATGGAGCGA GACGATTAGG ACAATGGTCA
3751  GGCTGCTGCC AGTGGCGATA AGTCGTGTCT TACCGGGTTG GACTCAAGAC
      CCGACGACGG TCACCGCTAT TCAGCACAGA ATGGCCCAAC CTGAGTTCTG
3801  GATAGTTACC GGATAAGGCG CAGCGGTCGG GCTGAACGGG GGGTTCGTGC
      CTATCAATGG CCTATTCCGC GTCGCCAGCC CGACTTGCCC CCCAAGCACG
3851  ACACAGCCCA GCTTGGAGCG AACGACCTAC ACCGAACTGA GATACCTACA
      TGTGTCGGGT CGAACCTCGC TTGCTGGATG TGGCTTGACT CTATGGATGT
3901  GCGTGAGCAT TGAGAAAGCG CCACGCTTCC CGAAGGGAGA AAGGCGGACA
      CGCACTCGTA ACTCTTTCGC GGTGCGAAGG GCTTCCCTCT TTCCGCCTGT
3951  GGTATCCGGT AAGCGGCAGG GTCGGAACAG GAGAGCGCAC GAGGGAGCTT
      CCATAGGCCA TTCGCCGTCC CAGCCTTGTC CTCTCGCGTG CTCCCTCGAA
4001  CCAGGGGGAA ACGCCTGGTA TCTTTATAGT CCTGTCGGGT TTCGCCACCT
      GGTCCCCCTT TGCGGACCAT AGAAATATCA GGACAGCCCA AAGCGGTGGA
4051  CTGACTTGAG CGTCGATTTT TGTGATGCTC GTCAGGGGGG CGGAGCCTAT
      GACTGAACTC GCAGCTAAAA ACACTACGAG CAGTCCCCCC GCCTCGGATA
4101  GGAAAAACGC CAGCAACGCG GCCTTTTTAC GGTTCCTGGC CTTTTGCTGG
      CCTTTTTGCG GTCGTTGCGC CGGAAAAATG CCAAGGACCG GAAAACGACC
4151  CCTTTTGCTC ACATGTTCTT TCCTGCGTTA TCCCCTGATT CTGTGGATAA
      GGAAAACGAG TGTACAAGAA AGGACGCAAT AGGGGACTAA GACACCTATT
4201  CCGTATTACC GCCTTTGAGT GAGCTGATAC CGCTCGCCGC AGCCGAACGA
      GGCATAATGG CGGAAACTCA CTCGACTATG GCGAGCGGCG TCGGCTTGCT
4251  CCGAGCGCAG CGAGTCAGTG AGCGAGGAAG CGGAAGAGCG CCTGATGCGG
      GGCTCGCGTC GCTCAGTCAC TCGCTCCTTC GCCTTCTCGC GGACTACGCC
4301  TATTTTCTCC TTACGCATCT GTGCGGTATT TCACACCGCA GACCAGCCGC
      ATAAAAGAGG AATGCGTAGA CACGCCATAA AGTGTGGCGT CTGGTCGGCG
4351  GTAACCTGGC AAAATCGGTT ACGGTTGAGT AATAAATGGA TGCCCTGCGT
      CATTGGACCG TTTTAGCCAA TGCCAACTCA TTATTTACCT ACGGGACGCA
4401  AAGCGGGTGT GGGCGGACAA TAAAGTCTTA AACTGAACAA AATAGATCTA
      TTCGCCCACA CCCGCCTGTT ATTTCAGAAT TTGACTTGTT TTATCTAGAT
4451  AACTATGACA ATAAAGTCTT AAACTAGACA GAATAGTTGT AAACTGAAAT
      TTGATACTGT TATTTCAGAA TTTGATCTGT CTTATCAACA TTTGACTTTA
4501  CAGTCCAGTT ATGCTGTGAA AAAGCATACT GGACTTTTGT TATGGCTAAA
      GTCAGGTCAA TACGACACTT TTTCGTATGA CCTGAAAACA ATACCGATTT
4551  GCAAACTCTT CATTTCTGA AGTGCAAATT GCCCGTCGTA TTAAAGAGGG
      CGTTTGAGAA GTAAAGACT TCACGTTTAA CGGGCAGCAT AATTTCTCCC
4601  GCGTGGCCAA GGGCATGGTA AAGACTATAT CGCGGCGTT GTGACAATTT
      CGCACCGGTT CCCGTACCAT TTCTGATATA AGCGCCGCAA CACTGTTAAA
4651  ACCGAACAAC TCCGCGGCCG GAAGCCGAT CTCGGCTTGA ACGAATTGTT
      TGGCTTGTTG AGGCGCCGGC CCTTCGGCTA GAGCCGAACT TGCTTAACAA
4701  AGGTGGCGGT ACTTGGGTCG ATATCAAAGT GCATCACTTC TTCCCGTATG
      TCCACCGCCA TGAACCCAGC TATAGTTTCA CGTAGTGAAG AAGGGCATAC
4751  CCCAACTTTG TATAGAGAGC CACTGCGGGA TCGTCACCGT AATCTGCTTG
      GGGTTGAAAC ATATCTCTCG GTGACGCCCT AGCAGTGGCA TTAGACGAAC
4801  CACGTAGATC ACATAAGCAC CAAGCGCGTT GGCCTCATGC TTGAGGAGAT
      GTGCATCTAG TGTATTCGTG GTTCGCGCAA CCGGAGTACG AACTCCTCTA
4851  TGATGAGCGC GGTGGCAATG CCCTGCCTCC GGTGCTCGCC GGAGACTGCG
```

Figure 44E

```
           ACTACTCGCG CCACCGTTAC GGGACGGAGG CCACGAGCGG CCTCTGACGC
    4901   AGATCATAGA TATAGATCTC ACTACGCGGC TGCTCAAACC TGGGCAGAAC
           TCTAGTATCT ATATCTAGAG TGATGCGCCG ACGAGTTTGG ACCCGTCTTG
    4951   GTAAGCCGCG AGAGCGCCAA CAACCGCTTC TTGGTCGAAG GCAGCAAGCG
           CATTCGGCGC TCTCGCGGTT GTTGGCGAAG AACCAGCTTC CGTCGTTCGC
    5001   CGATGAATGT CTTACTACGG AGCAAGTTCC CGAGGTAATC GGAGTCCGGC
           GCTACTTACA GAATGATGCC TCGTTCAAGG GCTCCATTAG CCTCAGGCCG
                                     Esp3I
                                    ~~~~~~
    5051   TGATGTTGGG AGTAGGTGGC TACGTCTCCG AACTCACGAC CGAAAAGATC
           ACTACAACCC TCATCCACCG ATGCAGAGGC TTGAGTGCTG GCTTTTCTAG
    5101   AAGAGCAGCC CGCATGGATT TGACTTGGTC AGGGCCGAGC CTACATGTGC
           TTCTCGTCGG GCGTACCTAA ACTGAACCAG TCCCGGCTCG GATGTACACG
    5151   GAATGATGCC CATACTTGAG CCACCTAACT TTGTTTTAGG GCGACTGCCC
           CTTACTACGG GTATGAACTC GGTGGATTGA AACAAAATCC CGCTGACGGG
    5201   TGCTGCGTAA CATCGTTGCT GCTGCGTAAC ATCGTTGCTG CTCCATAACA
           ACGACGCATT GTAGCAACGA CGACGCATTG TAGCAACGAC GAGGTATTGT
    5251   TCAAACATCG ACCCACGGCG TAACGCGCTT GCTGCTTGGA TGCCCGAGGC
           AGTTTGTAGC TGGGTGCCGC ATTGCGCGAA CGACGAACCT ACGGGCTCCG
    5301   ATAGACTGTA CAAAAAAACA GTCATAACAA GCCATGAAAA CCGCCACTGC
           TATCTGACAT GTTTTTTTGT CAGTATTGTT CGGTACTTTT GGCGGTGACG
    5351   GCCGTTACCA CCGCTGCGTT CGGTCAAGGT TCTGGACCAG TTGCGTGAGC
           CGGCAATGGT GGCGACGCAA GCCAGTTCCA AGACCTGGTC AACGCACTCG
    5401   GCATACGCTA CTTGCATTAC AGTTTACGAA CCGAACAGGC TTATGTCAAC
           CGTATGCGAT GAACGTAATG TCAAATGCTT GGCTTGTCCG AATACAGTTG
    5451   TGGGTTCGTG CCTTCATCCG TTTCCACGGT GTGCGTCACC CGGCAACCTT
           ACCCAAGCAC GGAAGTAGGC AAAGGTGCCA CACGCAGTGG GCCGTTGGAA
    5501   GGGCAGCAGC GAAGTCGAGG CATTTCTGTC CTGGCTGGCG AACGAGCGCA
           CCCGTCGTCG CTTCAGCTCC GTAAAGACAG GACCGACCGC TTGCTCGCGT
                      BsaI
                     ~~~~~~~
    5551   AGGTTTCGGT CTCCACGCAT CGTCAGGCAT TGGCGGCCTT GCTGTTCTTC
           TCCAAAGCCA GAGGTGCGTA GCAGTCCGTA ACCGCCGGAA CGACAAGAAG
    5601   TACGGCAAGG TGCTGTGCAC GGATCTGCCC TGGCTTCAGG AGATCGGAAG
           ATGCCGTTCC ACGACACGTG CCTAGACGGG ACCGAAGTCC TCTAGCCTTC
    5651   ACCTCGGCCG TCGCGGCGCT TGCCGGTGGT GCTGACCCCG GATGAAGTGG
           TGGAGCCGGC AGCGCCGCGA ACGGCCACCA CGACTGGGGC CTACTTCACC
    5701   TTCGCATCCT CGGTTTTCTG GAAGGCGAGC ATCGTTTGTT CGCCCAGGAC
           AAGCGTAGGA GCCAAAAGAC CTTCCGCTCG TAGCAAACAA GCGGGTCCTG
    5751   TCTAGCTATA GTTCTAGTGG TTGGCTACGT ATACTCCGGA ATATTAATAG
           AGATCGATAT CAAGATCACC AACCGATGCA TATGAGGCCT TATAATTATC
```

Figure 46A

```
   1 ATCCGGATAT AGTTCCTCCT TTCAGCAAAA AACCCCTCAA GACCCGTTTA
     TAGGCCTATA TCAAGGAGGA AAGTCGTTTT TTGGGGAGTT CTGGGCAAAT
  51 GAGGCCCCAA GGGGTTATGC TAGTTATTGC TCAGCGGTGG CAGCAGCCAA
     CTCCGGGGTT CCCCAATACG ATCAATAACG AGTCGCCACC GTCGTCGGTT
 101 CTCAGCTTCC TTTCGGGCTT TGTTAGCAGC GGATCTCAG TGGTGGTGGT
     GAGTCGAAGG AAAGCCCGAA ACAATCGTCG GCCTAGAGTC ACCACCACCA
                                          HindIII
                                         ~~~~~~
 151 GGTGGTGCTC GAGTGCGGCC GCAAGCTTGT CGACGGAGCT CGAATTCGGA
     CCACCACGAG CTCACGCCGG CGTTCGAACA GCTGCCTCGA GCTTAAGCCT
         BsaI
       ~~~~~~
 201 TCCGGTCTCA ACCTCCAATC TGTTCGCGGT GAGCCTCAAT AATATCGTTA
     AGGCCAGAGT TGGAGGTTAG ACAAGCGCCA CTCGGAGTTA TTATAGCAAT
 251 TCCTCCATGT CCAAATCTTC AGGGGTCTGA TCAGCTTGAA TTCTAATACC
     AGGAGGTACA GGTTTAGAAG TCCCCAGACT AGTCGAACTT AAGATTATGG
 301 GTCGTACAAG AATCTTAAGG AGTCCATTTC CTTACCCTGT CTTTTAGCGA
     CAGCATGTTC TTAGAATTCC TCAGGTAAAG GAATGGGACA GAAAATCGCT
 351 ACGCTTCCAT CAGCCTTCTT AAAGGAGTGG TCTTTTTGAT CTTGAAGAAG
     TGCGAAGGTA GTCGGAAGAA TTTCCTCACC AGAAAAACTA GAACTTCTTC
 401 ATCTCTGAAG ATCCATCGGA CACCTTTAAA TTGATGTGAG TCTCAGGCTT
     TAGAGACTTC TAGGTAGCCT GTGGAAATTT AACTACACTC AGAGTCCGAA
 451 GACTTCTGGC TTGACCTCTG GCTTAGCTTC TTGATTGACT TCTGAGTCCG
     CTGAAGACCG AACTGGAGAC CGAATCGAAG AACTAACTGA AGACTCAGGC
                                          NcoI
                                         ~~~~~~~
 501 ACCCGTGATG ATGATGGTGA TGACCCATGG TATATCTCCT TCTTAAAGTT
     TGGGCACTAC TACTACCACT ACTGGGTACC ATATAGAGGA AGAATTTCAA
                      XbaI
                    ~~~~~~
 551 AAACAAAATT ATTTCTAGAG GGAATTGTT ATCCGCTCAC AATTCCCCTA
     TTTGTTTTAA TAAAGATCTC CCCTTAACAA TAGGCGAGTG TTAAGGGGAT
 601 TAGTGAGTCG TATTAATTTC GCGGGATCGA GATCTCGATC CTCTACGCCG
     ATCACTCAGC ATAATTAAAG CGCCCTAGCT CTAGAGCTAG GAGATGCGGC
 651 GACGCATCGT GGCCGGCATC ACCGGCGCCA CAGGTGCGGT TGCTGGCGCC
     CTGCGTAGCA CCGGCCGTAG TGGCCGCGGT GTCCACGCCA ACGACCGCGG
 701 TATATCGCCG ACATCACCGA TGGGGAAGAT CGGGCTCGCC ACTTCGGGCT
     ATATAGCGGC TGTAGTGGCT ACCCCTTCTA GCCCGAGCGG TGAAGCCCGA
 751 CATGAGCGCT TGTTTCGGCG TGGGTATGGT GGCAGGCCCC GTGGCCGGGG
     GTACTCGCGA ACAAAGCCGC ACCCATACCA CCGTCCGGGG CACCGGCCCC
 801 GACTGTTGGG CGCCATCTCC TTGCATGCAC CATTCCTTGC GGCGGCGGTG
     CTGACAACCC GCGGTAGAGG AACGTACGTG GTAAGGAACG CCGCCGCCAC
 851 CTCAACGGCC TCAACCTACT ACTGGGCTGC TTCCTAATGC AGGAGTCGCA
     GAGTTGCCGG AGTTGGATGA TGACCCGACG AAGGATTACG TCCTCAGCGT
 901 TAAGGGAGAG CGTCGAGATC CCGGACACCA TCGAATGGCG CAAAACCTTT
     ATTCCCTCTC GCAGCTCTAG GGCCTGTGGT AGCTTACCGC GTTTTGGAAA
 951 CGCGGTATGG CATGATAGCG CCCGGAAGAG AGTCAATTCA GGGTGGTGAA
     GCGCCATACC GTACTATCGC GGGCCTTCTC TCAGTTAAGT CCCACCACTT
1001 TGTGAAACCA GTAACGTTAT ACGATGTCGC AGAGTATGCC GGTGTCTCTT
```

Figure 46B

```
           ACACTTTGGT CATTGCAATA TGCTACAGCG TCTCATACGG CCACAGAGAA
     1051  ATCAGACCGT TTCCCGCGTG GTGAACCAGG CCAGCCACGT TTCTGCGAAA
           TAGTCTGGCA AAGGGCGCAC CACTTGGTCC GGTCGGTGCA AAGACGCTTT
     1101  ACGCGGGAAA AAGTGGAAGC GGCGATGGCG GAGCTGAATT ACATTCCCAA
           TGCGCCCTTT TTCACCTTCG CCGCTACCGC CTCGACTTAA TGTAAGGGTT
     1151  CCGCGTGGCA CAACAACTGG CGGGCAAACA GTCGTTGCTG ATTGGCGTTG
           GGCGCACCGT GTTGTTGACC GCCCGTTTGT CAGCAACGAC TAACCGCAAC
     1201  CCACCTCCAG TCTGGCCCTG CACGCGCCGT CGCAAATTGT CGCGGCGATT
           GGTGGAGGTC AGACCGGGAC GTGCGCGGCA GCGTTTAACA GCGCCGCTAA
     1251  AAATCTCGCG CCGATCAACT GGGTGCCAGC GTGGTGGTGT CGATGGTAGA
           TTTAGAGCGC GGCTAGTTGA CCCACGGTCG CACCACCACA GCTACCATCT
     1301  ACGAAGCGGC GTCGAAGCCT GTAAAGCGGC GGTGCACAAT CTTCTCGCGC
           TGCTTCGCCG CAGCTTCGGA CATTTCGCCG CCACGTGTTA GAAGAGCGCG
     1351  AACGCGTCAG TGGGCTGATC ATTAACTATC CGCTGGATGA CCAGGATGCC
           TTGCGCAGTC ACCCGACTAG TAATTGATAG GCGACCTACT GGTCCTACGG
     1401  ATTGCTGTGG AAGCTGCCTG CACTAATGTT CCGGCGTTAT TTCTTGATGT
           TAACGACACC TTCGACGGAC GTGATTACAA GGCCGCAATA AAGAACTACA
     1451  CTCTGACCAG ACACCCATCA ACAGTATTAT TTTCTCCCAT GAAGACGGTA
           GAGACTGGTC TGTGGGTAGT TGTCATAATA AAAGAGGGTA CTTCTGCCAT
     1501  CGCGACTGGG CGTGGAGCAT CTGGTCGCAT TGGGTCACCA GCAAATCGCG
           GCGCTGACCC GCACCTCGTA GACCAGCGTA ACCCAGTGGT CGTTTAGCGC
     1551  CTGTTAGCGG GCCCATTAAG TTCTGTCTCG GCGCGTCTGC GTCTGGCTGG
           GACAATCGCC CGGGTAATTC AAGACAGAGC CGCGCAGACG CAGACCGACC
     1601  CTGGCATAAA TATCTCACTC GCAATCAAAT TCAGCCGATA GCGGAACGGG
           GACCGTATTT ATAGAGTGAG CGTTAGTTTA AGTCGGCTAT CGCCTTGCCC
     1651  AAGGCGACTG GAGTGCCATG TCCGGTTTTC AACAAACCAT GCAAATGCTG
           TTCCGCTGAC CTCACGGTAC AGGCCAAAAG TTGTTTGGTA CGTTTACGAC
     1701  AATGAGGGCA TCGTTCCCAC TGCGATGCTG GTTGCCAACG ATCAGATGGC
           TTACTCCCGT AGCAAGGGTG ACGCTACGAC CAACGGTTGC TAGTCTACCG
     1751  GCTGGGCGCA ATGCGCGCCA TTACCGAGTC CGGGCTGCGC GTTGGTGCGG
           CGACCCGCGT TACGCGCGGT AATGGCTCAG GCCCGACGCG CAACCACGCC
     1801  ATATCTCGGT AGTGGGATAC GACGATACCG AAGACAGCTC ATGTTATATC
           TATAGAGCCA TCACCCTATG CTGCTATGGC TTCTGTCGAG TACAATATAG
     1851  CCGCCGTTAA CCACCATCAA ACAGGATTTT CGCCTGCTGG GGCAAACCAG
           GGCGGCAATT GGTGGTAGTT TGTCCTAAAA GCGGACGACC CCGTTTGGTC
     1901  CGTGGACCGC TTGCTGCAAC TCTCTCAGGG CCAGGCGGTG AAGGGCAATC
           GCACCTGGCG AACGACGTTG AGAGAGTCCC GGTCCGCCAC TTCCCGTTAG
     1951  AGCTGTTGCC CGTCTCACTG GTGAAAAGAA AAACCACCCT GGCGCCCAAT
           TCGACAACGG GCAGAGTGAC CACTTTTCTT TTTGGTGGGA CCGCGGGTTA
     2001  ACGCAAACCG CCTCTCCCCG CGCGTTGGCC GATTCATTAA TGCAGCTGGC
           TGCGTTTGGC GGAGAGGGGC GCGCAACCGG CTAAGTAATT ACGTCGACCG
     2051  ACGACAGGTT TCCCGACTGG AAAGCGGGCA GTGAGCGCAA CGCAATTAAT
           TGCTGTCCAA AGGGCTGACC TTTCGCCCGT CACTCGCGTT GCGTTAATTA
     2101  GTAAGTTAGC TCACTCATTA GGCACCGGGA TCTCGACCGA TGCCCTTGAG
           CATTCAATCG AGTGAGTAAT CCGTGGCCCT AGAGCTGGCT ACGGGAACTC
     2151  AGCCTTCAAC CCAGTCAGCT CCTTCCGGTG GGCGCGGGGC ATGACTATCG
           TCGGAAGTTG GGTCAGTCGA GGAAGGCCAC CCGCGCCCCG TACTGATAGC
     2201  TCGCCGCACT TATGACTGTC TTCTTTATCA TGCAACTCGT AGGACAGGTG
           AGCGGCGTGA ATACTGACAG AAGAAATAGT ACGTTGAGCA TCCTGTCCAC
     2251  CCGGCAGCGC TCTGGGTCAT TTTCGGCGAG GACCGCTTTC GCTGGAGCGC
           GGCCGTCGCG AGACCCAGTA AAAGCCGCTC CTGGCGAAAG CGACCTCGCG
```

Figure 46C

```
2301  GACGATGATC GGCCTGTCGC TTGCGGTATT CGGAATCTTG CACGCCCTCG
      CTGCTACTAG CCGGACAGCG AACGCCATAA GCCTTAGAAC GTGCGGGAGC
2351  CTCAAGCCTT CGTCACTGGT CCCGCCACCA AACGTTTCGG CGAGAAGCAG
      GAGTTCGGAA GCAGTGACCA GGGCGGTGGT TTGCAAAGCC GCTCTTCGTC
2401  GCCATTATCG CCGGCATGGC GGCCCACGG GTGCGCATGA TCGTGCTCCT
      CGGTAATAGC GGCCGTACCG CCGGGGTGCC CACGCGTACT AGCACGAGGA
2451  GTCGTTGAGG ACCCGGCTAG GCTGGCGGGG TTGCCTTACT GGTTAGCAGA
      CAGCAACTCC TGGGCCGATC CGACCGCCCC AACGGAATGA CCAATCGTCT
2501  ATGAATCACC GATACGCGAG CGAACGTGAA GCGACTGCTG CTGCAAAACG
      TACTTAGTGG CTATGCGCTC GCTTGCACTT CGCTGACGAC GACGTTTTGC
2551  TCTGCGACCT GAGCAACAAC ATGAATGGTC TTCGGTTTCC GTGTTTCGTA
      AGACGCTGGA CTCGTTGTTG TACTTACCAG AAGCCAAAGG CACAAAGCAT
2601  AAGTCTGGAA ACGCGGAAGT CAGCGCCCTG CACCATTATG TTCCGGATCT
      TTCAGACCTT TGCGCCTTCA GTCGCGGGAC GTGGTAATAC AAGGCCTAGA
2651  GCATCGCAGG ATGCTGCTGG CTACCCTGTG GAACACCTAC ATCTGTATTA
      CGTAGCGTCC TACGACGACC GATGGGACAC CTTGTGGATG TAGACATAAT
2701  ACGAAGCGCT GGCATTGACC CTGAGTGATT TTTCTCTGGT CCCGCCGCAT
      TGCTTCGCGA CCGTAACTGG GACTCACTAA AAAGAGACCA GGGCGGCGTA
2751  CCATACCGCC AGTTGTTTAC CCTCACAACG TTCCAGTAAC CGGGCATGTT
      GGTATGGCGG TCAACAAATG GGAGTGTTGC AAGGTCATTG GCCCGTACAA
2801  CATCATCAGT AACCCGTATC GTGAGCATCC TCTCTCGTTT CATCGGTATC
      GTAGTAGTCA TTGGGCATAG CACTCGTAGG AGAGAGCAAA GTAGCCATAG
2851  ATTACCCCCA TGAACAGAAA TCCCCCTTAC ACGGAGGCAT CAGTGACCAA
      TAATGGGGGT ACTTGTCTTT AGGGGGAATG TGCCTCCGTA GTCACTGGTT
2901  ACAGGAAAAA ACCGCCCTTA ACATGGCCCG CTTTATCAGA AGCCAGACAT
      TGTCCTTTTT TGGCGGGAAT TGTACCGGGC GAAATAGTCT TCGGTCTGTA
2951  TAACGCTTCT GGAGAAACTC AACGAGCTGG ACGCGGATGA ACAGGCAGAC
      ATTGCGAAGA CCTCTTTGAG TTGCTCGACC TGCGCCTACT TGTCCGTCTG
3001  ATCTGTGAAT CGCTTCACGA CCACGCTGAT GAGCTTTACC GCAGCTGCCT
      TAGACACTTA GCGAAGTGCT GGTGCGACTA CTCGAAATGG CGTCGACGGA
3051  CGCGCGTTTC GGTGATGACG GTGAAAACCT CTGACACATG CAGCTCCCGG
      GCGCGCAAAG CCACTACTGC CACTTTTGGA GACTGTGTAC GTCGAGGGCC
3101  AGACGGTCAC AGCTTGTCTG TAAGCGGATG CCGGGAGCAG ACAAGCCCGT
      TCTGCCAGTG TCGAACAGAC ATTCGCCTAC GGCCCTCGTC TGTTCGGGCA
3151  CAGGGCGCGT CAGCGGGTGT TGGCGGGTGT CGGGGCGCAG CCATGACCCA
      GTCCCGCGCA GTCGCCCACA ACCGCCCACA GCCCCGCGTC GGTACTGGGT
3201  GTCACGTAGC GATAGCGGAG TGTATACTGG CTTAACTATG CGGCATCAGA
      CAGTGCATCG CTATCGCCTC ACATATGACC GAATTGATAC GCCGTAGTCT
3251  GCAGATTGTA CTGAGAGTGC ACCATATATG CGGTGTGAAA TACCGCACAG
      CGTCTAACAT GACTCTCACG TGGTATATAC GCCACACTTT ATGGCGTGTC
3301  ATGCGTAAGG AGAAAATACC GCATCAGGCG CTCTTCCGCT TCCTCGCTCA
      TACGCATTCC TCTTTTATGG CGTAGTCCGC GAGAAGGCGA AGGAGCGAGT
3351  CTGACTCGCT GCGCTCGGTC GTTCGGCTGC GGCGAGCGGT ATCAGCTCAC
      GACTGAGCGA CGCGAGCCAG CAAGCCGACG CCGCTCGCCA TAGTCGAGTG
3401  TCAAAGGCGG TAATACGGTT ATCCACAGAA TCAGGGGATA ACGCAGGAAA
      AGTTTCCGCC ATTATGCCAA TAGGTGTCTT AGTCCCTAT TGCGTCCTTT
3451  GAACATGTGA GCAAAAGGCC AGCAAAAGGC CAGGAACCGT AAAAAGGCCG
      CTTGTACACT CGTTTTCCGG TCGTTTTCCG GTCCTTGGCA TTTTTCCGGC
3501  CGTTGCTGGC GTTTTTCCAT AGGCTCCGCC CCCCTGACGA GCATCACAAA
      GCAACGACCG CAAAAGGTA TCCGAGGCGG GGGACTGCT CGTAGTGTTT
3551  AATCGACGCT CAAGTCAGAG GTGGCGAAAC CCGACAGGAC TATAAAGATA
```

Figure 46D

```
         TTAGCTGCGA GTTCAGTCTC CACCGCTTTG GCTGTCCTG  ATATTTCTAT
3601     CCAGGCGTTT CCCCCTGGAA GCTCCCTCGT GCGCTCTCCT GTTCCGACCC
         GGTCCGCAAA GGGGGACCTT CGAGGGAGCA CGCGAGAGGA CAAGGCTGGG
3651     TGCCGCTTAC CGGATACCTG TCCGCCTTTC TCCCTTCGGG AAGCGTGGCG
         ACGGCGAATG GCCTATGGAC AGGCGGAAAG AGGGAAGCCC TTCGCACCGC
3701     CTTTCTCATA GCTCACGCTG TAGGTATCTC AGTTCGGTGT AGGTCGTTCG
         GAAAGAGTAT CGAGTGCGAC ATCCATAGAG TCAAGCCACA TCCAGCAAGC
3751     CTCCAAGCTG GCTGTGTGC  ACGAACCCCC CGTTCAGCCC GACCGCTGCG
         GAGGTTCGAC CCGACACACG TGCTTGGGGG GCAAGTCGGG CTGGCGACGC
3801     CCTTATCCGG TAACTATCGT CTTGAGTCCA ACCCGGTAAG ACACGACTTA
         GGAATAGGCC ATTGATAGCA GAACTCAGGT TGGGCCATTC TGTGCTGAAT
3851     TCGCCACTGG CAGCAGCCAC TGGTAACAGG ATTAGCAGAG CGAGGTATGT
         AGCGGTGACC GTCGTCGGTG ACCATTGTCC TAATCGTCTC GCTCCATACA
3901     AGGCGGTGCT ACAGAGTTCT TGAAGTGGTG GCCTAACTAC GGCTACACTA
         TCCGCCACGA TGTCTCAAGA ACTTCACCAC CGGATTGATG CCGATGTGAT
3951     GAAGGACAGT ATTTGGTATC TGCGCTCTGC TGAAGCCAGT TACCTTCGGA
         CTTCCTGTCA TAAACCATAG ACGCGAGACG ACTTCGGTCA ATGGAAGCCT
4001     AAAAGAGTTG GTAGCTCTTG ATCCGGCAAA CAAACCACCG CTGGTAGCGG
         TTTTCTCAAC CATCGAGAAC TAGGCCGTTT GTTTGGTGGC GACCATCGCC
4051     TGGTTTTTTT GTTTGCAAGC AGCAGATTAC GCGCAGAAAA AAAGGATCTC
         ACCAAAAAAA CAAACGTTCG TCGTCTAATG CGCGTCTTTT TTTCCTAGAG
4101     AAGAAGATCC TTTGATCTTT TCTACGGGGT CTGACGCTCA GTGGAACGAA
         TTCTTCTAGG AAACTAGAAA AGATGCCCCA GACTGCGAGT CACCTTGCTT
4151     AACTCACGTT AAGGGATTTT GGTCATGAAC AATAAAACTG TCTGCTTACA
         TTGAGTGCAA TTCCCTAAAA CCAGTACTTG TTATTTTGAC AGACGAATGT
4201     TAAACAGTAA TACAAGGGGT GTTATGAGCC ATATTCAACG GGAAACGTCT
         ATTTGTCATT ATGTTCCCCA CAATACTCGG TATAAGTTGC CCTTTGCAGA
4251     TGCTCTAGGC CGCGATTAAA TTCCAACATG GATGCTGATT TATATGGGTA
         ACGAGATCCG GCGCTAATTT AAGGTTGTAC CTACGACTAA ATATACCCAT
4301     TAAATGGGCT CGCGATAATG TCGGGCAATC AGGTGCGACA ATCTATCGAT
         ATTTACCCGA GCGCTATTAC AGCCCGTTAG TCCACGCTGT TAGATAGCTA
4351     TGTATGGGAA GCCCGATGCG CCAGAGTTGT TTCTGAAACA TGGCAAAGGT
         ACATACCCTT CGGGCTACGC GGTCTCAACA AAGACTTTGT ACCGTTTCCA
4401     AGCGTTGCCA ATGATGTTAC AGATGAGATG GTCAGACTAA ACTGGCTGAC
         TCGCAACGGT TACTACAATG TCTACTCTAC CAGTCTGATT TGACCGACTG
4451     GGAATTTATG CCTCTTCCGA CCATCAAGCA TTTTATCCGT ACTCCTGATG
         CCTTAAATAC GGAGAAGGCT GGTAGTTCGT AAAATAGGCA TGAGGACTAC
4501     ATGCATGGTT ACTCACCACT GCGATCCCCG GGAAACAGC  ATTCCAGGTA
         TACGTACCAA TGAGTGGTGA CGCTAGGGGC CCTTTTGTCG TAAGGTCCAT
4551     TTAGAAGAAT ATCCTGATTC AGGTGAAAAT ATTGTTGATG CGCTGGCAGT
         AATCTTCTTA TAGGACTAAG TCCACTTTTA TAACAACTAC GCGACCGTCA
4601     GTTCCTGCGC CGGTTGCATT CGATTCCTGT TTGTAATTGT CCTTTTAACA
         CAAGGACGCG GCCAACGTAA GCTAAGGACA ACATTAACA  GGAAAATTGT
4651     GCGATCGCGT ATTTCGTCTC GCTCAGGCGC AATCACGAAT GAATAACGGT
         CGCTAGCGCA TAAAGCAGAG CGAGTCCGCG TTAGTGCTTA CTTATTGCCA
4701     TTGGTTGATG CGAGTGATTT TGATGACGAG CGTAATGGCT GGCCTGTTGA
         AACCAACTAC GCTCACTAAA ACTACTGCTC GCATTACCGA CCGGACAACT
4751     ACAAGTCTGG AAAGAAATGC ATAAACTTTT GCCATTCTCA CCGGATTCAG
         TGTTCAGACC TTTCTTTACG TATTTGAAAA CGGTAAGAGT GGCCTAAGTC
4801     TCGTCACTCA TGGTGATTTC TCACTTGATA ACCTTATTTT TGACGAGGGG
         AGCAGTGAGT ACCACTAAAG AGTGAACTAT TGGAATAAAA ACTGCTCCCC
```

Figure 46E

```
4851  AAATTAATAG GTTGTATTGA TGTTGGACGA GTCGGAATCG CAGACCGATA
      TTTAATTATC CAACATAACT ACAACCTGCT CAGCCTTAGC GTCTGGCTAT
4901  CCAGGATCTT GCCATCCTAT GGAACTGCCT CGGTGAGTTT TCTCCTTCAT
      GGTCCTAGAA CGGTAGGATA CCTTGACGGA GCCACTCAAA AGAGGAAGTA
4951  TACAGAAACG GCTTTTTCAA AAATATGGTA TTGATAATCC TGATATGAAT
      ATGTCTTTGC CGAAAAAGTT TTTATACCAT AACTATTAGG ACTATACTTA
5001  AAATTGCAGT TTCATTTGAT GCTCGATGAG TTTTTCTAAG AATTAATTCA
      TTTAACGTCA AAGTAAACTA CGAGCTACTC AAAAAGATTC TTAATTAAGT
5051  TGAGCGGATA CATATTTGAA TGTATTTAGA AAAATAAACA AATAGGGGTT
      ACTCGCCTAT GTATAAACTT ACATAAATCT TTTTATTTGT TTATCCCCAA
5101  CCGCGCACAT TTCCCCGAAA AGTGCCACCT GAAATTGTAA ACGTTAATAT
      GGCGCGTGTA AAGGGGCTTT TCACGGTGGA CTTTAACATT TGCAATTATA
5151  TTTGTTAAAA TTCGCGTTAA ATTTTTGTTA AATCAGCTCA TTTTTTAACC
      AAACAATTTT AAGCGCAATT TAAAAACAAT TTAGTCGAGT AAAAAATTGG
5201  AATAGGCCGA AATCGGCAAA ATCCCTTATA AATCAAAAGA ATAGACCGAG
      TTATCCGGCT TTAGCCGTTT TAGGGAATAT TTAGTTTTCT TATCTGGCTC
5251  ATAGGGTTGA GTGTTGTTCC AGTTTGGAAC AAGAGTCCAC TATTAAAGAA
      TATCCCAACT CACAACAAGG TCAAACCTTG TTCTCAGGTG ATAATTTCTT
5301  CGTGGACTCC AACGTCAAAG GGCGAAAAAC CGTCTATCAG GGCGATGGCC
      GCACCTGAGG TTGCAGTTTC CCGCTTTTG GCAGATAGTC CCGCTACCGG
5351  CACTACGTGA ACCATCACCC TAATCAAGTT TTTTGGGGTC GAGGTGCCGT
      GTGATGCACT TGGTAGTGGG ATTAGTTCAA AAAACCCCAG CTCCACGGCA
5401  AAAGCACTAA ATCGGAACCC TAAAGGGAGC CCCCGATTTA GAGCTTGACG
      TTTCGTGATT TAGCCTTGGG ATTTCCCTCG GGGGCTAAAT CTCGAACTGC
5451  GGGAAAGCCG GCGAACGTGG CGAGAAAGGA AGGGAAGAAA GCGAAGGAG
      CCCTTTCGGC CGCTTGCACC GCTCTTTCCT TCCCTTCTTT CGCTTCCTC
5501  CGGGCGCTAG GGCGCTGGCA AGTGTAGCGG TCACGCTGCG CGTAACCACC
      GCCCGCGATC CCGCGACCGT TCACATCGCC AGTGCGACGC GCATTGGTGG
5551  ACACCCGCCG CGCTTAATGC GCCGCTACAG GGCGCGTCCC ATTCGCCA
      TGTGGGCGGC GCGAATTACG CGGCGATGTC CCGCGCAGGG TAAGCGGT
```

METHODS AND COMPOSITIONS FOR PROTEIN EXPRESSION AND PURIFICATION

CROSS REFERENCE TO RELATED APPLICATION

This application is a divisional application of U.S. patent application Ser. No. 10/338,411 filed Jan. 7, 2003 now U.S. Pat. No. 7,060,461, which claims priority to U.S. Provisional Application 60/346,449 entitled "Methods for Protein Expression and Purification" filed Jan. 7, 2002. The foregoing applications are incorporated by reference herein.

FIELD OF THE INVENTION

The present invention relates to the field of recombinant gene expression and purification of expressed proteins. More specifically, the invention provides materials and methods which facilitate purification of heterologous proteins from a variety of different host species.

BACKGROUND OF THE INVENTION

Several publications and patent documents are cited throughout the specification in order to describe the state of the art to which this invention pertains. Full citations for these references can be found at the end of the specification. Each of these citations is incorporated herein as though set forth in full.

Functional genomic studies have been hampered by the inability to uniformly express and purify biologically active proteins in heterologous expression systems. Despite the use of identical transcriptional and translational signals in a given expression vector, expressed protein levels have been observed to vary dramatically (5, 7). For this reason, several strategies have been developed to express heterologous proteins in bacteria, yeast, mammalian and insect cells as gene-fusions.

The expression of heterologous genes in bacteria is by far the simplest and most inexpensive means available for research or commercial purposes. However, some heterologous gene products fail to attain their correct three-dimensional conformation in E. coli while others become sequestered in large insoluble aggregates or "inclusion bodies" when overproduced. Major denaturant-induced solubilization methods followed by removal of the denaturant under conditions that favor refolding are often required to produce a reasonable yield of the recombinant protein. Selection of ORFs for structural genomics projects has also shown that only about 20% of the genes expressed in E. coli render proteins that were soluble or correctly folded (36, 38). These numbers are startlingly disappointing especially given that most scientists rely on E. coli for initial attempts to express gene products. Several gene fusion systems such as NUS A, maltose binding protein (MBP), glutathione S transferase (GST), and thioredoxin (TRX) have been developed (17). All of these systems have certain drawbacks, ranging from inefficient expression to inconsistent cleavage from desired structure. Comprehensive data showing that a particular fusion is best for a certain family of proteins is not available.

Ubiquitin and ubiquitin like proteins (UBLs) have been described in the literature. The SUMO system has also been characterized. SUMO (small ubiquitin related modifier) is also known as Sentrin, SMT3, PIC1, GMP1 and UBL1. SUMO and the SUMO pathway are present throughout the eukaryotic kingdom and the proteins are highly conserved from yeast to humans (12, 15, 28). SUMO homologues have also been identified in C. elegans and plants. SUMO has 18% sequence identity with ubiquitin (28, 39). Yeast has only a single SUMO gene, which has also been termed SMT3 (23, 16). The yeast Smt3 gene is essential for viability (29). In contrast to yeast, three members of SUMO have been described in vertebrates: SUMO-1 and close homologues SUMO-2 and SUMO-3. Human SUMO-1, a 101 amino-acid polypeptide, shares 50% sequence identity with human SUMO-1/SUMO-2 (29). Yeast SUMO (SMT3) shares 47% sequence identity with mammalian SUMO-1. Although overall sequence homology between ubiquitin and SUMO is only 18%, structure determination by nuclear magnetic resonance (NMR) reveals that the two proteins share a common three dimensional structure that is characterized by a tightly packed globular fold with α-sheets wrapped around one α-helix (4). Examination of the chaperoning properties of SUMO reveals that attachment of a tightly packed globular structure to N-termini of proteins can act as nucleus for folding and protect the labile protein. All SUMO genes encode precursor proteins with a short C-terminal sequence that extends from the conserved C-terminal Gly-Gly motif. The extension sequence, 2-12 amino acids in length, is different in all cases. Cells contain potent SUMO proteases that remove the C-terminal extensions. The C-terminus of SUMO is conjugated to ε amino groups of lysine residues of target proteins. The similarity of the enzymes of the sumoylation pathway to ubiquitin pathway enzymes is remarkable, given the different effects of these two protein modification pathways. Sumoylation of cellular proteins has been proposed to regulate nuclear transport, signal transduction, stress response, and cell cycle progression (29). It is very likely that SUMO chaperones translocation of proteins among various cell compartments, however, the precise mechanistic details of this function of SUMO are not known.

Other fusions promote solubility of partner proteins presumably due to their large size (e.g., NUS A). Fusion of proteins with glutathione S-transferase (GST) or maltose binding protein (MBP) has been proposed to enhance expression and yield of fusion partners. However, enhanced expression is not always observed when GST is used as GST forms dimers and can retard protein solubility. Another problem with GST or other fusion systems is that the desired protein may have to be removed from the fusion. To circumvent this problem, protease sites, such as factor X, thrombin or Tev protease sites are often engineered downstream of the fusion partner. However, incomplete cleavage and inappropriate cleavage within the fusion protein is often observed. The present invention circumvents these problems.

SUMMARY OF THE INVENTION

In accordance with the present invention compositions and methods for enhancing expression levels of a protein of interest in a host cell are provided. An exemplary method comprises i) operably linking a nucleic acid sequence encoding molecule selected from the group consisting of SUMO, RUB, HUB, APG8, APG12, URM1, and ISG15 to a nucleic acid sequence encoding said protein of interest thereby generating a construct encoding a fusion protein, ii) introducing said nucleic acid into said host cell, whereby the presence of said molecule in said fusion protein increases the expression level of said protein of interest in said host cell. In a preferred embodiment the molecule is SUMO encoded by a nucleic acid of SEQ ID NO: 2. The method optionally entails cleavage of said fusion protein and isolation of the protein of interest.

In yet another embodiment of the invention, an exemplary method for generating a protein of interest having an altered amino terminus is provided. Such a method comprises i) providing a nucleic acid sequence encoding the protein of interest; ii) altering the N-terminal amino acid coding sequence in the nucleic acid; iii) operably linking a SUMO molecule to the nucleic acid sequence; and iv) expressing the nucleic acid in a eukaryotic cell, thereby producing the protein of interest in the cell, wherein the eukaryotic cell expresses endogenous SUMO cleaving enzymes, which effect cleavage of SUMO from the sequence encoding the protein of interest, thereby producing a protein of interest having an altered amino terminus. All amino acids with the exception of proline may be added to the amino terminus using this method.

The invention also provides a method for producing a sumolated protein for tracking protein localization within a host cell. An exemplary method comprises i) providing a nucleic acid sequence encoding said protein; ii) substituting the N-terminal amino acid coding sequence in the nucleic acid for a codon which encodes proline; iii) operably linking a SUMO molecule to said nucleic acid sequence; and iv) expressing said SUMO linked protein in said host cell.

In yet another aspect of the invention, a method for enhancing secretion levels of a protein of interest from a host cell is provided. Such a method comprises i) operably linking a nucleic acid sequence encoding molecule selected from the group consisting of SUMO, RUB, HUB, URM1, and ISG15 to a nucleic acid sequence encoding said protein of interest thereby generating a construct encoding a fusion protein, ii) introducing said nucleic acid into said host cell, whereby the presence of said molecule in said fusion protein increases the secretion of said protein of interest from said host cell.

BRIEF DESCRIPTION OF THE DRAWINGS

FIG. 3 is a circular map of pSUMO, an *E. coli* SUMO expression vector. The nucleic acid sequence provided (SEQ ID NO: 37) encompasses the SUMO encoding region and the multiple cloning site. The amino acid sequence provided (SEQ ID NO: 38) is 6×His tagged SUMO. Restriction enzymes are indicated above their recognition sequence. The pSUMO expression vector has been constructed in the backbone of the pET-24d expression vector (Novagen).

(FIG. 8A) and 20° C. (FIG. 8B). *E. coli* cells expressing a SUMO-fusion of MAPKAP2 kinase were induced with 0.1 (lanes 2-4), 0.25 (lanes 5-7), and 0.5 (lanes 8-10) mM IPTG. The original induction sample (I) in addition to the supernatant (S) and resuspended pellet (P) following lysis and centrifugation were analyzed by SDS-PAGE. The first lanes are BioRad low molecular weight markers.

FIG. 14 is a series of micrographs of eGFP expression in Hi-Five cells infected with different eGFP fusion baculoviruses. Pictures were taken with a Leitz Fluovert Inverted Microscope with excitation at 488 nm with Hammamatsu Orca Cooled CCD camera.

FIG. 15 contains stained SDS-polyacrylamide gels representing the in vitro Ulp1 cleavage of Ni-NTA resin purified His6SUMO-eGFP fusion proteins expressed in *E. coli*. The purified His6SUMO-eGFP fusions, containing a different amino acid at the +1 position of the Ulp1 cleavage site, were incubated at 30° C. for 3 hours with purified Ulp1 hydrolase. The lanes are marked with the single letter code of the +1 amino acid. The negative control (−Ve) is the incubation of His6SUMO-eGFP at 30° C. for 3 hours in the absence of enzyme. Low molecular weight markers (LMW) are also provided.

Figure 1:
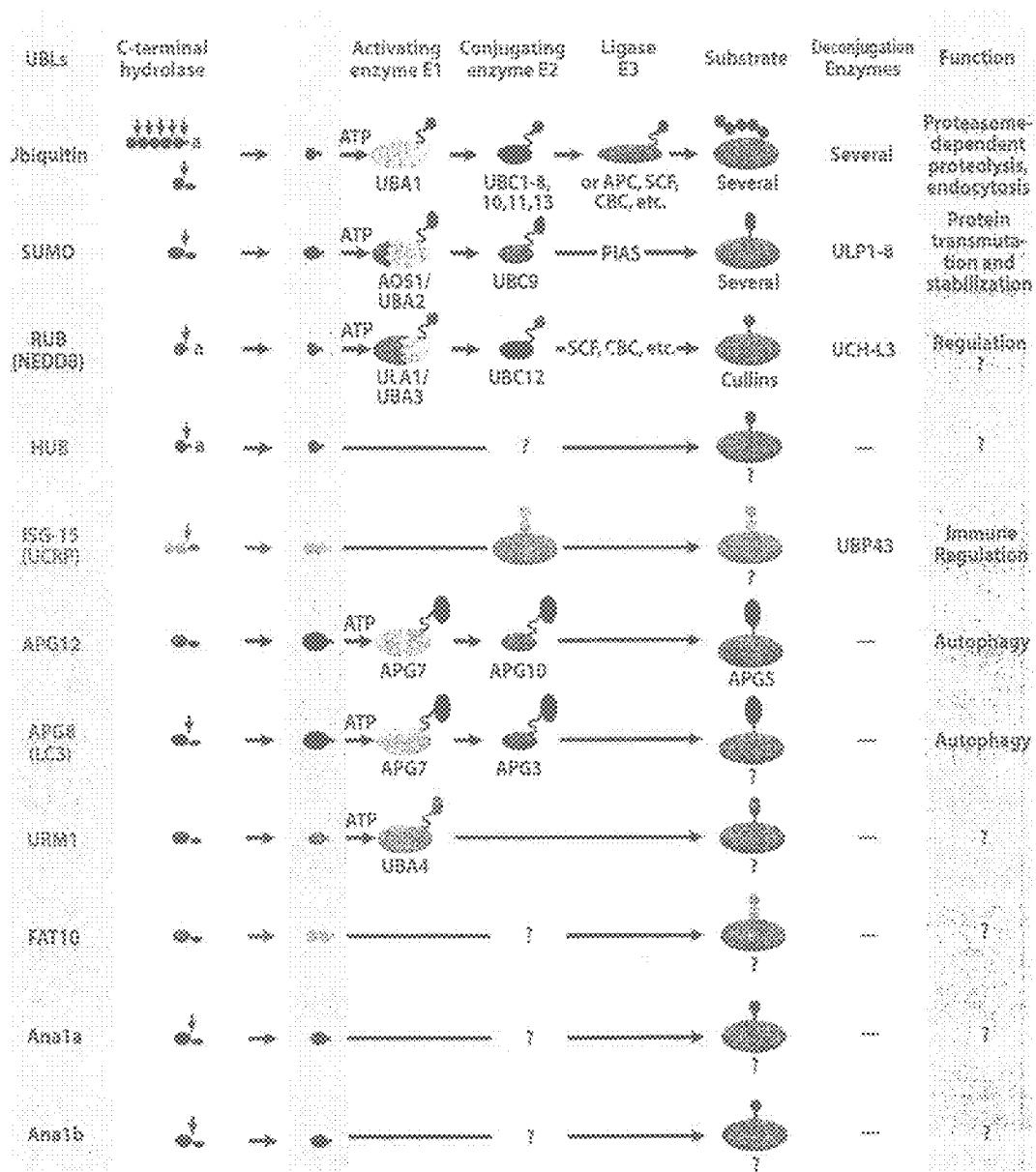
FIG. 1 is a schematic drawing illustrating the conjugation pathways for ubiquitin and ubiquitin-like proteins (UBLs). An arrow in the "C-terminal hydrolase" column indicates the cleavage of the precursor proteins. Only enzymes previously described are provided. The failure to list a particular enzyme in a particular pathway does not preclude the existence of that enzyme.

Lane markers: PMW is molecular weight markers; lane 1 is cellular proteins prior to treatment with guanidinium chloride, lane 2 is guanidinium chloride cell lysates, lane 3 is flow through from Ni-NTA column, lane 4 is elution, and lane 5 is Ulp1 cleavage of elution.

FIG. 23 is the amino acid (SEQ ID NO: 1) and nucleotide (SEQ ID NO: 2) sequences of SUMO.

FIGS. 24A and 24B are the amino acid (SEQ ID NO: 3) and nucleotide (SEQ ID NO: 4) sequences of GFP.

FIGS. 25A and 25B are the amino acid (SEQ ID NO: 5) and nucleotide (SEQ ID NO: 6) sequences of SUMO-GFP.

FIGS. 26A and 26B are the amino acid (SEQ ID NO: 7) and nucleotide (SEQ ID NO: 8) sequences of ubiquitin-GFP.

FIGS. 27A and 27B are the amino acid (SEQ ID NO: 9) and nucleotide (SEQ ID NO: 10) sequences of URM1-GFP.

FIGS. 28A and 28B are the amino acid (SEQ ID NO: 11) and nucleotide (SEQ ID NO: 12) sequences of HUB1-GFP.

FIGS. 29A and 29B are the amino acid (SEQ ID NO: 13) and nucleotide (SEQ ID NO: 14) sequences of RUB1-GFP.

FIGS. 30A and 30B are the amino acid (SEQ ID NO: 15) and nucleotide (SEQ ID NO: 16) sequences of APG8-GFP.

FIGS. 31A and 31B are the amino acid (SEQ ID NO: 17) and nucleotide (SEQ ID NO: 18) sequences of APG12-GFP.

FIGS. 32A and 32B are the amino acid (SEQ ID NO: 19) and nucleotide (SEQ ID NO: 20) sequences of ISG15-GFP.

FIG. 33 is the amino acid (SEQ ID NO: 21) and nucleotide (SEQ ID NO: 22) sequences of SUMO-Protein G.

FIGS. 34A, 34B, and 34C are the amino acid (SEQ ID NO: 23) and nucleotide (SEQ ID NO: 24) sequences of SUMO-β GUS.

FIGS. 35A, 35B, and 35C are the amino acid (SEQ ID NO: 25) and nucleotide (SEQ ID NO: 26) sequences of SUMO-LXRα.

FIGS. 36A and 36B are the amino acid (SEQ ID NO: 27) and nucleotide (SEQ ID NO: 28) sequences of SUMO-Tyrosine Kinase.

FIGS. 37A and 37B are the amino acid (SEQ ID NO: 29) and nucleotide (SEQ ID NO: 30) sequences of SUMO-MPA-KAP2 Kinase.

FIGS. 38A, 38B, 38C, 38D, and 38E are the amino acid (SEQ ID NO: 31) and nucleotide (SEQ ID NO: 32) sequences of SUMO-β GAL.

Figure 39:
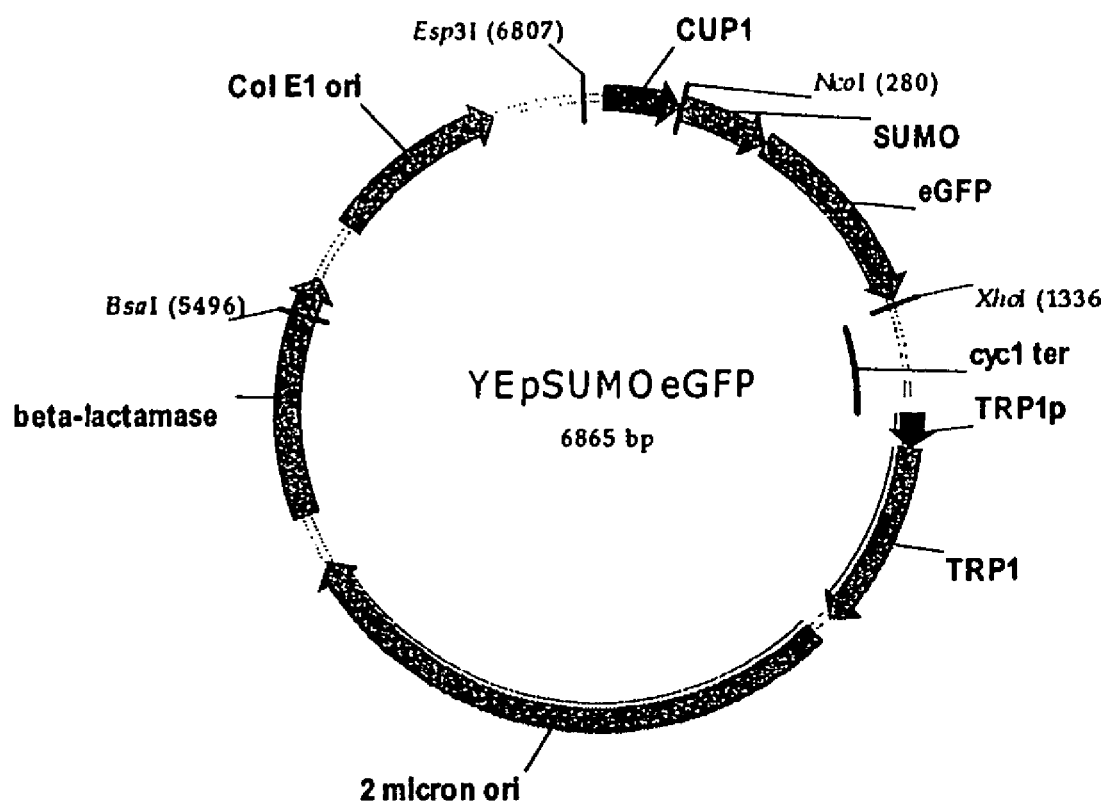

FIG. 39 is a circular map of YEpSUMO-eGFP.

FIGS. 40A, 40B, 40C, 40D, 40E, and 40F are the nucleotide sequence (SEQ ID NO: 33) of YEpSUMO-eGFP. Select restriction enzyme sites are indicated.

Figure 41:
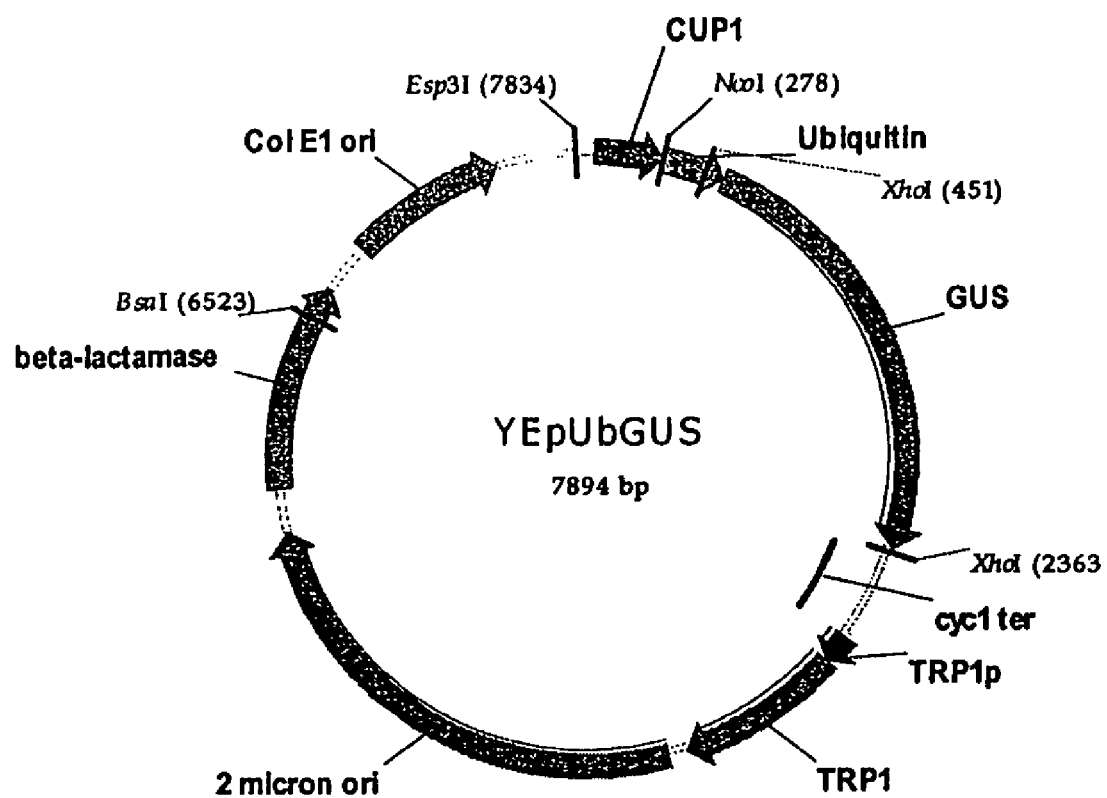

FIG. 41 is a circular map of YEpUbGUS.

FIGS. 42A, 42B, 42C, 42D, 42E, 42F, and 42G are the nucleotide sequence (SEQ ID NO: 34) of YEpUbGUS. Select restriction enzyme sites are indicated.

Figure 43:
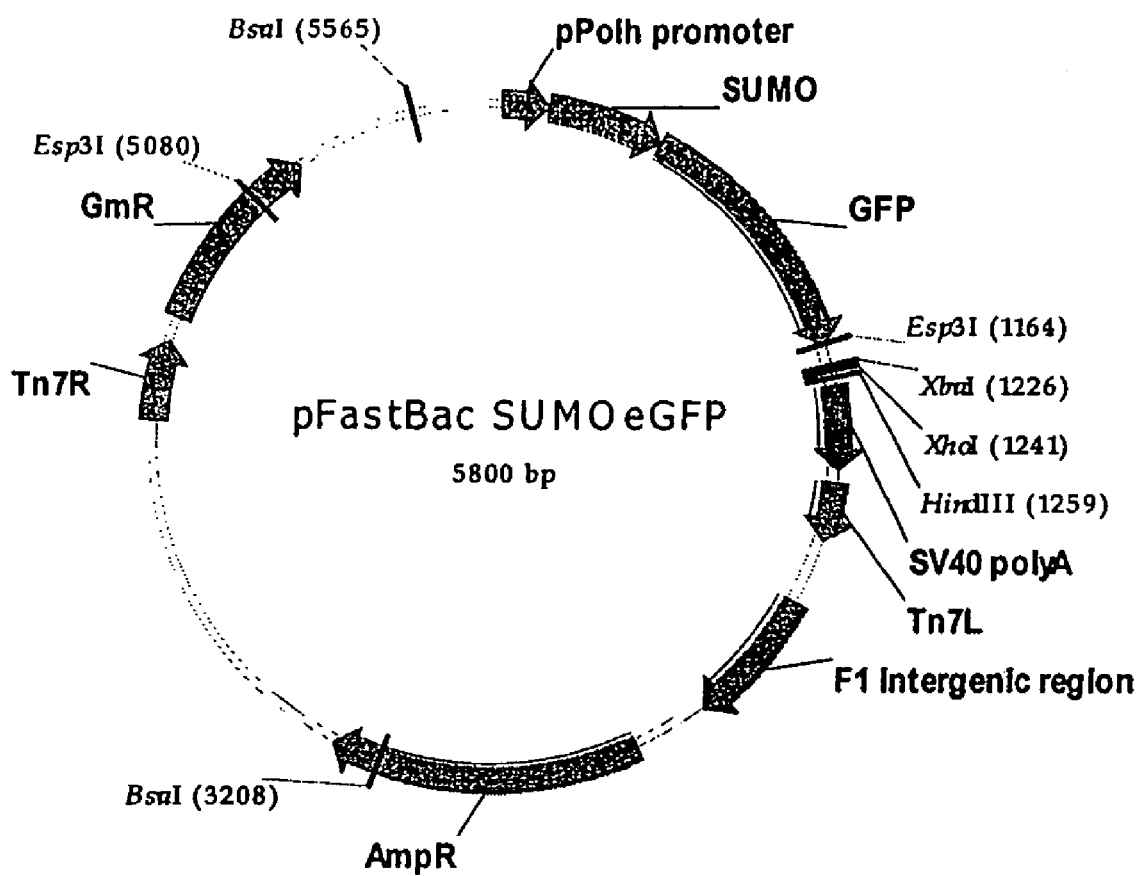

FIG. 43 is a circular map of pFastBac SUMO-eGFP.

FIGS. 44A, 44B, 44C, 44D, and 44E are the nucleotide sequence (SEQ ID NO: 35) of pFastBac SUMO-eGFP. Select restriction enzyme sites are indicated.

Figure 45:
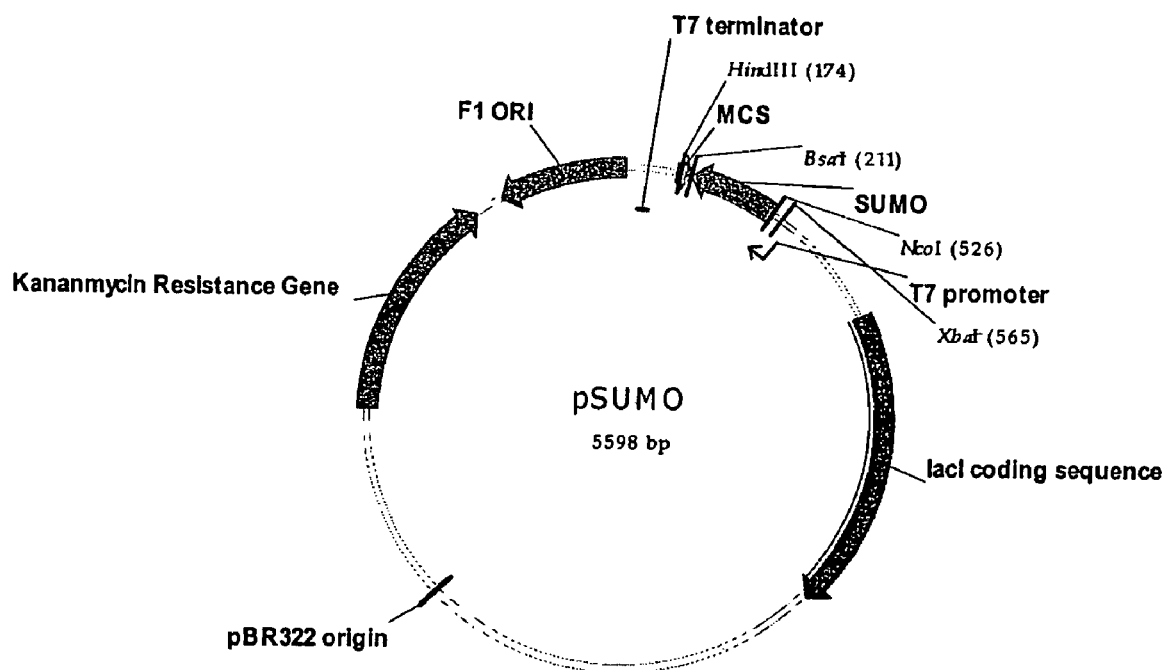

FIG. 45 is a circular map of pSUMO (pET24d6HisxSUMO).

FIGS. 46A, 46B, 46C, 46D, and 46E are the nucleotide sequence (SEQ ID NO: 36) of pSUMO (pET24d6HisxSUMO). Select restriction enzyme sites are indicated.

DETAILED DESCRIPTION OF THE INVENTION

There are a number of reasons for the lack of efficient recombinant protein expression in a host, including, for example, short half life, improper folding or compartmentalization and codon bias. While the Human Genome project has successfully created a DNA "map" of the human genome, the development of protein expression technologies that function uniformly in different expression platforms and for all the protein motifs has not yet been achieved.

In accordance with the present invention, it has been discovered that that N-terminal fusion of the ubiquitin homologue SUMO or Smt3 to otherwise unexpressed or poorly expressed proteins remarkably enhances the expression levels of biologically active proteins in both prokaryotes and eukaryotes. The Ubiquitin-Like protein (UBL) family contains many proteins, including for example, SUMO, Rub1, Hub1, ISG15, Apg12, Apg8, Urm1, Ana 1a and Ana 1b (15, 28). See Table 1. The hallmark of all of these proteins, exept APG12, and URM1, is that they are synthesized as precursors and processed by a hydrolase (or proteases) to generate mature carboxy-terminal sequence. Secondly, all of the UBLs share a common structure.

In *E. coli*, fusion proteins remained intact while in yeast or insect cells fusion proteins were efficiently cleaved, except when proline was the N-terminal residue of the target protein. While any of the UBLs set forth in Table 1 may be utilized in the compositions and methods of the invention to enhance expression of heterologous fusion proteins of interest, SUMO is exemplified in the gene fusion system provided herein.

TABLE 1

Properties of Ubiquitin-like Proteins (UBLs)

| UBL (yeast) | Function | Knockout phenotype | Substrate | % UB Identity | KDa | Hydrolase | COOH Residues |
|---|---|---|---|---|---|---|---|
| UB | Translocation to proteasome for degradation. | not viable | many | 100 | 8.5 | UCH/UBPs | LRLR GG (SEQ ID NO: 39) |
| SUMO (SMT3) | Translocation to nucleus | not viable | Sentrins, RanGap, others | 18 | 11.6 | Aut1/Aut2 | GG |
| RUB1 (NEDD8) | Regulation of mitosis. | viable; non-essential. | cullins, cytoskelet. proteins | 60 | 8.7 | not known | GG |
| HUB1 | Cell polarization during mating projections. | viable; deficient in mating. | Sph1, Hbt1 cell polarity factors | 22 | 8.2 | not known | YY |

TABLE 1-continued

Properties of Ubiquitin-like Proteins (UBLs)

| UBL (yeast) | Function | Knockout phenotype | Substrate | % UB Identity | KDa | Hydrolase | COOH Residues |
| --- | --- | --- | --- | --- | --- | --- | --- |
| ISG-15 (UCRP) | Unknown | IFN, LPS hypersensitivity; death | many | ~30; 28 (two domains) | 15.0 | UBP43 (USP18) | LRLR GG (SEQ ID NO: 39) |
| APG12 | Autophagy | viable, defective in autophagy | Apg5 | 18 | 21.1 | not cleaved | FG |
| URM1 | Unknown | ts growth; non-essential. | unknown | 20 | 11.0 | not known | GG |
| APG8 (LC3) | Autophagy | viable; no autophagocytosis or sporulation | phospatidyl-ethanol-amine | 18 | 13.6 | Apg4/Aut2 | FG |

The SUMO fusion system of the present invention has been successfully applied to express different molecular weight proteins such as 6 KDa Protein G domain to 110 KDa β-galactosidase in E. coli and eukaryotic cells. More specifically, the system allows one to: (1) enhance the expression of underexpressed proteins; (2) increase the solubility of proteins that are insoluble; (3) protect candidate proteins from degradation by intracellular proteases by fusing UBLs to their N-termini; (4) cleave the fusion protein to efficiently generate authentic proteins using naturally-present enzymes (5) generate proteins with novel amino termini; and (6) cleave all fusion proteins with remarkable efficiency irrespective of the N-terminal sequence of the fused protein, using UBL hydrolases such as SUMO hydrolase Ulp1. Because UBLs are small molecular weight proteins (~100 amino acids), they can also be used as purification tags as well. These remarkable properties of UBLs make them excellent candidates for enhancing expression and solubility of proteins. The method may also be utilized to generate novel amino termini on proteins of interest for a variety of research, diagnostic and therapeutic applications.

The ultimate fate of ubiquitinated or sumoylated proteins within a cell varies. A protein can be monoubiquitinated or polyubiquitinated. Ubiquitination of protein has multiple functions and gives rise to different fates for the protein within a cell (11). Ubiquitination primarily targets proteins to 26S proteosome for degradation (13). On the other hand, sumoylation of target proteins does not lead to degradation, but, rather, leads directly or indirectly to altered localization of proteins (15). There are about 17 deubiquitinating enzymes that cleave conjugated ubiquitin from target proteins as well as ubiquitin-ubiquitin and ubiquitin artificial-fusion proteins (1, 35). Thus far it appears that yeast has two cysteinyl proteases, called Ulp1 and Ulp2, that remove SUMO from ε-amino groups of lysine as well from the artificial linear SUMO-fusions (20, 21).

To determine if UBLs and SUMO fusion will enhance expression of recombinant proteins of different sizes and function, we have designed several UBL-GFP fusion proteins in addition to SUMO-fusion proteins and monitored their expression levels in E. coli, yeast and insect cells. In E. coli, the proteins are expressed as intact fusions, while in eukaryotes, the fusions were efficiently cleaved. A dramatic increase in the yield of proteins after fusion with SUMO and expression in E. coli was observed. In additional studies, SUMO-GFP protein was used as a model fusion for detailed studies in yeast and insect cells. We have designed SUMO-GFP fusion where all the N-terminal methionine residues have been replaced with the rest of the 19 amino acids. We have purified 20 sumo-GFP fusion proteins from E. coli and cleaved them in vitro with Ulp1. Ulp1 efficiently cleaved 19 out of the 20 possible amino acid junctions. The proline junction was not cleaved. As compared to deubiquitinating enzyme (3), Ulp1 demonstrated broad specificity and robustness in its digestion properties. Proteins having a wide range of molecular weights were cleaved efficiently by Ulp1. Similarly, in yeast, and insect cells, the fusion proteins were efficiently processed, yielding intact, biologically active proteins. In addition to enhancing protein expression levels, the SUMO-fusion approach can be used to advantage to generate desired N-termini to study novel N-terminal protein functions in the cell. Since SUMO fusion can both enhance recombinant protein yield and generate new N-termini, this technology provides an important tool for post-genomic biotechnology analyses.

The materials and methods set forth below are provided to facilitate the practice of the present invention.

Design and Construction of E. coli Expression Vectors:

The original vector backbone was developed using pET 24d vector from Novagen (see FIG. 3 as well as FIGS. 45-46A-E). pET24d uses a T7 promoter system that is inducible with IPTG. The vector has a kanamycin selection marker and does not contain any translation terminator.

Figure 2:
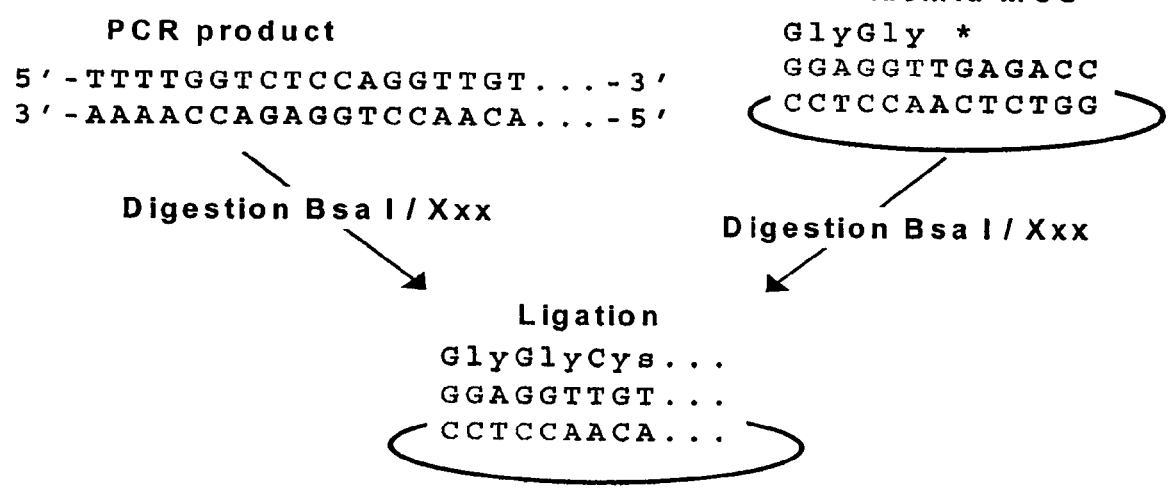
FIG. 2 is a schematic representation of the cloning strategy used to express SUMO fusion proteins. In this cloning strategy, a Bsa I site is introduced directly downstream of a SUMO sequence within a desired vector. The nucleic acid sequence encoding the protein to be expressed as a fusion with SUMO is amplified by PCR with primers that introduce a Bsa I site at the 5' end. The vector (SEQ ID NO: 62, top strand; SEQ ID NO: 63, bottom strand) and the PCR product (SEQ ID NO: 60, top strand; SEQ ID NO: 61, bottom strand) are cleaved by Bsa I and an appropriate restriction enzyme (represented by Xxx) that allows for insertion of the cleaved PCR product into the vector.

Construction of Variable His6SUMO-GFP Fusions:

A N-terminal six his-tagged SUMO (fusion vector was constructed as follows. A PCR product was generated with the primers 5'CCATGGGTCATCACCATCATCAT-CACGGGTCGGACTCAGAAGTCAATCAA-3' (SEQ ID NO: 40) and 5'-GGATCCGGTCTCAACCTCCAATCTGT-TCGCGGTGAG-3'(SEQ ID NO:41) using yeast Smt3 gene (16) as a template (kind gift of Erica Johnson). The PCR fragment was double digested with Nco I and Bam HI, and then ligated into pET24d, which had been similarly digested. It is important to note that the current invention utilizes a variant of the wild type yeast SUMO sequence. The A nucleotide at position 229 has been replaced with a G nucleotide, thus encoding an alanine instead of a threonine (SEQ ID NOS: 64 and 65). The detailed cloning strategy is provided in FIG. 2. The pET24d His6Smt3eGFP fusions, containing each of the twenty different amino acids at the +1 position of the cleavage site were generated as follows. The eGFP sequence was amplified a template, with the primers 5'-GGTCT-CAAGGT NNNGTGAGCAAGGGCGAGGAGC-3' (SEQ ID NO:42) and 5'-AAGCTTATTACTTGTACAGCTCGT CCATGCC-3'(SEQ ID NO: 43), where the NNN in the forward primer corresponding to the variable codon encoding one of the twenty amino acids. The PCR products were purified and double digested with Bsa I and Hind III, these were then ligated into the pET24dHisSUMO vector which had been similarly digested. Plasmids from clones containing the variable inserts, were sequenced to confirm the presence of the novel codon in each.

Construction of SUMO-Fusion Vectors from pSUMO:

The gene encoding the protein of interest is cloned in frame with the SUMO tag, in the pSUMO vector, by utilizing the encoded Bsa I site. Bsa I belongs to the family of Class IIS restriction enzymes, which recognize non-palindromic sequences, and cleave at a site that is separate from their recognition sequences. The latter trait gives Class IIS enzymes two useful properties. First, when a Class IIS enzyme recognition site is engineered at the end of a primer, the site is cleaved when digested. Second, overhangs created by Class IIS enzymes are template-derived and thus unique. This is in clear contrast to regular Class II restriction enzymes such as EcoRI, which creates an enzyme-defined overhang that will ligate to any EcoRI-digested end. The unique overhangs produced by Class IIS enzymes can be ligated only to their original partner.

It is often preferable to amplify the gene encoding the protein of interest via PCR prior to cloning into the pSUMO vector. The forward primer must contain the additional standard sequence:

5'-GGTCTCAAGGTNNN-3'(SEQ ID NO:44) where GGTCTC is the Bsa I site and NNN is the first codon of the gene encoding the protein of interest. Additional nucleotides are required for the primer to anneal specifically with the gene of interest during the PCR amplification. The reverse primer may contain another restriction enzyme such as Xho I to allow for directional cloning of a gene into pSUMO. Bsa I can also be employed in the reverse primer to simplify cloning steps, for example, in the following primer:

```
5'-GGTCTCCTCGAGTTANNN-3'      (SEQ ID NO: 45)
```

The PCR product can be digested with both Xho I and Bsa I. A digestion reaction containing just the latter enzyme generates a product that would directionally ligate into the pSUMO vector between the Bsa I and Xho I sites of the MCS.

Construction of pSUMO-Protein G fusion *E. coli* expression vector:

The B2 IgG binding domain (9) from *streptococcus* G148 protein was synthesized by three synthetic oligonucleotides. The sequence of the gene is 5'-GT CTTAAGA CTA AGA GGT GGC ACG CCG GCG GTG ACC ACC TAT AAA CTG GTG ATT AAC GGC AAA ACC CTG AAA GGC GAA ACC ACC-3'. (SEQ ID NO:46) The 81 bps oligo sequence is 5'-GCC GTT ATC GTT CGC ATA CTG TTT AAA CGC TTT TTC CGC GGT TTC CGC ATC CAC CGC TTT GGT GGT TTC GCC TTT CAG-3'. (SEQ ID NO:47) The 86 pbs oligo sequence is 5'-CAG TAT GCG AAC GAT AAC GGC GTG GAT GGC GTG TGG ACC TAT GAT GAT GCG ACC AAA ACC TTT ACC GTG ACC GAA TAA GGT ACC CC-3'(SEQ ID NO:48). The bolded nucleotides refer to the AflII and Kpn1 sites that flank the protein G domain. ACG is the first amino acid residue of the domain. The above three oligos were annealed using the Life Technologies protocol. The annealed fragments were extended by Pol1 enzyme. The resultant gene was PCR amplified by the following oligo primers G1 forward 5'-CTT GTC TTA AGA GGT-3' (SEQ ID NO:49) and G2 reverse primer 5'-GCT GGG TAC CTT ATT CGG TCA-3'(SEQ ID NO:50). The above protein G gene was cloned at the AflII and Kpn1 site of the human ubiquitin gene and expressed as ubiquitin-protein G fusion protein in an *E. coli* pET 22 expression vector (Novagen). The protein G sequence was in turn amplified from the ubiquitin-protein G fusion plasmid by using the primers 5'-GGTCTCAAGG-TACGCCGGCGGTGACCACCT-3'(SEQ ID NO: 51) and 5'-AAGCTTATTATTCGGTCACGGTAAAGGTTT-3'(SEQ ID NO:52) and inserted in pSUMO to generate pSUMO-protein G expression vector.

Construction of *E. coli* SUMO-β-Galactosidase Expression Vector.

*E. coli* β-galctosidase was amplified using pfu (Stratagene) a preparation of genomic DNA from BL21 (DE3) (Stratagene) as a template and the primers 5'-GGTCTCAAGGTAT-GACCATGATTACGGATTCACT-3' (SEQ ID NO:53) and 5'-AAGCTTATTATTATTATTTTTGACACCAGACC-3' (SEQ ID NO:54). The PCR products were purified and double digested with Bsa I and Hind III. These were then ligated into the vector pET24d6xHisSUMO, which had been similarly digested.

Construction of *E. coli* pSUMO-Liver X Receptor (LXR) Expression Vector:

The PCR products of the LXR from amino acid residue 189 to the end of the protein that spans the ligand binding domain was digested with BsaI and HindIII and ligated into the pSUMO vector, also digested with Bsa1 and HindIII.

Figure 8A:
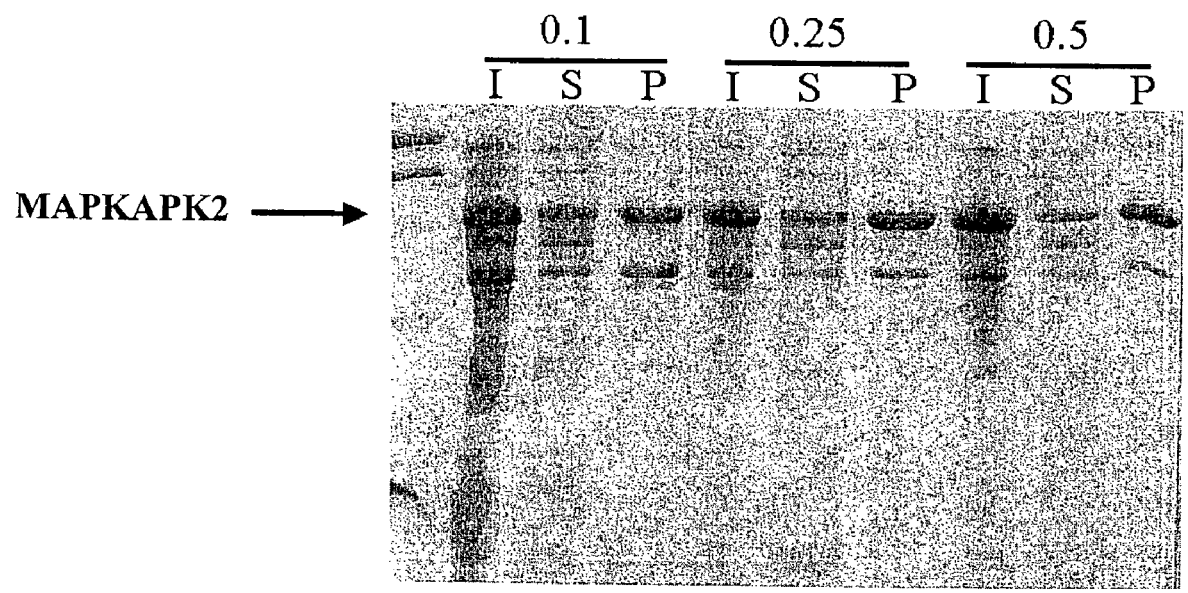
FIGS. 8A and 8B display stained SDS-polyacrylamide gels demonstrating the solubility of the SUMO-MAPKAPK2 fusion protein expressed at 37° C.
Figure 8B:
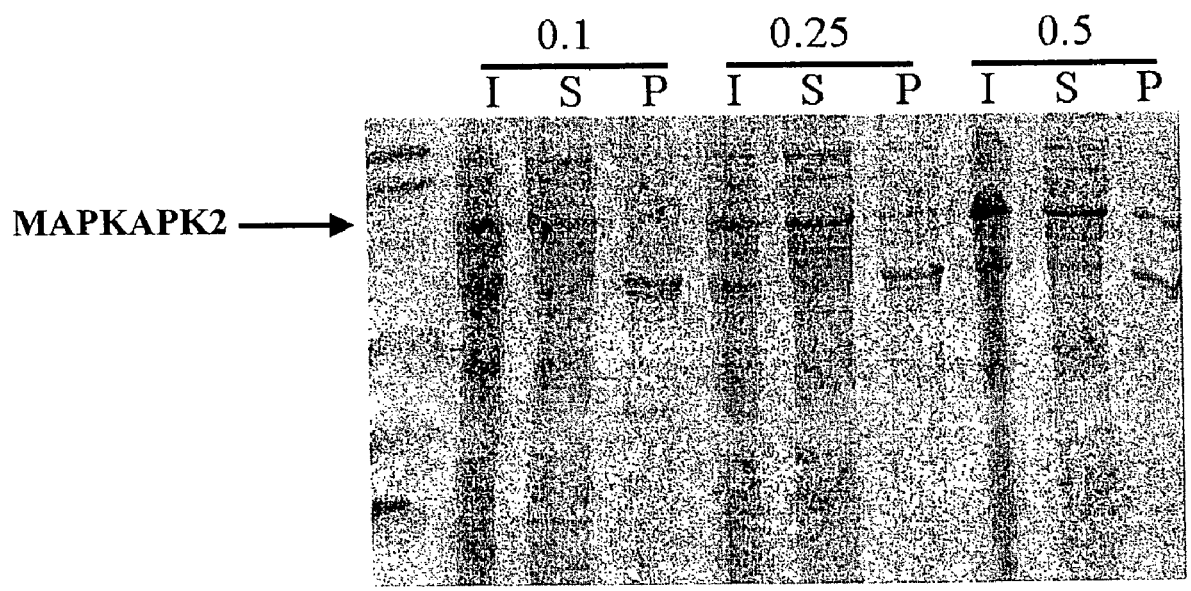

Construction of *E. coli* pSUMO-MAPKAP2 Expression Vector:

The fragment of MAPKAP2, encoded in the plasmid pMON45641, was amplified by PCR and cloned into pET24d 6H is SUMO vector by designing PCR primers that flank the sequence shown FIGS. 8A and 8B. The SUMO vector was digested with Bsa I site and Hind III. The cloning procedure yields a fusion protein, which, upon expression, purification and cleavage, generates the desired protein whose first amino acid is a glutamine (CAG).

Construction of *E. coli* pSUMO-Tyrosine Kinase Expression Vector:

For the tyrosine kinase, both, the SUMO fusion and unfused expression vectors were designed. As described above the region of kinase was cloned by PCR flanked with BsaI and Hind III sites that were cloned in to similarly digested pSUMO.

Construction of *E. coli* pSUMO-β-Glucuronidase Expression Vector:

*E. coli* β-glucuronidase was the kind gift of Ben Glick, University of Chicago) and amplified with the primers 5'-GGTCTCAAGGTATGCAGATCTTCGTCAAGACGTT-3'(SEQ ID NO:55) and 5'-AAGC TTATTATTGTTTGCCTC-CCTGCTGCG-3'(SEQ ID NO:56).

Construction of *E. coli* SUMO-Hydrolase Expression Vector:

C-terminal His-tagged SUMO hydrolase/protease Ulp (403-621)p (21) (27) was expressed from pET24d in Rosetta (DE3) pLysS (Novagen). The recombinant protein was purified using Ni-NTA agarose (Qiagen) and buffer exchanged into 20 mM Tris-HCl pH 8.0, 150 mM NaCl and 5 mM β-mercaptoethanol using a PD-10 column (AP Biotech). About 2 ug of the pure protein was analyzed on gels and data shown in FIG. 6 lane Ulp1. The protein was almost 90% pure as judged by SDS-PAGE analysis.

Construction of *E. coli* UBL-GFP Fusion Vectors.

DNA sequences encoding ubiquitin (Ub), SUMO, Urm1, Hub1, Rub1, Apg8, and Apg12 were PCR-amplified using Deep-Vent polymerase (NEB) and yeast strain DNA to generate a template. Full-length human ISG15 cDNA was a kind gift of Dr. A. Haas, Medical College of Wisconsin, Milwaukee. A unique NcoI site followed by 6His sequence was introduced by PCR at the 5'-end of each Ubl cDNA. Primer sequence at the 3'-end included unique Esp3I and HindIII sites. PCR products were digested with NcoI/HindIII and inserted into respective sites of pET24d vector (Novagen) as described above. Full length GFP sequence (Clontech Cat # 60610-1) flanked by Esp3I and HindIII sites, respectively, was PCR-amplified and cloned into pCR4-TOPO-TA vector (Invitrogen). Esp3I/HindIII digested GFP-encoding gene was inserted into respective sites of pET24d-UBL1 plasmids, creating final UBL-GFP expression vectors for *E. coli*. In toto, there were nine plasmid constructs coding for the following structures: 6His-Ubl-GFP. All plasmids were sequenced to confirm the expected structure.

Design and Construction of Yeast UBL-Fusion Vectors:

*Saccharomyces cerevisiae* has been used as a eukaryotic model for all the experiments involving yeast. All of the expression vectors for these studies were designed on multicopy yeast vectors that contain tryptophan or leucine as a selectable marker and 2µ as an origin of replication (22). Proteins were expressed as unfused products or as ubiquitin, SUMO or other UBL fusion proteins.

Construction of the β-Glucuronidase Yeast Expression Vectors:

To demonstrate that UBLs increase the level of secretion of the protein to the media, in addition to enhancing the level of expression, expression vectors were constructed with and without ubiquitin. We have also compared ubiquitin fusion and SUMO fusion using GFP as a model protein (see FIG. 9 and FIG. 10). pRS425-GUS plasmid was produced by cloning the XhoI-SacI fragment (containing *E. coli* β-Glucuronidase (GUS)) from plasmid pGUS1 (25, 22) into the XhoI-SacI sites of plasmid pRS425 (32). The next construction involved addition of a promoter, and resulted in the plasmid pRS425-ADH1p-GUS. The fragment XhoI-HindIII (containing the ADH1 promoter) was inserted into the XhoI-HindIII sites of the plasmid pRS425-GUS. The ADH1 promoter XhoI-HindIII fragment was cloned using polymerase chain reaction (PCR), amplifying the ADH1 promoter from the plasmid pGRIP1 (37). The following primers were used to amplify the full length ADH1 promoter: ADH1-XhoI: 5'-gctcgagagcacagatgcttcgttg-3'(SEQ ID NO:57), and ADH1-HindIII: 5'-gcaaagcttggagttgattgtatgc-3'(SEQ ID NO:58). The underlining indicates the nucleotide sequence of the XhoI and HindIII restriction sites. PCR of the DNA fragment involved amplification in 30 cycles (96° C.-30 sec., 54° C.—1 min. and 72° C.—3 min.) using high replication fidelity Deep Vent Polymerase (New England Biolabs). The PCR product was then digested with XhoI and HindIII, and subsequently cloned into the XhoI-HindIII sites of pRS425-GUS. Construction of the next set of plasmids involved a change in promoter. The following two plasmids were constructed to give expression vectors containing either a methionine or proline junction between the ubiquitin and the GUS. pRS425-GPDp-Ub(Methionine)-GUS and pRS425-GPDp-Ub(Proline)-GUS were similarly constructed using both pre-constructed plasmids and PCR amplification. The final expression construct was pRS425-CUP1p-SUMO-GUS, which was the only plasmid produced with the CUP1, copper regulated promoter. This plasmid was digested with the enzymes BglII and NsiI, releasing the CUP1 promoter (6). The CUP1 fragment was then ligated to pRS425-GPDp-Ub-GUS, having also been digested with BglII-NsiI.

Construction of SUMO-N-GFP Yeast Expression Vector:

To determine what variety of N-terminal variant amino acids at the junction of SUMO and GFP can be cleaved in yeast we designed SUMO-GFP vectors in which all 20 amino acid residues were encoded at the N-terminus of GFP. Essentially all 20 SUMO-X-GFP vectors designed for *E. coli* expression were digested with Bsa I-Hind III, and the inserts were purified. The 20 inserts were cloned in Yep12 that was slightly modified. Specifically, YeEpSW was generated by digesting Yep12 with Bam HI and SacI. The CUP1 promoter region was recovered from the fragment by PCR. A polylinker was created at the 3' end of CUP1 with a variety of restriction sites including NcoI and Xho1. All 20 SUMO-GFPs (N end variants) were digested with NcoI-XhoI enzymes and cloned directly YepSW. The resultant vector YepSW-SUMO-eGFP utilizes tryptophan selection and expresses SUMO-GFP proteins under the control of the copper promoter. All vectors were sequenced to ensure correct codons at the junction of SUMO and GFP.

Construction of UBL-GFP Fusion Yeast Expression Vectors:

Construction of the UBL-GFP fusion vectors for *E. coli* has been described above. In order to make UBL yeast expression vector NcoI/XhoI fragments carrying GFP alone and all the Ubl-GFP fusions were inserted into respective sites of pYEp SW (see above) that was similarly digested with NcoI/XhoI. Insertion of UBL-GFP cassette in Yep SW (See FIGS. 39 and 40A-40F), allows copper inducible expression of Ubl-GFP fusions in yeast system.

Figure 11A:
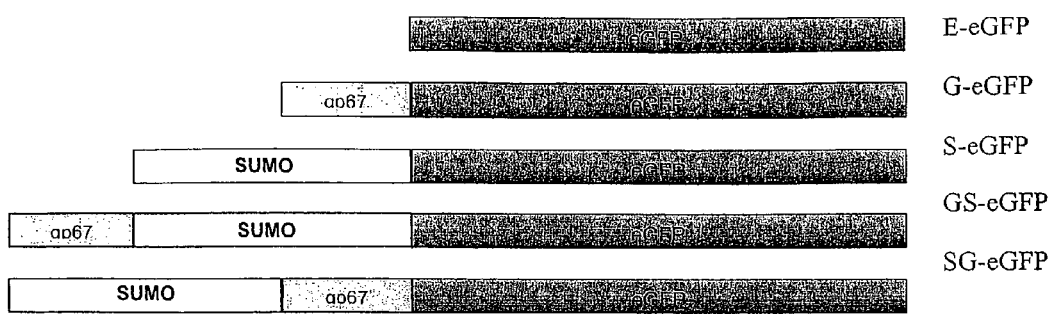
FIGS. 11A and 11B are schematic representations of the SUMO (FIG. 11A) and ubiquitin (FIG. 11B) GFP fusion proteins that also contain the gp67 secretory signal. In construct E, only unfused GFP protein is expressed. In construct G, a 7 kDa secretory sequence from gp67 was attached to the N-terminus of GFP. In constructs S and U, SUMO and ubiquitin sequences, respectively, are inserted in frame to the N-terminus of GFP. In constructs GS and GU, gp67 sequences are followed by SUMO and ubiquitin, respectively, and then GFP. In constructs SG and UG, gp67 sequences are inserted in between the C-terminus of SUMO and ubiquitin, repectively, and the N-terminus of GFP.
Figure 11B:
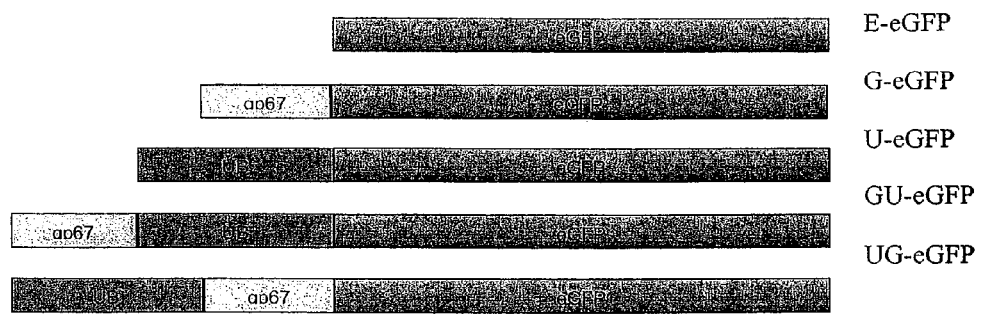

Design and Construction of Recombinant Baculovirus for SUMO and Ubiquitin GFP Fusion Expression:

To demonstrate that attachment of SUMO or ubiquitin to GFP increases its expression and enhances secretion into the media, several GFP fusion vectors were designed with different configurations of gp67 secretory signals. The basic GFP vector for expression is essentially based on *E. coli* vectors described above. Derivatives of this vector representing each candidate gene have been constructed by designing PCR primers. The construction of GFP plasmid transfer vectors for baculovirus is described. To help appreciate the rationale for the secretory signal in the context of GFP-fusion, see the diagrammatic representation shown in FIG. 11. Single letter code refers to unfused GFP (E); gp67-sec signal-GFP (G); ubiquitin-GFP (U); SUMO-GFP(S); gp67-Ub-GFP (GU); Ub-gp67-GFP (UG); gp67-SUMO-GFP (GS); and SUMO-gp67-GFP (SG).

(i) pFastbacE. A synthetic oligonucleotide containing the Esp3I site was inserted between BamHI and EcoRI cloning site of the transfer vector pFastbac1, which had been modified by removing Esp3I site from Gmr region. (ii) pFastbacG. The signal sequence of the gp67 gene derived from pACSecG2T was isolated by PCR using 2 primers (f-gp67 and r-gp67), digested with BglII and EcoRI in the next step, and then inserted between BamHI and EcoRI cloning sites of the transfer vector pFastbacE. (iii) pFastbacS. A full-length SUMO gene derived from pET SUMO was generated by PCR using 2 primers (f-bacsmt and r-bacsmt), digested with BsaI and EcoRI in the next step, and then inserted between BamHI and EcoRI cloning sites of the transfer vector pFastbacE. (iv) pFastbacG/S. The signal sequence of the gp67 gene in the pACSecG2T vector was generated by PCR using 2 primers (f-fusgp67 and r-fusgp67), and inserted between BamHI and EcoRI cloning sites of the transfer vector pFastbacE to create a new pFastbacG, which was used for fusion with SUMO afterward. A full-length SUMO gene derived from pET SUMO as described above (iii) was digested with BsaI and SacI and inserted between Esp3I and SacI cloning sites of the new transfer vector pFastbacG. (v) pFastbacS/G. A full-length SUMO gene derived from pET SUMO was generated by PCR using 2 primers (f-fussmt3 and r-fusgp67) and inserted between BamHI and EcoRI cloning sites of the transfer vector pFastbacE to create the new pFastbacS, used for fusion with gp67 afterward. The signal sequence of the gp67 gene derived from pACSecG2T as described above (ii) was digested with BsaI and SacI, and then inserted between the Esp3I and SacI cloning sites of the new transfer vector pFastbacS.

Preparation of Baculovirus Stocks and Cell Growth.

Transfer vector constructs based on the pFastbac 1 shuttle plasmid (Invitrogen, Inc.) were transposed in DH10Bac *E. coli* competent cells to transfer the respective e-GFP fusion sequences into recombinant virus DNA by site-specific integration. After alkaline lysis of transformed (white colonies) of *E. coli* cells, which contain recombinant virus (bacmid) DNA, and extraction of the recombinant bacmid DNA, the bacmid DNA was used to transfect *Spodoptera frugiperda* (Sf9) insect cells, in which virus replication occurs. The virus was then amplified to produce passage 2 (for long-term storage) and passage 3 virus (for working) stocks by infection of fresh Sf9 cell cultures and used directly to infect cells for fusion protein expression. Virus infectivity (pfu/ml) was determined by titration in Sf9 cells using the BacPAK™ Rapid Titer Kit (BD Sciences Clontech, Inc.). A 50 ml culture of Hi-Five cells at concentration of $1 \times 10^6$ cells/ml, was infected with recombinant virus at MOI=5 in Express Five media (serum free media). The cells were grown in 100 ml spinner flask at 27° C. Every 24 hours, cell viability was determined by trypan blue and cell counting. 5 ml of the suspension culture was removed at 24 hour intervals, centrifuged at 500×g at 4° C. in 10 minutes. The supernatant was transferred into a fresh tube to monitor any protein that may have been secreted into the media (see below).

Analysis of Proteins from Insect Cell Compartments:

Cell pellets (from above step) were gently washed in 1 ml PBS and recentrifuged at 500×g at 4° C. for 10 minutes. All supernatant and pellets are stored at −80° C. The presence of recombinant protein in cells and media was ascertained by SDS-PAGE and Western blotting of supernatant and cell pellets. The total intracellular protein was extracted by M-PER extraction buffer (Pierce), a neutral buffer for protein extraction. The cell pellet was mixed with rapid pipetting and incubated for 1 hour on an orbital shaker. The suspension was centrifuged at 500×g at 4° C. for 10 minutes to remove debris. The supernatant contained extracted cellular proteins that were either analyzed by PAGE or stored at −80° C. To analyze the proteins present in the media, the following procedure was adopted. Trichloroacetic acid was added to 5 ml media to a final concentration of 20%. The suspension was mixed well and left on ice for three hours, and then centrifuged 500×g at 4° C. for 10 minutes. The white pellet was washed with 80% ethyl alcohol twice, and then dried. The pellet was suspended in 1 ml of M-PER buffer for PAGE to compare the distribution of control (unfused) and SUMO-fused proteins inside and outside the cell.

Methods for Analysis of Yeast Expressed Fusion Proteins:

Yeast cultures were grown in synthetic or rich media. Standard yeast and *E. coli* media were prepared as described (31). The yeast strain Y4727: Matαhis3-Δ200 leu2-Δ0 lys2-Δ0 met5-Δ0 trp1-Δ63 ura3-Δ0 was used as a host (gift from Dr. Jeff Boeke) or BJ 1991. Yeast transformation was performed according to published procedures (8). Yeast transformants with autonomously replicating plasmids were maintained in yeast selective media. The *E. coli* β-Galactosidase and β-Glucuronidase proteins were expressed under the regulation of either the alcohol dehydrogenase (ADH), or Glyceraldehyde-Phosphate-Dehydrogenase (GPD) promoter or copper metallothioneine (CUP1) promoter in 2 μm multicopy plasmids with the LEU2 selective marker.

Yeast cells were transformed with appropriate expression vectors, and single colonies were grown in synthetic media minus the selectable marker. For each protein, at least two single colonies were independently analyzed for protein expression. Cells were grown in 5 ml culture overnight and, in the morning, the culture was diluted to an O.D. at 600 nm of 0.5. If the gene was under the control of copper inducible promoter, copper sulfate was added to 100 uM and the culture was allowed to grow for at least three hours. Cells were pelleted at 2000×g for 5 minutes, washed with 10 mM Tris-EDTA buffer pH 7.5. If enzymatic assays were performed, cells were disrupted in assay buffer with glass beads, 2× times the volume of the pellet. Cells were centrifuged and the supernatant was recovered for enzymatic or protein analysis. Alternatively, if the level and the type of protein was analyzed by SDS-PAGE, cell pellet was suspended in SDS-PAGE buffer and boiled for 5 mins. The suspension was centrifuged, and 10-20 ul aliquots were run on 12% SDS-PAGE.

Measurement of β-GUS Activity from Yeast:

β-Glucuronidase (GUS) is a 65 kDa protein that is a useful marker for protein trafficking. We have used GUS to determine the role of N-terminal ubiquitin on secretion of GUS in yeast. Yeast cells were transformed with various GUS vectors, grown overnight in selective liquid media at 30° C., and diluted in the liquid selective media to 0.1 OD600 (OD culture). Yeast cells were incubated in the presence of inducer in shaker at 30° C. After 4 hours of incubation, 100%1 of 2×"Z" Sarcosine-ONPG buffer (120 mM Na2HPO4, 80 mM NaH2PO4, 20 mM KCl, 2 mM MgSO4, 100 mM β-mercaptoethanol, pH 7.0, 0.4% lauroyl sarcosine) was added. (The 2×"Z" Sarcosine-buffer is freshly prepared or stored at −20° C. prior use.) We used a fluorometric assay with 4-methylumbelliferyl β-D-glucuronide as the substrate for β-GUS assay. After incubation at 37° C. for 1 hour (t incubation), the reaction was stopped by adding 100 μl of quenching solution, 0.5 M Na$_2$CO$_3$. The GUS activity was determined by reading the plates in a fluorometric plate reader. For calorimetric reactions, relative activity was calculated as following: (1000×OD reaction)/(t incubation×OD culture).

*E. coli* Growth, Compartmentalization and Protein Expression.

Protein expression studies were carried out in the Rosetta bacterial strain (Novagen). This strain is derived from the lambda DE3 lysogen strain and carries a chromosomal copy of the IPTG inducible T7 RNA polymerase along with tRNAs on a pACYC based plasmid. Cultures were grown in LB as well as minimal media and at growth temperatures of 37° C. and 20° C. with 100 ug/mL ampicillin and 30 ug/mL chloramphenicol. The culture was diluted 50 fold and grown to mid log (OD at 600 nm=0.5-0.7), at which time the culture was induced with 1 mM IPTG. Induction was allowed to proceed for 4-5 hrs. Upon completion of induction, cells were centrifuged and resuspended in a buffer containing 20% sucrose. To analyze protein induction in total cells, SDS-PAGE buffer was added and the protein was analyzed following SDS-PAGE and staining with Coomassie blue.

Separation of Soluble and Insoluble Fractions.

*E. coli* were harvested by mild centrifugation and washed once with PBS buffer. Cells were resuspended in 4 ml of PBS and ruptured by several pulses of sonication. Unbroken cells were removed by mild centrifugation (5 min at 1500×g) and supernatants were sonicated again to ensure complete cell lysis. An aliquot (5 µl) was mixed with 2% SDS to ensure that no viscosity is detected owing to lysis of unbroken cells. After ensuring that no unbroken cells remained in the lysate, insoluble material consisting of cell walls, inclusion bodies and membrane fragments was sedimented by centrifugation (18,000×g for 10 min). The supernatant was considered "Soluble fraction".

The pellets were washed from any remaining soluble proteins, lipids and peptidoglycan as follows. Pellets were resuspended in 600 µl of PBS and to the suspensions 600 µl of solution containing 3 M urea and 1% Triton X100 was added. The suspension was briefly vortexed and insoluble material was collected by centrifugation as above. The PBS/Urea/Triton wash was repeated two more times to ensure complete removal of soluble proteins. The washed pellets, designated as "insoluble fraction," consisted primarily of inclusion bodies formed by over expressed proteins. Approximately 10 µg of protein from each fraction was resolved on 12% SDS-PAGE minigels and stained with Coomassie Brilliant Blue.

Fluorescence (GFP Activity) Assessment.

GFP fluorescence was measured in soluble fractions (approx. 0.1 mg of soluble protein in a final volume of 40 µl) using Fluoroscan Accent FL fluorometer (LabSystems) with Excitation 485 nm/Emission 510 nm filter set with the exposure set to 40 sec. The data are presented in Arbitrary Units (AU).

Western Blotting.

Twenty µg of total yeast protein per lane were resolved on 12% SDS-PAGE minigel and electro-blotted to nitrocellulose membranes by standard methods. Membranes were blocked with 5% milk in TTBS buffer and incubated with rabbit anti-GFP antibodies (Clontech, cat no. 8367) at 1:100 dilution overnight at 4° C. Secondary HRP-conjugated antibodies were from Amersham. Identical gels were run in parallel and stained with Coomassie to ensure equal loading of the samples.

The various 6HisxSUMO-GFP (16) fusions were expressed in Rosetta(DE3) pLysS (Novagen) using the procedures recommended by the manufacturer. Expression levels in the absence and presence of the fusion proteins was compared by SDS-PAGE analysis. The recombinant proteins were purified using Ni-NTA agarose; (Qiagen) using procedures recommended by the manufacturer.

Cleavage of Proteins

For studies in E. coli, an organism that does not possess SUMO or ubiquitin cleaving enzymes, each cleavage reaction contained 100 ul of purified fusion protein, 99 ul of the buffer 20 mM Tris-HCl pH 8.0, 150 mM NaCl, 5 mM β-mercaptoethanol, and 1 ul of enzyme. The reactions were incubated for 3 hours at 30° C., and stopped by addition of 6× Laemmli SDS-page loading buffer followed by boiling at 95° C. for 5 minutes. The products of the cleavage reaction were analyzed by SDS-PAGE.

The following examples are provided to illustrate various embodiments of the present invention. They are not intended to limit the invention in any way.

EXAMPLE I

Attachment of C-Terminus of UBLs to N-Terminus of GFP Enhances the Expression and Solubility of the Protein in E. coli.

Figure 4A:
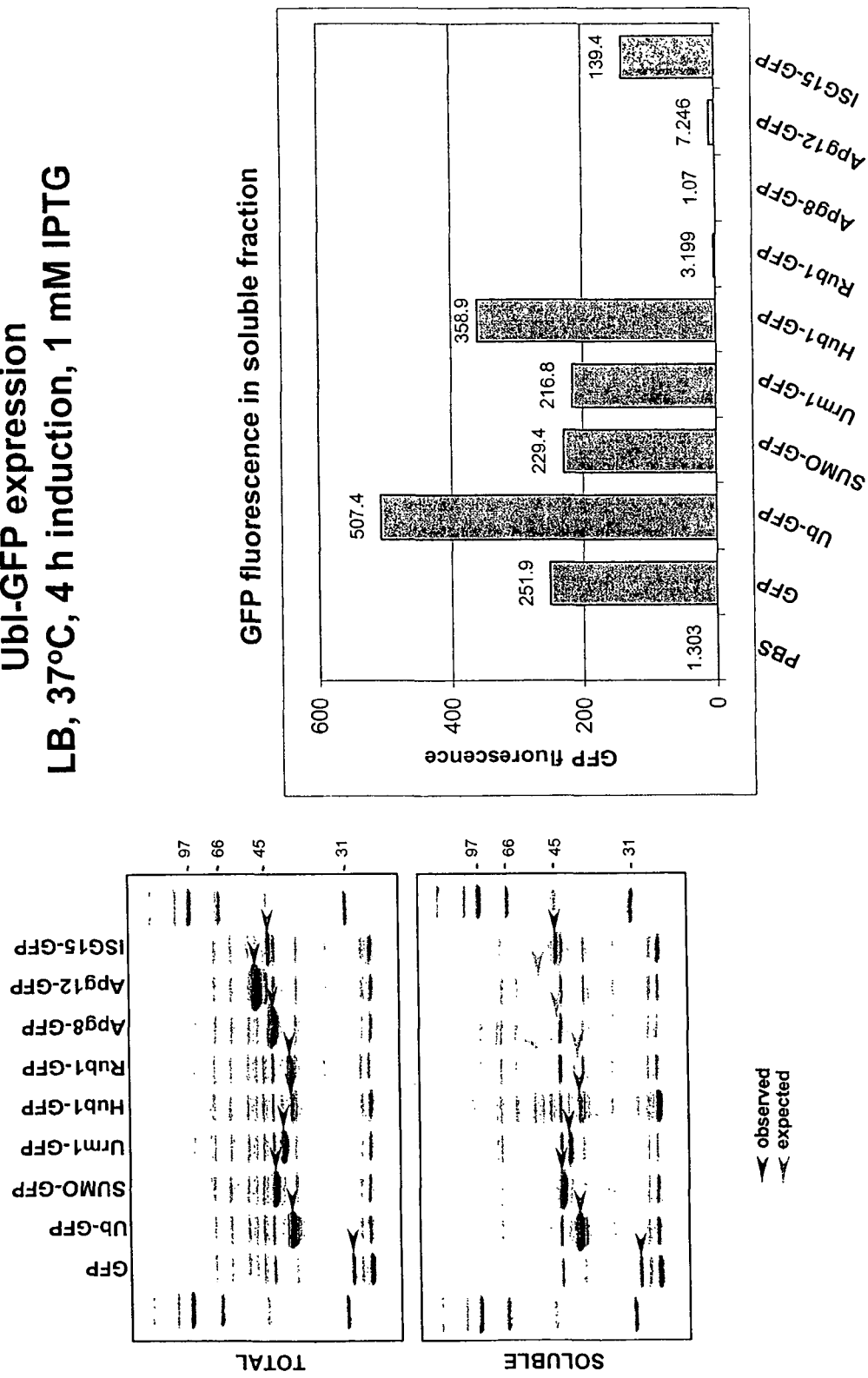
FIGS. 4A and 4B show Coomassie stained gels and graphic data that demonstrate that the attachment of the carboxy-terminus of UBLs to the amino-terminus of target proteins increases expression and/or enhances solubility of the protein in *E. coli*. Green fluorescence protein (GFP) and UBL-GFP fusions encoded in pET24d *E. coli* expression vectors were expressed in the *E. coli* Rosetta pLysS strain (Novagen). Expression was induced either at 37° C. with 1 mM IPTG for four hours either in LB medium (FIG. 4A) or in minimal media with 1 mM IPTG at 26° C. overnight (FIG. 4B). Left panels are Coomassie stained SDS-polyacrylamide gels of total cellular protein (top) and soluble proteins (bottom). The first lanes of each gel are molecular weight markers. Dark arrow indicates observed GFP species and light arrow indicates size of expected GFP species. Right panel is quantitative representation in Arbitrary Units (AU) of GFP fluorescence present in soluble fractions as measured in a Fluorscan Ascent FL fluorometer (LabSystems).

The design and construction of all the UBL E. coli expression vectors has been described above. The DNA sequences, accession numbers of the UBL-GFP fusion proteins, and translation frames are shown FIGS. 25-32. FIG. 4A shows the 37° C. expression pattern of GFP, Ub-GFP, SUMO-GFP, Urm1-GFP, Hub1-GFP, Rub1-GFP, Apg8-GFP, Apg12-GFP, ISG15-GFP. Un-fused GFP is generally poorly expressed in E. coli. The data show that all of the UBLs enhance the expression level of GFP to varying degrees. However, the greatest amount of induction was observed with Ub, SUMO, Urm1, Apg8 and Apg12. Induced cells were broken by sonication and soluble proteins were analyzed on SDS-polyacrylamide gels. The stained gel shows (FIG. 4A, Soluble Panel) that ubiquitin, SUMO, Urm1, Hub1 and ISG15 were able to solublize the GFP while Rub1, Apg8 and Apg12 fusion proteins were not soluble, however, fusion to these proteins did enhance the level of expression several fold. To determine if the fusion proteins were folded correctly, we determined the fluorescence properties of proteins in the soluble fraction. FIG. 4 A also shows GFP fluorescence in approximately 0.1 mg of soluble protein in a final volume of 40 ul using Fluoroscan Accent FL fluorometer (LabSystems) with Excitation 485 nm/Emission 510 nm filter set with the exposure set to 40 sec. The data are presented in Arbitrary Units (AU) and show that Ub, SUMO, Urm1, Hub1 and ISG15 produced GFP protein that was able to fluoresce and, thus, was folded correctly. Fusions of GFP with Rub1, Apg8 and Apg12 were induced in large amounts but were not soluble and did not show any fluorescence.

In addition, it is shown that ISG15 plays a role in immune response (24). Thus presentation of ISG15 as a fusion protein is a viable tool for novel vaccine candidates. Similarly, Apg8 and Apg12 translocate protein to compartments in the cell for autophagy (30).

Similar experiments were performed with all the UBL-GFP fusion proteins, but the induction was performed at 26° C. overnight. The data shown in FIG. 4B confirms the finding in FIG. 4A. Almost all of the UBLs except Hub 1 showed dramatically enhanced expression of GFP after fusion. In the case of SUMO, the level of expression was increased about 20 fold. Analysis of soluble fraction showed that Ub, SUMO, Urm and ISG15 were able to solubilize fused GFP (see FIG. 4B, Soluble panel). Functional analysis of fusion GFP was performed by fluorescence from the soluble fraction. This data confirms the observation made in FIG. 4A. Combining all the data from the induction studies demonstrates that fusion of all the UBLs to GFP enhances expression level from 2-40 fold. In addition, Ub, SUMO, Urm1, Hub1 and ISG15 also increase the solubility of the GFP. These UBLs are therefore capable of producing correctly folded proteins in E. coli.

Figure 5:
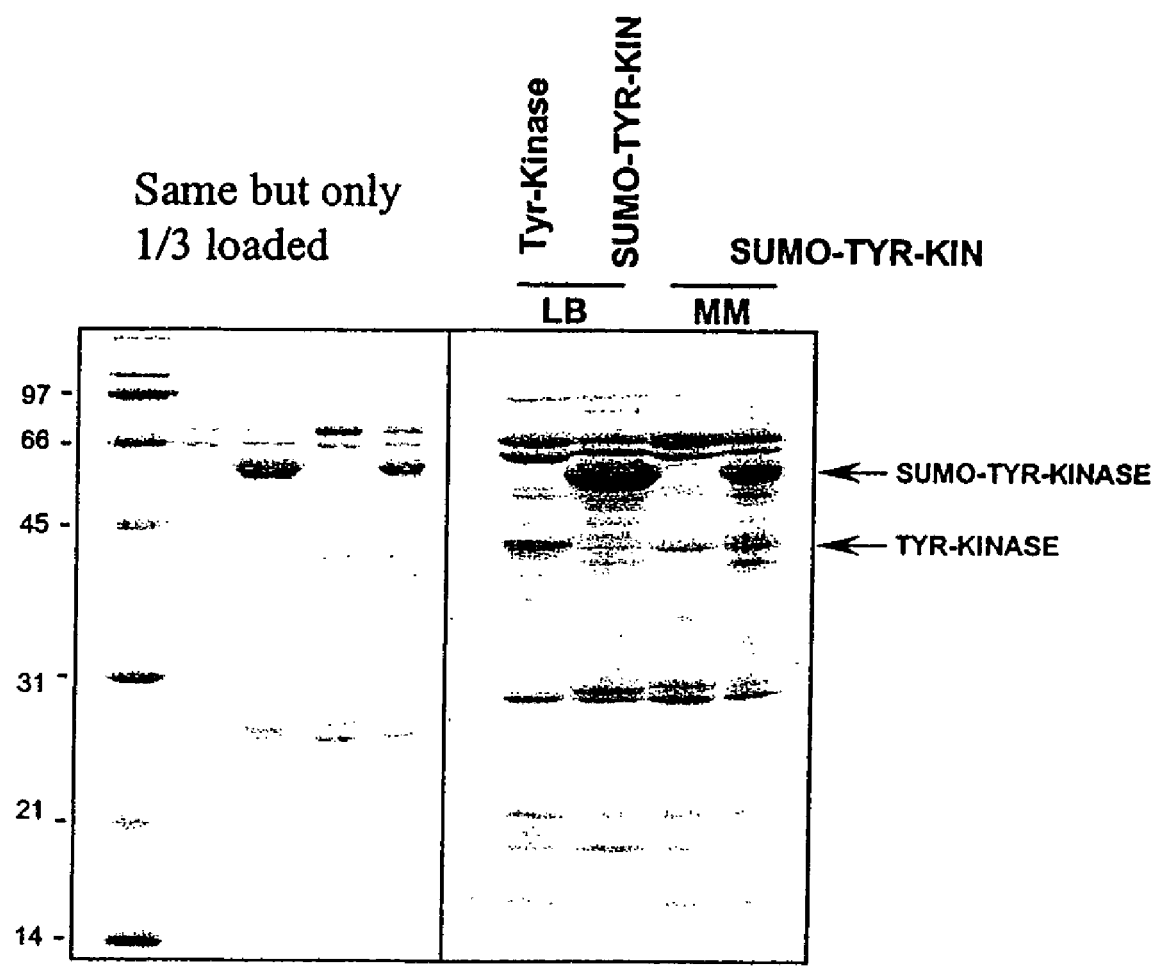
FIG. 5 is a Coomassie stained SDS-polyacrylamide gel demonstrating the expression and purification of a human tyrosine kinase as a SUMO fusion protein in *E. coli*. Tyrosine kinase and the fusion protein SUMO-tyrosine kinase were expressed in the Rossetta pLysS strain (Novagen) of *E. coli* in LB or minimal media (MM). The right panel shows the Ni-NTA resin purified proteins from the transformed *E. coli* cells. The left panel has the same lane arrangement as the right panel, but ⅓ of the amount protein was loaded on the SDS-polyacrylamide gel. Numbers indicate molecular weight standards in the first lane.
Figure 6:
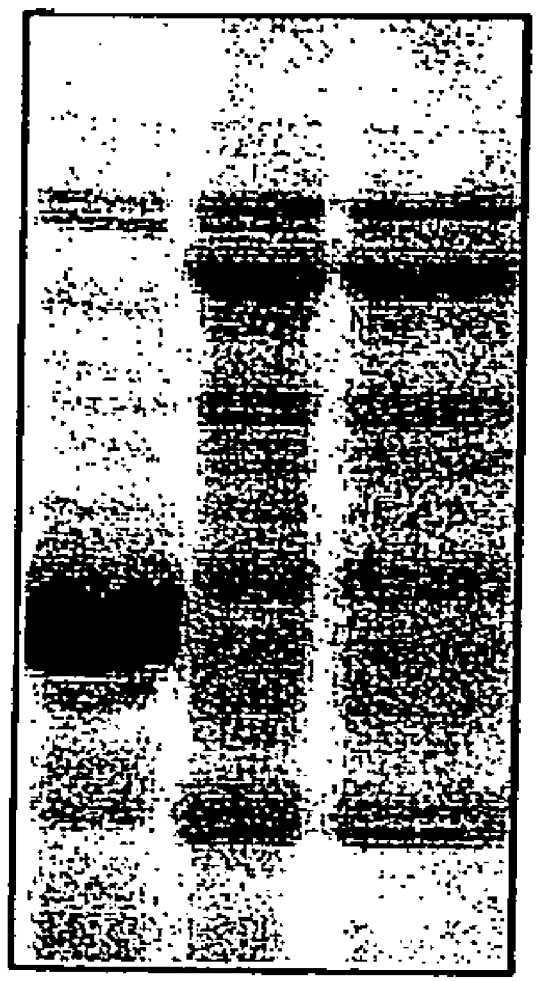
FIG. 6 shows a Coomassie stained SDS-polyacrylamide gel representing purified SUMO hydrolase from *E. coli* and the partial purification and elution of SUMO-tyrosine kinase fusion protein. *E. coli* cells were transformed with a vector expressing either SUMO hydrolase Ulp1 or SUMO-tyrosine kinase and cultured in minimal media. Proteins were subsequently purified by Ni-NTA resin. SUMO-tyrosine kinase was further purified by elution with either 100 mM EDTA or 250 mM imidazole. The gel shows that the current methods yield approximately 90% pure Ulp1 protein.

To gain more insight into the role of UBLs in enhancement of expression and solubility, we have tested the SUMO-fusion systems with other proteins as well. Serine threonine kinases, tyrosine kinase and human nuclear receptor have proven difficult to express in E. coli. Researchers have opted to use tissue culture systems to express soluble kinases of receptors. FIG. 5 shows expression 6His-SUMO-Tyr-Kinase and unfused Tyr-Kinase in E. coli using LB or minimal medium (MM), and purified on Ni-NTA resin as described previously. The small fraction of resin was boiled with 1×SDS-PAGE sample buffer and aliquots were resolved on the 12% SDS-PAGE. Equal amounts of E. coli culture were taken for SUMO-Tyr-kinase and unfused Tyr-kinase and purification was performed under identical conditions. The stained gel in FIG. 5 shows that SUMO fusion increases the yield of the kinase at least 20 fold, in cells grown in LB media. FIG. 6 also shows the pattern of the SUMO-Try kinase that was eluted from Ni-NTA by 100 mM EDTA or 250 mM imidazole. These data further demonstrate that SUMO fusion enhances the expression of difficult to express protein such as Tyrkinase, and that the expressed fusion protein is soluble.

Figure 7:
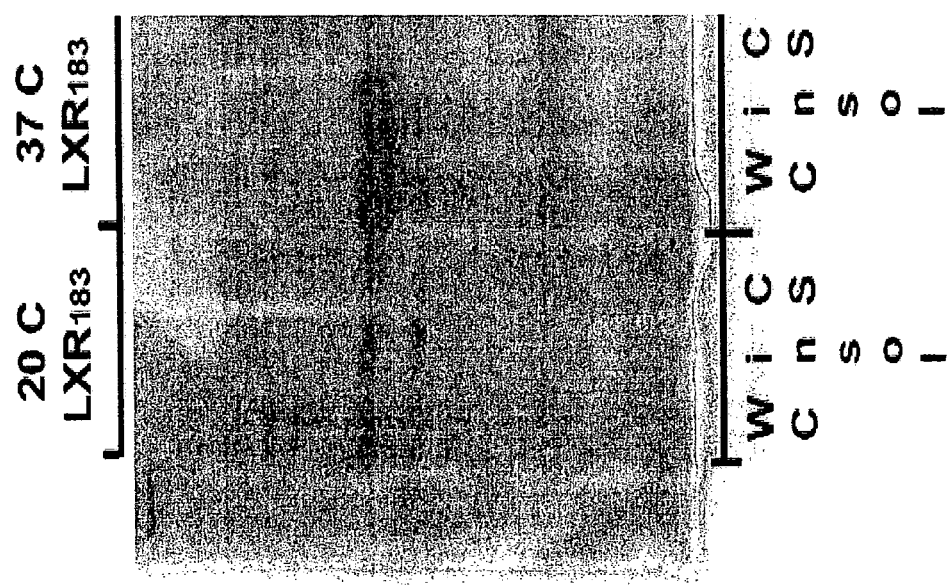
FIG. 7 is a stained SDS-polyacrylamide gel of the expression of the liver X receptor (LXR) ligand binding domain as a fusion protein with SUMO. *E. coli* cells were transformed with a SUMO-LXR expression vector. The cells were subsequently induced with 1 mM IPTG at 20° C. overnight or 37° C. for 3 hours. 10 μg of total protein (WC), soluble protein (CS), and insoluble protein (Insol) from each induction were loaded per well of a 12% SDS-polyacrylamide gel.

Human nuclear receptor proteins, such as steroid receptors, contain ligand-binding domains. These proteins have proven hard to express in soluble form in *E. coli*. We have used human liver X receptor (LXR) ligand binding domain to demonstrate that SUMO fusion promotes solubility of the protein in *E. coli*. The ligand-binding domain of LXR was expressed as SUMO fusion in Rosetta plysS cell at 20° C. or 37° C. and the pattern of soluble and insoluble protein was analyzed. FIG. 7 shows the stained SDS-polyacrylamide gel demonstrating that about 40% of the LXR protein was solublized by SUMO fusion, see lane CS in 20° C. box in FIG. 7 (predominant band in 40 kDa range). If the cells were induced at 37° C., hardly any SUMO-LXR was soluble although the level of protein induction had increased dramatically. Further proof that SUMO promotes solubility of previously insoluble proteins was gained by expressing MAPKAP2 kinase as a SUMO-fusion in *E. coli*. FIGS. 8A and 8B shows induction kinetics in *E. coli* cells expressing kinase at 20° C. and 37° C. Numbers at the top of the gel, 0.1, 0.25 and 0.5 refer to the mM concentration of inducer IPTG, in the culture. The original induced culture (I), supernatant from lysed cells (S) and resuspended pellet (P) were analyzed on 12% SDS-PAGE. The data clearly demonstrate that 90% of the SUMO kinase is soluble when the cells are induced at 20° C. with 0.25 mM IPTG. Although induction at 37° C. allows greater degree of expression, more than 50% of the kinase is still insoluble under these conditions. Cleavage of SUMO-MAPKKAP2 kinase by SUMO hydrolase is described in Example III. Also see FIG. 18.

Overall, these results show that in bacteria, fusion of UBLs to GFP increases the level of expression from 2-40 fold. Some of the UBLs such as Ub, SUMO, Urm1, Hub1, and ISG15 solublize otherwise insoluble proteins. In particular, SUMO has been demonstrated to increase solubility of kinases and LXR α under controlled temperature induction from 50-95% of the total expressed protein.

EXAMPLE II

SUMO-Fusion Expression in Yeast and Insect Cells

Fusions of C-Terminal UBLs to the N-Terminus of GFPs are Cleaved in Yeast

Figure 4B:
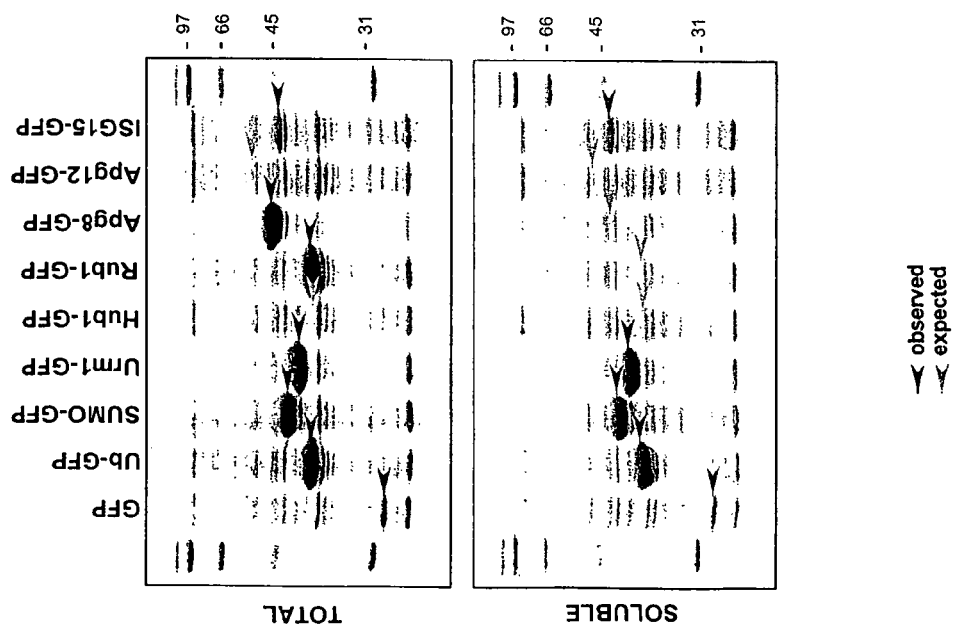
Figure 9:
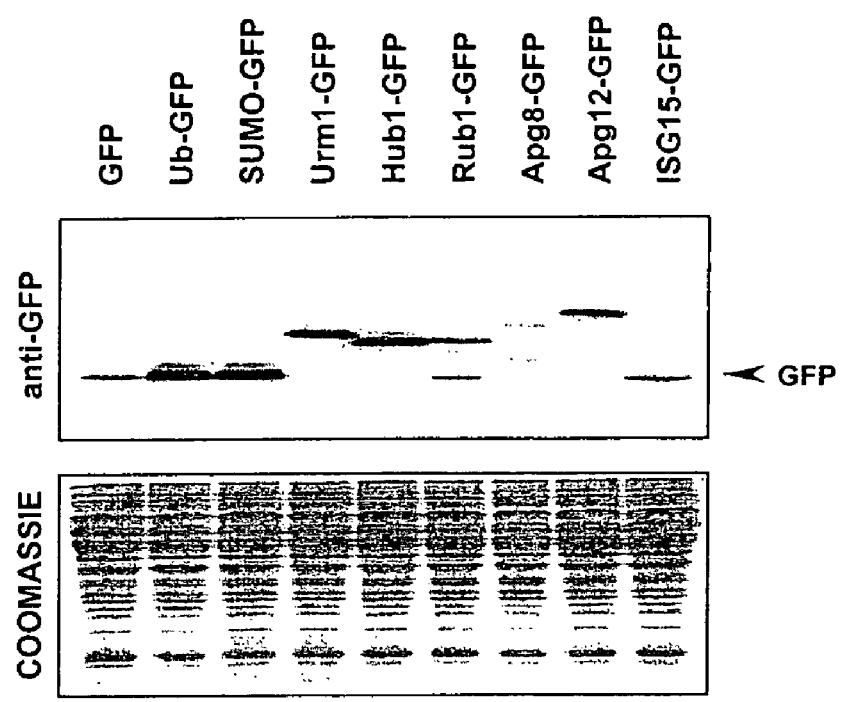
FIG. 9 is a Western blot (top panel) of UBL-GFP fusion proteins expressed in yeast cells demonstrating that UBL-GFP fusion proteins are co-translationally cleaved in yeast. Yeast strain BJ1991 was transformed with a vector expressing Ub-GFP, SUMO-GFP, Urm1-GFP, Hub1-GFP, Rub1-GFP, Apg8-GFP, Apg12-GFP or ISG15-GFP under the control of a copper sulfate regulated promoter. Total cell extracts were prepared by boiling the cells in SDS-PAGE buffer and briefly sonicating the sample to reduce viscosity. 20 μg of the total yeast proteins were resolved on 12% SDS-PAGE minigels and analyzed by Western blot with a rabbit polyclonal antibody against GFP and a secondary HRP-conjugated antibody. The arrow indicates the size of unfused GFP. An identical gel (bottom panel) was run in parallel and stained with Coomassie to ensure equal loading of the proteins from all samples.
Figure 10:
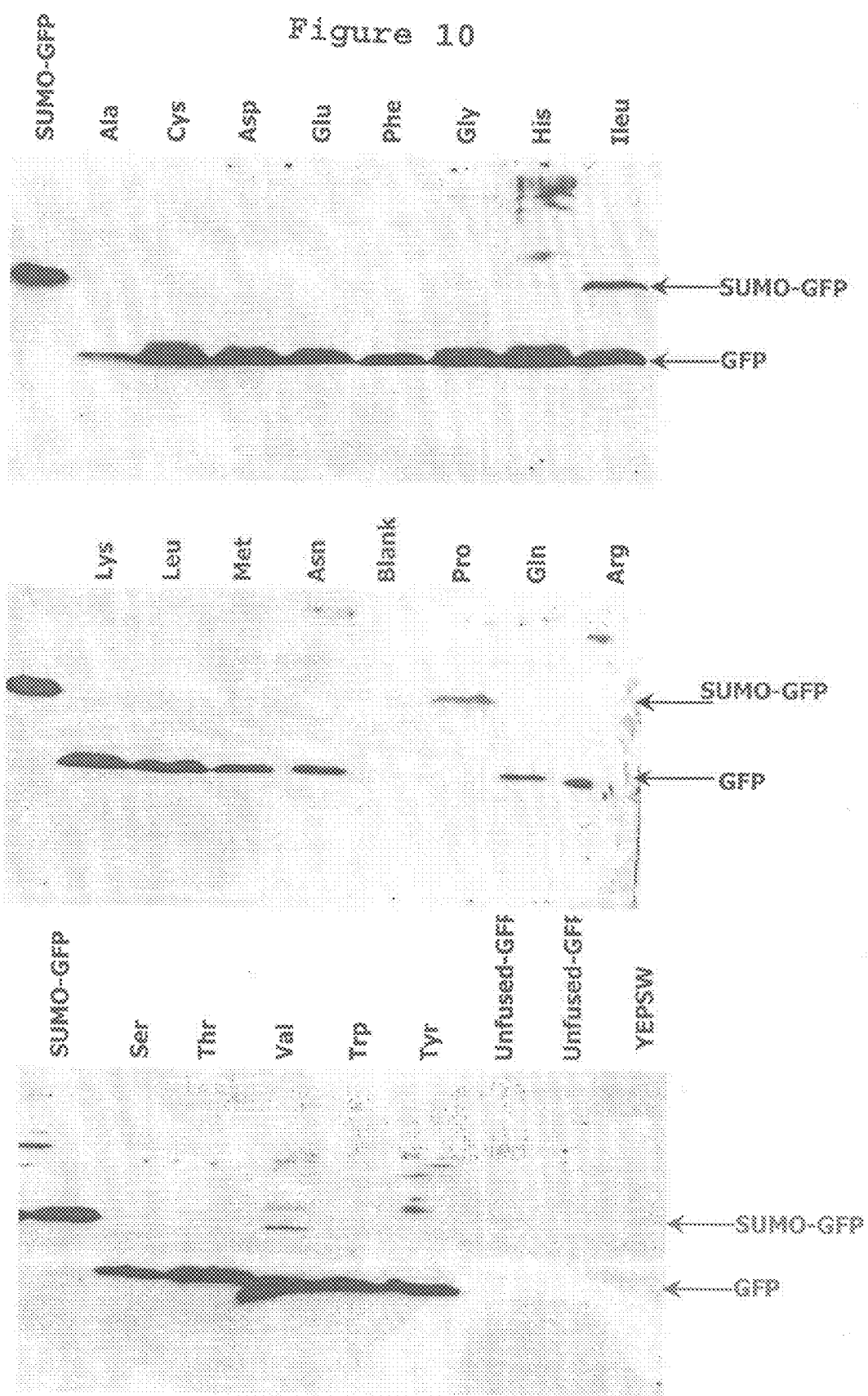
FIG. 10 is a series of Western blots that indicate SUMO-GFP Fusions are co-translationally cleaved in yeast generating novel amino termini. In addition to methionine as the first amino acid of GFP following the C-terminal Gly-Gly sequence of SUMO, we have engineered the remaining 19 amino acids as the amino-terminal residue of GFP in yeast SUMO-(X)20-GFP expression vectors. All expression vectors containing the 20 amino-terminal variants of GFP fusion proteins were expressed in yeast under the control of copper inducible promoter. Yeast lysates were separated by SDS-PAGE and analyzed by Western blot with antibodies against GFP. The "unfused-GFP" lanes represent the expression of GFP alone with no SUMO fusion. The "SUMO-GFP" lanes are bacterially expressed SUMO-GFP.

To further assess the utility of UBL fusion in eukaryotic cells we expressed all of the UBL-GFP fusions previously described in FIG. 4 in yeast. *S. cerevisiae* BJ1991 strain was transformed with either YEp-GFP or YEp-UBL-GFP fusion constructs using standard procedures. Positive clones were grown in YPD medium and induced with 100 μM CuSO$_4$ at cell density OD600=0.2 for 3.5 hours. Total cell extracts were prepared by boiling the yeast cells in SDS-PAGE buffer. Twenty ug of proteins were analyzed on 12% SDS gels. A replica gel was stained in Coomassie blue and another gel was blotted and probed with antibodies against GFP. Data in FIG. 9 shows that Ub-GFP, SUMO-GFP and ISG15-GFP fusions were efficiently cleaved in yeast, while Rub1-GFP fusion was partially cleaved. Apg8-GFP fusion was cleaved into two fragments. It is noteworthy that all the UBL-GFP fusions were designed with methionine as the first amino terminus. GFP fusion with Urm1, Hub1 and Apg12 expressed well, but were not cleaved in yeast. There was a modest increase in expression of GFP following fusion with Ub, SUMO, ISG15 and cleavage in yeast. Generally we have observed 10-20 fold increase in the level of protein expression following fusion to UBL in prokaryotes and eukaryotes (see FIGS. 4B, 10 and 11). The reason for the modest increase in GFP fusion following cleavage is that the cells were grown in induction media containing 100 uM copper sulfate in rich YPD media. Rich media contains many copper binding sites, and less free copper is available to induce the gene. A nearly 100-fold increase in GFP production has been observed with a variety of N-terminal fusions when cells were induced with 100 uM copper sulfate in synthetic media. See FIG. 10.

Generation of New Amino Termini:

The identity of the N-terminus of a protein has been proposed to control its half-life (the N-end Rule) (35). Many important biopharmaceuticals such as growth factors, chemokines, and other cellular proteins, require desired N-termini for therapeutic activity. It has not been possible to generate desired N-termini, as nature initiates translation from methionine, but the SUMO system offers a novel way to accomplish this.

To demonstrate that all N-termini of GFP in SUMO-GFP fusions were efficiently cleaved when expressed in yeast, a comprehensive study of SUMO-GFP with 20 N-termini was carried out. Multi-copy yeast expression plasmids were designed as described above. Plasmids were transformed in yeast strain BJ1991, four single colonies were selected, and the levels and cleavage patterns of two of the strains were analyzed by SDS-PAGE and western blotting. Data from Western blots of a single colony is presented in FIG. 10. These results are in agreement with our in vitro studies of purified SUMO-X-GFPs (from *E. coli*) and its cleavage pattern of SUMO hydrolase. All of the SUMO-GFP fusions were cleaved efficiently except those containing proline at the junction (see FIG. 10, middle panel lane "Pro"). It is also interesting to note that SUMO-Ileu-GFP was partially cleaved during the phase of copper induction. All of the genes are under the control of copper inducible promoter. It is possible that SUMO-Ileu-GFP is resistant to cleavage due to the nonpolar nature of the residue at the +1 active site of SUMO hydrolase. In this respect SUMO-Val-GFP was also partially resistant to cleavage in vivo (see lower most panel lane labeled "Val"). It is clear from these results that SUMO-Pro-GFP fusion was completely resistant to cleavage by yeast SUMO hydrolases as no GFP was observed (see lane "pro" in middle panel of FIG. 10). This data is consistent with our previous observations. See FIG. 15. Another important aspect of these findings is that fusion of SUMO with various N-termini of GFP appears to increase the expression of almost all the proteins, although to various degrees. For example Cys-GFP, Gly-GFP and His-GFP accumulated in greater amounts as compared to other N-terminal GFPs. A direct comparison of the increase in the level of GFP following fusion to SUMO can be made by comparing the level of un-fused GFP (see last lanes of lower most panel in FIG. 10). Although 20 ug of yeast proteins were loaded on SDS-PAGE the GFP signal was not detected. To ensure that we were not dealing with mutation or any artifact, we loaded a protein sample from another single colony that was induced in under similar conditions and the sample was loaded next to the previous GFP. No signal was detected, suggesting that unfused GFP is made in very small amounts that cannot be detected under the present experimental conditions, (i.e., a four hour induction with copper sulfate). These studies show that fusion with SUMO leads to a dramatic increase in the amount of protein expressed in yeast. All of the N-terminal fusions are cleaved by endogenous SUMO hydrolases except when the N-terminal residue is proline. Thus for enhanced expression of a protein in eukaryotes permanent attachment of SUMO is not required as significant (~100 fold) increased accumulation of the protein was observed even after the cleavage of SUMO. At the same time, SUMO-pro-fusions are also useful as 6xHis-SUMO can be used to purify the protein from yeast, and the SUMO moiety can be removed with 10 times greater amounts of the SUMO hydrolase (see example III).

Previous studies have shown that attachment of ubiquitin to the N-termini of proteins in yeast enhances expression, and protein fusions containing all amino acid at the N-terminal residue, except proline, are efficiently cleaved in yeast (2, 10, 34). However, these technologies have several drawbacks. Firstly, none of the deubiquitinating enzymes (DUBs) have been shown to efficiently cleave ubiquitin fusion proteins of varying sizes and structures (3,1), despite the fact that they were discovered more than 15 years ago (35, 19, 3). Secondly, and perhaps more importantly, ubiquitin predominantly functions as a signal for proteolysis (14). Therefore, for physiological reasons and for the lack of robust cleavage of artificial ubiquitin-fusions by DUBs, the ubiquitin gene fusion system has not been successfully developed for commercial applications. We have observed that the SUMO system appears to perform in a manner that is remarkably superior to that of ubiquitin, as SUMO and other UBL fusions enhance protein expression and solubility in prokaryotes. In addition, many of the UBLs increase expression of GFP, following the cleavage of UBL in yeast. Unlike the ubiquitin-fusion system, which may direct the protein to the ubiquitin proteosome pathway, the current cleavage of fusion-protein in yeast is the result of C-terminal fusion with SUMO, and proteins generated with novel N-termini are not subject to degradation by the ubiquitin-proteosome pathway. This is one of the reasons that large amount of GFP has accumulated in yeast after cleavage of the SUMO fusion (see FIG. 10).

N-Terminal Attachment of Ubiquitin Promotes Protein Secretion:

To date, a role for ubiquitin in the secretion of proteins has not been determined. We have assessed whether N-terminal fusion of ubiquitin to a protein promotes its secretion in yeast. Several yeast expression vectors that express E. coli β-glucoronidase (GUS) were designed. All of the yeast GUS expression vectors described in Table 2 are engineered under the control of the strong glycolytic GPD promoter that expresses constitutively. Some of the constructs were also expressed under the control of a copper regulated metallothionein promoter (CUP1) as well. CUP1 promoter driven synthesis of the SUMO-GUS constructs was induced by addition of 100 uM copper sulfate and incubation of 3 hours. To determine the level of GUS from media, cells were harvested by centrifugation at 2000×g for 10 mins. Supernatant was collected and equal amounts of aliquots were assayed for enzymatic activity or western blot analysis as described above. For the comparative study, all strains were treated identically and grown at the same time to equal O.D, and the assays were performed at the same time. To examine intracellular enzymatic activity, the cells were harvested by centrifugation and washed with Tris EDTA buffer, pH 7.5. The cell pellets were suspended in sarcosine buffer and ruptured with glass beads at 4° C., three times by vigorously vortexing. Supernatant was collected for assay of the enzymatic activity. The amount of protein secretion was determined by estimating relative activity of the enzyme in the media. The data is shown in Table 2.

TABLE 2

Ubiquitin-GUS Expression and Secretion in Yeast

| Vector (pRS425) | Promoter | Signal Sequence | GUS Activity Inside Cell | GUS Activity In Supernatant |
|---|---|---|---|---|
| ADH1-GUS1 | ADH1 | — | +++ | − |
| GPD-α-factor-GUS1 | GPD | α-factor | ++ | |
| GPD-Ub-GUS1 | GPD | Ubiquitin | ++++ | ++++ |
| GPD-Ub-α-factor-GUS1 | GPD | Ubiquitin-α-factor | ++++ | − |
| GPD-α-factor-Ub(pro)-GUS1 | GPD | α-factor-Ubiquitin(pro) | ++ | − |
| GPD-α-factor-Ub(met)-GUS1 | GPD | α-factor-Ubiquitin(met) | ++ | − |
| CUP1-Ub-GUS1 | CUP1 | Ubiquitin | ++++ | ++ |

GUS activity was measured as described. It was not possible to measure specific units of GUS in the media as yeast grown in synthetic media. Yeast secretes little protein and current methods of protein estimation, BioRad kit cannot estimate the protein, the data was presented as + where one + is equal to 2 units of GUS as described in invention.
− Sign means no GUS activity was detected.

The following conclusions are drawn from this study.
1) Fusion of ubiquitin to GUS leads to a several fold increase when yeast extracts were analyzed by enzymatic assays.
2) Insertion of proline at the junction of ubiquitin and GUS did not allow cleavage of the ubiquitin-GUS fusion protein.
3) The attachment of alpha factor secretory sequences to the N-terminus of ubiquitin-fusion did not have show any appreciable increase in secretion of the protein into the media.
4) Presence of alpha factor sequences between ubiquitin and GUS did not lead to any increase in extracellular level of GUS activity.
5) Greatest amount of secretion was observed with ubiquitin-Met-GUS. These observations suggest that endogenous secretory sequences of GUS in the context of ubiquitin promote the best secretion for GUS. To this end the current data from yeast correlates very well with the ubiquitin-GFP protein secretion in insect cells (see FIG. 13).

Fusion of SUMO and Ubiquitin to the N-Terminus of GFP Promotes Enhanced Expression and Secretion in Insect Cells.

Figure 12A:
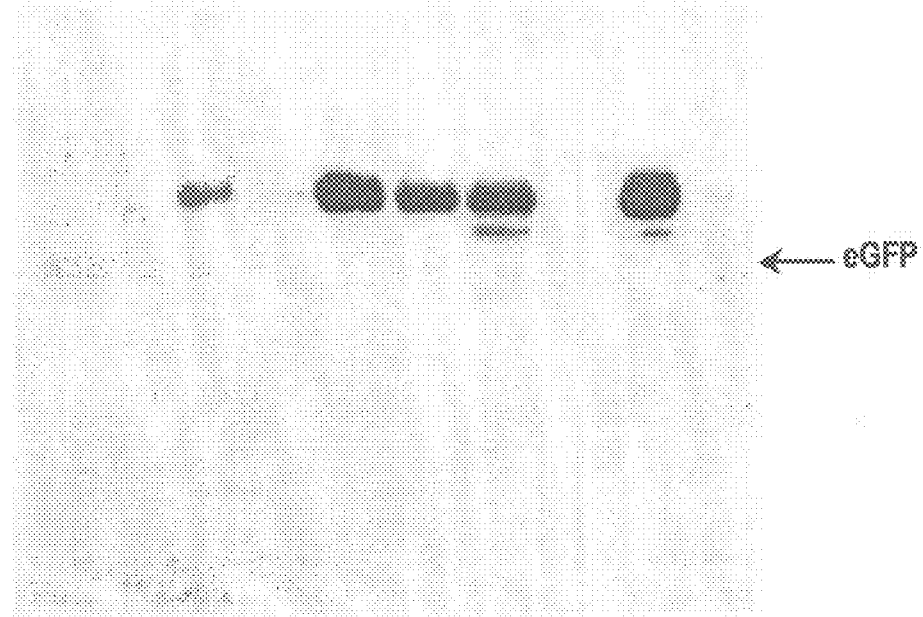
FIGS. 12A and 12B are Western blots demonstrating expression of SUMO and ubiquitin fusion proteins in insect cells. Hi-five insect cells were infected with recombinant baculovirus encoding for SUMO or ubiquitin fusion proteins. At 24 hours post-infection, equal amounts of cell lysates (FIG. 12A) and media (FIG. 12B) were separated by SDS-PAGE and analyzed by Western blot with antibodies against GFP. Lane markers: Hi5 is Hi Five cells, E is eGFP, G is gp67-eGFP, U is ubiquitin-eGFP, S is SUMO-eGFP, GU is gp67-ubiquitin-eGFP, UG is ubiquitin-gp67-eGFP, GS is gp67-SUMO-eGFP, SG is SUMO-gp67-eGFP, and eGFP is a positive control.
Figure 12B:
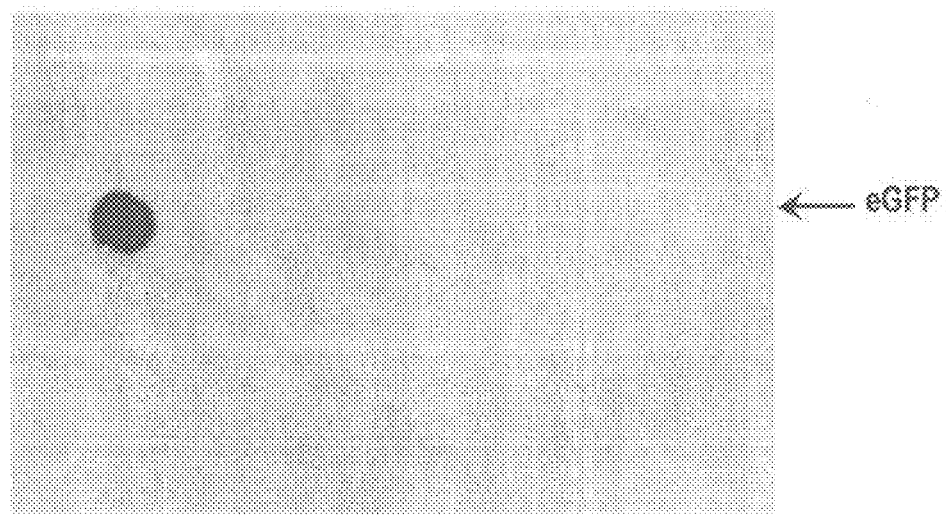

The role of SUMO in enhanced expression and secretion of proteins in cultured cells has also been studied in insect cells. Baculovirus vectors expressing SUMO-GFP constructs and appropriate controls have been described above. See FIG. 11A for the orientation gp67 secretory signals in the SUMO-GFP constructs. Data from a 24 hour infection is shown in FIG. 12. Panel A shows intracellular protein analysis by Western blots. It is clear that fusion with ubiquitin and SUMO promotes a large increase in the amount of protein (compare lane E with lane U and S). Insertion of gp67 signal sequences to the N-terminus of SUMO leads to further increase in the amount of protein in insect cells (compare unfused GFP lane E with gp67-SUMO-GFP lane GS). On the other hand attachment of gp67 signal sequence to the N-terminus of GFP (lane G, UG or SG) did not increase the level of protein expression, to the contrary there was diminution of signal when gp67 was attached to N-terminus of GFP (lane G) or between SUMO and GFP (lane SG). We estimate that in the level of expression in the context of gp67-SUMO-GFP is 20× fold higher as compared to unfused GFP (lane E) or 40× fold higher as compared to gp67-GFP (lane G). No unfused GFP was secreted by any of the constructs at 24 hour post infection, as shown in blot in FIG. 12 panel B. These results show that fusion with SUMO leads to a dramatic increase in expression of GFP in insect cells. Additionally, both SUMO-GFP and gp67-SUMO-GFP were efficiently cleaved by endogenous SUMO hydrolases.

Similar experiments were performed with cells 48 hours post infection. The data in FIGS. 13 A and B show that the pattern of intracellular expression was similar to the one seen in 24 hours of infection; however, large amounts of ubiquitin and SUMO-GFP protein were secreted at 48 hour post infection. Examination of the blots from media and intracellular protein show that reasonable expression of unfused GFP was observed inside the cell, but hardly any protein was secreted in the media (compare lane E of panel A and panel B in FIG. 13). Attachment of gp67 to the N-terminus of SUMO-GFP leads to the greatest amount of protein secreted into the media (see lane GS in panel B). Another important finding is that attachment of ubiquitin without any signal sequences shows very high secretion of GFP in the media. This result is completely consistent with our finding that attachment of ubiquitin to the N-terminus of GUS promotes the greatest amount of secretion of GUS into the yeast media.

Figure 13A:
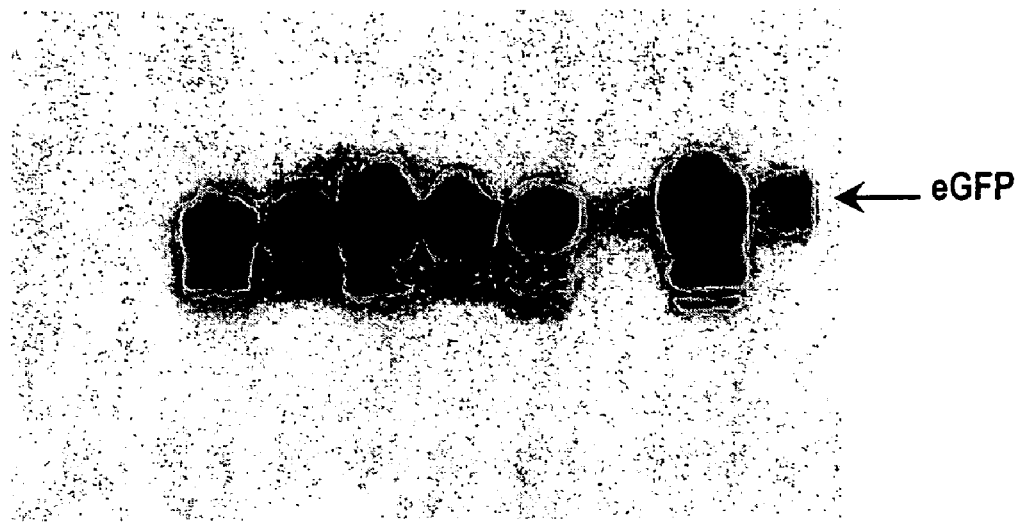
FIGS. 13A, 13B, and 13C are Western blots demonstrating expression of SUMO and ubiquitin fusion proteins in insect cells. Hi-five insect cells were infected with recombinant baculovirus encoding for SUMO or ubiquitin fusion proteins. At 48 hours post-infection, equal amounts of cell lysates (FIGS. 13A and 13C) and media (FIG. 13B) were separated by SDS-PAGE and analyzed by Western blot with antibodies against GFP. The lanes are: Hi5 is Hi Five cells, E is eGFP, G is gp67-eGFP, U is ubiquitin-eGFP, S is SUMO-eGFP, GU is gp67-ubiquitin-eGFP, UG is ubiquitin-gp67-eGFP, GS is gp67-SUMO-eGFP, SG is SUMO-gp67-eGFP, and S—P is SUMO-proline-GFP.
Figure 13B:
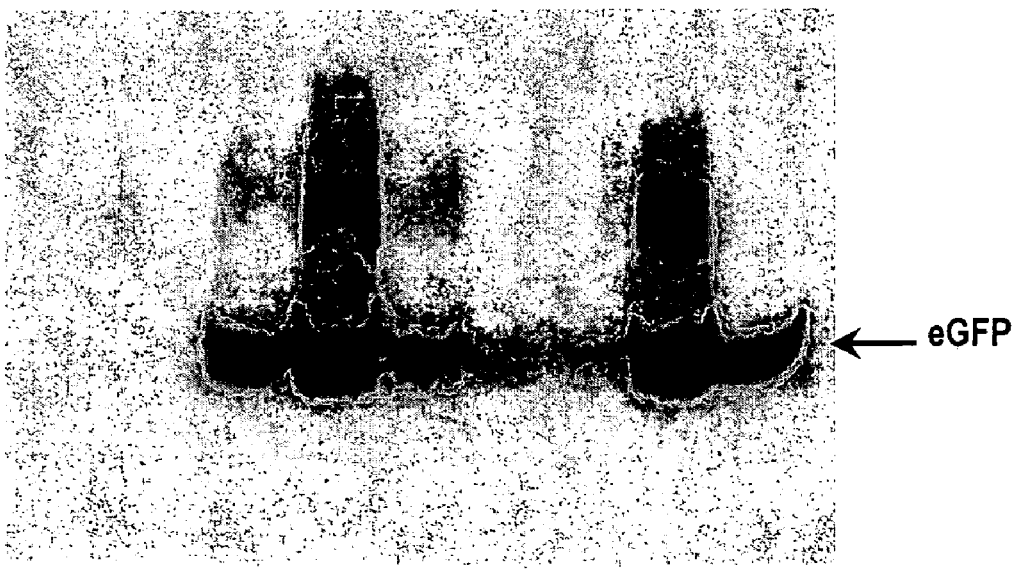
Figure 13C:
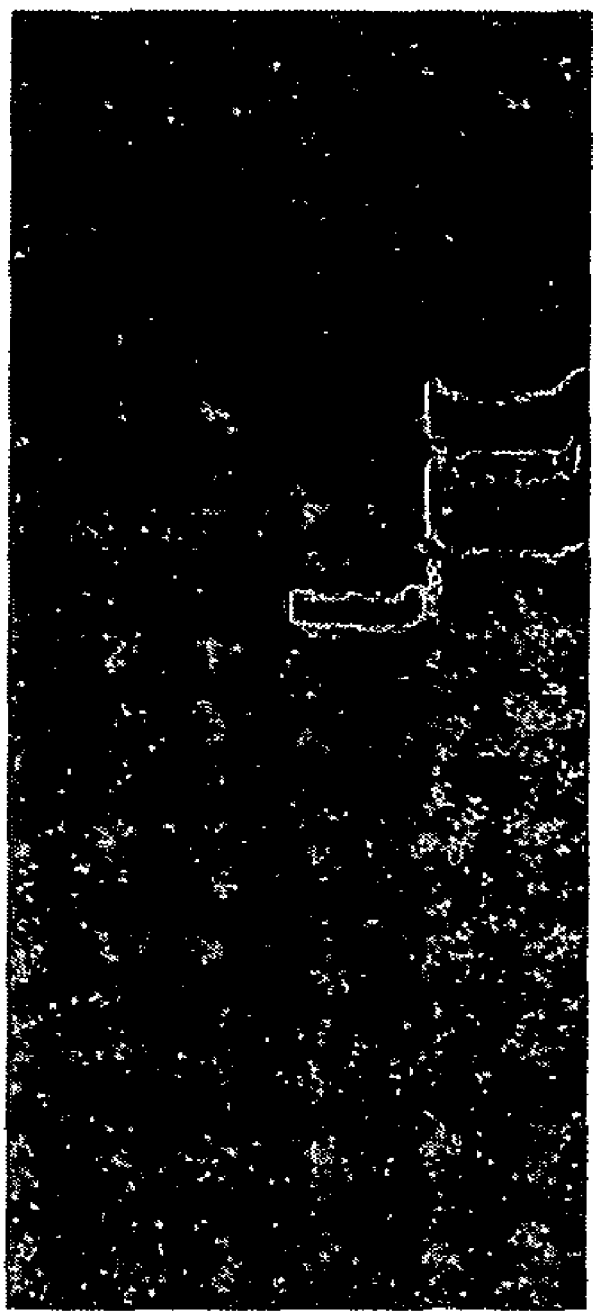

We have also discovered that SUMO-Pro-GFP fusion was not cleaved by endogenous SUMO hydrolases in insect cells (FIG. 13 C). Although some non-specific degradation of SUMO-Pro-GFP was observed in these experiments (see lane S-P in FIG. 13 C), we conclude that unlike SUMO-GFP, SUMO-Pro-GFP is not cleaved in insect cells. This observation is also consistent with the finding in yeast that SUMO-Pro-GFP is not cleaved in cells while other N-terminal GFP fusions are processed in yeast.

Further confirmation of these observations was obtained by fluorescence imaging of the cells expressing GFP fusion proteins. FIG. 14 shows that cells expressing GFP and fusion GFP fluoresce intensely. The fluorescence imaging was the strongest and most widely diffused in cell expressing gp67-SUMO-GFP and Ub-GFP. These cells show the largest amount of GFP secreted into the media (FIG. 13 panel B). It appears that secretory signal attachment directly the to N-terminus of GFP produces less GFP in the media and inside the cells. This observation is borne out by low fluorescence intensity and granulated pigmented fluorescence (see panel G-eGFP, S/G-eGFP and U/G-eGFP). These data have led to the following conclusions:

1) The increase in the amount of SUMO-fusion protein expression in insect cells was several-fold higher (20-40 fold) than that of unfused protein, as determined by and Western blot analysis.
2) All of the SUMO-GFP constructs that contain methionine at the +1 position were cleaved except SUMO-Proline-GUS. This aspect of the SUMO-fusion technology allows us to express proteins that are stably sumoylated.
3) Attachment of ubiquitin to the N-terminus of GFP led to dramatic enhancement in secretion of the protein in the media. Ubiquitin promotes secretion of proteins that may or may not have endogenous secretory signal. Thus, N-terminal ubiquitination may be utilized as a tool to enhance secretetion of proteins in eukaryotic cells.
4) N-terminal SUMO also promotes secretion of protein in insect cells.

EXAMPLE III

SUMO Protease ULP1 Cleaves a Variety of SUMO-Fusion Proteins:

Properties and Applications in Protein and Peptide Expression and Purification

Yeast cells contain two SUMO proteases, Ulp1 and Ulp2, which cleave sumoylated proteins in the cell. At least eight SUMO hydrolases have been identified in mammalian systems. The yeast SUMO hydrolase Ulp1 catalyzes two reactions. It processes full length SUMO into its mature form and it also de-conjugates SUMO from side chain lysines of target proteins. Examples I and II establish our findings that attachment of SUMO to the N-terminus of under-expressed proteins dramatically enhances their expression in E. coli, yeast and insect cells. To broaden the application of SUMO fusion technology as a tool for expression of proteins and peptides of different sizes and structures, the ability of Ulp1 to cleave a variety of proteins and peptides has been examined. Purified recombinant SUMO-GFPs were efficiently cleaved when any amino acid except Proline is present in the +1 position of the cleavage site. Similar properties of SUMO hydrolase Ulp1 were observed when Sumo-tyrosine kinase, Sumo-protein G, Sumo-β-GUS, and SUMO MAPKAP2 kinase were used as substrates. The in vitro activity of the enzyme showed that it was active under broad ranges of pH, temperature, and salt and imidazole concentration. These findings suggest that the Ulp1 is much more robust in cleavage of the SUMO-fusion proteins as compared to its counterpart, ubiquitin-fusion hydrolase. Broad specificity and highly efficient cleavage properties of the Ulp1 indicate that SUMO-fusion technology can be used as a universal tag to purify a variety of proteins and peptides, which are readily cleaved to render highly pure proteins.

The following materials and methods are provided to facilitate the practice of Example III.

Affinity Purification and Cleavage of SUMO Fusion Proteins with SUMO Hydrolase.

The following table lists the solutions required for the affinity purification and cleavage procedures:

| Solution | Components |
| --- | --- |
| Lysis buffer | 25 mM Tris pH 8.0; 50 mM NaCl |
| Wash Buffer | 25 mM imidazole; 50 mM Tris pH 8.0; 250 mM NaCl; (optional) 5-10 mM β-mercaptoethanol (protein dependent) |
| Elution Buffer | 300 mM imidazole; 50 mM Tris pH 8.0; 250 mM NaCl; (optional) 5-10 mM β-mercaptoethanol (protein dependent) |
| SUMO hydrolase (Ulp1) Cleavage Buffer | 50 mM Tris pH 8.0; 250 mM NaCl; 5 mM β-mercaptoethanol (protein dependent) |

From typical 250 ml cultures, the samples are pelleted by centrifugation, and supernatants are removed by decanting.

Generally, from 250 ml of culture, 1.0-1.5 grams of wet cells are produced. Pelleted cells are then resuspended in 5-10 ml of lysis buffer. RNase and DNase are added to final concentration of 10 ug/ml lysis solution. Samples are kept on ice throughout the sonication procedure. Using an appropriate tip, the samples are sonicated 3-5 times for 10 second pulses at 50% duty cycle. Sonicates are incubated on ice for 30 minutes; if the samples are viscous after this time, the sonication procedure is repeated. Lysed samples (in lysis solution) are loaded onto 1-ml columns. The columns are washed with 5 to 10 volumes of wash buffer (wash fractions are saved until the procedure is complete). Columns are developed with 2.5 ml of elution buffer, and SUMO hydrolase cleavage is performed by one of two methods: 1) cleavage is performed in elution buffer, with SUMO hydrolase added at 50 ul/250 ml buffer, samples incubated at room temperature for 2 hr or overnight at 4° C., and cleavage monitored by gel electrophoresis; 2) imidazole is first removed by dialysis, gel filtration, or desalting, samples are then resuspended in SUMO hydrolase cleavage buffer, SUMO hydrolase is added at 50 ul/2.5 ml buffer, and samples are incubated at room temperature for 2 hr or at 4° C. overnight, with cleavage monitored by gel electrophoresis. Units of SUMO hydrolase are defined as the amount of enzyme that cleaves 1 ug of pure SUMO-Met-GFP (up to 95%) in 50 mM Tris-HCl pH 8.0, 0.5 mM DTT, 150 mM NaCl at room temperature in 60 minutes.

After cleavage, protein can be stored at 4° C., or subjected to purification.

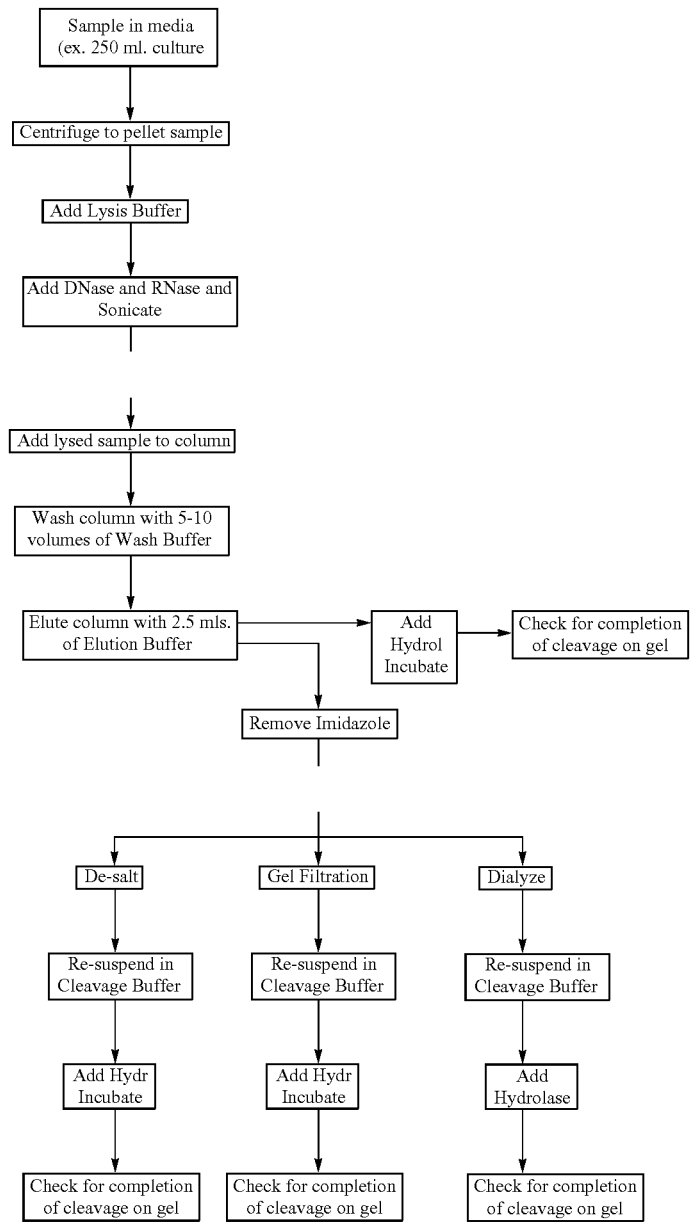

Flow Chart of Affinity Purification and Cleavage Options

The expression and purification of carboxy terminus of Ulp1p is described above.

In vitro cleavage experiments

The various His6smt3XeGFP fusions were expressed in Rosetta (DE3) pLysS (Novagen). The recombinant proteins were purified using Ni-NTA agarose (Qiagen). The comparative in vitro cleavage reactions were carried out by first normalizing the amount of the various fusions in each reaction. This was done by measuring the fluorescence properties of the purified fusion proteins using the fluorimeter Fluoriskan II (Lab Systems) and then diluting the more concentrated samples with the Ni-NTA agarose elution buffer (20 mM Tris-HCl pH 8.0, 150 mM NaCl 300 mM Imidazole and 5 mM beta-mercaptoethanol), such that their fluorescence values equaled that of the lowest yielder. Each cleavage reaction contained 100 ul of protein, 99 ul of the buffer 20 mM Tris-HCl pH 8.0, 150 mM NaCl and 5 mM beta-mercaptoethanol and 1 ul of enzyme. The reactions were incubated for 3 hours at 30° C. after which they were stopped by addition of 6× Laemmli SDS-page loading buffer followed by boiling at 95° C. for 5 minutes. The products of the cleavage reaction were analyzed by SDS-PAGE.

Proline cleavage experiments were carried out in a fashion similar to those described above. The purified His6smt3PeGFP was buffer exchanged into 20 mM Tris-HCl pH 8.0, 150 mM NaCl and 5 mM beta-mercaptoethanol using a PD-10 column. A 10 fold increase in the amount of Ulp1 were added to each reaction. Digestions were incubated for 3 hours at 30° C. All reactions were stopped by addition of Laemmli loading buffer and analyzed by SDS-page. FIG. 15 shows the stained SDS-PAGE analysis of all the SUMO-X-GFPs and their digestion by SUMO hydrolase. The findings clearly show that Ulp1 hydrolase was able to cleave all the SUMO-GFP fusions except proline. These finding are similar to the observations made in yeast (FIG. 10) and in insect cells (FIG. 13).

Conjugation of ubiquitin and SUMO to its target proteins is a highly regulated and dynamic process. Several deubiquitinating enzymes (DUBs) have been identified in yeast and other eukaryotic cells (1). Yeast genetics studies show that many of these enzymes are not essential suggesting that an overlapping function is performed by most of these enzymes. DUBs have been most extensively studied and shown to cleave linear ubiquitin fusions as well isopepetide bonds (3, 35). Much less is known about the enzymes that remove SUMO from isopeptide bonds or artificial SUMO-fusion proteins. Hochstrasser and Li have shown that Ulp1 and Ulp2 remove Smt3 and SUMO 1 from proteins and play a role in progression through the G2/M phase and recovery of cells from checkpoint arrest, respectively (20, 21). Ulp1 and Ulp2 cleave C-terminus of SUMO (-GGATY; SEQ ID NO: 59) to mature form (-GG) and de-conjugate Smt3 from the side chains of lysines (20, 21). The sequence similarity of two enzymes is restricted to a 200-amino acid sequence called ULP that contains the catalytically active region. The three-dimensional structure of the ULP domain from Ulp1 has been determined in a complex form with SUMO (Smt3) precursor (27). These studies show that conserved surfaces of SUMO determine the processing and de-conjugation of SUMO. Database searches of the human genome and recent findings suggest that there are at least 7 human ULPs with the size ranging from 238 to 1112 amino acid residues (18, 33, 39). It is intriguing to note that SUMO Ulps are not related to DUBs, suggesting that SUMO Ulps evolved separately from DUBs. The findings that ULP structure is distantly related to adenovirus processing protease, intracellular pathogen *Chlammydia trachomatis* and other proposed bacterial cystiene protease core domains suggest that this sequence evolved in prokaryotes (20, 21). Detailed properties of the SUMO proteases are provided in described in Table 3.

TABLE 3

SUMO Hydrolases/Proteases

| Enzyme | Properties (MW) | Reference |
| --- | --- | --- |
| UB1-specific Protease ULP1 | 72 KDa. 6 21 residues Cleaves linear fusion and SUMO isopeptides bonds. | Li and Hochstrasser, 1999 (REF 20) |
| ULP2 (Yeast) | 117 KDa, 1034 residues Cleaves linear fusions and SUMO isopeptide structures. | Li and Hochstrasser, 2000 (REF 21) |
| SUMO-I C-Terminal | 30 Kda Cleaves linear fusions and SUMO isopeptide structures | Suzuki, et al, 1999 (REF 33) |
| SUMO-I specific Protease SUSP I (Human) | 126 KDa 1112 residues Specific for SUMO-1 fusion but not Smt3 fusion. Does not cleave isopeptide bond. | Kim, et al, 2000 (REF 18) |
| Sentrin specific Proteases (SENP) SENP1 SENP2 SENP3 SENP4 SENP5 SENP6 SENP7 | All of the SENP enzymes have conserved C-terminal region with core catalytic cysteine. The smallest SENP7 is 238 residues and the largest SENP6 is 1112 residues. | Yeh, et al, 2000 (REF 39) |

Ulp1 has proven extremely robust in cleaving a variety of SUMO-fusion proteins expressed in *E. coli* as described in the present example. We have designed SUMO-GFP fusions in which the N-terminal methionine has been replaced with rest of the 19 amino acids. Attachment of 6×His to N-terminus of SUMO afforded easy purification of the 20 SUMO-GFP fusions from *E. coli*. The enzyme was active under broad ranges of pH, temperature, salts and imidazole concentration and was very effective in cleaving variety of proteins from SUMO fusion that includes BPTI a 6.49 KDa, Protein G a 7 KDa, β-Glucuronidase (GUS) and 110 KDa β-Galactosidase (GAL) genes. These findings suggest that the Ulp1 is much more robust in cleavage of the SUMO-fusion proteins as compared to its counterpart ubiquitin-fusion hydrolase.

SUMO Protease/Hydrolase is a Robust Enzyme:

Effects of Temperature and Additives

Figure 16:
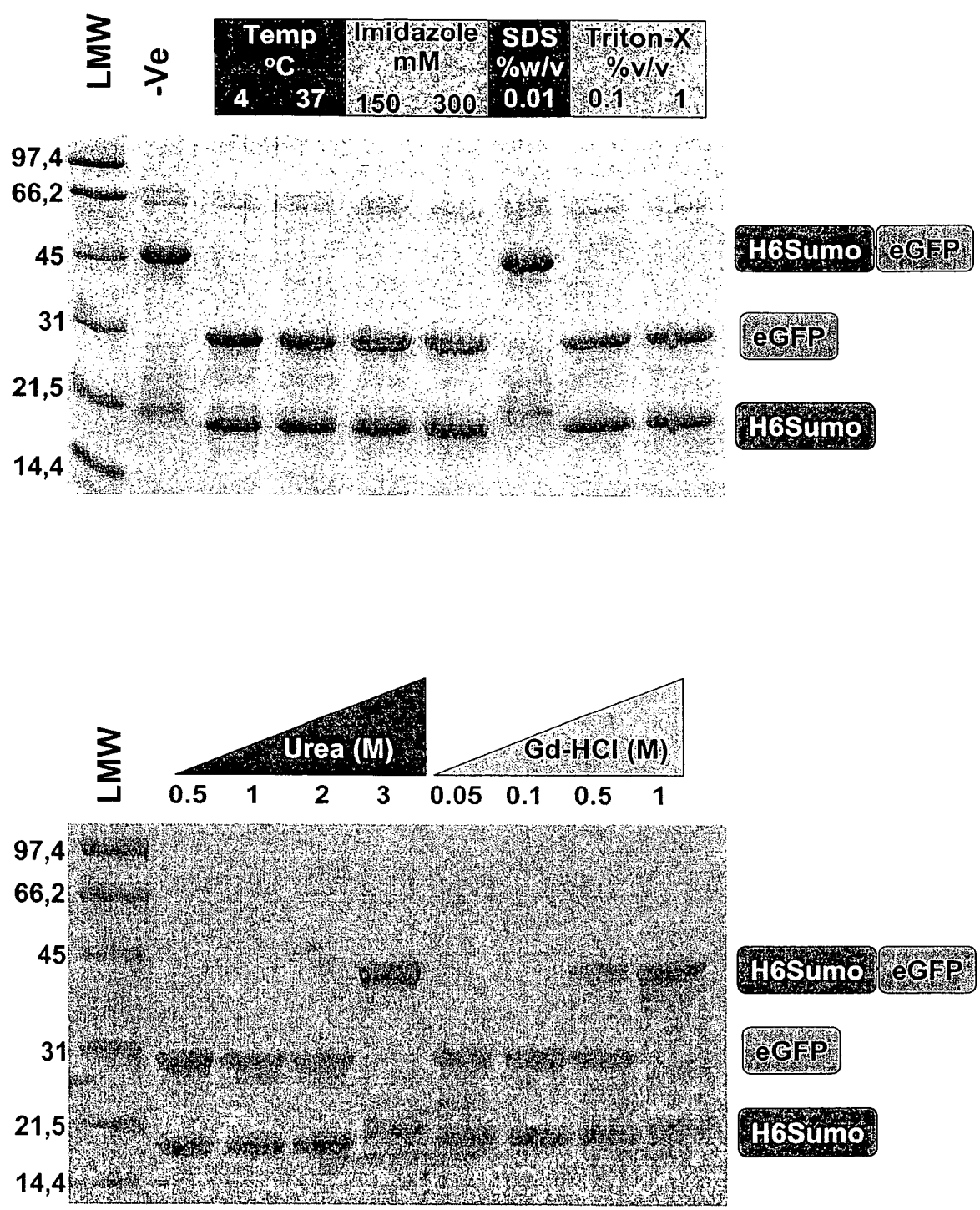
FIG. 16 contains a pair of stained SDS-polyacrylamide gels representing the effects of various conditions on Ulp1. Ni-NTA purified His6SUMO-GFP was incubated with Ulp1 under the indicated conditions for one hour at room temperature unless indicated otherwise. Low molecular weight markers (LMW) are also provided.
Figure 17:
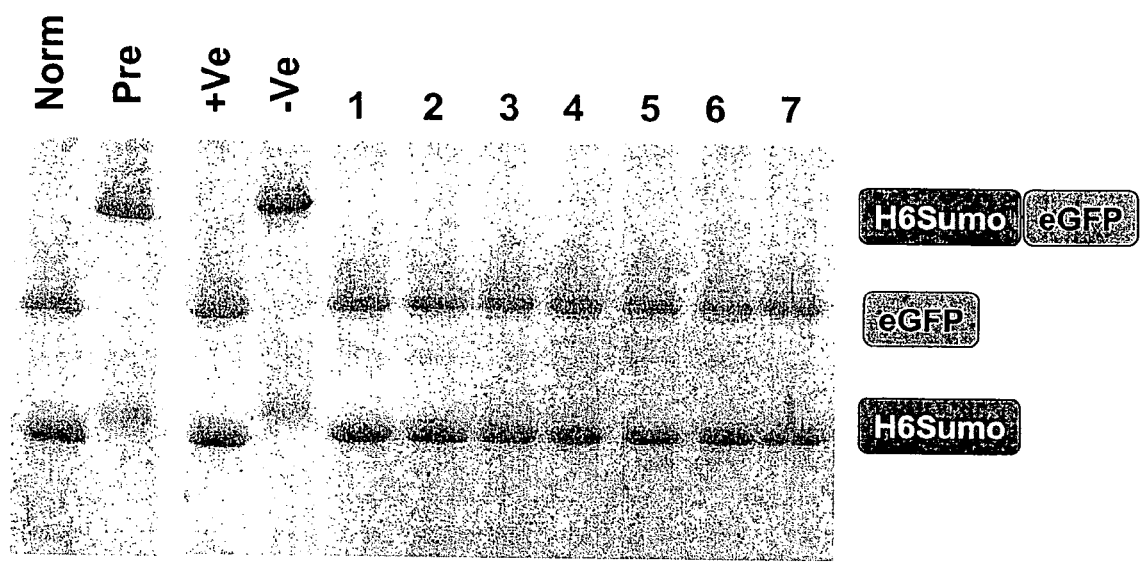
FIG. 17 is a stained SDS-polyacrylamide gel representing the effects of various protease inhibitors on Ulp1. Ni-NTA purified His6SUMO-GFP was incubated with Ulp1 and 10 mM of various protease inhibitors for 1 hour at room temperature. Lane markers: Norm is addition of Ulp1 and N-ethymaleimide (NEM) to the substrate at the same time, Pre is the incubation of Ulp1 with NEM prior to the addition of substrate, +Ve is the absence of any inhibitor, −Ve is in the absence of Ulp1, lane 1 is with E-64, lane 2 is with EDTA, lane 3 is with leupeptin, lane 4 is with NEM, lane 5 is with pepstatin, lane 6 is with TLCK. Low molecular weight markers (LMW) are also provided.

The effects of various additives/conditions and temperature upon the in vitro cleavage reaction were determined as follows: His6smt3MeGFP was expressed from pET24d in Rosetta(DE3) pLysS (Novagen). The recombinant protein was purified as before using Ni-NTA agarose (Qiagen) and then buffer exchanged into 20 mM Tris-HCl pH 8.0, 150 mM NaCl and 5 mM β-mercaptoethanol using a PD-10 column (AP Biotech). Cleavage reactions were performed with 100 ug of the purified protein, 0.5 ul of enzyme, the appropriate amount of a stock solution of additive to generate the final concentrations listed in Table 4, plus the exchange buffer up to a final volume of 200 ul. Reactions were incubated for 1 hour at 37° C. except for those at 4° C. were incubated for 3 hours. The data in FIG. 16 shows that Ulp1 was extremely active at 37° C. as well as at 4° C. Generally, His tagged proteins are purified on nickel columns and eluted with imidazole. We have discovered that the enzyme was remarkably active at 0-300 mM imidazole concentration. The enzyme was highly active at 0.01% SDS and up to 1% triton X 100. See Table 4. Similarly, chaotropic agents such as urea and did not effect the activity of the enzyme up to 2 M. Ulp1 showed 50% activity at 0.5M concentration of guanadinium hydrochloride (FIG. 16 and Table 4). A variety of reagents, including cysteine protease inhibitors, EDTA, PMSF. Pepstatin, Leupeptin, TLCK had no effect on the enzymatic activity (FIG. 17 and Table 4). N-ethymaleimide was active only if incubated with the enzyme prior to addition of the substrate. All the data shown in Table 2 demonstrate that this enzyme is extremely robust and thus constitutes a superior reagent for cleaving fusion proteins under variety of conditions.

TABLE 4

The Effect of Different Conditions on the Ulp1 Hydrolase Activity

| Conditions/Additions | Effect |
|---|---|
| Environmental: | |
| Temperature | Ulp1 is active over a broad range of temperatures, cleaving from 4 to 37° C. |
| Salts: | |
| Imidazole | Ulp1 shows similar activity in the range of 0 to 300 mM |
| Detergents: | |
| SDS | 0.01% SDS blocks activity |
| Triton-X | Ulp1 shows similar activity on the range of 0 to 0.1% |
| Chaotrophs | |
| Urea | Ulp1 shows complete activity up to and including a 2 M concentration |
| Gdm HCl | Ulp1 shows 50% activity in 0.5 M but is completely inactive in 1 M concentrations |
| Protease inhibitors: | |
| E-64 | Cysteine protease inhibitor; no affect |
| EDTA | Metalloprotease inhibitor; no affect |
| PMSF | Serine protease inhibitor; no affect |
| Pepstatin | Aspartate protease inhibitor; no affect |
| Leupeptin | Inhibits serine and cysteine proteases with trypsin-like specificity; no affect |
| TLCK-HCl | Inhibits serine and cysteine proteases with chymotrypsin-like specificity; no affect |
| N-ethylmaleimide | Cysteine protease inhibitor; on effective if enzyme is preincubated with inhibitor before addition of substrate |

Figure 18:
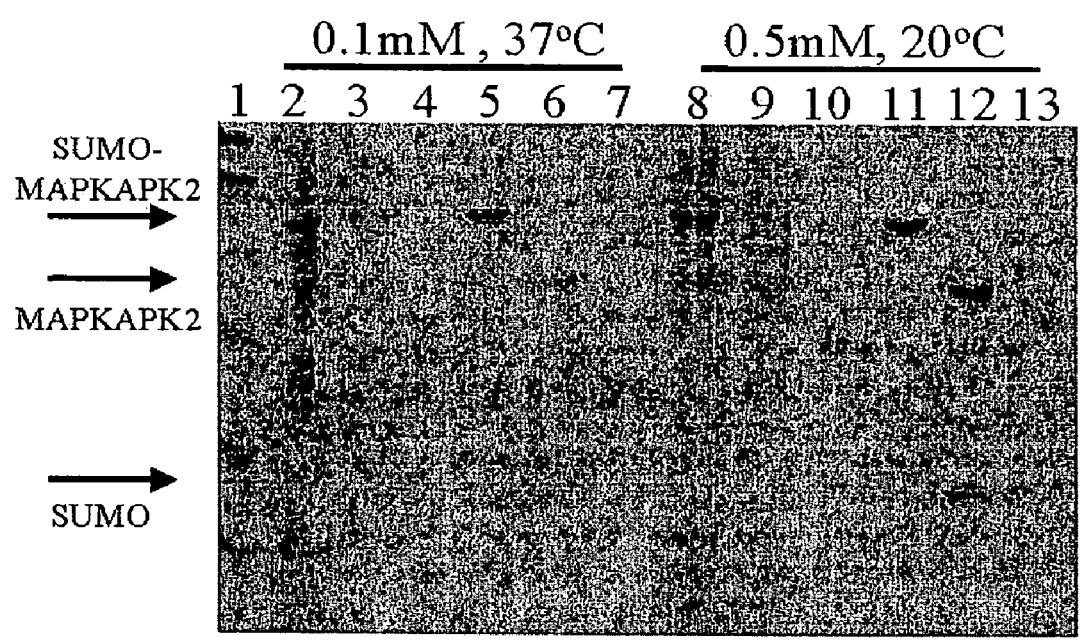
FIG. 18 is a stained SDS-polyacrylamide gel showing purification and cleavage of MAPKAP2. *E. coli* transformed with the expression vector for SUMO-MAPKAP2 where either grown at 37° C. and induced with 0.1 mM IPTG (lanes 2-7) or at 20° C. and induced with 0.5 mM IPTG (lanes 8-13). Cell lysates were Ni-NTA purified and separated by SDS-PAGE. Lane 1: BioRad low molecular weight marker; lanes 2 and 8: soluble fraction of cell lysates; lanes 3 and 9: flow through from Ni-NTA column; lanes 4 and 10: 15 mM imidazole wash of Ni-NTA column; lanes 5 and 11: 300 mm imidazole elution of Ni-NTA column; lanes 6 and 12: supernatant of 2 hour incubation of elution with SUMO hydrolase at 30° C.; and lanes 7 and 13: pellet of hydrolase incubation.

Robust Properties of SUMO Hydrolase: Cleavage of Different Size Fusion Proteins Under Broad pH Range:

FIG. 18 shows purification of a 40 kDa MAPKAP2 kinase that was difficult to express unless fused to SUMO. We have shown in Example I (FIG. 8) that this kinase was expressed in a highly soluble form (95%) as fusion to SUMO. FIG. 18 shows that whether purfied from cells expressing at 37° C. or 20° C., the SUMO fusion was efficiently cleaved under the conditions described.

Figure 19:
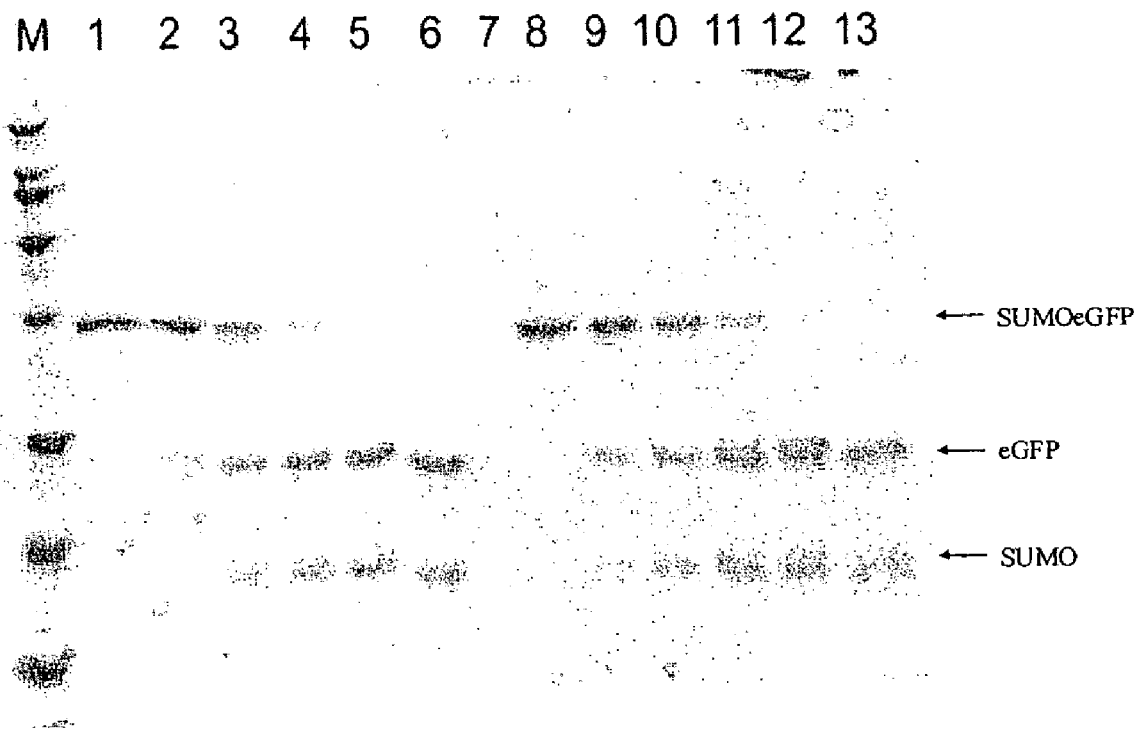
FIG. 19 is a stained SDS-polyacrylamide gel showing SUMO hydrolase function at pH 7.5 and 8.0. Purified SUMO-GFP was cleaved using 1/50 diluted purified stock of SUMO hydrolase in sodium phosphate buffer pH 7.5 (lanes 1-6) and 8.0 (lanes 8-13) at room temperature for the following length of times: lanes 1 and 8: 0 minutes, lanes 2 and 9: 1 min, lanes 3 and 10: 2.5 min, lanes 4 and 11: 5 min, lanes 5 and 12: 10 min, and lanes 6 and 13: 20 min. Lane 7 is blank and M is molecular weight markers.

The SUMO hydrolase also functions under broad pH range. FIG. 19 shows kinetics of cleavage at pH 7.5 and 8.0. The data shows that purified SUMO-GFP was completely digested at room temperature. We have also performed experiments from pH 5.5 to 10. The data (not shown) support the notion that this enzyme is active over broad range of pH.

Figure 20:
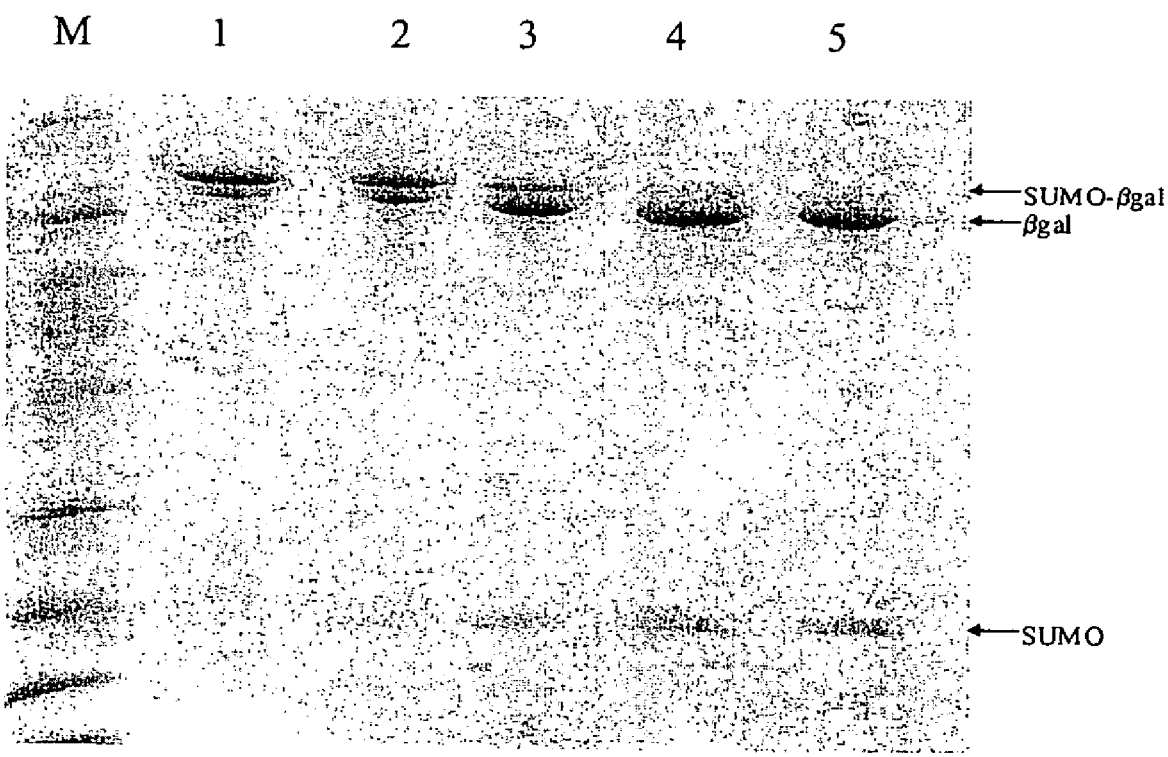
FIG. 20 is a stained SDS-polyacrylamide gel indicating SUMO hydrolase cleaves SUMO-β-Galactosidase. Purified SUMO hydrolase was incubated with *E. coli* produced SUMO-β-Galactosidase at room temperature for 0 minutes (lane 1), 2.5 min (lane 2), 5 min (lane 3), 10 min (lane 4), and 20 min (lane 5). Molecular weight markers are provided in lane M.

As discussed above, for broad utility of the system it is important that the enzyme be able to cleave fusion proteins of different sizes and structures in vitro. FIG. 20 shows the digestion pattern of SUMO-β-galactosidase (β-Gal) a 110 KDa protein. β-Gal enzyme is composed of tetrameric subunits. The digestion pattern demonstrates that in 20 minutes, SUMO hydrolase was able to cleave 100% of the protein.

Figure 21:
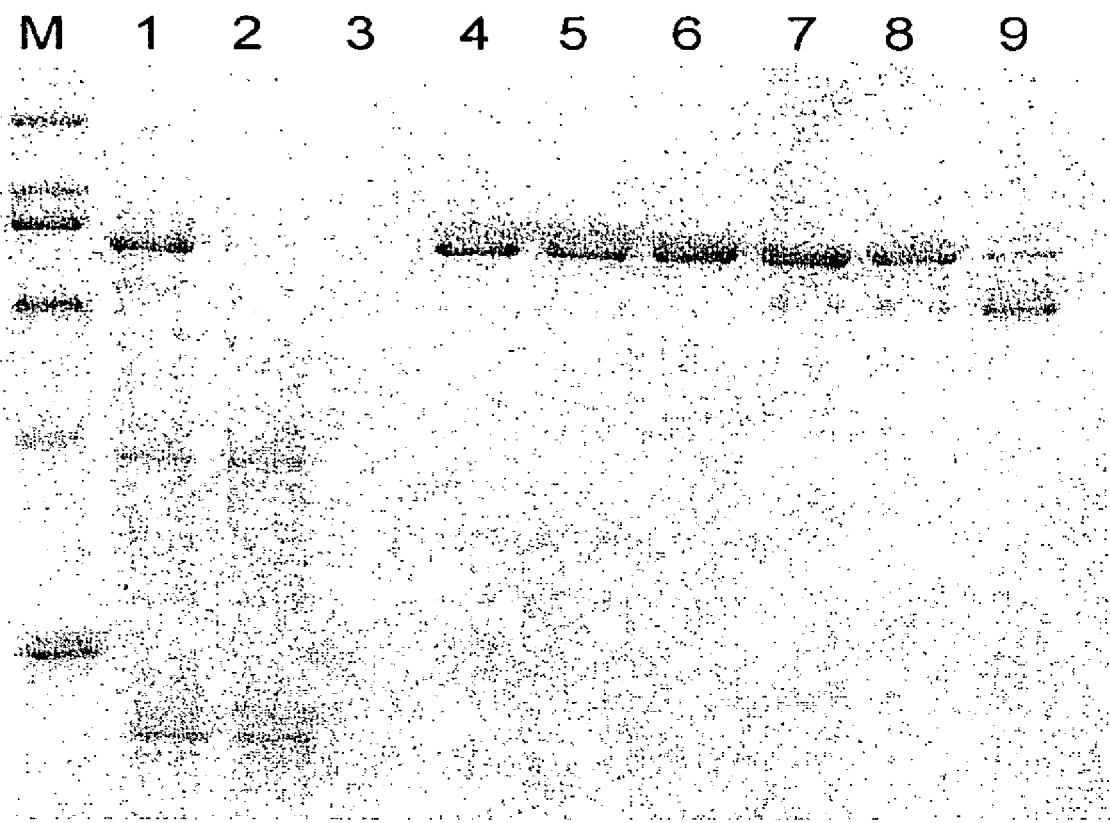
FIG. 21 is a stained SDS-polyacrylamide gel showing the cleavage of SUMO-GUS by SUMO Hydrolase in the presence of urea. Ni-NTA purified SUMO-β-GUS was incubated with 1/50 dilution of purified stock of SUMO hydrolase for 1 hour in increasing concentrations of urea at pH 8.0. Lane markers: M is broad range molecular weight marker; lane 1 is SUMO-GUS from soluble *E. coli* fraction; lane 2: flow through from nickel column; lane 3: wash; lane 4: elution; lanes 5-9: SUMO-GUS and hydrolase with various denaturants, specifically, lane 5: none; lane 6: 1 mM DTT; lane 7: 0.5 M Urea; lane 8: 1.0M Urea; lane 9: 2.0M Urea.

Among dozens of proteins expressed as SUMO fusions in our lab, only one, β-GUS, proved partially resistant to cleavage by the hydrolase. Configurations of artificial SUMO fusion are bound to occur wherein the structure of the protein will hinder the ability of the enzyme to recognize and bind the cleavage site of the fusion protein. This problem has been solved by adding small concentrations of urea, which does not inhibit the hydrolase, but results in cleavage the fusion that was previously resistant. FIG. 21 shows the digestion pattern of purified β-GUS and SUMO hydrolase before and after addition of urea. Lane 6 and 9 contain the same amount of SUMO hydrolase to which 2M urea was added during the incubation. Addition of urea allowed complete cleavage of 65 KDa β-GUS in 20 min at room temperature. This data further proves that the SUMO hydrolase cleaves broad spectrum of fusion protein efficiently. Additives such as urea can be added to aid complete cleavage of these structures that are resistant to hydrolase action.

High Throughput Protein Purification of Fusion Proteins:

Rapid Peptide Miniprep

Figure 22:
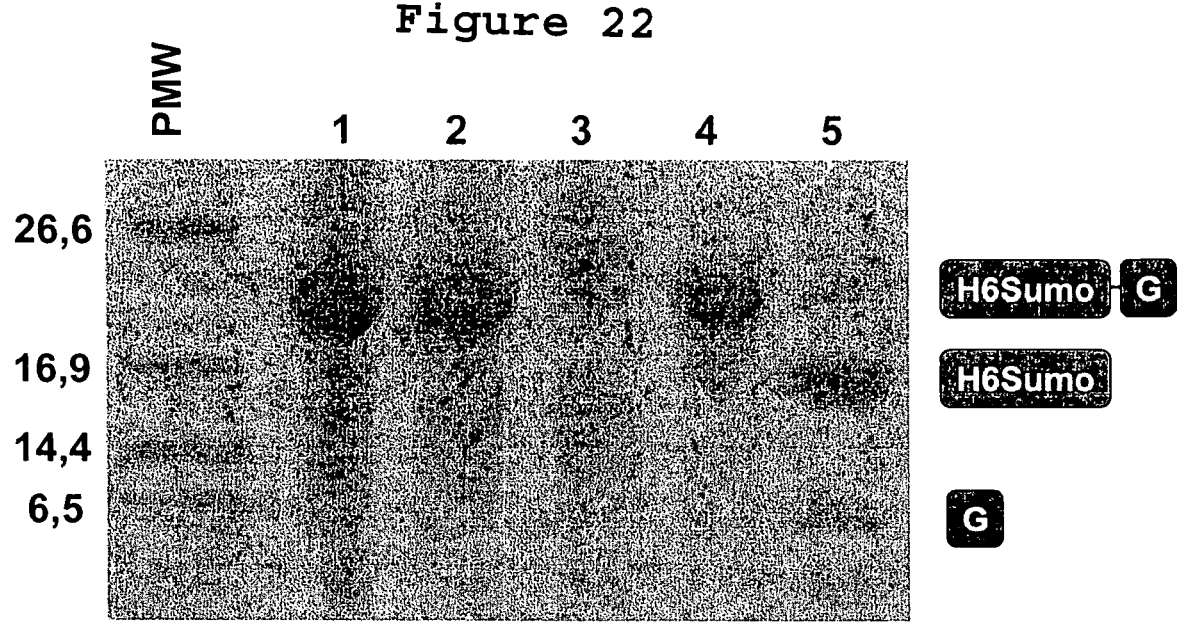
FIG. 22 is a stained SDS-polyacrylamide gel demonstrating the rapid isolation of a SUMO fusion protein. *E. coli* cells expressing a single IgG binding domain from Protein G fused to His6Smt3 were lysed with guanidinium chloride lysis buffer. Cell lysate supernatants were purified over Ni-NTA and eluted in a native buffer that allows for cleavage by Ulp1.

We have discovered that, due to the rapid folding properties of SUMO, the fused protein can also be rapidly re-natured after treatment of the crude protein mix with chaotropic agents such as guanidinium hydrochloride or urea. We have developed a simple and rapid procedure to purify SUMO-fused proteins that are expressed in prokaryotes and eukaryotes. This method was tested with SUMO-protein G fusion expressed in E. coli. Cells expressing 6×His-SUMO-G protein fusion were harvested and frozen until required for protein purification. Three times the weight per volume lysis buffer (6 M Guanidinium Chloride, 20 mM Tris-HCl, 150 mM NaCl, pH 8.0) was added to the cell pellet rapidly lyse the cells. The supernatant was loaded onto a pre-equilibrated column containing Ni-NTA agarose (Qiagen), the flow through was collected for analysis. The column was then washed, first with 2 column volumes (CV) of Lysis buffer, followed by 3 CV of wash buffer (20 nM Tris-HCl, 150 mM NaCl 15 mM Imidazole pH 8.0). The fusion protein was then eluted using 2 CV of elution buffer (20 mM Tris-HCl, 150 mM NaCl 300 mM Imidazole pH 8.0). The purified product is present in a native buffer that allows for cleavage and release of the peptide from the Sumo fusion using Ulp1. See FIG. 22. This data demonstrates that it is possible to rapidly purify the fusion protein and cleave it from the resin with Ulp1. It is possible that proteins of higher molecular weights may not rapidly re-nature and be amenable to cleavage by Ulp1. However, since the Ulp1 requires three-dimensional SUMO be intact the purification and cleavage properties are more dependent on the refolding of SUMO. Similar to DNA minipreps, rapid mini preps for the expression and purification analysis of the fused proteins may be readily employed. Table 5 summarizes the data showing the dramatic enhancement of protein production observed when utilizing the compositions and methods of the present invention. The sequences and vectors utilized in the practice of the invention are shown in FIGS. 23-46.

TABLE 5

Fusion with SUMO Enhances Protein Expression

| E. coli Expression of UBLs | All of the fusion have Met N-Termini |
| --- | --- |
| SUMO-GFP | 40 fold |
| Ub-GFP | 40 fold |
| Urm1-GFP | 50 fold |
| Hub1-GFP | 2 fold |
| Rub1-GFP | 50 fold |
| Apg8-GFP | 40 fold |
| Apg12-GFP | 20 fold |
| ISG15-GFP | 3-5 fold |

| Yeast | Met and Various N-Termini |
| --- | --- |
| Various UBLs expressed in rich media. | Copper induction not observed in rich media, however, Ub, SUMO, ISG15 fusions were processed and GFP induced 3-5 fold. |

TABLE 5-continued

Fusion with SUMO Enhances Protein Expression

| All of the twenty N-terminal variants were expressed in yeast as SUMO-X-GFP fusions. GFP was processed in all cases, except when N-terminal residue was proline. | Dramatic induction of GFP following fusion with SUMO. At least 50-100 fold induction as compared to unfused GFP expression. Under current loading conditions (20 ug) GFP was not detectable. |
| --- | --- |

| Insect Cells | Met as N-termini |
| --- | --- |
| SUMO-GFP | 10 fold compared to GFP |
| gp67-SUMO-GFP | 30 fold compared to gp-GFP |
| gp67-SUMO-GFP | 50 fold compared to SUMO-gp67-GFP |
| Secretion SUMO-GFP | At least 50 fold compared to GFP |
| Secretion Ub-GFP | At least 50 fold compared to GFP |

REFERENCES

1. Amerik, A. Y., S. J. Li, and M. Hochstrasser. 2000. Analysis of the deubiquitinating enzymes of the yeast *Saccharomyces cerevisiae*. Biol Chem 381:981-92.
2. Bachmair, A., D. Finley, and A. Varshavsky. 1986. In vivo half-life of a protein is a function of its amino-terminal residue. Science 234:179-86.
3. Baker, R. T. 1996. Protein expression using ubiquitin fusion and cleavage. Curr Opin Biotechnol 7:541-6.
4. Bayer, P., A. Arndt, S. Metzger, R. Mahajan, F. Melchior, R. Jaenicke, and J. Becker. 1998. Structure determination of the small ubiquitin-related modifier SUMO-1. J Mol Biol 280:275-86.
5. Butt, T. R., S. Jonnalagadda, B. P. Monia, E. J. Sternberg, J. A. Marsh, J. M. Stadel, D. J. Ecker, and S. T. Crooke. 1989. Ubiquitin fusion augments the yield of cloned gene products in *Escherichia coli*. Proc Natl Acad Sci USA 86:2540-4.
6. Butt, T. R., E. J. Sternberg, J. A. Gorman, P. Clark, D. Hamer, M. Rosenberg, and S. T. Crooke. 1984. Copper metallothionein of yeast, structure of the gene, and regulation of expression. Proc Natl Acad Sci USA 81:3332-6.
7. Ecker, D. J., J. M. Stadel, T. R. Butt, J. A. Marsh, B. P. Monia, D. A. Powers, J. A. Gorman, P. E. Clark, F. Warren, A. Shatzman, and et al. 1989. Increasing gene expression in yeast by fusion to ubiquitin. J Biol Chem 264:7715-9.
8. Gietz, D., A. St. Jean, R. A. Woods, and R. H. Schiestl. 1992. Improved method for high efficiency transformation of intact yeast cells. Nucleic Acids Res 20:1425.
9. Goward, C. R., J. P. Murphy, T. Atkinson, and D. A. Barstow. 1990. Expression and purification of a truncated recombinant streptococcal protein G. Biochem J 267:171-7.
10. Graumann, K., J. L. Wittliff, W. Raffelsberger, L. Miles, A. Jungbauer, and T. R. Butt. 1996. Structural and functional analysis of N-terminal point mutants of the human estrogen receptor. J Steroid Biochem Mol Biol 57:293-300.
11. Hicke, L. 1997. Ubiquitin-dependent internalization and down-regulation of plasma membrane proteins. Faseb J 11:1215-26.
12. Hochstrasser, M. 2000. Evolution and function of ubiquitin-like protein-conjugation systems. Nat Cell Biol 2:E153-7.
13. Hochstrasser, M. 1995. Ubiquitin, proteasomes, and the regulation of intracellular protein degradation. Curr Opin Cell Biol 7:215-23.

14. Hochstrasser, M. 1996. Ubiquitin-dependent protein degradation. Annu Rev Genet 30:405-39.
15. Jentsch, S., and G. Pyrowolakis. 2000. Ubiquitin and its kin: how close are the family ties? Trends Cell Biol 10:335-42. _00001785 _00001785.
16. Johnson, E. S., I. Schwienhorst, R. J. Dohmen, and G. Blobel. 1997. The ubiquitin-like protein Smt3p is activated for conjugation to other proteins by an Aos1p/Uba2p heterodimer. Embo J 16:5509-19.
17. Kapust, R. B., and D. S. Waugh. 1999. *Escherichia coli* maltose-binding protein is uncommonly effective at promoting the solubility of polypeptides to which it is fused. Protein Sci 8:1668-74.
18. Kim, K. I., S. H. Baek, Y. J. Jeon, S. Nishimori, T. Suzuki, S. Uchida, N. Shimbara, H. Saitoh, K. Tanaka, and C. H. Chung. 2000. A new SUMO-1-specific protease, SUSP1, that is highly expressed in reproductive organs. J Biol Chem 275:14102-6.
19. LaBean, T. H., S. A. Kauffman, and T. R. Butt. 1995. Libraries of random-sequence polypeptides produced with high yield as carboxy-terminal fusions with ubiquitin. Mol Divers 1:29-38.
20. Li, S. J., and M. Hochstrasser. 1999. A new protease required for cell-cycle progression in yeast. Nature 398:246-51.
21. Li, S. J., and M. Hochstrasser. 2000. The yeast ULP2 (SMT4) gene encodes a novel protease specific for the ubiquitin-like Smt3 protein. Mol Cell Biol 20:2367-77.
22. Lyttle, C. R., P. Damian-Matsumura, H. Juul, and T. R. Butt. 1992. Human estrogen receptor regulation in a yeast model system and studies on receptor agonists and antagonists. J Steroid Biochem Mol Biol 42:677-85.
23. Mahajan, R., L. Gerace, and F. Melchior. 1998. Molecular characterization of the SUMO-1 modification of Ran-GAP1 and its role in nuclear envelope association. J Cell Biol 140:259-70.
24. Malakhova, O., M. Malakhov, C. Hetherington, and D. E. Zhang. 2002. Lipopolysaccharide activates the expression of ISG15-specific protease UBP43 via interferon regulatory factor 3. J Biol Chem 277:14703-11.
25. Marathe, S. V., and J. E. McEwen. 1995. Vectors with the gus reporter gene for identifying and quantitating promoter regions in *Saccharomyces cerevisiae*. Gene 154:105-7.
26. Matunis, M. J., J. Wu, and G. Blobel. 1998. SUMO-1 modification and its role in targeting the Ran GTPase-activating protein, RanGAP1, to the nuclear pore complex. J Cell Biol 140:499-509.
27. Mossessova, E., and C. D. Lima. 2000. Ulp1-SUMO crystal structure and genetic analysis reveal conserved interactions and a regulatory element essential for cell growth in yeast. Mol Cell 5:865-76.
28. Muller, S., C. Hoege, G. Pyrowolakis, and S. Jentsch. 2001. SUMO, ubiquitin's mysterious cousin. Nat Rev Mol Cell Biol 2:202-10.
29. Muller, S., M. J. Matunis, and A. Dejean. 1998. Conjugation with the ubiquitin-related modifier SUMO-1 regulates the partitioning of PML within the nucleus. Embo J 17:61-70.
30. Ohsumi, Y. 2001. Molecular dissection of autophagy: two ubiquitin-like systems. Nat Rev Mol Cell Biol 2:211-6.
31. Sherman, F., G. Fink, and J. Hicks. 1986. Methods in yeast genetics. Cold Spring Harbor Laboratory, Cold Spring Harbor, N.Y.
32. Sikorski, R. S., and P. Hieter. 1989. A system of shuttle vectors and yeast host strains designed for efficient manipulation of DNA in *Saccharomyces cerevisiae*. Genetics 122:19-27.
33. Suzuki, T., A. Ichiyama, H. Saitoh, T. Kawakami, M. Omata, C. H. Chung, M. Kimura, N. Shimbara, and K. Tanaka. 1999. A new 30-kDa ubiquitin-related SUMO-1 hydrolase from bovine brain. J Biol Chem 274:31131-4.
34. Varshavsky, A. 1996. The N-end rule: functions, mysteries, uses. Proc Natl Acad Sci USA 93:12142-9.
35. Varshavsky, A. 2000. Ubiquitin fusion technique and its descendants. Methods Enzymol 327:578-93.
36. Waldo, G. S., B. M. Standish, J. Berendzen, and T. C. Terwilliger. 1999. Rapid protein-folding assay using green fluorescent protein. Nat Biotechnol 17:691-5.
37. Walfish, P. G., T. Yoganathan, Y. F. Yang, H. Hong, T. R. Butt, and M. R. Stallcup. 1997. Yeast hormone response element assays detect and characterize GRIP1 coactivator-dependent activation of transcription by thyroid and retinoid nuclear receptors. Proc Natl Acad Sci USA 94:3697-702.
38. Wright, L. C., J. Seybold, A. Robichaud, I. M. Adcock, and P. J. Barnes. 1998. Phosphodiesterase expression in human epithelial cells. Am J Physiol 275:L694-700.
39. Yeh, E. T., L. Gong, and T. Kamitani. 2000. Ubiquitin-like proteins: new wines in new bottles. Gene 248:1-14.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for enhancing expression levels of a protein of interest in a host cell comprising i) operably linking a nucleic acid sequence encoding a ubiquitin like molecule (UBL) molecule selected from the group consisting of RUB, HUB, APG8, APG12, URM1, and ISG15 to a nucleic acid sequence encoding said protein of interest thereby generating a construct encoding a fusion protein, wherein the carboxy terminus of said UBL molecule is directly attached to the amino terminus of said protein of interest in said fusion protein, and wherein the carboxy terminal amino acids of said related-to ubiquitin (RUB), homologous-to-ubiquitin (HUB), autophagy 8 (APG8), autophagy 12 (APG12), ubiquitin-related modifier 1 (URM1), and interferon stimulated gene 15 (ISG15) are Gly-Gly, Tyr-Tyr, Phe-Gly, Phe-Gly, Gly-Gly, and Gly-Gly, respectively; and ii) introducing said nucleic acid into said host cell, whereby the presence of said UBL molecule in said fusion protein increases the expression level of said protein of interest in said host cell.

2. The method of claim 1, wherein said host cell is selected from the group consisting of a yeast cell, *E. coli*, and an insect cell.

3. The method of claim 1, further comprising isolation of said fusion protein.

4. The method of claim 3, further comprising cleavage of said fusion protein to release said protein of interest from said UBL molecule.

5. A method for generating an altered amino terminus in a protein of interest in a host cell comprising;
   a) providing a nucleic acid sequence encoding said protein of interest;
   b) altering the N-terminal amino acid coding sequence in said nucleic acid;
   c) operably linking a nucleic acid molecule encoding a ubiquitin like molecule (UBL) selected from the group consisting of related-to ubiquitin (RUB), homologous-to-ubiquitin (HUB), autophagy 8 (APG8), autophagy 12 (APG12), ubiquitin-related modifier 1 (URM1), and interferon stimulated gene 15 (ISG15) to said nucleic acid sequence of step b) thereby generating a construct encoding a fusion protein, wherein the carboxy terminus of said UBL molecule is directly attached to the amino terminus of said protein of interest with altered amino terminus in said fusion protein, and wherein the carboxy terminal amino acids of said RUB, HUB, APG8, APG12, URM1, and ISG15 are Gly-Gly, Tyr-Tyr, Phe-Gly, Phe-Gly, Gly-Gly, and Gly-Gly, respectively; and
   d) expressing said nucleic acid in a eukaryotic cell, thereby producing said protein of interest in said cell, said eukaryotic cell expressing endogenous UBL cleaving enzymes which cleave the UBL operably linked to the protein of interest, thereby producing a protein of interest having an altered amino terminus.

6. A method for enhancing secretion levels of a protein of interest from a host cell comprising
   i) operably linking a nucleic acid sequence encoding a ubiquitin like molecule (UBL) selected from the group consisting of related-to ubiquitin (RUB), homologous-to- ubiquitin (HUB), ubiquitin-related modifier 1 (URM1), and interferon stimulated gene 15 (ISG15) to a nucleic acid sequence encoding said protein of interest thereby generating a construct encoding a fusion protein, wherein the carboxy terminus of said UBL molecule is directly attached to the amino terminus of said protein of interest in said fusion protein, and wherein the carboxy terminal amino acids of said RUB, HUB, URM1, and ISG15 are Gly-Gly, Tyr-Tyr, Gly-Gly, and Gly-Gly, respectively; and
   ii) introducing said nucleic acid into said host cell, whereby the presence of said UBL molecule in said fusion protein increases the secretion of said protein of interest from said host cell.

7. The method of claim 6, wherein said host cell is selected from the group consisting of a yeast cell, *E. coli*, and an insect cell.

8. The method of claim 6, further comprising isolation of said fusion protein.

9. The method of claim 6, further comprising cleavage of said fusion protein to release said protein of interest from said UBL molecule.

* * * * *

SEQUENCE LISTING

<160> NUMBER OF SEQ ID NOS: 65

<210> SEQ ID NO 1
<211> LENGTH: 106
<212> TYPE: PRT
<213> ORGANISM: Artificial Sequence
<220> FEATURE:
<223> OTHER INFORMATION: Synthetic Sequence

<400> SEQUENCE: 1

Met Gly His His His His His His Gly Ser Asp Ser Glu Val Asn Gln
 1               5                  10                  15

Glu Ala Lys Pro Glu Val Lys Pro Glu Val Lys Pro Glu Thr His Ile
            20                  25                  30

```
Asn Leu Lys Val Ser Asp Gly Ser Ser Glu Ile Phe Phe Lys Ile Lys
         35                  40                  45

Lys Thr Thr Pro Leu Arg Arg Leu Met Glu Ala Phe Ala Lys Arg Gln
 50                  55                  60

Gly Lys Glu Met Asp Ser Leu Arg Phe Leu Tyr Asp Gly Ile Arg Ile
 65                  70                  75                  80

Gln Ala Asp Gln Ala Pro Glu Asp Leu Asp Met Glu Asp Asn Asp Ile
             85                  90                  95

Ile Glu Ala His Arg Glu Gln Ile Gly Gly
            100                 105

<210> SEQ ID NO 2
<211> LENGTH: 320
<212> TYPE: DNA
<213> ORGANISM: Artificial Sequence
<220> FEATURE:
<223> OTHER INFORMATION: Synthetic Sequence

<400> SEQUENCE: 2
ccatgggtca tcaccatcat catcacgggt cggactcaga agtcaatcaa gaagctaagc     60
cagaggtcaa gccagaagtc aagcctgaga ctcacatcaa tttaaaggtg tccgatggat    120
cttcagagat cttcttcaag atcaaaaaga ccactccttt aagaaggctg atggaagcgt    180
tcgctaaaag acagggtaag gaaatggact ccttaagatt cttgtacgac ggtattagaa    240
ttcaagctga tcaggcccct gaagatttgg acatggagga taacgatatt attgaggctc    300
accgcgaaca gattggaggt                                                320

<210> SEQ ID NO 3
<211> LENGTH: 239
<212> TYPE: PRT
<213> ORGANISM: Artificial Sequence
<220> FEATURE:
<223> OTHER INFORMATION: Synthetic Sequence

<400> SEQUENCE: 3

Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
             20                  25                  30

Glu Gly Glu Gly Asp Ala Thr Tyr Gly Lys Leu Thr Leu Lys Phe Ile
         35                  40                  45

Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
             85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175
```

```
Val Gln Leu Ala Asp His Tyr Gln Gln Asn Thr Pro Ile Gly Asp Gly
                180                 185                 190

Pro Val Leu Leu Pro Asp Asn His Tyr Leu Ser Thr Gln Ser Ala Leu
            195                 200                 205

Ser Lys Asp Pro Asn Glu Lys Arg Asp His Met Val Leu Leu Glu Phe
        210                 215                 220

Val Thr Ala Ala Gly Ile Thr Leu Gly Met Asp Glu Leu Tyr Lys
225                 230                 235

<210> SEQ ID NO 4
<211> LENGTH: 727
<212> TYPE: DNA
<213> ORGANISM: Artificial Sequence
<220> FEATURE:
<223> OTHER INFORMATION: Synthetic Sequence

<400> SEQUENCE: 4
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagtaa     720
taagctt                                                              727

<210> SEQ ID NO 5
<211> LENGTH: 345
<212> TYPE: PRT
<213> ORGANISM: Artificial Sequence
<220> FEATURE:
<223> OTHER INFORMATION: Synthetic Sequence

<400> SEQUENCE: 5

Met Gly His His His His His His Gly Ser Asp Ser Glu Val Asn Gln
1               5                   10                  15

Glu Ala Lys Pro Glu Val Lys Pro Glu Val Lys Pro Glu Thr His Ile
            20                  25                  30

Asn Leu Lys Val Ser Asp Gly Ser Ser Glu Ile Phe Phe Lys Ile Lys
        35                  40                  45

Lys Thr Thr Pro Leu Arg Arg Leu Met Glu Ala Phe Ala Lys Arg Gln
    50                  55                  60

Gly Lys Glu Met Asp Ser Leu Arg Phe Leu Tyr Asp Gly Ile Arg Ile
65                  70                  75                  80

Gln Ala Asp Gln Ala Pro Glu Asp Leu Asp Met Glu Asp Asn Asp Ile
                85                  90                  95

Ile Glu Ala His Arg Glu Gln Ile Gly Gly Met Val Ser Lys Gly Glu
            100                 105                 110
```

```
Glu Leu Phe Thr Gly Val Val Pro Ile Leu Val Glu Leu Asp Gly Asp
            115                 120                 125

Val Asn Gly His Lys Phe Ser Val Ser Gly Glu Gly Glu Gly Asp Ala
        130                 135                 140

Thr Tyr Gly Lys Leu Thr Leu Lys Phe Ile Cys Thr Thr Gly Lys Leu
145                 150                 155                 160

Pro Val Pro Trp Pro Thr Leu Val Thr Thr Leu Thr Tyr Gly Val Gln
                165                 170                 175

Cys Phe Ser Arg Tyr Pro Asp His Met Lys Gln His Asp Phe Phe Lys
            180                 185                 190

Ser Ala Met Pro Glu Gly Tyr Val Gln Glu Arg Thr Ile Phe Phe Lys
        195                 200                 205

Asp Asp Gly Asn Tyr Lys Thr Arg Ala Glu Val Lys Phe Glu Gly Asp
    210                 215                 220

Thr Leu Val Asn Arg Ile Glu Leu Lys Gly Ile Asp Phe Lys Glu Asp
225                 230                 235                 240

Gly Asn Ile Leu Gly His Lys Leu Glu Tyr Asn Tyr Asn Ser His Asn
                245                 250                 255

Val Tyr Ile Met Ala Asp Lys Gln Lys Asn Gly Ile Lys Val Asn Phe
            260                 265                 270

Lys Ile Arg His Asn Ile Glu Asp Gly Ser Val Gln Leu Ala Asp His
        275                 280                 285

Tyr Gln Gln Asn Thr Pro Ile Gly Asp Gly Pro Val Leu Leu Pro Asp
    290                 295                 300

Asn His Tyr Leu Ser Thr Gln Ser Ala Leu Ser Lys Asp Pro Asn Glu
305                 310                 315                 320

Lys Arg Asp His Met Val Leu Leu Glu Phe Val Thr Ala Ala Gly Ile
                325                 330                 335

Thr Leu Gly Met Asp Glu Leu Tyr Lys
            340                 345

<210> SEQ ID NO 6
<211> LENGTH: 1047
<212> TYPE: DNA
<213> ORGANISM: Artificial Sequence
<220> FEATURE:
<223> OTHER INFORMATION: Synthetic Sequence

<400> SEQUENCE: 6
ccatgggtca tcaccatcat catcacgggt cggactcaga agtcaatcaa gaagctaagc    60
cagaggtcaa gccagaagtc aagcctgaga ctcacatcaa tttaaaggtg tccgatggat   120
cttcagagat cttcttcaag atcaaaaaga ccactccttt aagaaggctg atggaagcgt   180
tcgctaaaag acagggtaag gaaatggact ccttaagatt cttgtacgac ggtattagaa   240
ttcaagctga tcaggcccct gaagatttgg acatggagga taacgatatt attgaggctc   300
accgcgaaca gattggaggt atggtgagca agggcgagga gctgttcacc ggggtggtgc   360
ccatcctggt cgagctggac ggcgacgtaa acggccacaa gttcagcgtg tccggcgagg   420
gcgagggcga tgccacctac ggcaagctga ccctgaagtt catctgcacc accggcaagc   480
tgcccgtgcc ctggcccacc ctcgtgacca ccctgaccta cggcgtgcag tgcttcagcc   540
gctaccccga ccacatgaag cagcacgact tcttcaagtc cgccatgccc gaaggctacg   600
tccaggagcg caccatcttc ttcaaggacg acggcaacta caagacccgc gccgaggtga   660
agttcgaggg cgacaccctg gtgaaccgca tcgagctgaa gggcatcgac ttcaaggagg   720
```

-continued

```
acggcaacat cctggggcac aagctggagt acaactacaa cagccacaac gtctatatca    780
tggccgacaa gcagaagaac ggcatcaagg tgaacttcaa gatccgccac aacatcgagg    840
acggcagcgt gcagctcgcc gaccactacc agcagaacac ccccatcggc gacggccccg    900
tgctgctgcc cgacaaccac tacctgagca cccagtccgc cctgagcaaa gaccccaacg    960
agaagcgcga tcacatggtc ctgctggagt tcgtgaccgc cgccgggatc actctcggca   1020
tggacgagct gtacaagtaa taagctt                                       1047
```

<210> SEQ ID NO 7
<211> LENGTH: 323
<212> TYPE: PRT
<213> ORGANISM: Artificial Sequence
<220> FEATURE:
<223> OTHER INFORMATION: Synthetic Sequence

<400> SEQUENCE: 7

```
Met Gly His His His His His His Gly Gln Ile Phe Val Lys Thr Leu
  1               5                  10                  15

Thr Gly Lys Thr Ile Thr Leu Glu Val Glu Pro Ser Asp Thr Ile Glu
             20                  25                  30

Asn Val Lys Ala Lys Ile Gln Asp Lys Glu Gly Ile Pro Pro Asp Gln
         35                  40                  45

Gln Arg Leu Ile Phe Ala Gly Lys Gln Leu Glu Asp Gly Arg Thr Leu
     50                  55                  60

Ser Asp Tyr Asn Ile Gln Lys Glu Ser Thr Leu His Leu Val Leu Arg
 65                  70                  75                  80

Leu Arg Gly Gly Met Val Ser Lys Gly Glu Glu Leu Phe Thr Gly Val
                 85                  90                  95

Val Pro Ile Leu Val Glu Leu Asp Gly Asp Val Asn Gly His Lys Phe
            100                 105                 110

Ser Val Ser Gly Glu Gly Glu Gly Asp Ala Thr Tyr Gly Lys Leu Thr
        115                 120                 125

Leu Lys Phe Ile Cys Thr Thr Gly Lys Leu Pro Val Pro Trp Pro Thr
    130                 135                 140

Leu Val Thr Thr Leu Thr Tyr Gly Val Gln Cys Phe Ser Arg Tyr Pro
145                 150                 155                 160

Asp His Met Lys Gln His Asp Phe Phe Lys Ser Ala Met Pro Glu Gly
                165                 170                 175

Tyr Val Gln Glu Arg Thr Ile Phe Phe Lys Asp Asp Gly Asn Tyr Lys
            180                 185                 190

Thr Arg Ala Glu Val Lys Phe Glu Gly Asp Thr Leu Val Asn Arg Ile
        195                 200                 205

Glu Leu Lys Gly Ile Asp Phe Lys Glu Asp Gly Asn Ile Leu Gly His
    210                 215                 220

Lys Leu Glu Tyr Asn Tyr Asn Ser His Asn Val Tyr Ile Met Ala Asp
225                 230                 235                 240

Lys Gln Lys Asn Gly Ile Lys Val Asn Phe Lys Ile Arg His Asn Ile
                245                 250                 255

Glu Asp Gly Ser Val Gln Leu Ala Asp His Tyr Gln Gln Asn Thr Pro
            260                 265                 270

Ile Gly Asp Gly Pro Val Leu Leu Pro Asp Asn His Tyr Leu Ser Thr
        275                 280                 285

Gln Ser Ala Leu Ser Lys Asp Pro Asn Glu Lys Arg Asp His Met Val
    290                 295                 300
```

-continued

| Leu Leu Glu Phe Val Thr Ala Ala Gly Ile Thr Leu Gly Met Asp Glu |
| 305 310 315 320 |

Leu Tyr Lys

<210> SEQ ID NO 8
<211> LENGTH: 981
<212> TYPE: DNA
<213> ORGANISM: Artificial Sequence
<220> FEATURE:
<223> OTHER INFORMATION: Synthetic Sequence

<400> SEQUENCE: 8

```
ccatgggtca tcaccatcat catcacgggc agatcttcgt caagacgtta accggtaaaa    60
ccataactct agaagttgaa ccatccgata ccatcgaaaa cgttaaggct aaaattcaag   120
acaaggaagg cattccacct gatcaacaaa gattgatctt tgccggtaag cagctcgagg   180
acggtagaac gctgtctgat tacaacattc agaaggagtc gaccttacat cttgtcttac   240
gcctacgtgg aggtatggtg agcaagggcg aggagctgtt caccggggtg gtgcccatcc   300
tggtcgagct ggacggcgac gtaaacggcc acaagttcag cgtgtccggc gagggcgagg   360
gcgatgccac ctacggcaag ctgaccctga agttcatctg caccaccggc aagctgcccg   420
tgccctggcc caccctcgtg accaccctga cctacggcgt gcagtgcttc agccgctacc   480
ccgaccacat gaagcagcac gacttcttca gtccgccat gcccgaaggc tacgtccagg   540
agcgcaccat cttcttcaag gacgacggca actacaagac ccgcgccgag gtgaagttcg   600
agggcgacac cctggtgaac cgcatcgagc tgaagggcat cgacttcaag gaggacggca   660
acatcctggg gcacaagctg gagtacaact acaacagcca caacgtctat atcatggccg   720
acaagcagaa gaacggcatc aaggtgaact tcaagatccg ccacaacatc gaggacggca   780
gcgtgcagct cgccgaccac taccagcaga caccccccat cggcgacggc cccgtgctgc   840
tgcccgacaa ccactacctg agcacccagt ccgccctgag caaagacccc aacgagaagc   900
gcgatcacat ggtcctgctg gagttcgtga ccgccgccgg gatcactctc ggcatggacg   960
agctgtacaa gtaataagct t                                             981
```

<210> SEQ ID NO 9
<211> LENGTH: 346
<212> TYPE: PRT
<213> ORGANISM: Artificial Sequence
<220> FEATURE:
<223> OTHER INFORMATION: Synthetic Sequence

<400> SEQUENCE: 9

| Met Gly His His His His His His Gly Val Asn Val Lys Val Glu Phe |
| 1 5 10 15 |

| Leu Gly Gly Leu Asp Ala Ile Phe Gly Lys Gln Arg Val His Lys Ile |
| 20 25 30 |

| Lys Met Asp Lys Glu Asp Pro Val Thr Val Gly Asp Leu Ile Asp His |
| 35 40 45 |

| Ile Val Ser Thr Met Ile Asn Asn Pro Asn Asp Val Ser Ile Phe Ile |
| 50 55 60 |

| Glu Asp Asp Ser Ile Arg Pro Gly Ile Ile Thr Leu Ile Asn Asp Thr |
| 65 70 75 80 |

| Asp Trp Glu Leu Glu Gly Glu Lys Asp Tyr Ile Leu Glu Asp Gly Asp |
| 85 90 95 |

| Ile Ile Ser Phe Thr Ser Thr Leu His Gly Gly Met Val Ser Lys Gly |
| 100 105 110 |

```
Glu Glu Leu Phe Thr Gly Val Val Pro Ile Leu Val Glu Leu Asp Gly
            115                 120                 125
Asp Val Asn Gly His Lys Phe Ser Val Ser Gly Glu Gly Glu Gly Asp
        130                 135                 140
Ala Thr Tyr Gly Lys Leu Thr Leu Lys Phe Ile Cys Thr Thr Gly Lys
145                 150                 155                 160
Leu Pro Val Pro Trp Pro Thr Leu Val Thr Thr Leu Thr Tyr Gly Val
                165                 170                 175
Gln Cys Phe Ser Arg Tyr Pro Asp His Met Lys Gln His Asp Phe Phe
            180                 185                 190
Lys Ser Ala Met Pro Glu Gly Tyr Val Gln Glu Arg Thr Ile Phe Phe
        195                 200                 205
Lys Asp Asp Gly Asn Tyr Lys Thr Arg Ala Glu Val Lys Phe Glu Gly
210                 215                 220
Asp Thr Leu Val Asn Arg Ile Glu Leu Lys Gly Ile Asp Phe Lys Glu
225                 230                 235                 240
Asp Gly Asn Ile Leu Gly His Lys Leu Glu Tyr Asn Tyr Asn Ser His
                245                 250                 255
Asn Val Tyr Ile Met Ala Asp Lys Gln Lys Asn Gly Ile Lys Val Asn
            260                 265                 270
Phe Lys Ile Arg His Asn Ile Glu Asp Gly Ser Val Gln Leu Ala Asp
        275                 280                 285
His Tyr Gln Gln Asn Thr Pro Ile Gly Asp Gly Pro Val Leu Leu Pro
    290                 295                 300
Asp Asn His Tyr Leu Ser Thr Gln Ser Ala Leu Ser Lys Asp Pro Asn
305                 310                 315                 320
Glu Lys Arg Asp His Met Val Leu Leu Glu Phe Val Thr Ala Ala Gly
                325                 330                 335
Ile Thr Leu Gly Met Asp Glu Leu Tyr Lys
            340                 345

<210> SEQ ID NO 10
<211> LENGTH: 1050
<212> TYPE: DNA
<213> ORGANISM: Artificial Sequence
<220> FEATURE:
<223> OTHER INFORMATION: Synthetic Sequence

<400> SEQUENCE: 10
ccatgggtca tcaccatcat catcacgggg taaacgtgaa agtggagttt ctaggtggac      60
ttgatgctat ttttggaaaa caaagagtac ataaaattaa gatggacaaa gaagatcctg     120
tcacagtggg cgatttgatt gaccacattg tatctactat gatcaataac cctaatgacg     180
ttagtatctt catcgaagat gattctataa gacccggtat catcacatta atcaacgaca     240
ccgactggga gctcgaaggc gaaaaagact acatattgga agacggtgac atcatctctt     300
ttacttcaac attacatgga ggtatggtga gcaagggcga ggagctgttc accggggtgg     360
tgcccatcct ggtcgagctg gacggcgacg taaacggcca agttcagc gtgtccggcg       420 agggcgaggg cgatgccacc tacggcaagc tgaccctgaa gttcatctgc accaccggca     480
agctgcccgt gccctggccc accctcgtga ccaccctgac ctacggcgtg cagtgcttca     540
gccgctaccc cgaccacatg aagcagcacg acttcttcaa gtccgccatg cccgaaggct     600
acgtccagga gcgcaccatc ttcttcaagg acgacggcaa ctacaagacc cgcgccgagg     660
tgaagttcga gggcgacacc ctggtgaacc gcatcgagct gaagggcatc gacttcaagg     720
```

```
aggacggcaa catcctgggg cacaagctgg agtacaacta caacagccac aacgtctata    780
tcatggccga caagcagaag aacggcatca aggtgaactt caagatccgc cacaacatcg    840
aggacggcag cgtgcagctc gccgaccact accagcagaa cacccccatc ggcgacggcc    900
ccgtgctgct gcccgacaac cactacctga gcacccagtc cgccctgagc aaagacccca    960
acgagaagcg cgatcacatg gtcctgctgg agttcgtgac cgccgccggg atcactctcg   1020
gcatggacga gctgtacaag taataagctt                                    1050
```

<210> SEQ ID NO 11
<211> LENGTH: 320
<212> TYPE: PRT
<213> ORGANISM: Artificial Sequence
<220> FEATURE:
<223> OTHER INFORMATION: Synthetic Sequence

<400> SEQUENCE: 11

```
Met Gly His His Tyr His His His Gly Met Ile Glu Val Val Val Asn
  1               5                  10                  15

Asp Arg Leu Gly Lys Lys Val Arg Val Lys Cys Leu Ala Glu Asp Ser
             20                  25                  30

Val Gly Asp Phe Lys Lys Val Leu Ser Leu Gln Ile Gly Thr Gln Pro
         35                  40                  45

Asn Lys Ile Val Leu Gln Lys Gly Gly Ser Val Leu Lys Asp His Ile
     50                  55                  60

Ser Leu Glu Asp Tyr Glu Val His Asp Gln Thr Asn Leu Glu Leu Tyr
 65                  70                  75                  80

Tyr Met Val Ser Lys Gly Glu Glu Leu Phe Thr Gly Val Val Pro Ile
                 85                  90                  95

Leu Val Glu Leu Asp Gly Asp Val Asn Gly His Lys Phe Ser Val Ser
            100                 105                 110

Gly Glu Gly Glu Gly Asp Ala Thr Tyr Gly Lys Leu Thr Leu Lys Phe
        115                 120                 125

Ile Cys Thr Thr Gly Lys Leu Pro Val Pro Trp Pro Thr Leu Val Thr
    130                 135                 140

Thr Leu Thr Tyr Gly Val Gln Cys Phe Ser Arg Tyr Pro Asp His Met
145                 150                 155                 160

Lys Gln His Asp Phe Phe Lys Ser Ala Met Pro Glu Gly Tyr Val Gln
                165                 170                 175

Glu Arg Thr Ile Phe Phe Lys Asp Asp Gly Asn Tyr Lys Thr Arg Ala
            180                 185                 190

Glu Val Lys Phe Glu Gly Asp Thr Leu Val Asn Arg Ile Glu Leu Lys
        195                 200                 205

Gly Ile Asp Phe Lys Glu Asp Gly Asn Ile Leu Gly His Lys Leu Glu
    210                 215                 220

Tyr Asn Tyr Asn Ser His Asn Val Tyr Ile Met Ala Asp Lys Gln Lys
225                 230                 235                 240

Asn Gly Ile Lys Val Asn Phe Lys Ile Arg His Asn Ile Glu Asp Gly
                245                 250                 255

Ser Val Gln Leu Ala Asp His Tyr Gln Gln Asn Thr Pro Ile Gly Asp
            260                 265                 270

Gly Pro Val Leu Leu Pro Asp Asn His Tyr Leu Ser Thr Gln Ser Ala
        275                 280                 285
```

```
Leu Ser Lys Asp Pro Asn Glu Lys Arg Asp His Met Val Leu Leu Glu
    290                 295                 300

Phe Val Thr Ala Ala Gly Ile Thr Leu Gly Met Asp Glu Leu Tyr Lys
305                 310                 315                 320

<210> SEQ ID NO 12
<211> LENGTH: 972
<212> TYPE: DNA
<213> ORGANISM: Artificial Sequence
<220> FEATURE:
<223> OTHER INFORMATION: Synthetic Sequence

<400> SEQUENCE: 12
ccatgggtca tcactatcat catcacggga tgattgaggt agttgtgaat gaccgattag       60
gcaaaaaagt cagagtgaag tgccttgctg aagatagtgt aggtgatttc aaaaaagtat      120
tgtccttgca aattggcacc caaccaaaca aaattgtgtt gcagaagggt ggaagtgttt      180
taaaagacca tatctctctg gaagattatg aggtacatga tcagacaaat ttggagctgt      240
attacatggt gagcaagggc gaggagctgt tcaccggggt ggtgcccatc ctggtcgagc      300
tggacggcga cgtaaacggc cacaagttca gcgtgtccgg cgagggcgag ggcgatgcca      360
cctacggcaa gctgaccctg aagttcatct gcaccaccgg caagctgccc gtgccctggc      420
ccaccctcgt gaccaccctg acctacggcg tgcagtgctt cagccgctac cccgaccaca      480
tgaagcagca cgacttcttc aagtccgcca tgcccgaagg ctacgtccag gagcgcacca      540
tcttcttcaa ggacgacggc aactacaaga cccgcgccga ggtgaagttc gagggcgaca      600
ccctggtgaa ccgcatcgag ctgaagggca tcgacttcaa ggaggacggc aacatcctgg      660
ggcacaagct ggagtacaac tacaacagcc acaacgtcta tatcatggcc gacaagcaga      720
agaacggcat caaggtgaac ttcaagatcc gccacaacat cgaggacggc agcgtgcagc      780
tcgccgacca ctaccagcag aacaccccca tcggcgacgg ccccgtgctg ctgcccgaca      840
accactacct gagcacccag tccgccctga gcaaagaccc caacgagaag cgcgatcaca      900
tggtcctgct ggagttcgtg accgccgccg ggatcactct cggcatggac gagctgtaca      960
agtaataagc tt                                                          972

<210> SEQ ID NO 13
<211> LENGTH: 323
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (0)...(0)
<223> OTHER INFORMATION: Xaa = unknown

<400> SEQUENCE: 13

Met Gly His His His His His Gly Ile Val Lys Xaa Lys Thr Leu
1               5                   10                  15

Thr Gly Lys Glu Ile Ser Val Glu Leu Lys Glu Ser Asp Leu Val Tyr
                20                  25                  30

His Ile Lys Glu Leu Leu Glu Glu Lys Glu Gly Ile Pro Pro Ser Gln
            35                  40                  45

Gln Arg Leu Ile Phe Gln Gly Lys Gln Ile Asp Asp Lys Leu Thr Val
        50                  55                  60

Thr Asp Ala His Xaa Val Glu Gly Met Gln Leu His Leu Val Leu Thr
65                  70                  75                  80
```

Leu Arg Gly Gly Met Val Ser Lys Gly Glu Glu Leu Phe Thr Gly Val
                85                  90                  95

Val Pro Ile Leu Val Glu Leu Asp Gly Asp Val Asn Gly His Lys Phe
            100                 105                 110

Ser Val Ser Gly Glu Gly Glu Gly Asp Ala Thr Tyr Gly Lys Leu Thr
        115                 120                 125

Leu Lys Phe Ile Cys Thr Thr Gly Lys Leu Pro Val Pro Trp Pro Thr
130                 135                 140

Leu Val Thr Thr Leu Thr Tyr Gly Val Gln Cys Phe Ser Arg Tyr Pro
145                 150                 155                 160

Asp His Met Lys Gln His Asp Phe Phe Lys Ser Ala Met Pro Glu Gly
                165                 170                 175

Tyr Val Gln Glu Arg Thr Ile Phe Phe Lys Asp Asp Gly Asn Tyr Lys
            180                 185                 190

Thr Arg Ala Glu Val Lys Phe Glu Gly Asp Thr Leu Val Asn Arg Ile
        195                 200                 205

Glu Leu Lys Gly Ile Asp Phe Lys Glu Asp Gly Asn Ile Leu Gly His
210                 215                 220

Lys Leu Glu Tyr Asn Tyr Asn Ser His Asn Val Tyr Ile Met Ala Asp
225                 230                 235                 240

Lys Gln Lys Asn Gly Ile Lys Val Asn Phe Lys Ile Arg His Asn Ile
                245                 250                 255

Glu Asp Gly Ser Val Gln Leu Ala Asp His Tyr Gln Gln Asn Thr Pro
            260                 265                 270

Ile Gly Asp Gly Pro Val Leu Leu Pro Asp Asn His Tyr Leu Ser Thr
        275                 280                 285

Gln Ser Ala Leu Ser Lys Asp Pro Asn Glu Lys Arg Asp His Met Val
290                 295                 300

Leu Leu Glu Phe Val Thr Ala Ala Gly Ile Thr Leu Gly Met Asp Glu
305                 310                 315                 320

Leu Tyr Lys

```
<210> SEQ ID NO 14
<211> LENGTH: 981
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (0)...(0)
<223> OTHER INFORMATION: n = a, c, g, or t
```

<400> SEQUENCE: 14

| | | | | | | |
|---|---|---|---|---|---|---|
| ccatgggtca | tcaccatcat | catcacggga | ttgttaaagn | gaagacactg | actgggaagg | 60 |
| agatctctgt | tgagctgaag | gaatcagatc | tcgtatatca | catcaaggaa | cttttggagg | 120 |
| aaaaagaagg | gattccacca | tctcaacaaa | gacttatatt | ccaggaaaaa | caaattgatg | 180 |
| ataaattaac | agtaacggat | gcacatntag | tagagggaat | gcaactccac | ttggtattaa | 240 |
| cactacgcgg | aggtatggtg | agcaagggcg | aggagctgtt | caccggggtg | gtgcccatcc | 300 |
| tggtcgagct | ggacggcgac | gtaaacggcc | acaagttcag | cgtgtccggc | gagggcgagg | 360 |
| gcgatgccac | ctacggcaag | ctgaccctga | agttcatctg | caccaccggc | aagctgcccg | 420 |
| tgccctggcc | cacccctgtg | accacccctga | cctacggcgt | gcagtgcttc | agccgctacc | 480 |
| ccgaccacat | gaagcagcac | gacttcttca | agtccgccat | gcccgaaggc | tacgtccagg | 540 |

-continued

```
agcgcaccat cttcttcaag gacgacggca actacaagac ccgcgccgag gtgaagttcg    600
agggcgacac cctggtgaac cgcatcgagc tgaagggcat cgacttcaag gaggacggca    660
acatcctggg gcacaagctg gagtacaact acaacagcca acgtctat atcatggccg      720 acaagcagaa gaacggcatc aaggtgaact tcaagatccg ccacaacatc gaggacggca    780
gcgtgcagct cgccgaccac taccagcaga cacccccat cggcgacggc cccgtgctgc     840
tgcccgacaa ccactacctg agcacccagt ccgccctgag caaagacccc aacgagaagc    900
gcgatcacat ggtcctgctg gagttcgtga ccgccgccgg gatcactctc ggcatggacg    960
agctgtacaa gtaataagct t                                              981
```

<210> SEQ ID NO 15
<211> LENGTH: 363
<212> TYPE: PRT
<213> ORGANISM: Artificial Sequence
<220> FEATURE:
<223> OTHER INFORMATION: Synthetic Sequence

<400> SEQUENCE: 15

```
Met Gly His His His His His His Gly Lys Ser Thr Phe Lys Ser Glu
 1               5                  10                  15

Tyr Pro Phe Glu Lys Arg Lys Ala Glu Ser Glu Arg Ile Ala Asp Arg
            20                  25                  30

Phe Lys Asn Arg Ile Pro Val Ile Cys Glu Lys Ala Glu Lys Ser Asp
        35                  40                  45

Ile Pro Glu Ile Asp Lys Arg Lys Tyr Leu Val Pro Ala Asp Leu Thr
    50                  55                  60

Val Gly Gln Phe Val Tyr Val Ile Arg Lys Arg Ile Met Leu Pro Pro
65                  70                  75                  80

Glu Lys Ala Ile Phe Ile Phe Val Asn Asp Thr Leu Pro Pro Thr Ala
                85                  90                  95

Ala Leu Met Ser Ala Ile Tyr Gln Glu His Lys Asp Lys Asp Gly Phe
            100                 105                 110

Leu Tyr Val Thr Tyr Ser Gly Glu Asn Thr Phe Gly Met Val Ser Lys
        115                 120                 125

Gly Glu Glu Leu Phe Thr Gly Val Val Pro Ile Leu Val Glu Leu Asp
    130                 135                 140

Gly Asp Val Asn Gly His Lys Phe Ser Val Ser Gly Glu Gly Glu Gly
145                 150                 155                 160

Asp Ala Thr Tyr Gly Lys Leu Thr Leu Lys Phe Ile Cys Thr Thr Gly
                165                 170                 175

Lys Leu Pro Val Pro Trp Pro Thr Leu Val Thr Thr Leu Thr Tyr Gly
            180                 185                 190

Val Gln Cys Phe Ser Arg Tyr Pro Asp His Met Lys Gln His Asp Phe
        195                 200                 205

Phe Lys Ser Ala Met Pro Glu Gly Tyr Val Gln Glu Arg Thr Ile Phe
    210                 215                 220

Phe Lys Asp Asp Gly Asn Tyr Lys Thr Arg Ala Glu Val Lys Phe Glu
225                 230                 235                 240

Gly Asp Thr Leu Val Asn Arg Ile Glu Leu Lys Gly Ile Asp Phe Lys
                245                 250                 255

Glu Asp Gly Asn Ile Leu Gly His Lys Leu Glu Tyr Asn Tyr Asn Ser
            260                 265                 270

His Asn Val Tyr Ile Met Ala Asp Lys Gln Lys Asn Gly Ile Lys Val
        275                 280                 285
```

```
Asn Phe Lys Ile Arg His Asn Ile Glu Asp Gly Ser Val Gln Leu Ala
        290                 295                 300

Asp His Tyr Gln Gln Asn Thr Pro Ile Gly Asp Gly Pro Val Leu Leu
305                 310                 315                 320

Pro Asp Asn His Tyr Leu Ser Thr Gln Ser Ala Leu Ser Lys Asp Pro
                325                 330                 335

Asn Glu Lys Arg Asp His Met Val Leu Leu Glu Phe Val Thr Ala Ala
            340                 345                 350

Gly Ile Thr Leu Gly Met Asp Glu Leu Tyr Lys
            355                 360

<210> SEQ ID NO 16
<211> LENGTH: 1099
<212> TYPE: DNA
<213> ORGANISM: Artificial Sequence
<220> FEATURE:
<223> OTHER INFORMATION: Synthetic Sequence

<400> SEQUENCE: 16
atgggtcatc accatcatca tcacgggaag tctacattta agtctgaata tccatttgaa      60
aaaaggaagg cggagtcgga gaggattgct gacaggttca agaataggat acctgtgatt     120
tgcgaaaaag ctgaaaagtc agatattcca gagattgata agcgtaaata tctagttcct     180
gctgacctta ccgtagggca atttgtttat gttataagaa agaggattat gctaccccct     240
gagaaggcca tcttcatttt tgtcaatgat actttgccac ctactgcggc gttgatgtct     300
gccatatatc aagaacacaa ggataaggac gggttttgt atgtcactta ctcaggagaa      360
aatacatttg gtatggtgag caagggcgag gagctgttca ccggggtggt gcccatcctg     420
gtcgagctgg acggcgacgt aaacggccac aagttcagcg tgtccggcga gggcgagggc     480
gatgccacct acggcaagct gaccctgaag ttcatctgca ccaccggcaa gctgcccgtg     540
ccctggccca ccctcgtgac caccctgacc tacggcgtgc agtgcttcag ccgctacccc     600
gaccacatga agcagcacga cttcttcaag tccgccatgc ccgaaggcta cgtccaggag     660
cgcaccatct tcttcaagga cgacggcaac tacaagaccc gcgccgaggt gaagttcgag     720
ggcgacaccc tggtgaaccg catcgagctg aagggcatcg acttcaagga ggacggcaac     780
atcctggggc acaagctgga gtacaactac aacagccaca cgtctatat catggccgac     840 aagcagaaga acggcatcaa ggtgaacttc aagatccgcc acaacatcga ggacggcagc     900
gtgcagctcg ccgaccacta ccagcagaac ccccccatcg gcgacggccc cgtgctgctg     960
cccgacaacc actacctgag cacccagtcc gccctgagca agacccccaa cgagaagcgc    1020
gatcacatgg tcctgctgga gttcgtgacc gccgccggga tcactctcgg catggacgag    1080
ctgtacaagt aataagctt                                                 1099

<210> SEQ ID NO 17
<211> LENGTH: 433
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (0)...(0)
<223> OTHER INFORMATION: Xaa = unknown
```

<400> SEQUENCE: 17

```
Met Gly His His His His His Gly Ser Arg Ile Leu Glu Ser Glu
 1               5                  10                  15

Asn Glu Thr Glu Ser Asp Glu Ser Ser Ile Ile Ser Thr Asn Asn Gly
            20                  25                  30

Thr Ala Met Glu Arg Ser Arg Asn Asn Gln Glu Leu Arg Ser Ser Pro
        35                  40                  45

His Thr Val Gln Asn Arg Leu Glu Leu Phe Ser Arg Arg Leu Ser Gln
50                  55                  60

Leu Gly Leu Ala Ser Asp Ile Ser Val Asp Gln Gln Val Glu Asp Ser
65                  70                  75                  80

Ser Ser Gly Thr Tyr Glu Gln Glu Thr Ile Lys Thr Asn Ala Gln
                85                  90                  95

Thr Ser Lys Gln Lys Ser His Lys Asp Glu Lys Asn Ile Gln Lys Ile
            100                 105                 110

Gln Ile Lys Phe Gln Pro Ile Gly Ser Ile Gly Gln Leu Lys Pro Ser
        115                 120                 125

Val Cys Lys Ile Ser Met Ser Gln Ser Phe Ala Met Val Ile Leu Phe
130                 135                 140

Leu Lys Arg Arg Leu Lys Met Asp His Val Tyr Cys Tyr Ile Asn Asn
145                 150                 155                 160

Ser Phe Ala Pro Ser Pro Gln Gln Asn Ile Gly Glu Leu Trp Met Xaa
                165                 170                 175

Phe Lys Thr Asn Asp Glu Leu Ile Val Ser Tyr Cys Ala Ser Val Ala
            180                 185                 190

Phe Gly Met Val Ser Lys Gly Glu Glu Leu Phe Thr Gly Val Val Pro
        195                 200                 205

Ile Leu Val Glu Leu Asp Gly Asp Val Asn Gly His Lys Phe Ser Val
210                 215                 220

Ser Gly Glu Gly Glu Gly Asp Ala Thr Tyr Gly Lys Leu Thr Leu Lys
225                 230                 235                 240

Phe Ile Cys Thr Thr Gly Lys Leu Pro Val Pro Trp Pro Thr Leu Val
                245                 250                 255

Thr Thr Leu Thr Tyr Gly Val Gln Cys Phe Ser Arg Tyr Pro Asp His
            260                 265                 270

Met Lys Gln His Asp Phe Phe Lys Ser Ala Met Pro Glu Gly Tyr Val
        275                 280                 285

Gln Glu Arg Thr Ile Phe Phe Lys Asp Asp Gly Asn Tyr Lys Thr Arg
290                 295                 300

Ala Glu Val Lys Phe Glu Gly Asp Thr Leu Val Asn Arg Ile Glu Leu
305                 310                 315                 320

Lys Gly Ile Asp Phe Lys Glu Asp Gly Asn Ile Leu Gly His Lys Leu
                325                 330                 335

Glu Tyr Asn Tyr Asn Ser His Asn Val Tyr Ile Met Ala Asp Lys Gln
            340                 345                 350

Lys Asn Gly Ile Lys Val Asn Phe Lys Ile Arg His Asn Ile Glu Asp
        355                 360                 365

Gly Ser Val Gln Leu Ala Asp His Tyr Gln Gln Asn Thr Pro Ile Gly
370                 375                 380

Asp Gly Pro Val Leu Leu Pro Asp Asn His Tyr Leu Ser Thr Gln Ser
385                 390                 395                 400
```

```
Ala Leu Ser Lys Asp Pro Asn Glu Lys Arg Asp His Met Val Leu Leu
            405                 410                 415

Glu Phe Val Thr Ala Ala Gly Ile Thr Leu Gly Met Asp Glu Leu Tyr
        420                 425                 430

Lys

<210> SEQ ID NO 18
<211> LENGTH: 1311
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (0)...(0)
<223> OTHER INFORMATION: n = a, c, g, or t

<400> SEQUENCE: 18
ccatgggtca tcaccatcat catcacggga gtaggatcct agagagcgaa aatgaaacag    60
aaagtgacga agctccatc atatccacaa ataatggaac ggcaatggaa agatccagaa   120
ataatcaaga attaagatca tctcctcata ccgttcaaaa tagattggaa cttttagca   180 ggagattgtc tcagcttggt ttggcgagtg acatttctgt cgaccagcaa gttgaagatt   240
cctctagtgg cacttatgaa caggaagaga caatcaaaac gaatgcacaa acaagcaaac   300
aaaaaagcca taaagacgaa aaaaacatac aaaagataca gataaaattt cagcccattg   360
gttctattgg gcagttaaaa ccatctgttt gtaaatatc natgtcacag tcttttgcaa   420
tggttatttt atttcttaag agacggctga aaatggacca tgtttattgt tatataaata   480
attcgtttgc gccaagtccg cagcaaaata ttggtgaact ttggatgcna ttcaagacta   540
atgatgagct tattgtaagt tattgtgcat ccgtagcgtt tggtatggtg agcaagggcg   600
aggagctgtt caccggggtg gtgcccatcc tggtcgagct ggacggcgac gtaaacggcc   660
acaagttcag cgtgtccggc gagggcgagg gcgatgccac ctacggcaag ctgaccctga   720
agttcatctg caccaccggc aagctgcccg tgccctggcc caccctcgtg accaccctga   780
cctacggcgt gcagtgcttc agccgctacc ccgaccacat gaagcagcac gacttcttca   840
agtccgccat gcccgaaggc tacgtccagg agcgcaccat cttcttcaag gacgacggca   900
actacaagac ccgcgccgag gtgaagttcg agggcgacac cctggtgaac cgcatcgagc   960
tgaagggcat cgacttcaag gaggacggca acatcctggg gcacaagctg gagtacaact  1020
acaacagcca caacgtctat atcatggccg acaagcagaa gaacggcatc aaggtgaact  1080
tcaagatccg ccacaacatc gaggacggca gcgtgcagct cgccgaccac taccagcaga  1140 acaccccat cggcgacggc cccgtgctgc tgcccgacaa ccactacctg agcacccagt  1200
ccgccctgag caaagacccc aacgagaagc gcgatcacat ggtcctgctg gagttcgtga  1260
ccgccgccgg gatcactctc ggcatggacg agctgtacaa gtaataagct t           1311

<210> SEQ ID NO 19
<211> LENGTH: 410
<212> TYPE: PRT
<213> ORGANISM: Artificial Sequence
<220> FEATURE:
<223> OTHER INFORMATION: Synthetic Sequence
```

<400> SEQUENCE: 19

```
Met Gly His His His His His Gly Gly Trp Asp Leu Thr Val Lys
 1               5                  10                  15
Met Leu Ala Gly Asn Glu Phe Gln Val Ser Leu Ser Ser Met Ser
            20                  25                  30
Val Ser Glu Leu Lys Ala Gln Ile Thr Gln Lys Ile Gly Val His Ala
        35                  40                  45
Phe Gln Gln Arg Leu Ala Val His Pro Ser Gly Val Ala Leu Gln Asp
    50                  55                  60
Arg Val Pro Leu Ala Ser Gln Gly Leu Gly Pro Gly Ser Thr Val Leu
65                  70                  75                  80
Leu Val Val Asp Lys Cys Asp Glu Pro Leu Ser Ile Leu Val Arg Asn
                85                  90                  95
Asn Lys Gly Arg Ser Ser Thr Tyr Glu Val Arg Leu Thr Gln Thr Val
            100                 105                 110
Ala His Leu Lys Gln Gln Val Ser Gly Leu Glu Gly Val Gln Asp Asp
        115                 120                 125
Leu Phe Trp Leu Thr Phe Glu Gly Lys Pro Leu Glu Asp Gln Leu Pro
    130                 135                 140
Leu Gly Glu Tyr Gly Leu Lys Pro Leu Ser Thr Val Phe Met Asn Leu
145                 150                 155                 160
Arg Leu Arg Gly Gly Gly Thr Glu Pro Gly Gly Met Val Ser Lys Gly
                165                 170                 175
Glu Glu Leu Phe Thr Gly Val Val Pro Ile Leu Val Glu Leu Asp Gly
            180                 185                 190
Asp Val Asn Gly His Lys Phe Ser Val Ser Gly Glu Gly Glu Gly Asp
        195                 200                 205
Ala Thr Tyr Gly Lys Leu Thr Leu Lys Phe Ile Cys Thr Thr Gly Lys
    210                 215                 220
Leu Pro Val Pro Trp Pro Thr Leu Val Thr Thr Leu Thr Tyr Gly Val
225                 230                 235                 240
Gln Cys Phe Ser Arg Tyr Pro Asp His Met Lys Gln His Asp Phe Phe
                245                 250                 255
Lys Ser Ala Met Pro Glu Gly Tyr Val Gln Glu Arg Thr Ile Phe Phe
            260                 265                 270
Lys Asp Asp Gly Asn Tyr Lys Thr Arg Ala Glu Val Lys Phe Glu Gly
        275                 280                 285
Asp Thr Leu Val Asn Arg Ile Glu Leu Lys Gly Ile Asp Phe Lys Glu
    290                 295                 300
Asp Gly Asn Ile Leu Gly His Lys Leu Glu Tyr Asn Tyr Asn Ser His
305                 310                 315                 320
Asn Val Tyr Ile Met Ala Asp Lys Gln Lys Asn Gly Ile Lys Val Asn
                325                 330                 335
Phe Lys Ile Arg His Asn Ile Glu Asp Gly Ser Val Gln Leu Ala Asp
            340                 345                 350
His Tyr Gln Gln Asn Thr Pro Ile Gly Asp Gly Pro Val Leu Leu Pro
        355                 360                 365
Asp Asn His Tyr Leu Ser Thr Gln Ser Ala Leu Ser Lys Asp Pro Asn
    370                 375                 380
Glu Lys Arg Asp His Met Val Leu Leu Glu Phe Val Thr Ala Ala Gly
385                 390                 395                 400
Ile Thr Leu Gly Met Asp Glu Leu Tyr Lys
                405                 410
```

<210> SEQ ID NO 20
<211> LENGTH: 1242
<212> TYPE: DNA
<213> ORGANISM: Artificial Sequence
<220> FEATURE:
<223> OTHER INFORMATION: Synthetic Sequence

<400> SEQUENCE: 20

```
ccatgggtca tcaccatcat catcacgggg gctgggacct gacggtgaag atgctggcgg      60
gcaacgaatt ccaggtgtcc ctgagcagct ccatgtcggt gtcagagctg aaggcgcaga     120
tcacccagaa gattggcgtg cacgccttcc agcagcgtct ggctgtccac ccagcggtg      180
tggcgctgca ggacagggtc ccccttgcca gccagggcct gggccctggc agcacggtcc     240
tgctggtggt ggacaaatgc gacgaacctc tgagcatcct ggtgaggaat aacaagggcc     300
gcagcagcac ctacgaggtc cggctgacgc agaccgtggc ccacctgaag cagcaagtga     360
gcgggctgga gggtgtgcag gacgaccgt tctggctgac cttcgagggg aagcccctgg     420
aggaccagct cccgctgggg gagtacggcc tcaagcccct gagcaccgtg ttcatgaatc     480
tgcgcctgcg gggaggcggc acagagcctg gaggtatggt gagcaagggc gaggagctgt     540
tcaccggggt ggtgcccatc ctggtcgagc tggacggcga cgtaaacggc cacaagttca     600
gcgtgtccgg cgagggcgag ggcgatgcca cctacggcaa gctgaccctg aagttcatct     660
gcaccaccgg caagctgccc gtgccctggc ccaccctcgt gaccaccctg acctacggcg     720
tgcagtgctt cagccgctac cccgaccaca tgaagcagca cgacttcttc aagtccgcca     780
tgcccgaagg ctacgtccag gagcgcacca tcttcttcaa ggacgacggc aactacaaga     840
cccgcgccga ggtgaagttc gagggcgaca ccctggtgaa ccgcatcgag ctgaagggca     900
tcgacttcaa ggaggacggc aacatcctgg ggcacaagct ggagtacaac tacaacagcc     960
acaacgtcta tatcatggcc gacaagcaga agaacggcat caaggtgaac ttcaagatcc    1020
gccacaacat cgaggacggc agcgtgcagc tcgccgacca ctaccagcag aacacccca    1080
tcggcgacgg ccccgtgctg ctgcccgaca accactacct gagcacccag tccgccctga    1140
gcaaagaccc caacgagaag cgcgatcaca tggtcctgct ggagttcgtg accgccgccg    1200
ggatcactct cggcatggac gagctgtaca agtaataagc tt                       1242
```

<210> SEQ ID NO 21
<211> LENGTH: 166
<212> TYPE: PRT
<213> ORGANISM: Artificial Sequence
<220> FEATURE:
<223> OTHER INFORMATION: Synthetic Sequence

<400> SEQUENCE: 21

```
Met Gly His His His His His His Gly Ser Asp Ser Glu Val Asn Gln
  1               5                  10                  15

Glu Ala Lys Pro Glu Val Lys Pro Glu Val Lys Pro Glu Thr His Ile
             20                  25                  30

Asn Leu Lys Val Ser Asp Gly Ser Ser Glu Ile Phe Phe Lys Ile Lys
         35                  40                  45

Lys Thr Thr Pro Leu Arg Arg Leu Met Glu Ala Phe Ala Lys Arg Gln
     50                  55                  60

Gly Lys Glu Met Asp Ser Leu Arg Phe Leu Tyr Asp Gly Ile Arg Ile
 65                  70                  75                  80

Gln Ala Asp Gln Thr Pro Glu Asp Leu Asp Met Glu Asp Asn Asp Ile
                 85                  90                  95
```

```
Ile Glu Ala His Arg Glu Gln Ile Gly Gly Thr Pro Ala Val Thr Thr
            100                 105                 110

Tyr Lys Leu Val Ile Asn Gly Lys Thr Leu Lys Gly Glu Thr Thr Thr
            115                 120                 125

Lys Ala Val Asp Ala Glu Thr Ala Glu Lys Ala Phe Lys Gln Tyr Ala
            130                 135                 140

Asn Asp Asn Gly Val Asp Gly Val Trp Thr Tyr Asp Asp Ala Thr Lys
145                 150                 155                 160

Thr Phe Thr Val Thr Glu
                165

<210> SEQ ID NO 22
<211> LENGTH: 510
<212> TYPE: DNA
<213> ORGANISM: Artificial Sequence
<220> FEATURE:
<223> OTHER INFORMATION: Synthetic Sequence

<400> SEQUENCE: 22
ccatgggtca tcaccatcat catcacgggt cggactcaga agtcaatcaa gaagctaagc      60
cagaggtcaa gccagaagtc aagcctgaga ctcacatcaa tttaaaggtg tccgatggat     120
cttcagagat cttcttcaag atcaaaaaga ccactccttt aagaaggctg atggaagcgt     180
tcgctaaaag acagggtaag gaaatggact ccttaagatt cttgtacgac ggtattagaa     240
ttcaagctga tcagacccct gaagatttgg acatggagga taacgatatt attgaggctc     300
accgcgaaca gattggaggt acgccggcgg tgaccaccta taaactggtg attaacggca     360
aaaccctgaa aggcgaaacc accaccaaag cggtggatgc ggaaaccgcg gaaaaagcgt     420
ttaaacagta tgcgaacgat aacggcgtgg atggcgtgtg gacctatgat gatgcgacca     480 aaaccttta cgtgaccgaa taataagctt                                       510

<210> SEQ ID NO 23
<211> LENGTH: 711
<212> TYPE: PRT
<213> ORGANISM: Artificial Sequence
<220> FEATURE:
<223> OTHER INFORMATION: Synthetic Sequence

<400> SEQUENCE: 23

Met Gly His His His His His His Gly Ser Asp Ser Glu Val Asn Gln
1               5                   10                  15

Glu Ala Lys Pro Glu Val Lys Pro Glu Val Lys Pro Glu Thr His Ile
            20                  25                  30

Asn Leu Lys Val Ser Asp Gly Ser Ser Glu Ile Phe Phe Lys Ile Lys
        35                  40                  45

Lys Thr Thr Pro Leu Arg Arg Leu Met Glu Ala Phe Ala Lys Arg Gln
    50                  55                  60

Gly Lys Glu Met Asp Ser Leu Arg Phe Leu Tyr Asp Gly Ile Arg Ile
65                  70                  75                  80

Gln Ala Asp Gln Thr Pro Glu Asp Leu Asp Met Glu Asp Asn Asp Ile
            85                  90                  95

Ile Glu Ala His Arg Glu Gln Ile Gly Gly Met Glu Phe Met Leu Arg
            100                 105                 110

Pro Val Glu Thr Pro Thr Arg Glu Ile Lys Lys Leu Asp Gly Leu Trp
            115                 120                 125

Ala Phe Ser Leu Asp Arg Glu Asn Cys Gly Ile Asp Gln Arg Trp Trp
            130                 135                 140
```

-continued

```
Glu Ser Ala Leu Gln Glu Ser Arg Ala Ile Ala Val Pro Gly Ser Phe
145                 150                 155                 160

Asn Asp Gln Phe Ala Asp Ala Asp Ile Arg Asn Tyr Ala Gly Asn Val
            165                 170                 175

Trp Tyr Gln Arg Glu Val Phe Ile Pro Lys Gly Trp Ala Gly Gln Arg
        180                 185                 190

Ile Val Leu Arg Phe Asp Ala Val Thr His Tyr Gly Lys Val Trp Val
    195                 200                 205

Asn Asn Gln Glu Val Met Glu His Gln Gly Gly Tyr Thr Pro Phe Glu
210                 215                 220

Ala Asp Val Thr Pro Tyr Val Ile Ala Gly Lys Ser Val Arg Ile Thr
225                 230                 235                 240

Val Cys Val Asn Glu Leu Asn Trp Gln Thr Ile Pro Pro Gly Met
                245                 250                 255

Val Ile Thr Asp Glu Asn Gly Lys Lys Lys Gln Ser Tyr Phe His Asp
            260                 265                 270

Phe Phe Asn Tyr Ala Gly Ile His Arg Ser Val Met Leu Tyr Thr Thr
        275                 280                 285

Pro Asn Thr Trp Val Asp Asp Ile Thr Val Val Thr His Val Ala Gln
    290                 295                 300

Asp Cys Asn His Ala Ser Val Asp Trp Gln Val Val Ala Asn Gly Asp
305                 310                 315                 320

Val Ser Val Glu Leu Arg Asp Ala Asp Gln Gln Val Val Ala Thr Gly
            325                 330                 335

Gln Gly Thr Ser Gly Thr Leu Gln Val Val Asn Pro His Leu Trp Gln
        340                 345                 350

Pro Gly Glu Gly Tyr Leu Tyr Glu Leu Cys Val Thr Ala Lys Ser Gln
    355                 360                 365

Thr Glu Cys Asp Ile Tyr Pro Leu Arg Val Gly Ile Arg Ser Val Ala
    370                 375                 380

Val Lys Gly Gln Gln Phe Leu Ile Asn His Lys Pro Phe Tyr Phe Thr
385                 390                 395                 400

Gly Phe Gly Arg His Glu Asp Ala Asp Leu Arg Gly Lys Gly Phe Asp
            405                 410                 415

Asn Val Leu Met Val His Asp His Ala Leu Met Asp Trp Ile Gly Ala
        420                 425                 430

Asn Ser Tyr Arg Thr Ser His Tyr Pro Tyr Ala Glu Glu Met Leu Asp
    435                 440                 445

Trp Ala Asp Glu His Gly Ile Val Val Ile Asp Glu Thr Ala Ala Val
450                 455                 460

Gly Phe Asn Leu Ser Leu Gly Ile Gly Phe Glu Ala Gly Asn Lys Pro
465                 470                 475                 480

Lys Glu Leu Tyr Ser Glu Glu Ala Val Asn Gly Glu Thr Gln Gln Ala
            485                 490                 495

His Leu Gln Ala Ile Lys Glu Leu Ile Ala Arg Asp Lys Asn His Pro
        500                 505                 510

Ser Val Val Met Trp Ser Ile Ala Asn Glu Pro Asp Thr Arg Pro Gln
    515                 520                 525

Val His Gly Asn Ile Ser Pro Leu Ala Glu Ala Thr Arg Lys Leu Asp
530                 535                 540

Pro Thr Arg Pro Ile Thr Cys Val Asn Val Met Phe Cys Asp Ala His
545                 550                 555                 560
```

```
Thr Asp Thr Ile Ser Asp Leu Phe Asp Val Leu Cys Leu Asn Arg Tyr
            565                 570                 575

Tyr Gly Trp Tyr Val Gln Ser Gly Asp Leu Glu Thr Ala Glu Lys Val
        580                 585                 590

Leu Glu Lys Glu Leu Leu Ala Trp Gln Glu Lys Leu His Gln Pro Ile
        595                 600                 605

Ile Ile Thr Glu Tyr Gly Val Asp Thr Leu Ala Gly Leu His Ser Met
        610                 615                 620

Tyr Thr Asp Met Trp Ser Glu Glu Tyr Gln Cys Ala Trp Leu Asp Met
625                 630                 635                 640

Tyr His Arg Val Phe Asp Arg Val Ser Ala Val Val Gly Glu Gln Val
                645                 650                 655

Trp Asn Phe Ala Asp Phe Ala Thr Ser Gln Gly Ile Leu Arg Val Gly
            660                 665                 670

Gly Asn Lys Lys Gly Ile Phe Thr Arg Asp Arg Lys Pro Lys Ser Ala
        675                 680                 685

Ala Phe Leu Leu Gln Lys Arg Trp Thr Gly Met Asn Phe Gly Glu Lys
        690                 695                 700

Pro Gln Gln Gly Gly Lys Gln
705                 710

<210> SEQ ID NO 24
<211> LENGTH: 2133
<212> TYPE: DNA
<213> ORGANISM: Artificial Sequence
<220> FEATURE:
<223> OTHER INFORMATION: Synthetic Sequence

<400> SEQUENCE: 24
atgggtcatc accatcatca tcacgggtcg gactcagaag tcaatcaaga agctaagcca      60
gaggtcaagc cagaagtcaa gcctgagact cacatcaatt taaaggtgtc cgatggatct     120
tcagagatct tcttcaagat caaaaagacc actcctttaa aaggctgatg gaagcgttc      180 gctaaaagac agggtaagga aatggactcc ttaagattct tgtacgacgg tattagaatt     240
caagctgatc agaccctga agatttggac atggaggata cgatattat tgaggctcac       300 cgcgaacaga ttggaggtat ggaattcatg ttacgtcctg tagaaacccc aacccgtgaa     360
atcaaaaaac tcgacggcct gtgggcattc agtctggatc gcgaaaactg tggaattgat     420
cagcgttggt gggaaagcgc gttacaagaa agccgggcaa ttgctgtgcc aggcagtttt     480
aacgatcagt tcgccgatgc agatattcgt aattatgcgg gcaacgtctg gtatcagcgc     540
gaagtcttta taccgaaagg ttgggcaggc cagcgtatcg tgctgcgttt cgatgcggtc     600
actcattacg gcaaagtgtg ggtcaataat caggaagtga tggagcatca gggcggctat     660
acgccatttg aagccgatgt cacgccgtat gttattgccg ggaaaagtgt acgtatcacc     720
gtttgtgtga caacgaact gaactggcag actatcccgc cgggaatggt gattaccgac     780
gaaaacggca gaaaaagca gtcttacttc catgatttct ttaactatgc cggaatccat     840
cgcagcgtaa tgctctacac cacgccgaac acctgggtgg acgatatcac cgtggtgacg     900
catgtcgcgc aagactgtaa ccacgcgtct gttgactggc aggtggtggc caatggtgat     960
gtcagcgttg aactgcgtga tgcggatcaa caggtggttg caactggaca aggcactagc    1020 gggacttgc aagtggtgaa tccgcacctc tggcaaccgg gtgaaggtta tctctatgaa    1080
ctgtgcgtca gccaaaaag ccagacagag tgtgatatct accgcttcg cgtcggcatc     1140 cggtcagtgg cagtgaaggg ccaacagttc ctgattaacc acaaaccgtt ctactttact    1200
```

-continued

```
ggctttggtc gtcatgaaga tgcggactta cgtggcaaag gattcgataa cgtgctgatg    1260
gtgcacgacc acgcattaat ggactggatt ggggccaact cctaccgtac ctcgcattac    1320
ccttacgctg aagagatgct cgactgggca gatgaacatg gcatcgtggt gattgatgaa    1380
actgctgctg tcggctttaa cctctcttta ggcattggtt tcgaagcggg caacaagccg    1440
aaagaactgt acagcgaaga ggcagtcaac ggggaaactc agcaagcgca cttacaggcg    1500 attaagagc tgatagcgcg tgacaaaaac cacccaagcg tggtgatgtg gagtattgcc     1560
aacgaaccgg atacccgtcc gcaagtgcac gggaatattt cgccactggc ggaagcaacg    1620
cgtaaactcg acccgacgcg tccgatcacc tgcgtcaatg taatgttctg cgacgctcac    1680
accgatacca tcagcgatct ctttgatgtg ctgtgcctga accgttatta cggatggtat    1740
gtccaaagcg gcgatttgga acggcagag aaggtactgg aaaaagaact tctggcctgg    1800
caggagaaac tgcatcagcc gattatcatc accgaatacg gcgtggatac gttagccggg    1860
ctgcactcaa tgtacaccga catgtggagt gaagagtatc agtgtgcatg gctggatatg    1920
tatcaccgcg tctttgatcg cgtcagcgcc gtcgtcggtg aacaggtatg gaatttcgcc    1980
gattttgcga cctcgcaagg catattgcgc gttggcggta acaagaaagg gatcttcact    2040
cgcgaccgca aaccgaagtc ggcggctttt ctgctgcaaa aacgctggac tggcatgaac    2100
ttcggtgaaa aaccgcagca gggaggcaaa caa                                 2133
```

<210> SEQ ID NO 25
<211> LENGTH: 553
<212> TYPE: PRT
<213> ORGANISM: Artificial Sequence
<220> FEATURE:
<223> OTHER INFORMATION: Synthetic Sequence

<400> SEQUENCE: 25

```
Met Gly His His His His His His Gly Ser Asp Ser Glu Val Asn Gln
  1               5                  10                  15

Glu Ala Lys Pro Glu Val Lys Pro Glu Val Lys Pro Glu Thr His Ile
             20                  25                  30

Asn Leu Lys Val Ser Asp Gly Ser Ser Glu Ile Phe Phe Lys Ile Lys
         35                  40                  45

Lys Thr Thr Pro Leu Arg Arg Leu Met Glu Ala Phe Ala Lys Arg Gln
     50                  55                  60

Gly Lys Glu Met Asp Ser Leu Arg Phe Leu Tyr Asp Gly Ile Arg Ile
 65                  70                  75                  80

Gln Ala Asp Gln Thr Pro Glu Asp Leu Asp Met Glu Asp Asn Asp Ile
             85                  90                  95

Ile Glu Ala His Arg Glu Gln Ile Gly Gly Met Ser Leu Trp Leu Gly
            100                 105                 110

Ala Pro Val Pro Asp Ile Pro Pro Asp Ser Ala Val Glu Leu Trp Lys
        115                 120                 125

Pro Gly Ala Gln Asp Ala Ser Ser Gln Ala Gln Gly Gly Ser Ser Cys
    130                 135                 140

Ile Leu Arg Glu Glu Ala Arg Met Pro His Ser Ala Gly Gly Thr Ala
145                 150                 155                 160

Gly Val Gly Leu Glu Ala Ala Glu Pro Thr Ala Leu Leu Thr Arg Ala
                165                 170                 175

Glu Pro Pro Ser Glu Pro Thr Glu Ile Arg Pro Gln Lys Arg Lys Lys
            180                 185                 190
```

```
Gly Pro Ala Pro Lys Met Leu Gly Asn Glu Leu Cys Ser Val Cys Gly
            195                 200                 205

Asp Lys Ala Ser Gly Phe His Tyr Asn Val Leu Ser Cys Glu Gly Cys
        210                 215                 220

Lys Gly Phe Phe Arg Arg Ser Val Ile Lys Gly Ala His Tyr Ile Cys
225                 230                 235                 240

His Ser Gly Gly His Cys Pro Met Asp Thr Tyr Met Arg Arg Lys Cys
            245                 250                 255

Gln Glu Cys Arg Leu Arg Lys Cys Arg Gln Ala Gly Met Arg Glu Glu
        260                 265                 270

Cys Val Leu Ser Glu Glu Gln Ile Arg Leu Lys Lys Leu Lys Arg Gln
        275                 280                 285

Glu Glu Glu Gln Ala His Ala Thr Ser Leu Pro Pro Arg Arg Ser Ser
        290                 295                 300

Pro Pro Gln Ile Leu Pro Gln Leu Ser Pro Glu Gln Leu Gly Met Ile
305                 310                 315                 320

Glu Lys Leu Val Ala Ala Gln Gln Cys Asn Arg Arg Ser Phe Ser
                325                 330                 335

Asp Arg Leu Arg Val Thr Pro Trp Pro Met Ala Pro Asp Pro His Ser
            340                 345                 350

Arg Glu Ala Arg Gln Gln Arg Phe Ala His Phe Thr Glu Leu Ala Ile
        355                 360                 365

Val Ser Val Gln Glu Ile Val Asp Phe Ala Lys Gln Leu Pro Gly Phe
        370                 375                 380

Leu Gln Leu Ser Arg Glu Asp Gln Ile Ala Leu Leu Lys Thr Ser Ala
385                 390                 395                 400

Ile Glu Val Met Leu Leu Glu Thr Ser Arg Arg Tyr Asn Pro Gly Ser
                405                 410                 415

Glu Ser Ile Thr Phe Leu Lys Asp Phe Ser Tyr Asn Arg Glu Asp Phe
            420                 425                 430

Ala Lys Ala Gly Leu Gln Val Glu Phe Ile Asn Pro Ile Phe Glu Phe
        435                 440                 445

Ser Arg Ala Met Asn Glu Leu Gln Leu Asn Asp Ala Glu Phe Ala Leu
    450                 455                 460

Leu Ile Ala Ile Ser Ile Phe Ser Ala Asp Arg Pro Asn Val Gln Asp
465                 470                 475                 480

Gln Leu Gln Val Glu Arg Leu Gln His Thr Tyr Val Glu Ala Leu His
                485                 490                 495

Ala Tyr Val Ser Ile His His Pro His Asp Arg Leu Met Phe Pro Arg
            500                 505                 510

Met Leu Met Lys Leu Val Ser Leu Arg Thr Leu Ser Ser Val His Ser
        515                 520                 525

Glu Gln Val Phe Ala Leu Arg Leu Gln Asp Lys Lys Leu Pro Pro Leu
        530                 535                 540

Leu Ser Glu Ile Trp Asp Val His Glu
545                 550

<210> SEQ ID NO 26
<211> LENGTH: 1662
<212> TYPE: DNA
<213> ORGANISM: Artificial Sequence
<220> FEATURE:
<223> OTHER INFORMATION: Synthetic Sequence
```

<400> SEQUENCE: 26

```
atgggtcatc accatcatca tcacgggtcg gactcagaag tcaatcaaga agctaagcca      60
gaggtcaagc cagaagtcaa gcctgagact cacatcaatt taaaggtgtc cgatggatct     120
tcagagatct tcttcaagat caaaaagacc actcctttaa aaggctgat ggaagcgttc      180
gctaaaagac agggtaagga aatggactcc ttaagattct tgtacgacgg tattagaatt     240
caagctgatc agacccctga agatttggac atggaggata cgatattat tgaggctcac     300
cgcgaacaga ttggaggtat gtccttgtgg ctgggggccc ctgtgcctga cattcctcct    360
gactctgcgg tggagctgtg gaagccaggc gcacaggatg caagcagcca ggcccaggga    420
ggcagcagct gcatcctcag agaggaagcc aggatgcccc actctgctgg gggtactgca    480
ggggtggggc tggaggctgc agagcccaca gccctgctca ccagggcaga gcccccttca    540
gaacccacag agatccgtcc acaaaagcgg aaaaggggc cagcccccaa aatgctgggg     600
aacgagctat gcgcgtgtg tggggacaag gcctcgggct ccactacaa tgttctgagc      660
tgcgagggct gcaagggatt cttccgccgc agcgtcatca agggagcgca ctacatctgc    720
cacagtggcg ccactgcccc catggacacc tacatgcgtc gcaagtgcca ggagtgtcgg    780
cttcgcaaat gccgtcaggc tggcatgcgg gaggagtgtg tcctgtcaga gaacagatc    840
cgcctgaaga aactgaagcg gcaagaggag aacaggctc atgccacatc cttgcccccc    900
aggcgttcct caccccccca aatcctgccc cagctcagcc cggaacaact gggcatgatc    960
gagaagctcg tcgctgccca gcaacagtgt aaccggcgct ccttttctga ccggcttcga   1020
gtcacgcctt ggcccatggc accagatccc catagccggg aggcccgtca gcagcgctt    1080
gcccacttca ctgagctggc catcgtctct gtgcaggaga tagttgactt tgctaaacag    1140
ctacccggct tcctgcagct cagccgggag gaccagattg ccctgctgaa gacctctgcg   1200
atcgaggtga tgcttctgga gacatctcgg aggtacaacc tgggagtga gagtatcacc    1260
ttcctcaagg atttcagtta taaccgggaa gactttgcca aagcagggct gcaagtggaa    1320
ttcatcaacc ccatcttcga gttctccagg gccatgaatg agctgcaact caatgatgcc    1380
gagtttgcct tgctcattgc tatcagcatc ttctctgcag accggcccaa cgtgcaggac   1440
cagctccagg tggagaggct gcagcacaca tatgtggaag ccctgcatgc ctacgtctcc    1500
atccaccatc cccatgaccg actgatgttc ccacggatgc taatgaaact ggtgagcctc    1560
cggaccctga gcagcgtcca ctcagagcaa gtgtttgcac tgcgtctgca ggacaaaaag    1620
ctcccaccgc tgctctctga gatctgggat gtgcacgaat ga                      1662
```

<210> SEQ ID NO 27
<211> LENGTH: 473
<212> TYPE: PRT
<213> ORGANISM: Artificial Sequence
<220> FEATURE:
<223> OTHER INFORMATION: Synthetic Sequence

<400> SEQUENCE: 27

```
Met Gly His His His His His His Gly Ser Asp Ser Glu Val Asn Gln
  1               5                  10                  15

Glu Ala Lys Pro Glu Val Lys Pro Glu Val Lys Pro Glu Thr His Ile
             20                  25                  30

Asn Leu Lys Val Ser Asp Gly Ser Ser Glu Ile Phe Phe Lys Ile Lys
         35                  40                  45

Lys Thr Thr Pro Leu Arg Arg Leu Met Glu Ala Phe Ala Lys Arg Gln
     50                  55                  60
```

-continued

```
Gly Lys Glu Met Asp Ser Leu Arg Phe Leu Tyr Asp Gly Ile Arg Ile
 65                  70                  75                  80

Gln Ala Asp Gln Thr Pro Glu Asp Leu Asp Met Glu Asp Asn Asp Ile
                 85                  90                  95

Ile Glu Ala His Arg Glu Gln Ile Gly Gly Met Cys Pro Asn Ser Ser
            100                 105                 110

Ala Ser Asn Ala Ser Gly Ala Ala Pro Thr Leu Pro Ala His Pro
        115                 120                 125

Ser Thr Leu Thr His Pro Gln Arg Arg Ile Asp Thr Leu Asn Ser Asp
    130                 135                 140

Gly Tyr Thr Pro Glu Pro Ala Arg Ile Thr Ser Pro Asp Lys Pro Arg
145                 150                 155                 160

Pro Met Pro Met Asp Thr Ser Val Tyr Glu Ser Pro Tyr Ser Asp Pro
                165                 170                 175

Glu Glu Leu Lys Asp Lys Lys Leu Phe Leu Lys Arg Asp Asn Leu Leu
            180                 185                 190

Ile Ala Asp Ile Glu Leu Gly Cys Gly Asn Phe Gly Ser Val Arg Gln
        195                 200                 205

Gly Val Tyr Arg Met Arg Lys Lys Gln Ile Asp Val Ala Ile Lys Val
    210                 215                 220

Leu Lys Gln Gly Thr Glu Lys Ala Asp Thr Glu Glu Met Met Arg Glu
225                 230                 235                 240

Ala Gln Ile Met His Gln Leu Asp Asn Pro Tyr Ile Val Arg Leu Ile
                245                 250                 255

Gly Val Cys Gln Ala Glu Ala Leu Met Leu Val Met Glu Met Ala Gly
            260                 265                 270

Gly Gly Pro Leu His Lys Phe Leu Val Gly Lys Arg Glu Glu Ile Pro
        275                 280                 285

Val Ser Asn Val Ala Glu Leu Leu His Gln Val Ser Met Gly Met Lys
    290                 295                 300

Tyr Leu Glu Glu Lys Asn Phe Val His Arg Asp Leu Ala Ala Arg Asn
305                 310                 315                 320

Val Leu Leu Val Asn Arg His Tyr Ala Lys Ile Ser Asp Phe Gly Leu
                325                 330                 335

Ser Lys Ala Leu Gly Ala Asp Asp Ser Tyr Tyr Thr Ala Arg Ser Ala
            340                 345                 350

Gly Lys Trp Pro Leu Lys Trp Tyr Ala Pro Glu Cys Ile Asn Phe Arg
        355                 360                 365

Lys Phe Ser Ser Arg Ser Asp Val Trp Ser Tyr Gly Val Thr Met Trp
    370                 375                 380

Glu Ala Leu Ser Tyr Gly Gln Lys Pro Tyr Lys Met Lys Gly Pro
385                 390                 395                 400

Glu Val Met Ala Phe Ile Glu Gln Gly Lys Arg Met Glu Cys Pro Pro
                405                 410                 415

Glu Cys Pro Pro Glu Leu Tyr Ala Leu Met Ser Asp Cys Trp Ile Tyr
            420                 425                 430

Lys Trp Glu Asp Arg Pro Asp Phe Leu Thr Val Glu Gln Arg Met Arg
        435                 440                 445

Ala Cys Tyr Tyr Ser Leu Ala Ser Lys Val Glu Gly Pro Pro Gly Ser
    450                 455                 460

Thr Gln Lys Ala Glu Ala Cys Ala
465                 470
```

<210> SEQ ID NO 28
<211> LENGTH: 1422
<212> TYPE: DNA
<213> ORGANISM: Artificial Sequence
<220> FEATURE:
<223> OTHER INFORMATION: Synthetic Sequence

<400> SEQUENCE: 28

```
atgggtcatc accatcatca tcacgggtcg gactcagaag tcaatcaaga agctaagcca      60
gaggtcaagc cagaagtcaa gcctgagact cacatcaatt taaaggtgtc cgatggatct     120
tcagagatct tcttcaagat caaaaagacc actcctttaa aaggctgat ggaagcgttc      180
gctaaaagac agggtaagga atggactcc ttaagattct tgtacgacgg tattagaatt      240
caagctgatc agacccctga agatttggac atggaggata cgatattat tgaggctcac      300
cgcgaacaga ttggaggtat gtgccccaac agcagtgcca gcaacgcctc aggggctgct     360
gctcccacac tcccagccca cccatccacg ttgactcatc ctcagagacg aatcgacacc     420
ctcaactcag atggatacac ccctgagcca gcacgcataa cgtccccaga caaaccgcgg     480
ccgatgccca tggacacgag cgtgtatgag agcccctaca cgacccaga ggagctcaag      540
gacaagaagc tcttcctgaa gcgcgataac ctcctcatag ctgacattga acttggctgc     600
ggcaactttg gctcagtgcg ccagggcgtg taccgcatgc gcaagaagca gatcgacgtg     660
gccatcaagg tgctgaagca gggcacggag aaggcagaca cggaagagat gatgcgcgag     720
gcgcagatca tgcaccagct ggacaacccc tacatcgtgc ggctcattgg cgtctgccag     780
gccgaggccc tcatgctggt catggagatg gctgggggcg gccgctgca caagttcctg      840
gtcggcaaga gggaggagat ccctgtgagc aatgtggccg agctgctgca ccaggtgtcc     900
atggggatga agtacctgga ggagaagaac tttgtgcacc gtgacctggc ggcccgcaac     960
gtcctgctgg ttaaccggca ctacgccaag atcagcgact ttggcctctc caagcactg     1020
ggtgccgacg acagctacta cactgcccgc tcagcaggga gtggccgct caagtggtac     1080
gcacccgaat gcatcaactt ccgcaagttc tccagccgca gcgatgtctg gagctatggg     1140
gtcaccatgt ggaggccctt gtcctacggc cagaagccct acaagaagat gaagggccg     1200
gaggtcatgg ccttcatcga gcagggcaag cggatggagt gcccaccaga gtgtccaccc     1260
gaactgtacg cactcatgag tgactgctgg atctacaagt gggaggatcg ccccgacttc     1320
ctgaccgtgg agcagcgcat gcgagcctgt tactacagcc tggccagcaa ggtggaaggg     1380
cccccaggca gcacacagaa ggctgaggct gcctgtgcct ga                       1422
```

<210> SEQ ID NO 29
<211> LENGTH: 434
<212> TYPE: PRT
<213> ORGANISM: Artificial Sequence
<220> FEATURE:
<223> OTHER INFORMATION: Synthetic Sequence

<400> SEQUENCE: 29

```
Met Gly His His His His His His Gly Ser Asp Ser Glu Val Asn Gln
  1               5                  10                  15

Glu Ala Lys Pro Glu Val Lys Pro Glu Val Lys Pro Glu Thr His Ile
             20                  25                  30

Asn Leu Lys Val Ser Asp Gly Ser Ser Glu Ile Phe Phe Lys Ile Lys
         35                  40                  45

Lys Thr Thr Pro Leu Arg Arg Leu Met Glu Ala Phe Ala Lys Arg Gln
     50                  55                  60
```

```
Gly Lys Glu Met Asp Ser Leu Arg Phe Leu Tyr Gly Ile Arg Ile
 65                  70                  75                  80

Gln Ala Asp Gln Thr Pro Glu Asp Leu Asp Met Glu Asp Asn Asp Ile
                 85                  90                  95

Ile Glu Ala His Arg Glu Gln Ile Gly Gly Met Gln Phe His Val Lys
            100                 105                 110

Ser Gly Leu Gln Ile Lys Lys Asn Ala Ile Ile Asp Asp Tyr Lys Val
        115                 120                 125

Thr Ser Gln Val Leu Gly Leu Gly Ile Asn Gly Lys Val Leu Gln Ile
    130                 135                 140

Phe Asn Lys Arg Thr Gln Glu Lys Phe Ala Leu Lys Met Leu Gln Asp
145                 150                 155                 160

Cys Pro Lys Ala Arg Arg Glu Val Glu Leu His Trp Arg Ala Ser Gln
                165                 170                 175

Cys Pro His Ile Val Arg Ile Val Asp Val Tyr Glu Asn Leu Tyr Ala
            180                 185                 190

Gly Arg Lys Cys Leu Leu Ile Val Met Glu Cys Leu Asp Gly Gly Glu
        195                 200                 205

Leu Phe Ser Arg Ile Gln Asp Arg Gly Asp Gln Ala Phe Thr Glu Arg
    210                 215                 220

Glu Ala Ser Glu Ile Met Lys Ser Ile Gly Glu Ala Ile Gln Tyr Leu
225                 230                 235                 240

His Ser Ile Asn Ile Ala His Arg Asp Val Lys Pro Glu Asn Leu Leu
                245                 250                 255

Tyr Thr Ser Lys Arg Pro Asn Ala Ile Leu Lys Leu Thr Asp Phe Gly
            260                 265                 270

Phe Ala Lys Glu Thr Thr Ser His Asn Ser Leu Thr Thr Pro Cys Tyr
        275                 280                 285

Thr Pro Tyr Tyr Val Ala Pro Glu Val Leu Gly Pro Glu Lys Tyr Asp
    290                 295                 300

Lys Ser Cys Asp Met Trp Ser Leu Gly Val Ile Met Tyr Ile Leu Leu
305                 310                 315                 320

Cys Gly Tyr Pro Pro Phe Tyr Ser Asn His Gly Leu Ala Ile Ser Pro
                325                 330                 335

Gly Met Lys Thr Arg Ile Arg Met Gly Gln Tyr Glu Phe Pro Asn Pro
            340                 345                 350

Glu Trp Ser Glu Val Ser Glu Glu Val Lys Met Leu Ile Arg Asn Leu
        355                 360                 365

Leu Lys Thr Glu Pro Thr Gln Arg Met Thr Ile Thr Glu Phe Met Asn
    370                 375                 380

His Pro Trp Ile Met Gln Ser Thr Lys Val Pro Gln Thr Pro Leu His
385                 390                 395                 400

Thr Ser Arg Val Leu Lys Glu Asp Lys Glu Arg Trp Glu Asp Val Lys
                405                 410                 415

Glu Glu Met Thr Ser Ala Leu Ala Thr Met Arg Val Asp Tyr Glu Gln
            420                 425                 430

Ile Lys
```

```
<210> SEQ ID NO 30
<211> LENGTH: 1305
<212> TYPE: DNA
<213> ORGANISM: Artificial Sequence
<220> FEATURE:
<223> OTHER INFORMATION: Synthetic Sequence
```

<400> SEQUENCE: 30

```
atgggtcatc accatcatca tcacgggtcg gactcagaag tcaatcaaga agctaagcca      60
gaggtcaagc cagaagtcaa gcctgagact cacatcaatt taaaggtgtc cgatggatct     120
tcagagatct tcttcaagat caaaaagacc actcctttaa aaggctgat ggaagcgttc      180
gctaaaagac agggtaagga aatggactcc ttaagattct tgtacgacgg tattagaatt     240
caagctgatc agacccctga agatttggac atggaggata cgatattat tgaggctcac      300
cgcgaacaga ttggaggtat gcagttccac gtcaagtccg gcctgcagat caagaagaac     360
gccatcatcg atgactacaa ggtcaccagc caggtcctgg ggctgggcat caacggcaaa     420
gttttgcaga tcttcaacaa gaggacccag gagaaattcg ccctcaaaat gcttcaggac     480
tgccccaagg cccgcaggga ggtggagctg cactggcggg cctcccagtg cccgcacatc     540
gtacggatcg tggatgtgta cgagaatctg tacgcaggga ggaagtgcct gctgattgtc     600
atggaatgtt tggacggtgg agaactcttt agccgaatcc aggatcgagg agaccaggca     660
ttcacagaaa gagaagcatc cgaaatcatg aagagcatcg gtgaggccat ccagtatctg     720
cattcaatca acattgccca tcgggatgtc aagcctgaga tctcttata cacctccaaa      780
aggcccaacg ccatcctgaa actcactgac tttggctttg ccaaggaaac caccagccac     840
aactctttga ccactccttg ttatacaccg tactatgtgg ctccagaagt gctgggtcca     900
gagaagtatg acaagtcctg tgacatgtgg tccctgggtg tcatcatgta catcctgctg     960
tgtgggtatc ccccttcta ctccaaccac ggccttgcca tctctccggg catgaagact     1020
cgcatccgaa tgggccagta tgaatttccc aacccagaat ggtcagaagt atcagaggaa    1080
gtgaagatgc tcattcggaa tctgctgaaa acagagccca cccagagaat gaccatcacc    1140
gagtttatga ccaccccttg gatcatgcaa tcaacaaagg tccctcaaac cccactgcac    1200
accagccggg tcctgaagga ggacaaggag cggtgggagg atgtcaagga ggagatgacc    1260
agtgccttgg ccacaatgcg cgttgactac gagcagatca agtaa                    1305
```

<210> SEQ ID NO 31
<211> LENGTH: 1130
<212> TYPE: PRT
<213> ORGANISM: Artificial Sequence
<220> FEATURE:
<223> OTHER INFORMATION: Synthetic Sequence

<400> SEQUENCE: 31

```
Met Gly His His His His His Gly Ser Asp Ser Glu Val Asn Gln
  1               5                  10                  15

Glu Ala Lys Pro Glu Val Lys Pro Glu Val Lys Pro Glu Thr His Ile
                 20                  25                  30

Asn Leu Lys Val Ser Asp Gly Ser Ser Glu Ile Phe Phe Lys Ile Lys
         35                  40                  45

Lys Thr Thr Pro Leu Arg Arg Leu Met Glu Ala Phe Ala Lys Arg Gln
     50                  55                  60

Gly Lys Glu Met Asp Ser Leu Arg Phe Leu Tyr Asp Gly Ile Arg Ile
 65                  70                  75                  80

Gln Ala Asp Gln Thr Pro Glu Asp Leu Asp Met Glu Asp Asn Asp Ile
                 85                  90                  95

Ile Glu Ala His Arg Glu Gln Ile Gly Gly Met Thr Met Ile Thr Asp
                100                 105                 110

Ser Leu Ala Val Val Leu Gln Arg Arg Asp Trp Glu Asn Pro Gly Val
            115                 120                 125
```

```
Thr Gln Leu Asn Arg Leu Ala Ala His Pro Pro Phe Ala Ser Trp Arg
    130                 135                 140
Asn Ser Glu Glu Ala Arg Thr Asp Arg Pro Ser Gln Gln Leu Arg Ser
145                 150                 155                 160
Leu Asn Gly Glu Trp Arg Phe Ala Trp Phe Pro Ala Pro Glu Ala Val
                165                 170                 175
Pro Glu Ser Trp Leu Glu Cys Asp Leu Pro Glu Ala Asp Thr Val Val
            180                 185                 190
Val Pro Ser Asn Trp Gln Met His Gly Tyr Asp Ala Pro Ile Tyr Thr
        195                 200                 205
Asn Val Thr Tyr Pro Ile Thr Val Asn Pro Pro Phe Val Pro Thr Glu
    210                 215                 220
Asn Pro Thr Gly Cys Tyr Ser Leu Thr Phe Asn Val Asp Glu Ser Trp
225                 230                 235                 240
Leu Gln Glu Gly Gln Thr Arg Ile Ile Phe Asp Gly Val Asn Ser Ala
                245                 250                 255
Phe His Leu Trp Cys Asn Gly Arg Trp Val Gly Tyr Gly Gln Asp Ser
            260                 265                 270
Arg Leu Pro Ser Glu Phe Asp Leu Ser Ala Phe Leu Arg Ala Gly Glu
        275                 280                 285
Asn Arg Leu Ala Val Met Val Leu Arg Trp Ser Asp Gly Ser Tyr Leu
    290                 295                 300
Glu Asp Gln Asp Met Trp Arg Met Ser Gly Ile Phe Arg Asp Val Ser
305                 310                 315                 320
Leu Leu His Lys Pro Thr Thr Gln Ile Ser Asp Phe His Val Ala Thr
                325                 330                 335
Arg Phe Asn Asp Asp Phe Ser Arg Ala Val Leu Glu Ala Glu Val Gln
            340                 345                 350
Met Cys Gly Glu Leu Arg Asp Tyr Leu Arg Val Thr Val Ser Leu Trp
        355                 360                 365
Gln Gly Glu Thr Gln Val Ala Ser Gly Thr Ala Pro Phe Gly Gly Glu
    370                 375                 380
Ile Ile Asp Glu Arg Gly Gly Tyr Ala Asp Arg Val Thr Leu Arg Leu
385                 390                 395                 400
Asn Val Glu Asn Pro Lys Leu Trp Ser Ala Glu Ile Pro Asn Leu Tyr
                405                 410                 415
Arg Ala Val Val Glu Leu His Thr Ala Asp Gly Thr Leu Ile Glu Ala
            420                 425                 430
Glu Ala Cys Asp Val Gly Phe Arg Glu Val Arg Ile Glu Asn Gly Leu
        435                 440                 445
Leu Leu Leu Asn Gly Lys Pro Leu Leu Ile Arg Gly Val Asn Arg His
    450                 455                 460
Glu His His Pro Leu His Gly Gln Val Met Asp Glu Gln Thr Met Val
465                 470                 475                 480
Gln Asp Ile Leu Leu Met Lys Gln Asn Asn Phe Asn Ala Val Arg Cys
                485                 490                 495
Ser His Tyr Pro Asn His Pro Leu Trp Tyr Thr Leu Cys Asp Arg Tyr
            500                 505                 510
Gly Leu Tyr Val Val Asp Glu Ala Asn Ile Glu Thr His Gly Met Val
        515                 520                 525
Pro Met Asn Arg Leu Thr Asp Asp Pro Arg Trp Leu Pro Ala Met Ser
    530                 535                 540
```

-continued

```
Glu Arg Val Thr Arg Met Val Gln Arg Asp Arg Asn His Pro Ser Val
545                 550                 555                 560

Ile Ile Trp Ser Leu Gly Asn Glu Ser Gly His Gly Ala Asn His Asp
                565                 570                 575

Ala Leu Tyr Arg Trp Ile Lys Ser Val Asp Pro Ser Arg Pro Val Gln
            580                 585                 590

Tyr Glu Gly Gly Gly Ala Asp Thr Thr Ala Thr Asp Ile Ile Cys Pro
        595                 600                 605

Met Tyr Ala Arg Val Asp Glu Asp Gln Pro Phe Pro Ala Val Pro Lys
    610                 615                 620

Trp Ser Ile Lys Lys Trp Leu Ser Leu Pro Gly Glu Thr Arg Pro Leu
625                 630                 635                 640

Ile Leu Cys Glu Tyr Ala His Ala Met Gly Asn Ser Leu Gly Gly Phe
                645                 650                 655

Ala Lys Tyr Trp Gln Ala Phe Arg Gln Tyr Pro Arg Leu Gln Gly Gly
            660                 665                 670

Phe Val Trp Asp Trp Val Asp Gln Ser Leu Ile Lys Tyr Asp Glu Asn
        675                 680                 685

Gly Asn Pro Trp Ser Ala Tyr Gly Gly Asp Phe Gly Asp Thr Pro Asn
    690                 695                 700

Asp Arg Gln Phe Cys Met Asn Gly Leu Val Phe Ala Asp Arg Thr Pro
705                 710                 715                 720

His Pro Ala Leu Thr Glu Ala Lys His Gln Gln Gln Phe Phe Gln Phe
                725                 730                 735

Arg Leu Ser Gly Gln Thr Ile Glu Val Thr Ser Glu Tyr Leu Phe Arg
            740                 745                 750

His Ser Asp Asn Glu Leu Leu His Trp Met Val Ala Leu Asp Gly Lys
        755                 760                 765

Pro Leu Ala Ser Gly Glu Val Pro Leu Asp Val Ala Pro Gln Gly Lys
    770                 775                 780

Gln Leu Ile Glu Leu Pro Glu Leu Pro Gln Pro Glu Ser Ala Gly Gln
785                 790                 795                 800

Leu Trp Leu Thr Val Arg Val Val Gln Pro Asn Ala Thr Ala Trp Ser
                805                 810                 815

Glu Ala Gly His Ile Ser Ala Trp Gln Gln Trp Arg Leu Ala Glu Asn
            820                 825                 830

Leu Ser Val Thr Leu Pro Ala Ala Ser His Ala Ile Pro His Leu Thr
        835                 840                 845

Thr Ser Glu Met Asp Phe Cys Ile Glu Leu Gly Asn Lys Arg Trp Gln
    850                 855                 860

Phe Asn Arg Gln Ser Gly Phe Leu Ser Gln Met Trp Ile Gly Asp Lys
865                 870                 875                 880

Lys Gln Leu Leu Thr Pro Leu Arg Asp Gln Phe Thr Arg Ala Pro Leu
                885                 890                 895

Asp Asn Asp Ile Gly Val Ser Glu Ala Thr Arg Ile Asp Pro Asn Ala
            900                 905                 910

Trp Val Glu Arg Trp Lys Ala Ala Gly His Tyr Gln Ala Glu Ala Ala
        915                 920                 925

Leu Leu Gln Cys Thr Ala Asp Thr Leu Ala Asp Ala Val Leu Ile Thr
    930                 935                 940

Thr Ala His Ala Trp Gln His Gln Gly Lys Thr Leu Phe Ile Ser Arg
945                 950                 955                 960
```

```
Lys Thr Tyr Arg Ile Asp Gly Ser Gly Gln Met Ala Ile Thr Val Asp
                965                 970                 975

Val Glu Val Ala Ser Asp Thr Pro His Pro Ala Arg Ile Gly Leu Asn
            980                 985                 990

Cys Gln Leu Ala Gln Val Ala Glu Arg Val Asn Trp Leu Gly Leu Gly
        995                 1000                1005

Pro Gln Glu Asn Tyr Pro Asp Arg Leu Thr Ala Ala Cys Phe Asp Arg
    1010                1015                1020

Trp Asp Leu Pro Leu Ser Asp Met Tyr Thr Pro Tyr Val Phe Pro Ser
1025                1030                1035                1040

Glu Asn Gly Leu Arg Cys Gly Thr Arg Glu Leu Asn Tyr Gly Pro His
                1045                1050                1055

Gln Trp Arg Gly Asp Phe Gln Phe Asn Ile Ser Arg Tyr Ser Gln Gln
            1060                1065                1070

Gln Leu Met Glu Thr Ser His Arg His Leu Leu His Ala Glu Glu Gly
        1075                1080                1085

Thr Trp Leu Asn Ile Asp Gly Phe His Met Gly Ile Gly Gly Asp Asp
    1090                1095                1100

Ser Trp Ser Pro Ser Val Ser Ala Glu Phe Gln Leu Ser Ala Gly Arg
1105                1110                1115                1120

Tyr His Tyr Gln Leu Val Trp Cys Gln Lys
                1125                1130

<210> SEQ ID NO 32
<211> LENGTH: 3396
<212> TYPE: DNA
<213> ORGANISM: Artificial Sequence
<220> FEATURE:
<223> OTHER INFORMATION: Synthetic Sequence

<400> SEQUENCE: 32
atgggtcatc accatcatca tcacgggtcg gactcagaag tcaatcaaga agctaagcca        60
gaggtcaagc cagaagtcaa gcctgagact cacatcaatt taaaggtgtc cgatggatct      120
tcagagatct tcttcaagat caaaaagacc actcctttaa gaaggctgat ggaagcgttc      180
gctaaaagac agggtaagga aatggactcc ttaagattct tgtacgacgg tattagaatt      240
caagctgatc agaccccctga agatttggac atggaggata cgatattat tgaggctcac      300 cgcgaacaga ttggaggtat gaccatgatt acggattcac tggccgtcgt tttacaacgt      360
cgtgactggg aaaaccctgg cgttacccaa cttaatcgcc ttgcagcaca tcccccttc      420 gccagctggc gtaatagcga agaggcccgc accgatcgcc cttcccaaca gttgcgcagc      480
ctgaatggcg aatggcgctt tgcctggttt ccggcaccag aagcggtgcc ggaaagctgg      540
ctggagtgcg atcttcctga ggccgatact gtcgtcgtcc cctcaaactg gcagatgcac      600
ggttacgatg cgcccatcta caccaacgta acctatccca ttacggtcaa tccgccgttt      660
gttcccacgg agaatccgac gggttgttac tcgctcacat ttaatgttga tgaaagctgg      720
ctacaggaag gccagacgcg aattattttt gatggcgtta actcggcgtt catctgtgg      780 tgcaacgggc gctgggtcgg ttacggccag acagtcgtt tgccgtctga atttgacctg      840
agcgcatttt tacgcgccgg agaaaaccgc ctcgcggtga tggtgctgcg ttggagtgac      900
ggcagttatc tggaagatca ggatatgtgg cggatgagcg gcattttccg tgacgtctcg      960
ttgctgcata aaccgactac acaaatcagc gatttccatg ttgccactcg ctttaatgat     1020
gatttcagcc gcgctgtact ggaggctgaa gttcagatgt gcggcgagtt gcgtgactac     1080
```

```
ctacgggtaa cagtttcttt atggcagggt gaaacgcagg tcgccagcgg caccgcgcct    1140
ttcggcggtg aaattatcga tgagcgtggt ggttatgccg atcgcgtcac actacgtctg    1200
aacgtcgaaa acccgaaact gtggagcgcc gaaatcccga atctctatcg tgcggtggtt    1260
gaactgcaca ccgccgacgg cacgctgatt gaagcagaag cctgcgatgt cggtttccgc    1320
gaggtgcgga ttgaaaatgg tctgctgctg ctgaacggca agccgttgct gattcgaggc    1380
gttaaccgtc acgagcatca tcctctgcat ggtcaggtca tggatgagca gacgatggtg    1440
caggatatcc tgctgatgaa gcagaacaac tttaacgccg tgcgctgttc gcattatccg    1500
aaccatccgc tgtggtacac gctgtgcgac cgctacggcc tgtatgtggt ggatgaagcc    1560
aatattgaaa cccacggcat ggtgccaatg aatcgtctga ccgatgatcc gcgctggcta    1620
ccggcgatga gcgaacgcgt aacgcgaatg gtgcagcgcg atcgtaatca cccgagtgtg    1680
atcatctggt cgctggggaa tgaatcaggc cacggcgcta atcacgacgc gctgtatcgc    1740
tggatcaaat ctgtcgatcc ttcccgcccg gtgcagtatg aaggcggcgg agccgacacc    1800
acggccaccg atattatttg cccgatgtac gcgcgcgtgg atgaagacca gcccttcccg    1860
gctgtgccga atggtccat caaaaaatgg ctttcgctac ctggagagac gcgcccgctg    1920
atcctttgcg aatacgccca cgcgatgggt aacagtcttg gcggtttcgc taaatactgg    1980
caggcgtttc gtcagtatcc ccgtttacag ggcggcttcg tctgggactg ggtggatcag    2040
tcgctgatta aatatgatga aaacggcaac ccgtggtcgg cttacggcgg tgattttggc    2100
gatacgccga cgatcgcca gttctgtatg aacggtctgg tctttgccga ccgcacgccg    2160
catccagcgc tgacggaagc aaaacaccag cagcagtttt ccagttccg tttatccggg    2220 caaaccatcg aagtgaccag cgaataccctg ttccgtcata gcgataacga gctcctgcac    2280
tggatggtgg cgctggatgg taagccgctg gcaagcggtg aagtgcctct ggatgtcgct    2340
ccacaaggta acagttgat tgaactgcct gaactaccgc agccggagag cgccgggcaa    2400
ctctggctca cagtacgcgt agtgcaaccg aacgcgaccg catggtcaga agccgggcac    2460
atcagcgcct ggcagcagtg gcgtctggcg gaaaacctca gtgtgacgct ccccgccgcg    2520
tcccacgcca tcccgcatct gaccaccagc gaaatggatt tttgcatcga gctgggtaat    2580
aagcgttggc aatttaaccg ccagtcaggc tttctttcac agatgtggat tggcgataaa    2640
aaacaactgc tgacgccgct gcgcgatcag ttcacccgtg caccgctgga taacgacatt    2700
ggcgtaagtg aagcgacccg cattgaccct aacgcctggg tcgaacgctg gaaggcggcg    2760
ggccattacc aggccgaagc agcgttgttg cagtgcacgg cagatacact tgctgatgcg    2820
gtgctgatta cgaccgctca cgcgtggcag catcagggga aaaccttatt tatcagccgg    2880
aaaacctacc ggattgatgg tagtggtcaa atggcgatta ccgttgatgt tgaagtggcg    2940
agcgatacac cgcatccggc gcggattggc ctgaactgcc agctggcgca ggtagcagag    3000
cgggtaaact ggctcggatt agggccgcaa gaaaactatc ccgaccgcct tactgccgcc    3060 tgtttttgacc gctgggatct gccattgtca gacatgtata cccgtacgt cttcccgagc    3120 gaaaacggtc tgcgctgcgg gacgcgcgaa ttgaattatg ccacaccca gtggcgcggc    3180 gacttccagt tcaacatcag ccgctacagt caacagcaac tgatggaaac cagccatcgc    3240
catctgctgc acgcggaaga aggcacatgg ctgaatatcg acggtttcca tatgggggatt    3300 ggtggcgacg actcctggag cccgtcagta tcggcggaat tccagctgag cgccggtcgc    3360
taccattacc agttggtctg tgtgtcaaaaa taataa                             3396
```

<210> SEQ ID NO 33
<211> LENGTH: 6865
<212> TYPE: DNA
<213> ORGANISM: Artificial Sequence
<220> FEATURE:
<223> OTHER INFORMATION: Synthetic Sequence

<400> SEQUENCE: 33

```
cgccttgtta ctagttagaa aaagacattt tgctgtcag tcactgtcaa gagattcttt      60
tgctggcatt tcttctagaa gcaaaaagag cgatgcgtct tttccgctga accgttccag     120
caaaaaagac taccaacgca atatggattg tcagaatcat ataaaagaga agcaaataac     180
tccttgtctt gtatcaattg cattataata tcttcttgtt agtgcaatat catatagaag     240
tcatcgaaat agatattaag aaaaacaaac tgtacaatcc atgggtcatc accatcatca     300
tcacgggtcg gactcagaag tcaatcaaga agctaagcca gaggtcaagc cagaagtcaa     360
gcctgagact cacatcaatt taaaggtgtc cgatggatct tcagagatct tcttcaagat     420
caaaaagacc actcctttaa gaaggctgat ggaagcgttc gctaaaagac agggtaagga     480
aatggactcc ttaagattct tgtacgacgg tattagaatt caagctgatc agacccctga     540
agatttggac atggaggata cgatattat tgaggctcac cgcgaacaga ttggaggtat     600
ggtgagcaag ggcgaggagc tgttcaccgg ggtggtgccc atcctggtcg agctggacgg     660
cgacgtaaac ggccacaagt tcagcgtgtc cggcgagggc gagggcgatg ccacctacgg     720
caagctgacc ctgaagttca tctgcaccac cggcaagctg cccgtgccct ggcccaccct     780
cgtgaccacc ctgacctacg gcgtgcagtg cttcagccgc taccccgacc acatgaagca     840
gcacgacttc ttcaagtccg ccatgcccga aggctacgtc caggagcgca ccatcttctt     900
caaggacgac ggcaactaca agacccgcgc cgaggtgaag ttcgagggcg acaccctggt     960
gaaccgcatc gagctgaagg gcatcgactt caaggaggac ggcaacatcc tggggcacaa    1020
gctggagtac aactacaaca gccacaacgt ctatatcatg gccgacaagc agaagaacgg    1080
catcaaggtg aacttcaaga tccgccacaa catcgaggac ggcagcgtgc agctcgccga    1140
ccactaccag cagaacaccc ccatcggcga cggccccgtg ctgctgcccg acaaccacta    1200
cctgagcacc cagtccgccc tgagcaaaga ccccaacgag aagcgcgatc acatggtcct    1260
gctggagttc gtgaccgccg ccgggatcac tctcggcatg gacgagctgt acaagtaata    1320
agcttgcggc cgcactcgag gagctccctg gcgaattgta ccaagatggc ctttggtggg    1380
ttgaagaagg aaaagacag aaacgactta attacctact tgaaaaaagc ctgtgagtaa    1440
acaggcccct tttcctttgt cgatatcatg taattagtta tgtcacgctt acattcacgc    1500
cctccccca catccgctct aaccgaaaag gaaggagtta caacctga agtctaggtc     1560
cctatttatt tttttatagt tatgttagta ttaagaacgt tatttatatt tcaaattttt    1620
ctttttttc tgtacagacg cgtgtacgca tgtaacatta tactgaaaac cttgcttgag    1680
aaggttttgg gacgctcgaa ggctttaatt tgcaagctta tcgatgataa gctgtcaaac    1740
atgagaattc ggtcgaaaaa agaaaaggag agggccaaga gggagggcat tggtgactat    1800
tgagcacgtg agtatacgtg attaagcaca caaaggcagc ttggagtatg tctgttatta    1860
atttcacagg tagttctggt ccattggtga agtttgcgg cttgcagagc acagaggccg    1920
cagaatgtgc tctagattcc gatgctgact tgctgggtat tatatgtgtg cccaatagaa    1980
agagaacaat tgacccggtt attgcaagga aatttcaag tcttgtaaaa gcatataaaa    2040
atagttcagg cactccgaaa tacttggttg gcgtgtttcg taatcaacct aaggaggatg    2100
```

```
ttttggctct ggtcaatgat tacggcattg atatcgtcca actgcatgga gatgagtcgt    2160
ggcaagaata ccaagagttc ctcggtttgc cagttattaa aagactcgta tttccaaaag    2220
actgcaacat actactcagt gcagcttcac agaaacctca ttcgtttatt cccttgtttg    2280
attcagaagc aggtgggaca ggtgaacttt tggattggaa ctcgatttct gactgggttg    2340
gaaggcaaga gagccccgaa agcttacatt ttatgttagc tggtggactg acgccagaaa    2400
atgttggtga tgcgcttaga ttaaatggcg ttattggtgt tgatgtaagc ggaggtgtgg    2460
agacaaatgg tgtaaaagac tctaacaaaa tagcaaattt cgtcaaaaat gctaagaaat    2520
aggttattac tgagtagtat ttatttaagt attgtttgtg cacttgcctg cagcttctca    2580
atgatattcg aatacgcttt gaggagatac agcctaatat ccgacaaact gttttacaga    2640
tttacgatcg tacttgttac ccatcattga attttgaaca tccgaacctg ggagttttcc    2700
ctgaaacaga tagtatattt gaacctgtat aataatatat agtctagcgc tttacggaag    2760
acaatgtatg tatttcggtt cctggagaaa ctattgcatc tattgcatag gtaatcttgc    2820
acgtcgcatc cccggttcat tttctgcgtt tccatcttgc acttcaatag catatctttg    2880
ttaacgaagc atctgtgctt catttttgtag aacaaaaatg caacgcgaga gcgctaattt    2940
ttcaaacaaa gaatctgagc tgcattttta cagaacagaa atgcaacgcg aaagcgctat    3000
tttaccaacg aagaatctgt gcttcatttt tgtaaaacaa aaatgcaacg cgagagcgct    3060 aattttcaa acaaagaatc tgagctgcat ttttacagaa cagaaatgca acgcgagagc    3120
gctattttac caacaaagaa tctatacttc ttttttgttc tacaaaatg catcccgaga    3180 gcgctatttt tctaacaaag catcttagat tactttttt ctcctttgtg cgctctataa    3240
tgcagtctct tgataacttt ttgcactgta ggtccgttaa ggttagaaga aggctacttt    3300
ggtgtctatt ttctcttcca taaaaaaagc ctgactccac ttcccgcgtt tactgattac    3360
tagcgaagct gcgggtgcat tttttcaaga taaaggcatc cccgattata ttctataccg    3420
atgtggattg cgcatacttt gtgaacagaa agtgatagcg ttgatgattc ttcattggtc    3480
agaaaattat gaacggtttc ttctattttg tctctatata ctacgtatag gaaatgttta    3540
cattttcgta ttgttttcga ttcactctat gaatagttct tactacaatt tttttgtcta    3600
aagagtaata ctagagataa acataaaaaa tgtagaggtc gagtttagat gcaagttcaa    3660
ggagcgaaag gtggatgggt aggttatata gggatatagc acagagatat atagcaaaga    3720 gatactttg agcaatgttt gtggaagcgg tattcgcaat attttagtag ctcgttacag    3780
tccggtgcgt ttttggtttt ttgaaagtgc gtcttcagag cgcttttggt tttcaaaagc    3840
gctctgaagt tcctatactt tctagagaat aggaacttcg gaataggaac ttcaaagcgt    3900
ttccgaaaac gagcgcttcc gaaaatgcaa cgcgagctgc gcacatacag ctcactgttc    3960
acgtcgcacc tatatctgcg tgttgcctgt atatatat acatgagaag aacggcatag    4020
tgcgtgttta tgcttaaatg cgtacttata tgcgtctatt tatgtaggat gaaaggtagt    4080
ctagtacctc ctgtgatatt atcccattcc atgcggggta tcgtatgctt ccttcagcac    4140 tacccttag ctgttctata tgctgccact cctcaattgg attagtctca tccttcaatg    4200
ctatcatttc ctttgatatt ggatcatatg catagtaccg agaaactagt gcgaagtagt    4260
gatcaggtat tgctgttatc tgatgagtat acgttgtcct ggccacggca gaagcacgct    4320
tatcgctcca atttcccaca acattagtca actccgttag gcccttcatt gaaagaaatg    4380
aggtcatcaa atgtcttcca atgtgagatt ttggccatt ttttatagca agattgaat    4440 aaggcgcatt tttcttcaaa gctttattgt acgatctgac taagttatct tttaataatt    4500
```

```
ggtattcctg tttattgctt gaagaattgc cggtcctatt tactcgtttt aggactggtt    4560
cagaattctt gaagacgaaa gggcctcgtg atacgcctat ttttataggt taatgtcatg    4620
ataataatgg tttcttagac gtcaggtggc acttttcggg gaaatgtgcg cggaacccct    4680
atttgtttat ttttctaaat acattcaaat atgtatccgc tcatgagaca ataaccctga    4740
taaatgcttc aataatattg aaaaaggaag agtatgagta ttcaacattt ccgtgtcgcc    4800
cttattccct tttttgcggc attttgcctt cctgtttttg ctcacccaga aacgctggtg    4860
aaagtaaaag atgctgaaga tcagttgggt gcacgagtgg gttacatcga actggatctc    4920
aacagcggta agatccttga gagttttcgc cccgaagaac gttttccaat gatgagcact    4980
tttaaagttc tgctatgtgg cgcggtatta tcccgtgttg acgccgggca agagcaactc    5040
ggtcgccgca tacactattc tcagaatgac ttggttgagt actcaccagt cacagaaaag    5100
catcttacgg atggcatgac agtaagagaa ttatgcagtg ctgccataac catgagtgat    5160
aacactgcgg ccaacttact tctgacaacg atcggaggac cgaaggagct aaccgctttt    5220
ttgcacaaca tgggggatca tgtaactcgc cttgatcgtt gggaaccgga gctgaatgaa    5280
gccataccaa acgacgagcg tgacaccacg atgcctgcag caatggcaac aacgttgcgc    5340
aaactattaa ctggcgaact acttactcta gcttcccggc aacaattaat agactggatg    5400
gaggcggata aagttgcagg accacttctg cgctcggccc ttccggctgg ctggtttatt    5460
gctgataaat ctggagccgg tgagcgtggg tctcgcggta tcattgcagc actggggcca    5520
gatggtaagc cctcccgtat cgtagttatc tacacgacgg ggagtcaggc aactatggat    5580
gaacgaaata gacagatcgc tgagataggt gcctcactga ttaagcattg gtaactgtca    5640
gaccaagttt actcatatat actttagatt gatttaaaac ttcatttttt atttaaaagg    5700
atctaggtga agatcctttt tgataatctc atgaccaaaa tcccttaacg tgagttttcg    5760
ttccactgag cgtcagaccc cgtagaaaag atcaaaggat cttcttgaga tcctttttttt    5820 ctgcgcgtaa tctgctgctt gcaaacaaaa aaaccaccgc taccagcggt ggtttgtttg    5880
ccggatcaag agctaccaac tctttttccg aaggtaactg gcttcagcag agcgcagata    5940
ccaaatactg tccttctagt gtagccgtag ttaggccacc acttcaagaa ctctgtagca    6000
ccgcctacat acctcgctct gctaatcctg ttaccagtgg ctgctgccag tggcgataag    6060
tcgtgtctta ccgggttgga ctcaagacga tagttaccgg ataaggcgca gcggtcgggc    6120
tgaacggggg gttcgtgcac acagcccagc ttggagcgaa cgacctacac cgaactgaga    6180
tacctacagc gtgagctatg agaaagcgcc acgcttcccg aagggagaaa ggcggacagg    6240
tatccggtaa gcggcagggt cggaacagga gagcgcacga gggagcttcc agggggaaac    6300
gcctggtatc tttatagtcc tgtcgggttt cgccacctct gacttgagcg tcgatttttg    6360
tgatgctcgt caggggggcg gagcctatgg aaaaacgcca gcaacgcggc ctttttacgg    6420
ttcctggcct tttgctggcc ttttgctcac atgttctttc ctgcgttatc ccctgattct    6480
gtggataacc gtattaccgc ctttgagtga gctgataccg ctcgccgcag ccgaacgacc    6540
gagcgcagcg agtcagtgag cgaggaagcg gaagagcgcc tgatgcggta ttttctcctt    6600
acgcatctgt gcggtatttc acaccgcata tggtgcactc tcagtacaat ctgctctgat    6660
gccgcatagt taagccagta tacactccgc tatcgctacg tgactgggtc atggctgcgc    6720
cccgacaccc gccaacaccc gctgacgcgc cctgacgggc ttgtctgctc ccggcatccg    6780
cttacagaca agctgtgacc gtctccggga gctgcatgtg tcagaggttt tcaccgtcat    6840
caccgaaacg cgcgaggcag ggatc                                          6865
```

```
<210> SEQ ID NO 34
<211> LENGTH: 7894
<212> TYPE: DNA
<213> ORGANISM: Artificial Sequence
<220> FEATURE:
<223> OTHER INFORMATION: Synthetic Sequence

<400> SEQUENCE: 34
ccttgttact agttagaaaa agacatttt gctgtcagtc actgtcaaga gattcttttg      60
ctggcatttc ttctagaagc aaaaagagcg atgcgtcttt ccgctgaac cgttccagca     120 aaaaagacta ccaacgcaat atggattgtc agaatcatat aaaagagaag caaataactc    180
cttgtcttgt atcaattgca ttataatatc ttcttgttag tgcaatatca tatagaagtc    240
atcgaaatag atattaagaa aaacaaactg tacaatccat gggtcatcac catcatcatc    300
acgggcagat cttcgtcaag acgttaaccg gtaaaccat aactctagaa gttgaaccat     360
ccgataccat cgaaaacgtt aaggctaaaa ttcaagacaa ggaaggcatt ccacctgatc    420
aacaaagatt gatctttgcc ggtaagcagc tcgaggacgg tagaacgctg tctgattaca    480
acattcagaa ggagtcgacc ttacatcttg tcttacgcct acgtggaggt atggaattca    540
tgttacgtcc tgtagaaacc caacccgtg aaatcaaaaa actcgacggc ctgtgggcat     600
tcagtctgga tcgcgaaaac tgtggaattg atcagcgttg gtgggaaagc gcgttacaag    660 aaagccggc aattgctgtg ccaggcagtt ttaacgatca gttcgccgat gcagatattc     720
gtaattatgc gggcaacgtc tggtatcagc gcgaagtctt tataccgaaa ggttgggcag    780
gccagcgtat cgtgctgcgt ttcgatgcgg tcactcatta cggcaaagtg tgggtcaata    840
atcaggaagt gatggagcat cagggcggct atacgccatt tgaagccgat gtcacgccgt    900
atgttattgc cgggaaaagt gtacgtatca ccgtttgtgt gaacaacgaa ctgaactggc    960
agactatccc gccgggaatg gtgattaccg acgaaacgg caagaaaaag cagtcttact   1020
tccatgattt ctttaactat gccggaatcc atcgcagcgc aatgctctac accacgccga   1080
acacctgggt ggacgatatc accgtggtga cgcatgtcgc gcaagactgt aaccacgcgt   1140
ctgttgactg gcaggtggtg gccaatgtg atgtcagcgc tgaactgcgt gatgcggatc    1200
aacaggtggt tgcaactgga caaggcacta gcgggacttt gcaagtggtg aatccgcacc   1260
tctggcaacc gggtgaaggt tatctctatg aactgtgcgt cacagccaaa gccagacag    1320 agtgtgatat ctacccgctt cgcgtcggca tccggtcagt ggcagtgaag gccaacagt    1380 tcctgattaa ccacaaaccg ttctacttta ctggctttgg tcgtcatgaa gatgcggact   1440
tacgtggcaa aggattcgat aacgtgctga tggtgcacga ccacgcatta atggactgga   1500
ttggggccaa ctcctaccgt acctcgcatt acccttacgc tgaagagatg ctcgactggg   1560
cagatgaaca tggcatcgtg gtgattgatg aaactgctgc tgtcggcttt aacctctctt   1620
taggcattgg tttcgaagcg gcaacaagc cgaaagaact gtacagcgaa gaggcagtca   1680 acgggaaac tcagcaagcg cacttacagg cgattaaaga gctgatagcg cgtgacaaaa   1740
accacccaag cgtggtgatg tggagtattg ccaacgaacc ggataccgt ccgcaagtgc    1800 acgggaatat ttcgccactg gcggaagcaa cgcgtaaact cgaccgacg cgtccgatca    1860 cctgcgtcaa tgtaatgttc tgcgacgctc acaccgatac catcagcgat ctctttgatg   1920
tgctgtgcct gaaccgttat tacgatggt atgtccaaag cggcgatttg gaaacggcag   1980
agaaggtact ggaaaaagaa cttctggcct ggcaggagaa actgcatcag ccgattatca   2040
tcaccgaata cggcgtggat acgttagccg ggctgcactc aatgtacacc gacatgtgga   2100
```

```
gtgaagagta tcagtgtgca tggctggata tgtatcaccg cgtctttgat cgcgtcagcg   2160
ccgtcgtcgg tgaacaggta tggaatttcg ccgattttgc gacctcgcaa ggcatattgc   2220
gcgttggcgg taacaagaaa gggatcttca ctcgcgaccg caaaccgaag tcggcggctt   2280
ttctgctgca aaaacgctgg actggcatga acttcggtga aaaaccgcag cagggaggca   2340
aacaataagc ttgcggccgc actcgaggag ctccctggcg aattgtacca agatggcctt   2400
tggtgggttg aagaaggaaa aagacagaaa cgacttaatt acctacttga aaaaagcctg   2460
tgagtaaaca ggccccttttt cctttgtcga tatcatgtaa ttagttatgt cacgcttaca   2520
ttcacgccct ccccccacat ccgctctaac cgaaaaggaa ggagttagac aacctgaagt   2580
ctaggtccct atttattttt ttatagttat gttagtatta agaacgttat ttatatttca   2640
aatttttctt ttttttctgt acagacgcgt gtacgcatgt aacattatac tgaaaacctt   2700
gcttgagaag gttttgggac gctcgaaggc tttaatttgc aagcttatcg atgataagct   2760
gtcaaacatg agaattcggt cgaaaaaaga aaggagagg ccaagaggg agggcattgg    2820 tgactattga gcacgtgagt atacgtgatt aagcacacaa aggcagcttg gagtatgtct   2880
gttattaatt tcacaggtag ttctggtcca ttggtgaaag tttgcggctt gcagagcaca   2940
gaggccgcag aatgtgctct agattccgat gctgacttgc tgggtattat atgtgtgccc   3000
aatagaaaga gaacaattga cccggttatt gcaaggaaaa tttcaagtct tgtaaaagca   3060
tataaaaata gttcaggcac tccgaaatac ttggttggcg tgtttcgtaa tcaacctaag   3120
gaggatgttt tggctctggt caatgattac ggcattgata tcgtccaact gcatggagat   3180
gagtcgtggc aagaatacca agagttcctc ggtttgccag ttattaaaag actcgtatt    3240 ccaaaagact gcaacatact actcagtgca gcttcacaga aacctcattc gtttattccc   3300
ttgtttgatt cagaagcagg tgggacaggt gaacttttgg attggaactc gatttctgac   3360
tgggttggaa ggcaagagag ccccgaaagc ttacatttta tgttagctgg tggactgacg   3420
ccagaaaatg ttggtgatgc gcttagatta aatggcgtta ttggtgttga tgtaagcgga   3480
ggtgtggaga caaatggtgt aaaagactct aacaaaatag caaatttcgt caaaaatgct   3540
aagaaatagg ttattactga gtagtattta tttaagtatt gtttgtgcac ttgcctgcag   3600
cttctcaatg atattcgaat acgctttgag gagatacagc ctaatatccg acaaactgtt   3660
ttacagattt acgatcgtac ttgttaccca tcattgaatt ttgaacatcc gaacctggga   3720
gttttccctg aaacagatag tatatttgaa cctgtataat aatatatagt ctagcgcttt   3780
acggaagaca atgtatgtat ttcggttcct ggagaaacta ttgcatctat tgcataggta   3840
atcttgcacg tcgcatcccc ggttcatttt ctgcgtttcc atcttgcact tcaatagcat   3900
atctttgtta acgaagcatc tgtgcttcat tttgtagaac aaaaatgcaa cgcgagagcg   3960 ctaattttc aaacaaagaa tctgagctgc attttacag aacagaaatg caacgcgaaa     4020
gcgctatttt accaacgaag aatctgtgct tcattttgt aaaacaaaaa tgcaacgcga    4080
gagcgctaat ttttcaaaca aagaatctga gctgcatttt tacagaacag aaatgcaacg   4140
cgagagcgct attttaccaa caaagaatct atacttcttt tttgttctac aaaaatgcat   4200
cccgagagcg ctatttttct aacaaagcat cttagattac ttttttttctc ctttgtgcgc   4260 tctataatgc agtctcttga taactttttg cactgtaggt ccgttaaggt tagaagaagg   4320
ctactttggt gtctattttc tcttccataa aaaaagcctg actccacttc ccgcgtttac   4380
tgattactag cgaagctgcg ggtgcatttt ttcaagataa aggcatcccc gattatattc   4440
tataccgatg tggattgcgc atactttgtg aacagaaagt gatagcgttg atgattcttc   4500
```

```
attggtcaga aaattatgaa cggtttcttc tattttgtct ctatatacta cgtataggaa    4560
atgtttacat tttcgtattg ttttcgattc actctatgaa tagttcttac tacaattttt    4620
ttgtctaaag agtaatacta gagataaaca taaaaaatgt agaggtcgag tttagatgca    4680
agttcaagga gcgaaaggtg gatgggtagg ttatataggg atatagcaca gagatatata    4740
gcaaagagat acttttgagc aatgtttgtg gaagcggtat tcgcaatatt ttagtagctc    4800
gttacagtcc ggtgcgtttt tggttttttg aaagtgcgtc ttcagagcgc ttttggtttt    4860
caaaagcgct ctgaagttcc tatactttct agagaatagg aacttcggaa taggaacttc    4920
aaagcgtttc cgaaacgag cgcttccgaa atgcaacgc gagctgcgca catacagctc    4980
actgttcacg tcgcacctat atctgcgtgt tgcctgtata tatatataca tgagaagaac    5040
ggcatagtgc gtgtttatgc ttaaatgcgt acttatatgc gtctatttat gtaggatgaa    5100
aggtagtcta gtacctcctg tgatattatc ccattccatg cggggtatcg tatgcttcct    5160
tcagcactac cctttagctg ttctatatgc tgccactcct caattggatt agtctcatcc    5220
ttcaatgcta tcatttcctt tgatattgga tcatatgcat agtaccgaga aactagtgcg    5280
aagtagtgat caggtattgc tgttatctga tgagtatacg ttgtcctggc cacggcagaa    5340
gcacgcttat cgctccaatt tcccacaaca ttagtcaact ccgttaggcc cttcattgaa    5400
agaaatgagg tcatcaaatg tcttccaatg tgagattttg ggccattttt tatagcaaag    5460
attgaataag gcgcattttt cttcaaagct ttattgtacg atctgactaa gttatctttt    5520
aataattggt attcctgttt attgcttgaa gaattgccgg tcctatttac tcgttttagg    5580
actggttcag aattcttgaa gacgaaaggg cctcgtgata cgcctatttt tataggttaa    5640
tgtcatgata ataatggttt cttagacgtc aggtggcact tttcggggaa atgtgcgcgg    5700
aacccctatt tgtttatttt tctaaataca ttcaaatatg tatccgctca tgagacaata    5760
accctgataa atgcttcaat aatattgaaa aaggaagagt atgagtattc aacatttccg    5820
tgtcgccctt attccctttt tgcggcatt ttgccttcct gtttttgctc acccagaaac    5880
gctggtgaaa gtaaaagatg ctgaagatca gttgggtgca cgagtgggtt acatcgaact    5940
ggatctcaac agcggtaaga tccttgagag ttttcgcccc gaagaacgtt ttccaatgat    6000
gagcactttt aaagttctgc tatgtggcgc ggtattatcc cgtgttgacg ccgggcaaga    6060
gcaactcggt cgccgcatac actattctca gaatgacttg gttgagtact caccagtcac    6120
agaaaagcat cttacggatg gcatgacagt aagagaatta tgcagtgctg ccataaccat    6180
gagtgataac actgcggcca acttacttct gacaacgatc ggaggaccga aggagctaac    6240
cgcttttttg cacaacatgg ggatcatgt aactcgcctt gatcgttggg aaccggagct    6300
gaatgaagcc ataccaaacg acgagcgtga caccacgatg cctgcagcaa tggcaacaac    6360
gttgcgcaaa ctattaactg gcgaactact tactctagct tcccggcaac aattaataga    6420
ctggatggag gcggataaag ttgcaggacc acttctgcgc tcggcccttc cggctggctg    6480
gtttattgct gataaatctg gagccggtga gcgtgggtct cgcggtatca ttgcagcact    6540
ggggccagat ggtaagccct cccgtatcgt agttatctac acgacgggga gtcaggcaac    6600
tatggatgaa cgaaatagac agatcgctga gataggtgcc tcactgatta agcattggta    6660
actgtcagac caagtttact catatatact ttagattgat ttaaaacttc atttttaatt    6720
taaaaggatc taggtgaaga tcctttttga taatctcatg accaaaatcc cttaacgtga    6780
gttttcgttc cactgagcgt cagaccccgt agaaaagatc aaaggatctt cttgagatcc    6840 ttttttttctg cgcgtaatct gctgcttgca aacaaaaaaa ccaccgctac cagcggtggt    6900
```

| | | | |
|---|---|---|---|
| ttgtttgccg | gatcaagagc taccaactct | ttttccgaag gtaactggct | tcagcagagc | 6960 |
| gcagatacca | aatactgtcc ttctagtgta | gccgtagtta ggccaccact | tcaagaactc | 7020 |
| tgtagcaccg | cctacatacc tcgctctgct | aatcctgtta ccagtggctg | ctgccagtgg | 7080 |
| cgataagtcg | tgtcttaccg ggttggactc | aagacgatag ttaccggata | aggcgcagcg | 7140 |
| gtcgggctga | acgggggtt cgtgcacaca | gcccagcttg gagcgaacga | cctacaccga | 7200 |
| actgagatac | ctacagcgtg agctatgaga | aagcgccacg cttcccgaag | ggagaaaggc | 7260 |
| ggacaggtat | ccggtaagcg gcagggtcgg | aacaggagag cgcacgaggg | agcttccagg | 7320 |
| gggaaacgcc | tggtatcttt atagtcctgt | cgggtttcgc cacctctgac | ttgagcgtcg | 7380 |
| attttgtga | tgctcgtcag gggggcggag | cctatggaaa aacgccagca | acgcggcctt | 7440 |
| tttacggttc | ctggccttt gctggccttt | tgctcacatg ttctttcctg | cgttatcccc | 7500 |
| tgattctgtg | gataaccgta ttaccgcctt | tgagtgagct gataccgctc | gccgcagccg | 7560 |
| aacgaccgag | cgcagcgagt cagtgagcga | ggaagcggaa gagcgcctga | tgcggtattt | 7620 |
| tctccttacg | catctgtgcg gtatttcaca | ccgcatatgg tgcactctca | gtacaatctg | 7680 |
| ctctgatgcc | gcatagttaa gccagtatac | actccgctat cgctacgtga | ctgggtcatg | 7740 |
| gctgcgcccc | gacacccgcc aacacccgct | gacgcgccct gacgggcttg | tctgctcccg | 7800 |
| gcatccgctt | acagacaagc tgtgaccgtc | tccgggagct gcatgtgtca | gaggttttca | 7860 |
| ccgtcatcac | cgaaacgcgc gaggcaggga | tccg | 7894 |

<210> SEQ ID NO 35
<211> LENGTH: 5800
<212> TYPE: DNA
<213> ORGANISM: Artificial Sequence
<220> FEATURE:
<223> OTHER INFORMATION: Synthetic Sequence

<400> SEQUENCE: 35

| | | | |
|---|---|---|---|
| atcatggaga | taattaaaat gataaccatc | tcgcaaataa ataagtattt | tactgttttc | 60 |
| gtaacagttt | tgtaataaaa aaacctataa | atattccgga ttattcatac | cgtcccacca | 120 |
| tcgggcgcga | tgggtcatca ccatcatcat | cacgggtcgg actcagaagt | caatcaagaa | 180 |
| gctaagccag | aggtcaagcc agaagtcaag | cctgagactc acatcaattt | aaaggtgtcc | 240 |
| gatggatctt | cagagatctt cttcaagatc | aaaaagacca ctcctttaag | aaggctgatg | 300 |
| gaagcgttcg | ctaaaagaca gggtaaggaa | atggactcct taagattctt | gtacgacggt | 360 |
| attagaattc | aagctgatca gacccctgaa | gatttggaca tggaggataa | cgatattatt | 420 |
| gaggctcacc | gcgaacagat tggaggtatg | gtgagcaagg gcgaggagct | gttcaccggg | 480 |
| gtggtgccca | tcctggtcga gctggacggc | gacgtaaacg gccacaagtt | cagcgtgtcc | 540 |
| ggcgagggcg | agggcgatgc cacctacggc | aagctgaccc tgaagttcat | ctgcaccacc | 600 |
| ggcaagctgc | ccgtgccctg gcccaccctc | gtgaccaccc tgacctacgg | cgtgcagtgc | 660 |
| ttcagccgct | accccgacca catgaagcag | cacgacttct tcaagtccgc | catgcccgaa | 720 |
| ggctacgtcc | aggagcgcac catcttcttc | aaggacgacg gcaactacaa | gacccgcgcc | 780 |
| gaggtgaagt | tcgagggcga caccctggtg | aaccgcatcg agctgaaggg | catcgacttc | 840 |
| aaggaggacg | gcaacatcct ggggcacaag | ctggagtaca actacaacag | ccacaacgtc | 900 |
| tatatcatgg | ccgacaagca gaagaacggc | atcaaggtga acttcaagat | ccgccacaac | 960 |
| atcgaggacg | gcagcgtgca gctcgccgac | cactaccagc agaacacccc | catcggcgac | 1020 |
| ggccccgtgc | tgctgcccga caaccactac | ctgagcaccc agtccgccct | gagcaaagac | 1080 |

-continued

```
cccaacgaga agcgcgatca catggtcctg ctggagttcg tgaccgccgc cgggatcact    1140
ctcggcatgg acgagctgta caagtaatga gacggaattc aaaggcctac gtcgacgagc    1200
tcactagtcg cggccgcttt cgaatctaga gcctgcagtc tcgaggcatg cggtaccaag    1260
cttgtcgaga agtactagag gatcataatc agccatacca catttgtaga ggttttactt    1320
gctttaaaaa acctcccaca cctcccctg aacctgaaac ataaaatgaa tgcaattgtt    1380
gttgttaact tgtttattgc agcttataat ggttacaaat aaagcaatag catcacaaat    1440
ttcacaaata aagcattttt ttcactgcat tctagttgtg gtttgtccaa actcatcaat    1500
gtatcttatc atgtctggat ctgatcactg cttgagccta ggagatccga accagataag    1560
tgaaatctag ttccaaacta ttttgtcatt tttaattttc gtattagctt acgacgctac    1620
acccagttcc catctatttt gtcactcttc cctaaataat ccttaaaaac tccatttcca    1680
cccctcccag ttcccaacta ttttgtccgc ccacagcggg gcattttct tcctgttatg     1740 tttttaatca aacatcctgc caactccatg tgacaaaccg tcatcttcgg ctactttttc    1800
tctgtcacag aatgaaaatt tttctgtcat ctcttcgtta ttaatgtttg taattgactg    1860
aatatcaacg cttatttgca gcctgaatgg cgaatgggac gcgccctgta gcggcgcatt    1920
aagcgcggcg ggtgtggtgg ttacgcgcag cgtgaccgct acacttgcca gcgccctagc    1980
gcccgctcct ttcgctttct tcccttcctt tctcgccacg ttcgccggct ttccccgtca    2040
agctctaaat cggggggctcc ctttagggtt ccgatttagt gctttacggc acctcgaccc    2100
caaaaaactt gattagggtg atggttcacg tagtgggcca tcgccctgat agacggtttt    2160 tcgcccttg acgttggagt ccacgttctt taatagtgga ctcttgttcc aaactggaac    2220
aacactcaac cctatctcgg tctattcttt tgatttataa gggattttgc cgatttcggc    2280
ctattggtta aaaaatgagc tgatttaaca aaaatttaac gcgaatttta acaaaatatt    2340
aacgtttaca atttcaggtg gcacttttcg gggaaatgtg cgcggaaccc ctatttgttt    2400
atttttctaa atacattcaa atatgtatcc gctcatgaga caataaccct gataaatgct    2460
tcaataatat tgaaaaagga agagtatgag tattcaacat ttccgtgtcg cccttattcc    2520
cttttttgcg gcattttgcc ttcctgtttt tgctcaccca gaaacgctgg tgaaagtaaa    2580
agatgctgaa gatcagttgg gtgcacgagt gggttacatc gaactggatc tcaacagcgg    2640
taagatcctt gagagttttc gccccgaaga acgttttcca atgatgagca cttttaaagt    2700
tctgctatgt ggcgcggtat tatcccgtat tgacgccggg caagagcaac tcggtcgccg    2760
catacactat tctcagaatg acttggttga gtactcacca gtcacagaaa agcatcttac    2820
ggatggcatg acagtaagag aattatgcag tgctgccata accatgagtg ataacactgc    2880
ggccaactta cttctgacaa cgatcggagg accgaaggag ctaaccgctt ttttgcacaa    2940
catgggggat catgtaactc gccttgatcg ttgggaaccg gagctgaatg aagccatacc    3000
aaacgacgag cgtgacacca cgatgcctgt agcaatggca acaacgttgc gcaaactatt    3060
aactggcgaa ctacttactc tagcttcccg gcaacaatta atagactgga tggaggcgga    3120
taaagttgca ggaccacttc tgcgctcggc ccttccggct ggctggttta ttgctgataa    3180
atctggagcc ggtgagcgtg ggtctcgcgg tatcattgca gcactggggc cagatggtaa    3240
gccctcccgt atcgtagtta tctacacgac ggggagtcag gcaactatgg atgaacgaaa    3300
tagacagatc gctgagatag gtgcctcact gattaagcat tggtaactgt cagaccaagt    3360
ttactcatat atactttaga ttgatttaaa acttcatttt taatttaaaa ggatctaggt    3420
gaagatcctt tttgataatc tcatgaccaa atcccttaa cgtgagtttt cgttccactg    3480
```

```
agcgtcagac cccgtagaaa agatcaaagg atcttcttga gatcctttttt ttctgcgcgt   3540
aatctgctgc ttgcaaacaa aaaaaccacc gctaccagcg gtggtttgtt tgccggatca   3600
agagctacca actctttttc cgaaggtaac tggcttcagc agagcgcaga taccaaatac   3660
tgtccttcta gtgtagccgt agttaggcca ccacttcaag aactctgtag caccgcctac   3720
atacctcgct ctgctaatcc tgttaccagt ggctgctgcc agtggcgata agtcgtgtct   3780
taccgggttg gactcaagac gatagttacc ggataaggcg cagcggtcgg gctgaacggg   3840
gggttcgtgc acacagccca gcttggagcg aacgacctac accgaactga gatacctaca   3900
gcgtgagcat tgagaaagcg ccacgcttcc cgaagggaga aaggcggaca ggtatccggt   3960
aagcggcagg gtcggaacag gagagcgcac gagggagctt ccaggggaa acgcctggta    4020
tctttatagt cctgtcgggt ttcgccacct ctgacttgag cgtcgatttt tgtgatgctc   4080
gtcaggggg cggagcctat ggaaaaacgc cagcaacgcg gcctttttac ggttcctggc    4140
cttttgctgg ccttttgctc acatgttctt tcctgcgtta tcccctgatt ctgtggataa   4200
ccgtattacc gcctttgagt gagctgatac cgctcgccgc agccgaacga ccgagcgcag   4260
cgagtcagtg agcgaggaag cggaagagcg cctgatgcgg tattttctcc ttacgcatct   4320
gtgcggtatt tcacaccgca gaccagccgc gtaacctggc aaaatcggtt acggttgagt   4380
aataaatgga tgccctgcgt aagcgggtgt gggcggacaa taaagtctta aactgaacaa   4440
aatagatcta aactatgaca ataaagtctt aaactagaca gaatagttgt aaactgaaat   4500
cagtccagtt atgctgtgaa aaagcatact ggacttttgt tatggctaaa gcaaactctt   4560
cattttctga agtgcaaatt gcccgtcgta ttaaagaggg gcgtggccaa gggcatggta   4620
aagactatat cgcggcgtt gtgacaattt accgaacaac tccgcggccg ggaagccgat    4680
ctcggcttga acgaattgtt aggtggcggt acttgggtcg atatcaaagt gcatcacttc   4740
ttcccgtatg cccaactttg tatagagagc cactgcggga tcgtcaccgt aatctgcttg   4800
cacgtagatc acataagcac caagcgcgtt ggcctcatgc ttgaggagat tgatgagcgc   4860
ggtggcaatg ccctgcctcc ggtgctcgcc ggagactgcg agatcataga tatagatctc   4920
actacgcggc tgctcaaacc tgggcagaac gtaagccgcg agagcgccaa caaccgcttc   4980
ttggtcgaag gcagcaagcg cgatgaatgt cttactacgg agcaagttcc cgaggtaatc   5040
ggagtccggc tgatgttggg agtaggtggc tacgtctccg aactcacgac cgaaaagatc   5100
aagagcagcc cgcatggatt tgacttggtc agggccgagc ctacatgtgc gaatgatgcc   5160
catacttgag ccacctaact ttgttttagg gcgactgccc tgctgcgtaa catcgttgct   5220
gctgcgtaac atcgttgctg ctccataaca tcaaacatcg acccacggcg taacgcgctt   5280
gctgcttgga tgcccgaggc atagactgta caaaaaaaca gtcataacaa gccatgaaaa   5340
ccgccactgc gccgttacca ccgctgcgtt cggtcaaggt tctggaccag ttgcgtgagc   5400
gcatacgcta cttgcattac agtttacgaa ccgaacaggc ttatgtcaac tgggttcgtg   5460
ccttcatccg tttccacggt gtgcgtcacc cggcaacctt gggcagcagc gaagtcgagg   5520
catttctgtc ctggctggcg aacgagcgca aggtttcggt ctccacgcat cgtcaggcat   5580
tggcggcctt gctgttcttc tacggcaagg tgctgtgcac ggatctgccc tggcttcagg   5640
agatcggaag acctcggccg tcgcggcgct tgccggtggt gctgaccccg gatgaagtgg   5700
ttcgcatcct cggttttctg gaaggcgagc atcgtttgtt cgcccaggac tctagctata   5760
gttctagtgg ttggctacgt atactccgga atattaatag                          5800
```

<210> SEQ ID NO 36
<211> LENGTH: 5598
<212> TYPE: DNA
<213> ORGANISM: Artificial Sequence
<220> FEATURE:
<223> OTHER INFORMATION: Synthetic Sequence

<400> SEQUENCE: 36

```
atccggatat agttcctcct ttcagcaaaa aaccccctcaa gacccgttta gaggccccaa      60
ggggttatgc tagttattgc tcagcggtgg cagcagccaa ctcagcttcc tttcgggctt     120
tgttagcagc cggatctcag tggtggtggt ggtggtgctc gagtgcggcc gcaagcttgt     180
cgacggagct cgaattcgga tccggtctca acctccaatc tgttcgcggt gagcctcaat     240
aatatcgtta tcctccatgt ccaaatcttc aggggtctga tcagcttgaa ttctaatacc     300
gtcgtacaag aatcttaagg agtccatttc cttaccctgt cttttagcga acgcttccat     360
cagccttctt aaaggagtgg tcttttttgat cttgaagaag atctctgaag atccatcgga     420
caccttttaaa ttgatgtgag tctcaggctt gacttctggc ttgacctctg gcttagcttc     480
ttgattgact tctgagtccg acccgtgatg atgatggtga tgacccatgg tatatctcct     540
tcttaaagtt aaacaaaatt atttctagag gggaattgtt atccgctcac aattccccta     600
tagtgagtcg tattaattc gcgggatcga gatctcgatc ctctacgccg gacgcatcgt     660
ggccggcatc accggcgcca caggtgcggt tgctggcgcc tatatcgccg acatcaccga     720
tggggaagat cgggctcgcc acttcgggct catgagcgct tgtttcggcg tgggtatggt     780
ggcaggcccc gtggccgggg gactgttggg cgccatctcc ttgcatgcac cattccttgc     840
ggcggcggtg ctcaacggcc tcaacctact actgggctgc ttcctaatgc aggagtcgca     900
taagggagag cgtcgagatc ccggacacca tcgaatggcg caaaaccttt cgcggtatgg     960
catgatagcg cccggaagag agtcaattca gggtggtgaa tgtgaaacca gtaacgttat    1020
acgatgtcgc agagtatgcc ggtgtctctt atcagaccgt ttcccgcgtg gtgaaccagg    1080
ccagccacgt ttctgcgaaa acgcgggaaa aagtggaagc ggcgatggcg gagctgaatt    1140
acattcccaa ccgcgtggca caacaactgg cgggcaaaca gtcgttgctg attggcgttg    1200
ccacctccag tctggccctg cacgcgccgt cgcaaattgt cgcggcgatt aaatctcgcg    1260
ccgatcaact gggtgccagc gtggtggtgt cgatggtaga acgaagcggc gtcgaagcct    1320
gtaaagcggc ggtgcacaat cttctcgcgc aacgcgtcag tgggctgatc attaactatc    1380
cgctggatga ccaggatgcc attgctgtgg aagctgcctg cactaatgtt ccggcgttat    1440
ttcttgatgt ctctgaccag acacccatca acagtattat tttctcccat gaagacggta    1500
cgcgactggg cgtggagcat ctggtcgcat gggtcacca gcaaatcgcg ctgttagcgg    1560
gcccattaag ttctgtctcg gcgcgtctgc gtctggctgg ctggcataaa tatctcactc    1620
gcaatcaaat tcagccgata gcggaacggg aaggcgactg gagtgccatg tccggttttc    1680
aacaaaccat gcaaatgctg aatgagggca tcgttcccac tgcgatgctg gttgccaacg    1740
atcagatggc gctgggcgca atgcgcgcca ttaccgagtc cgggctgcgc gttggtgcgg    1800
atatctcggt agtgggatac gacgataccg aagacagctc atgttatatc ccgccgttaa    1860
ccaccatcaa acaggatttt cgcctgctgg ggcaaaccag cgtggaccgc ttgctgcaac    1920
tctctcaggg ccaggcggtg aagggcaatc agctgttgcc cgtctcactg gtgaaaagaa    1980
aaaccaccct ggcgcccaat acgcaaaccg cctctccccg cgcgttggcc gattcattaa    2040
tgcagctggc acgacaggtt tcccgactgg aaagcgggca gtgagcgcaa cgcaattaat    2100
```

```
gtaagttagc tcactcatta ggcaccggga tctcgaccga tgcccttgag agccttcaac    2160
ccagtcagct ccttccggtg ggcgcgggc atgactatcg tcgccgcact tatgactgtc    2220
ttctttatca tgcaactcgt aggacaggt ccggcagcgc tctgggtcat tttcggcgag    2280
gaccgctttc gctggagcgc gacgatgatc ggcctgtcgc ttgcggtatt cggaatcttg    2340
cacgccctcg ctcaagcctt cgtcactggt cccgccacca aacgtttcgg cgagaagcag    2400
gccattatcg ccggcatggc ggcccacgg gtgcgcatga tcgtgctcct gtcgttgagg    2460
acccggctag gctggcgggg ttgccttact ggttagcaga atgaatcacc gatacgcgag    2520
cgaacgtgaa gcgactgctg ctgcaaaacg tctgcgacct gagcaacaac atgaatggtc    2580
ttcggtttcc gtgtttcgta aagtctggaa acgcggaagt cagcgccctg caccattatg    2640
ttccggatct gcatcgcagg atgctgctgg ctaccctgtg aacacctac atctgtatta    2700 acgaagcgct ggcattgacc ctgagtgatt tttctctggt cccgccgcat ccataccgcc    2760
agttgtttac cctcacaacg ttccagtaac cgggcatgtt catcatcagt aacccgtatc    2820
gtgagcatcc tctctcgttt catcggtatc attaccccca tgaacagaaa tccccttac    2880 acggaggcat cagtgaccaa acaggaaaaa accgccctta acatggcccg ctttatcaga    2940
agccagacat taacgcttct ggagaaactc aacgagctgg acgcggatga acaggcagac    3000
atctgtgaat cgcttcacga ccacgctgat gagctttacc gcagctgcct cgcgcgtttc    3060
ggtgatgacg gtgaaaacct ctgacacatg cagctcccgg agacggtcac agcttgtctg    3120
taagcggatg ccgggagcag acaagcccgt cagggcgcgt cagcgggtgt tggcgggtgt    3180
cggggcgcag ccatgaccca gtcacgtagc gatagcggag tgtatactgg cttaactatg    3240
cggcatcaga gcagattgta ctgagagtgc accatatatg cggtgtgaaa taccgcacag    3300
atgcgtaagg agaaaatacc gcatcaggcg ctcttccgct tcctcgctca ctgactcgct    3360
gcgctcggtc gttcggctgc ggcgagcggt atcagctcac tcaaaggcgg taatacggtt    3420
atccacagaa tcagggata acgcaggaaa gaacatgtga gcaaaaggcc agcaaaaggc    3480
caggaaccgt aaaaaggccg cgttgctggc gtttttccat aggctccgcc cccctgacga    3540
gcatcacaaa aatcgacgct caagtcagag gtggcgaaac ccgacaggac tataaagata    3600
ccaggcgttt ccccctggaa gctccctcgt gcgctctcct gttccgaccc tgccgcttac    3660
cggatacctg tccgcctttc tcccttcggg aagcgtggcg ctttctcata gctcacgctg    3720
taggtatctc agttcggtgt aggtcgttcg ctccaagctg ggctgtgtgc acgaaccccc    3780
cgttcagccc gaccgctgcg ccttatccgg taactatcgt cttgagtcca acccggtaag    3840
acacgactta tcgccactgg cagcagccac tggtaacagg attagcagag cgaggtatgt    3900
aggcggtgct acagagttct tgaagtggtg gcctaactac ggctacacta aggacagt    3960 atttggtatc tgcgctctgc tgaagccagt taccttcgga aaaagagttg gtagctcttg    4020
atccggcaaa caaccaccg ctggtagcgg tggttttttt gtttgcaagc agcagattac    4080
gcgcagaaaa aaaggatctc aagaagatcc tttgatcttt tctacggggt ctgacgctca    4140
gtggaacgaa aactcacgtt aagggatttt ggtcatgaac aataaaactg tctgcttaca    4200
taaacagtaa tacaaggggt gttatgagcc atattcaacg ggaaacgtct gctctaggc    4260 cgcgattaaa ttccaacatg gatgctgatt tatatgggta aaatgggct cgcgataatg    4320 tcgggcaatc aggtgcgaca atctatcgat tgtatgggaa gcccgatgcg ccagagttgt    4380
ttctgaaaca tggcaaaggt agcgttgcca atgatgttac agatgagatg gtcagactaa    4440
actggctgac ggaatttatg cctcttccga ccatcaagca ttttatccgt actcctgatg    4500
```

```
atgcatggtt actcaccact gcgatccccg ggaaaacagc attccaggta ttagaagaat    4560
atcctgattc aggtgaaaat attgttgatg cgctggcagt gttcctgcgc cggttgcatt    4620
cgattcctgt ttgtaattgt ccttttaaca gcgatcgcgt atttcgtctc gctcaggcgc    4680
aatcacgaat gaataacggt ttggttgatg cgagtgattt tgatgacgag cgtaatggct    4740
ggcctgttga acaagtctgg aaagaaatgc ataaactttt gccattctca ccggattcag    4800
tcgtcactca tggtgatttc tcacttgata acctttattt tgacgagggg aaattaatag    4860
gttgtattga tgttggacga gtcggaatcc cagaccgata ccaggatctt gccatcctat    4920
ggaactgcct cggtgagttt tctccttcat tacagaaacg gcttttttcaa aaatatggta    4980 ttgataatcc tgatatgaat aaattgcagt ttcatttgat gctcgatgag ttttttctaag    5040 aattaattca tgagcggata catatttgaa tgtatttaga aaaataaaca aataggggtt    5100
ccgcgcacat ttccccgaaa agtgccacct gaaattgtaa acgttaatat tttgttaaaa    5160
ttcgcgttaa attttttgtta aatcagctca ttttttaacc aataggccga aatcggcaaa    5220
atcccttata aatcaaaaga atagaccgag atagggttga gtgttgttcc agtttggaac    5280
aagagtccac tattaaagaa cgtggactcc aacgtcaaag ggcgaaaaac cgtctatcag    5340
ggcgatggcc cactacgtga accatcaccc taatcaagtt ttttgggtc gaggtgccgt    5400 aaagcactaa atcggaaccc taaagggagc ccccgattta gagcttgacg gggaaagccg    5460
gcgaacgtgg cgagaaagga agggaagaaa gcgaaaggag cgggcgctag ggcgctggca    5520
agtgtagcgg tcacgctgcg cgtaaccacc acacccgccg cgcttaatgc gccgctacag    5580
ggcgcgtccc attcgcca                                                  5598

<210> SEQ ID NO 37
<211> LENGTH: 478
<212> TYPE: DNA
<213> ORGANISM: Artificial Sequence
<220> FEATURE:
<223> OTHER INFORMATION: Synthetic Sequence

<400> SEQUENCE: 37
agatctcgat cccgcgaaat taatacgact cactataggg gaattgtgag cggataacaa     60
ttcccctcta gaaataattt tgtttaactt taagaaggag atataccatg ggtcatcacc    120
atcatcatca cggtcggac tcagaagtca atcaagaagc taagccagag gtcaagccag    180
aagtcaagcc tgagactcac atcaatttaa aggtgtccga tggatcttca gagatcttct    240
tcaagatcaa aaagaccact cctttaagaa ggctgatgga agcgttcgct aaaagacagg    300
gtaaggaaat ggactcctta agattcttgt acgacggtat tagaattcaa gctgatcaga    360
cccctgaaga tttggacatg aggataacg atattattga ggctcaccgc gaacagattg    420
gaggttgaga ccggatccga attcgagctc cgtcgacaag cttgcggccg cactcgag     478

<210> SEQ ID NO 38
<211> LENGTH: 106
<212> TYPE: PRT
<213> ORGANISM: Saccharomtces cerevisiae

<400> SEQUENCE: 38

Met Gly His His His His His His Gly Ser Asp Ser Glu Val Asn Gln
1               5                   10                  15

Glu Ala Lys Pro Glu Val Lys Pro Glu Val Lys Pro Glu Thr His Ile
            20                  25                  30
```

```
Asn Leu Lys Val Ser Asp Gly Ser Glu Ile Phe Phe Lys Ile Lys
         35                  40                  45

Lys Thr Thr Pro Leu Arg Arg Leu Met Glu Ala Phe Ala Lys Arg Gln
 50                  55                  60

Gly Lys Glu Met Asp Ser Leu Arg Phe Leu Tyr Asp Gly Ile Arg Ile
 65                  70                  75                  80

Gln Ala Asp Gln Thr Pro Glu Asp Leu Asp Met Glu Asp Asn Asp Ile
                 85                  90                  95

Ile Glu Ala His Arg Glu Gln Ile Gly Gly
            100                 105

<210> SEQ ID NO 39
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 39

Leu Arg Leu Arg Gly Gly
 1               5

<210> SEQ ID NO 40
<211> LENGTH: 50
<212> TYPE: DNA
<213> ORGANISM: Artificial Sequence
<220> FEATURE:
<223> OTHER INFORMATION: primer

<400> SEQUENCE: 40
ccatgggtca tcaccatcat catcacgggt cggactcaga agtcaatcaa           50

<210> SEQ ID NO 41
<211> LENGTH: 36
<212> TYPE: DNA
<213> ORGANISM: Artificial Sequence
<220> FEATURE:
<223> OTHER INFORMATION: primer

<400> SEQUENCE: 41
ggatccggtc tcaacctcca atctgttcgc ggtgag                          36

<210> SEQ ID NO 42
<211> LENGTH: 33
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (0)...(0)
<223> OTHER INFORMATION: n = a, c, g, or t

<400> SEQUENCE: 42
ggtctcaagg tnnngtgagc aagggcgagg agc                             33

<210> SEQ ID NO 43
<211> LENGTH: 31
<212> TYPE: DNA
<213> ORGANISM: Artificial Sequence
<220> FEATURE:
<223> OTHER INFORMATION: primer

<400> SEQUENCE: 43
aagcttatta cttgtacagc tcgtccatgc c                               31
```

```
<210> SEQ ID NO 44
<211> LENGTH: 14
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (0)...(0)
<223> OTHER INFORMATION: n = a, c, g, or t

<400> SEQUENCE: 44
ggtctcaagg tnnn                                                      14

<210> SEQ ID NO 45
<211> LENGTH: 18
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (0)...(0)
<223> OTHER INFORMATION: n = a, c, g, or t

<400> SEQUENCE: 45
ggtctcctcg agttannn                                                  18

<210> SEQ ID NO 46
<211> LENGTH: 84
<212> TYPE: DNA
<213> ORGANISM: Artificial Sequence
<220> FEATURE:
<223> OTHER INFORMATION: Synthetic Sequence

<400> SEQUENCE: 46
gtcttaagac taagaggtgg cacgccggcg gtgaccacct ataaactggt gattaacggc    60
aaaaccctga aggcgaaac cacc                                            84

<210> SEQ ID NO 47
<211> LENGTH: 78
<212> TYPE: DNA
<213> ORGANISM: Artificial Sequence
<220> FEATURE:
<223> OTHER INFORMATION: Synthetic Sequence

<400> SEQUENCE: 47
gccgttatcg ttcgcatact gtttaaacgc tttttccgcg gtttccgcat ccaccgcttt    60
ggtggtttcg cctttcag                                                  78

<210> SEQ ID NO 48
<211> LENGTH: 86
<212> TYPE: DNA
<213> ORGANISM: Artificial Sequence
<220> FEATURE:
<223> OTHER INFORMATION: Synthetic Sequence

<400> SEQUENCE: 48
cagtatgcga acgataacgg cgtggatggc gtgtggacct atgatgatgc gaccaaaacc    60
tttaccgtga ccgaataagg tacccc                                         86

<210> SEQ ID NO 49
<211> LENGTH: 15
<212> TYPE: DNA
<213> ORGANISM: Artificial Sequence
```

```
<220> FEATURE:
<223> OTHER INFORMATION: primer

<400> SEQUENCE: 49
cttgtcttaa gaggt                                                          15

<210> SEQ ID NO 50
<211> LENGTH: 21
<212> TYPE: DNA
<213> ORGANISM: Artificial Sequence
<220> FEATURE:
<223> OTHER INFORMATION: primer

<400> SEQUENCE: 50
gctgggtacc ttattcggtc a                                                   21

<210> SEQ ID NO 51
<211> LENGTH: 30
<212> TYPE: DNA
<213> ORGANISM: Artificial Sequence
<220> FEATURE:
<223> OTHER INFORMATION: primer

<400> SEQUENCE: 51
ggtctcaagg tacgccggcg gtgaccacct                                          30

<210> SEQ ID NO 52
<211> LENGTH: 30
<212> TYPE: DNA
<213> ORGANISM: Artificial Sequence
<220> FEATURE:
<223> OTHER INFORMATION: primer

<400> SEQUENCE: 52
aagcttatta ttcggtcacg gtaaaggttt                                          30

<210> SEQ ID NO 53
<211> LENGTH: 34
<212> TYPE: DNA
<213> ORGANISM: Artificial Sequence
<220> FEATURE:
<223> OTHER INFORMATION: primer

<400> SEQUENCE: 53
ggtctcaagg tatgaccatg attacggatt cact                                     34

<210> SEQ ID NO 54
<211> LENGTH: 32
<212> TYPE: DNA
<213> ORGANISM: Artificial Sequence
<220> FEATURE:
<223> OTHER INFORMATION: primer

<400> SEQUENCE: 54
aagcttatta ttattatttt tgacaccaga cc                                       32

<210> SEQ ID NO 55
<211> LENGTH: 34
<212> TYPE: DNA
<213> ORGANISM: Artificial Sequence
<220> FEATURE:
<223> OTHER INFORMATION: primer

<400> SEQUENCE: 55
ggtctcaagg tatgcagatc ttcgtcaaga cgtt                                     34
```

```
<210> SEQ ID NO 56
<211> LENGTH: 30
<212> TYPE: DNA
<213> ORGANISM: Artificial Sequence
<220> FEATURE:
<223> OTHER INFORMATION: primer

<400> SEQUENCE: 56
aagcttatta ttgtttgcct ccctgctgcg                              30

<210> SEQ ID NO 57
<211> LENGTH: 25
<212> TYPE: DNA
<213> ORGANISM: Artificial Sequence
<220> FEATURE:
<223> OTHER INFORMATION: primer

<400> SEQUENCE: 57
gctcgagagc acagatgctt cgttg                                   25

<210> SEQ ID NO 58
<211> LENGTH: 25
<212> TYPE: DNA
<213> ORGANISM: Artificial Sequence
<220> FEATURE:
<223> OTHER INFORMATION: primer

<400> SEQUENCE: 58
gcaaagcttg gagttgattg tatgc                                   25

<210> SEQ ID NO 59
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 59

Gly Gly Ala Thr Tyr
 1               5

<210> SEQ ID NO 60
<211> LENGTH: 18
<212> TYPE: DNA
<213> ORGANISM: Artificial Sequence
<220> FEATURE:
<223> OTHER INFORMATION: primer

<400> SEQUENCE: 60
ttttggtctc caggttgt                                           18

<210> SEQ ID NO 61
<211> LENGTH: 18
<212> TYPE: DNA
<213> ORGANISM: Artificial Sequence
<220> FEATURE:
<223> OTHER INFORMATION: primer

<400> SEQUENCE: 61
acaacctgga gaccaaaa                                           18

<210> SEQ ID NO 62
<211> LENGTH: 13
<212> TYPE: DNA
<213> ORGANISM: Artificial Sequence
<220> FEATURE:
<223> OTHER INFORMATION: primer
```

-continued

```
<400> SEQUENCE: 62
ggaggttgag acc                                                          13

<210> SEQ ID NO 63
<211> LENGTH: 13
<212> TYPE: DNA
<213> ORGANISM: Artificial Sequence
<220> FEATURE:
<223> OTHER INFORMATION: primer

<400> SEQUENCE: 63
ggtctcaacc tcc                                                          13

<210> SEQ ID NO 64
<211> LENGTH: 294
<212> TYPE: DNA
<213> ORGANISM: Artificial Sequence
<220> FEATURE:
<223> OTHER INFORMATION: Synthetic Sequence

<400> SEQUENCE: 64
atgtcggact cagaagtcaa tcaagaagct aagccagagg tcaagccaga agtcaagcct       60
gagactcaca tcaatttaaa ggtgtccgat ggatcttcag agatcttctt caagatcaaa     120
aagaccactc ctttaagaag gctgatggaa gcgttcgcta aaagacaggg taaggaaatg     180
gactccttaa gattcttgta cgacggtatt agaattcaag ctgatcaggc ccctgaagat     240
ttggacatgg aggataacga tattattgag gctcaccgcg aacagattgg aggt           294

<210> SEQ ID NO 65
<211> LENGTH: 98
<212> TYPE: PRT
<213> ORGANISM: Artificial Sequence
<220> FEATURE:
<223> OTHER INFORMATION: Synthetic Sequence

<400> SEQUENCE: 65

Met Ser Asp Ser Glu Val Asn Gln Glu Ala Lys Pro Glu Val Lys Pro
 1               5                  10                  15

Glu Val Lys Pro Glu Thr His Ile Asn Leu Lys Val Ser Asp Gly Ser
            20                  25                  30

Ser Glu Ile Phe Phe Lys Ile Lys Lys Thr Thr Pro Leu Arg Arg Leu
        35                  40                  45

Met Glu Ala Phe Ala Lys Arg Gln Gly Lys Glu Met Asp Ser Leu Arg
    50                  55                  60

Phe Leu Tyr Asp Gly Ile Arg Ile Gln Ala Asp Gln Ala Pro Glu Asp
65                  70                  75                  80

Leu Asp Met Glu Asp Asn Asp Ile Ile Glu Ala His Arg Glu Gln Ile
                85                  90                  95

Gly Gly
```